(12) United States Patent
Fujihara et al.

(10) Patent No.: US 8,586,591 B2
(45) Date of Patent: *Nov. 19, 2013

(54) AMINOPYRAZINE DERIVATIVE AND MEDICINE

(71) Applicants: Hidetaka Fujihara, Kyoto (JP); Tetsuo Asaki, Uji (JP); Katsutoshi Hori, Kusatsu (JP); Haruna Naito, Kyoto (JP)

(72) Inventors: Hidetaka Fujihara, Kyoto (JP); Tetsuo Asaki, Uji (JP); Katsutoshi Hori, Kusatsu (JP); Haruna Naito, Kyoto (JP)

(73) Assignee: Nippon Shinyaku Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/743,550

(22) Filed: Jan. 17, 2013

(65) Prior Publication Data

US 2013/0131082 A1    May 23, 2013

Related U.S. Application Data

(63) Continuation of application No. 13/147,001, filed as application No. PCT/JP2010/051722 on Feb. 5, 2010.

(30) Foreign Application Priority Data

Feb. 6, 2009  (JP) ................................ 2009-026470
Dec. 4, 2009  (JP) ................................ 2009-276133

(51) Int. Cl.
  *A61K 31/497*   (2006.01)
  *C07D 401/14*   (2006.01)

(52) U.S. Cl.
  USPC ..................... 514/255.05; 544/405

(58) Field of Classification Search
  USPC ..................... 514/255.05; 544/405
  See application file for complete search history.

(56) References Cited

U.S. PATENT DOCUMENTS

2011/0288065 A1* 11/2011 Fujihara et al. .......... 514/210.02

FOREIGN PATENT DOCUMENTS

| WO | 00/71536 A1 | 11/2000 |
| WO | 2004/043936 A1 | 5/2004 |
| WO | 2009/017838 A2 | 2/2009 |

OTHER PUBLICATIONS

Van Etten et al., "Focus on myeloproliferative diseases and myelodysplastic syndromes", Cancer Cell, Dec. 2004, pp. 547-552, vol. 6, Cell Press.
Kralovics et al., "A Gain-of-Function Mutation of JAK2 in Myeloproliferative Disorders", The New England Journal of Medicine, Apr. 28, 2005, pp. 1779-1790, vol. 352;17, Massachusets Medical Society.
Campbell et al., "The Myeloproliferative Disorders", The New England Journal of Medicine, Dec. 7, 2006, pp. 2452-2466, vol. 355;23, Massachusets Medical Society.
Grunebach et al., "Detection of a new JAK2 D620E mutation in addition to V617F in a patient with polycythemia vera", Leukemia, Sep. 28, 2006, pp. 2210-2211, vol. 20.
Pikman et al., "MPLW515L Is a Novel Somatic Activating Mutation in Myelofibrosis with Myeloid Metaplasia", PLoS Medicine, Jul. 2006, pp. 1140-1151, vol. 3, Issue 7, e270.
Pardanani et al., "MPL515 mutations in myeloproliferative and other myeloid disorders: a study of 1182 patients", Blood, Jul. 25, 2006, pp. 3472-3476, vol. 108, American Society of Hematology.
Ceesay et al., "The JAK2 V617F mutation is rare in RARS but common in RARS-T", Leukemia, Aug. 2006, pp. 2060-2061, vol. 20.
Mullighan et al., "JAK mutations in high-risk childhood acute lymphoblastic leukemia", Proceedings of the National Academy of Science U.S.A., Jun. 9, 2009, pp. 9414-9418, vol. 106, No. 23.
Gaikwad et al., "Prevalence and clinical correlates of JAK2 mutations in Down syndrome acute lymphoblastic leukaemia", British Journal of Haematology, Dec. 22, 2008, pp. 930-932, vol. 144, Blackwell Publishing Ltd.
Valentino et al., "JAK/STAT signal transduction: Regulators and implication in hematological malignancies", Biochemical Pharmacology, 2006, pp. 713-721, vol. 71, Elsevier.
Samanta et al., "Janus Kinase 2: A Critical Target in Chronic Myelogenous Leukemia", Cancer Research, Jul. 3, 2006, pp. 6468-6472, vol. 66, American Association for Cancer Research.
Yu et al., "STATs in cancer inflammation and immunity: a leading role for STAT3", Nature Reviews Cancer, Nov. 2009, pp. 798-809, vol. 9, Macmillan Publishers Limited.
Ogura et al., "Interleukin-17 Promotes Autoimmunity by Triggering a Positive-Feedback Loop via Interleukin-6 Induction", Immunity, Oct. 17, 2008, pp. 628-636, vol. 29, Elsevier Inc.

(Continued)

*Primary Examiner* — Kristin Vajda

(57) ABSTRACT

The present invention relates to a compound represented by general formula [1] satisfying the following (I) or (II), or a pharmaceutically acceptable salt of the compound.

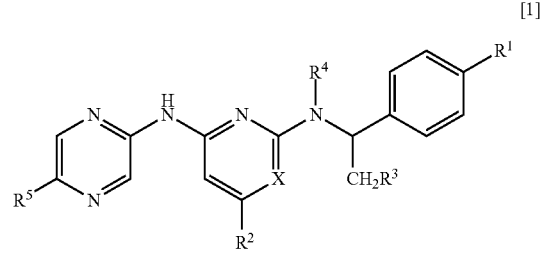

[1]

(I) is CH or N; $R^1$ is a halogen atom; and $R^2$ is H, a halogen atom, CN, [2], [3], [8], [9], an —O-alkyl, an —O— (saturated ring), etc.
[2]: —$C(R^C)(R^D)(R^E)$ ($R^C$ to $R^E$ each are H, an alkyl, etc.)
[3]: —$N(R^F)(R^G)$ ($R^F$ and $R^G$ each are H, OH, amino, a (hetero)aryl, etc.)
[8]: —$C(=O)R^L$ ($R^L$ is an alkyl, OH, an alkoxy, amino, etc.)
[9]: a (substituted)phenyl;
(II) X is >C—$C(=O)R^B$ ($R^B$ is a (substituted)amino, an alkoxy, OH, etc.);
$R^1$ is a halogen atom; and $R^2$ is H;
and
$R^3$ is H or OH; and $R^4$ and $R^5$ each are H or an alkyl.

12 Claims, No Drawings

(56) References Cited

OTHER PUBLICATIONS

Catlett-Falcone et al., "Constitutive Activation of Stat3 Signaling Confers Resistance to Apoptosis in Human U266 Myeloma Cells", Immunity, Jan. 1999, pp. 105-115, vol. 10, Cell Press.

Narazaki et al., "Activation of JAK2 kinase mediated by the interleukin 6 signal transducer gp130", Proceedings of the National Academy of Science U.S.A., Mar. 1994, pp. 2285-2289, vol. 91, Cell Biology.

Heinrich et al., "Principles of interleukin (IL)-6-type cytokine signalling and its regulation", Biochemical Journal, 2003, pp. 1-20, vol. 374, Biochemical Society, Great Britain.

Steiner et al., "Interleukin-6 Overexpression Induces Pulmonary Hypertension", Circulation Research, Dec. 12, 2008, pp. 236-244, vol. 104, American Heart Association.

Sprague et al., "Inflammatory cytokines in vascular dysfunction and vascular disease", Biochemical Pharmacology, Apr. 2009, pp. 539-552, vol. 78, Elsevier.

Neilson et al., "Coactivation of Janus Tyrosine Kinase (Jak)1 Positively Modulates Prolactin-Jak2 Signaling in Breast Cancer: Recruitment of ERK and Signal Transducer and Activator of Transcription (Stat)3 and Enhancement of Akt and Stat5a/b Pathways", Molecular Endocrinology, Sep. 2007, pp. 2218-2232, vol. 21, Endocrine Society.

Changelian et al., "Prevention of Organ Allograft Rejection by a Specific Janus Kinase 3 Inhibitor", Science, Oct. 31, 2003, pp. 875-878, vol. 302.

T. R. Golub et al., "Molecular Classification of Cancer: Class Discovery and Class Prediction by Gene Expression Monitoring," Science, vol. 286, No. 5439, pp. 531-537 (1999).

P. K. Lala and A. Orucevic "Role of Nitric Oxide in Tumor Progression: Lessons from Experimental Tumors," Cancer and Metastasis Reviews, vol. 17, No. 1, pp. 91-106 (1998).

"Cancer [online], [retrieved on Jul. 6, 2007], Retrieved from the Internet, URL: http://www.nlm.nih.gov/medlineplus/cancer.html," cited in Non-Final Office Action issued on Mar. 7, 2013, in parent U.S. Appl. No. 13/147,001.

\* cited by examiner

AMINOPYRAZINE DERIVATIVE AND MEDICINE

CROSS-REFERENCE TO RELATED APPLICATIONS

This patent application is a continuation of pending U.S. application Ser. No. 13/147,001 filed on Jul. 29, 2011, which is a U.S. national stage entry under 35 U.S.C. §371 of International Patent Application No. PCT/JP2010/051722 filed on Feb. 5, 2010, which claims the benefit of foreign priority to Japanese Patent Application Nos. JP 2009-026470 filed on Feb. 6, 2009, and JP 2009-276133 filed on Dec. 4, 2009, the disclosures of all of which are hereby incorporated by reference in their entireties. The U.S. application Ser. No. 13/147,001 was published on Nov. 24, 2011, as US 2011/0288065 A1. The International Application was published in Japanese on Aug. 12, 2010, as International Publication No. WO 2010/090290 A1 under PCT Article 21(2). The present application incorporates the corrections made to the specification in the First Preliminary Amendment filed in 13/147,001 on Jul. 29, 2011.

FIELD OF THE INVENTION

The present invention relates to a new aminopyrazine derivative and a pharmaceutical composition containing the aminopyrazine derivative as an active ingredient.

BACKGROUND OF THE INVENTION

Myeloidproliferative neoplasms (chronic myeloid proliferative diseases) are a class of diseases mainly involving abnormal growth of hemocytes, which is caused by aberrant hematopoietic stem cells. Specifically, diseases such as polycythemia vera, essential thrombocythemia, and idiopathic myelofibrosis are known (see, for example, Van Etten, et al., 2004, Cancer Cell, 6, 547-552). At present, there is no available therapy for myeloidproliferative neoplasms (chronic myeloid proliferative diseases) and thus there is an earnest desire of therapeutic agent for these diseases.

In 2005, an activated mutation of JAK2, a kind of JAK family tyrosine kinases (JAK2 V617F mutation), was reported in a patient suffering from myeloidproliferative neoplasm (chronic myeloid proliferative disease) (see, for example, Robert Kralovics, et al., 2005, New England Journal of Medicine, 352, 1779-1790). In a subsequent study, the activated mutation was confirmed in about 95% of polycythemia vera patients, about 50% of essential thrombocythemia patients, and about 50% of idiopathic myelofibrosis patients (see, for example, Peter J. Campbell, et al., 2006, New England Journal of Medicine, 355, 2452-2466). Further, another activated mutation of JAK2 (JAK2 D620E mutation) was found in a few cases of polycythemia vera patients (see, for example, L. Richeldi, et al., 2006, Leukemia, 20, 2210-2211). Moreover, activated mutations of c-Mpl in a thrombopoietin receptor (MPL W515L mutation and MPL W515K mutation) were found in about 10% of idiopathic myelofibrosis patients in whom JAK2 V617F was negative.

Since JAK2 is located downstream of the intracellular signal transduction pathway of c-Mpl, a compound having a JAK2 tyrosine kinase inhibitory activity is expected to be an active ingredient for therapeutics in treatment of diseases caused not only by JAK2-activated mutation but also by c-Mpl mutation, e.g., myeloidproliferative neoplasms (chronic myeloid proliferative diseases) (see, for example, Yana Pikman, et al., 2006, PLoS Medicine, 3, 1140-1151, and Animesh D, et al., 2006, Blood, 108, 3472-3476).

JAK2-activated mutations have also been found in other than myeloidproliferative neoplasms (chronic myeloid proliferative diseases). For example, it has been reported that a JAK2 V617F mutation is found at a high rate inpatients belonging to a class of myelodysplastic syndrome (RARS-T) (see, for example, MM Ceesay, et al., 2006, Leukemia, 20, 2060-2061). JAK2-activated mutation (JAK2 R683S/G mutation etc.) has also been found in 16 (about 9%) of 187 cases in infantile acute lymphocytic leukemia patients (see, for example, C. Mullighan, et al., 2009, Proceedings of the National Academy of Science U.S.A, 106, 9414-9418), and in about 20% of infantile acute lymphocytic leukemia patients with Down's syndrome (see, for example, A. Gaikwad, et al., 2008, British Journal of Haematology, 144, 930-932).

It has also been reported that the activation of JAK2 tyrosine kinase generated by JAK2 fusion gene is involved in pathological formation. For example, a TEL-JAK2 fusion protein was found in patients of myeloidproliferative neoplasms (acute myeloid proliferative diseases) and of acute myeloid leukemia, and a BCR-JAK2 fusion protein and a PCM1-JAK2 fusion protein were found in patients of chronic myeloid leukemia-like hematic cancer (see, for example, Lyne Valentino, et al., 2006, Biochemical Pharmacology, 71, 713-721 ("Valentino")). JAK2 signal transduction pathway is involved in the growth of Bcr-Abl-positive chronic myeloid leukemia cells, suggesting that a compound having a JAK2 tyrosine kinase inhibitory activity will be effective for imatinib-resistant chronic myeloid leukemia (see, for example, Ajoy K. Samanta, et al., 2006, Cancer Research, 66, 6468-6472). In general, the JAK2 signal transduction pathway is one of important pathways in the growth of hematic cancer cell, and thus, a compound having a JAK2 tyrosine kinase inhibitory activity is expected to have a therapeutic effect for a variety of hematic cancers (see, for example, Valentino).

JAK2 tyrosine kinase is also involved in intracellular signal transduction of cytokine receptors or hormone receptors. Interleukin-6 (IL-6) is an inflammatory cytokine which plays an important role in inflammation, immunoresponse and onset of cancers (see, for example, H. Yu, et al., 2009, Nature Reviews Cancer, 9, 798-809, H. Ogura, et al., 2008, Immunity, 29, 628-636, and R. Catlett-Falcone, et al., 1999, Immunity, 10, 105-115), and the IL-6 signal is transduced through JAK2 tyrosine kinase (see, for example, M. Narazaki, et al., 1994, Proceedings of the National Academy of Science U.S.A, 91, 2285-2289). Diseases in which IL-6 is involved include inflammatory diseases (e.g., rheumatoid arthritis, inflammatory bowel disease, osteoporosis, multiple sclerosis), hematic cancers (e.g., multiple myeloma), solid cancer (e.g., prostatic cancer), and angiopathy (e.g., pulmonary hypertension, arteriosclerosis, aneurysm, varicose vein) (see, for example, P. Heinrich, et al., 2003, Biochemical Journal, 374, 1-20, M. Steiner, et al., 2009, Circulation Research, 104, 236-244, and H. Alexander, et al., 2009, Biochemical Pharmacology, 78, 539-552). Further, it is known that JAK2 tyrosine kinase contributes to intracellular signal transduction of prolactin receptors, and the expressed amount of prolactin receptor increases in breast cancer, resulting in acceleration of the proliferation of cancer cells by prolactin (for example, L. Neilson, et al., 2007, Molecular Endocrinology, 21, 2218-2232).

Thus, it is expected that a compound having a JAK2 tyrosine kinase inhibitory activity exhibits a therapeutic effect for a variety of diseases such as inflammatory diseases, hematic cancers, solid cancers, and angiopathy since JAK2 tyrosine kinase is involved in transduction of extracellular stimulation.

JAK3 is a tyrosine kinase which plays an important role in signal transduction of cytokine, and has attracted considerable attention as a target molecule of immunosuppressants since 10 or more years ago. In fact, compounds having a JAK3 tyrosine kinase inhibitory activity have been subjected to clinical trial as therapeutics for organ transplantation and rheumatoid arthritis (see, for example, Paul S. Changelian, et al., 2003, Science, 302, 875-878).

BRIEF SUMMARY OF THE INVENTION

The main purpose of the present invention is to provide a new aminopyrazine derivative. Another purpose of the present invention is to provide a pharmaceutical composition which contains such an aminopyrazine derivative as an active ingredient.

In the present invention, the compound represented by the following general formula [1] (hereinafter referred to as "the compound of the invention") or a pharmaceutically acceptable salt thereof is exemplified, wherein the compound is defined by the following (I) or (II).

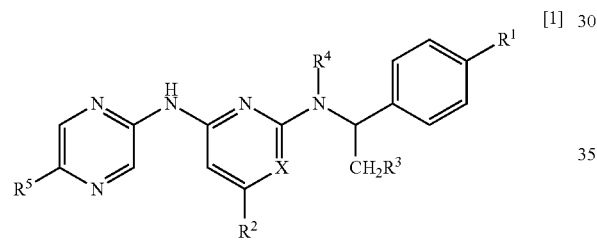

[1]

(I):

X represents CH or N;

$R^1$ represents a halogen;

$R^2$ represents:

(1) H, (2) a halogen, (3) cyano, (4) a group represented by the following general formula [2]:

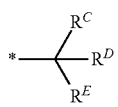

[2]

(wherein * indicates the binding position; and $R^C$, $R^D$ and $R^E$ are the same or different and each represents (a) H, or (b) alkyl optionally substituted by hydroxy or alkoxy, or alternatively two of $R^C$, $R^D$ and $R^E$ are taken together with the adjacent C to represent a N-containing saturated heterocyclic group and the other one is H, the saturated heterocyclic group optionally substituted by alkylsulfonyl), (5) a group represented by the following general formula [3]:

[3]

(wherein * has the same meaning as described above; and $R^F$ and $R^G$ are the same or different and each represents (a) H, (b) alkyl optionally substituted by one or two groups selected from the group consisting of hydroxy, amino, dialkylamino, a saturated cyclic amino group, alkylcarbonylamino, alkylsulfonylamino, aryl, heteroaryl optionally substituted by alkyl, tetrahydrofuranyl, and carbamoyl, (c) alkylcarbonyl, (d) alkylsulfonyl, (e) carbamoyl, or (f) heteroaryl optionally substituted by alkyl, or alternatively $R^F$ and $R^G$ are taken together with the adjacent N to represent a saturated cyclic amino group, which may optionally be substituted by one or two groups selected from the group consisting of (a) halogen, (b) cyano, (c) hydroxy, (d) alkyl optionally substituted by one or two groups selected from the group consisting of hydroxy, alkoxy, amino, alkoxycarbonylamino, alkylsulfonylamino, and alkylcarbonylamino, (e) cycloalkyl, (f) haloalkyl, (g) alkoxy, (h) oxo, (i) a group represented by the following general formula [4]:

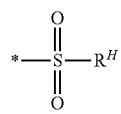

[4]

(wherein * has the same meaning as described above; and $R^H$ represents alkyl or aryl), (j) a group represented by the following general formula [5]:

[5]

(wherein * has the same meaning as described above; and $R^I$ and $R^J$ are the same or different and each represents H, alkyl, carbamoyl, alkylcarbonyl, or alkylsulfonyl), (k) a group represented by the following general formula [6]:

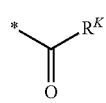

[6]

(wherein * has the same meaning as described above; and $R^K$ represents alkyl, hydroxy, amino, alkylamino, dialkylamino, cycloalkylamino, (cycloalkyl)alkylamino, (hydroxyalkyl) amino, (alkoxyalkyl)amino, alkoxy, alkylsulfonylamino, or a saturated cyclic amino group), and (l) a saturated cyclic amino group optionally substituted by hydroxy; and the saturated cyclic amino group, which is formed by combining $R^F$, $R^G$ and the adjacent N, may form a spiro-linkage with a group represented by the following general formula [7A] or [7B]:

[7A]

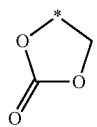

[7B]

(wherein * has the same meaning as described above)), (6) a group represented by the following general formula [8]:

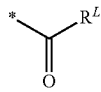

[8]

(wherein * has the same meaning as described above; and $R^L$ represents (a) alkyl, (b) hydroxy, (c) alkoxy, (d) saturated cyclic amino group optionally substituted by alkyl or alkylsulfonyl, or (e) an amino optionally substituted by one or two groups selected from the group consisting of alkyl, cycloalkyl, (cycloalkyl)alkyl, aralkyl, haloalkyl, dialkylaminoalkyl, alkoxyalkyl, and hydroxyalkyl), (7) a group represented by the following general formula [9]:

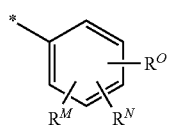

[9]

(wherein * has the same meaning as described above; and $R^M$, $R^N$ and $R^O$ are the same or different and each represents H, halogen, cyano, alkoxy, carbamoyl, sulfamoyl, monoalkylaminosulfonyl, or alkylsulfonyl, or alternatively two of $R^M$, $R^N$ and $R^O$ are taken together to represent methylenedioxy), (8) —$OR^P$ ($R^P$ represents an alkyl optionally substituted by a group selected from the group consisting of hydroxy, dialkylamino, alkoxy, tetrahydrofuranyl, and cycloalkyl, or an optionally O-containing saturated cyclic group optionally substituted by hydroxy), or (9) a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl;

$R^3$ represents H or hydroxy;

$R^4$ represents H or alkyl; and $R^5$ represents H or alkyl;

(II):

X represents —$CR^A$;

$R^A$ represents a group represented by the following general formula [10]:

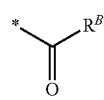

[10]

(wherein * has the same meaning as described above; and $R^B$ represents (a) amino optionally substituted by one or two groups selected from the group consisting of alkyl, cycloalkyl, (cycloalkyl)alkyl, and alkoxyalkyl, (b) alkoxy, (c) hydroxy, or (d) a saturated cyclic amino group);

$R^1$ represents a halogen;

$R^2$ represents H;

$R^3$ represents H or hydroxy;

$R^4$ represents H or alkyl; and $R^5$ represents H or alkyl.

Among the compounds of the invention, the compound represented by the general formula [1], particularly the compound as defined by the following [i] or [ii], or pharmaceutically acceptable salts thereof, are preferred.

[i]:

X is CH or N; and $R^2$ is:

(1) a group represented by the following general formula [11]:

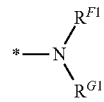

[11]

(wherein * has the same meaning as described above; and $R^{F1}$ and $R^{G1}$ are the same or different and each represents (a) H, (b) alkyl optionally substituted by one or two groups selected from the group consisting of hydroxy, amino, dialkylamino, a saturated cyclic amino group, alkylcarbonylamino, alkylsulfonylamino, aryl, heteroaryl optionally substituted by alkyl, tetrahydrofuranyl, and carbamoyl, (c) alkylcarbonyl, (d) alkylsulfonyl, (e) carbamoyl, or (f) heteroaryl optionally substituted by alkyl, or alternatively, $R^{F1}$ and $R^{G1}$ are taken together with the adjacent N to represent a saturated cyclic amino group, which may optionally be substituted by one or two groups selected from the group consisting of (a) halogen, (b) cyano, (c) hydroxy, (d) alkyl optionally substituted by one or two groups selected from the group consisting of hydroxy, alkoxy, amino, alkoxycarbonylamino, alkylsulfonylamino and alkylcarbonylamino, (e) cycloalkyl, (f) haloalkyl, (g) alkoxy, (h) oxo, (i) a group represented by the following general formula [4]:

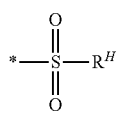

[4]

(wherein * and $R^P$ have the same meanings as described above), (j) a group represented by the following general formula [5]:

[5]

(wherein *, $R^I$ and $R^J$ have the same meanings as described above), (k) a group represented by the following general formula [6]:

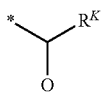

[6]

(wherein * and $R^K$ have the same meanings as described above), and (l) a saturated cyclic amino group optionally substituted by hydroxyl;

(2) a group represented by the following general formula [8]:

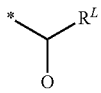

[8]

(wherein * and $R^L$ have the same meanings as described above), (3) a group represented by the following general formula [9]:

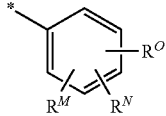

[9]

(wherein *, $R^M$, $R^N$ and $R^O$ have the same meanings as described above), (4) $-OR^{P1}$ (wherein $R^{P1}$ represents an alkyl optionally substituted by a group selected from the group consisting of hydroxy, dialkylamino, alkoxy, tetrahydrofuranyl, and cycloalkyl), or (5) a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl;

[ii]:
X is $-CR^A$;
$R^A$ is a group represented by the following general formula [10]:

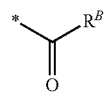

[10]

(wherein * and $R^B$ have the same meanings as described above); and
$R^2$ is H.

Among the compounds of the invention, those in which:
X is CH;
$R^2$ is:
(1) a group represented by the following general formula [11]:

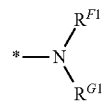

[11]

(wherein *, $R^{F1}$ and $R^{G1}$ have the same meanings as described above), (2) a group represented by the following general formula [8]:

[8]

(wherein * and $R^L$ have the same meanings as described above), (3) a group represented by the following general formula [9]:

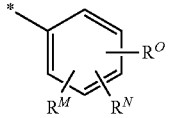

[9]

(wherein *, $R^M$, $R^N$ and $R^O$ have the same meanings as described above), (4) $-OR^{P1}$ (wherein $R^{P1}$ has the same meaning as described above), or (5) a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl; or pharmaceutically acceptable salts thereof are particularly preferred.

Among the compounds of the invention, the following specific compounds or pharmaceutically acceptable salts thereof are preferred.
(1) (S)-4-{2-[1-(4-fluorophenyl)ethylamino]-6-(pyrazin-2-ylamino) pyrimidin-4-yl}piperazin-2-one, (2) N-{(S)-1-[2-{[(S)-1-(4-fluorophenyl)ethyl]amino}-6-(pyrazin-2-ylamino)pyrimidin-4-yl]pyrrolidin-3-yl}acetamide,
(3) (S)-6-(3,3-difluoroazetidin-1-yl)-$N^2$-[1-(4-fluorophenyl)ethyl]-$N^4$-(pyrazin-2-yl)pyrimidine-2,4-diamine,
(4) (S)—$N^2$-[1-(4-fluorophenyl)ethyl]-4-(1-methyl-1H-pyrazol-4-yl)-$N^6$-(pyrazin-2-yl)pyridine-2,6-diamine,
(5) (S)—$N^{2'}$-[1-(4-fluorophenyl)ethyl]-$N^{6'}$-(pyrazin-2-yl)-3,4'-bipyridine-2',6'-diamine,
(6) (S)—$N^{2'}$-[1-(4-fluorophenyl)ethyl]-6-methoxy-$N^{6'}$-(pyrazin-2-yl)-3,4'-bipyridine-2',6'-diamine,
(7) (S)-2'-[1-(4-fluorophenyl)ethylamino]-6'-(pyrazin-2-ylamino)-3,4'-bipyridin-6-ol,
(8) (S)—$N^2$-[1-(4-fluorophenyl)ethyl]-4-(oxazol-5-yl)-$N^6$-(pyrazin-2-yl)pyridine-2,6-diamine,
(9) (S)-6-chloro-$N^2$-[1-(4-fluorophenyl)ethyl]-$N^4$-(pyrazin-2-yl)pyrimidine-2,4-diamine,
(10) (S)—$N^2$-[1-(4-fluorophenyl)ethyl]-6-[4-(methylsulfonyl)phenyl]-$N^4$-(pyrazin-2-yl)pyrimidine-2,4-diamine,
(11) (S)—$N^2$-[1-(4-fluorophenyl)ethyl]-$N^4$-(pyrazin-2-yl)-6-(1H-pyrazol-4-yl)pyrimidine-2,4-diamine,
(12) (S)-2-{2-[1-(4-fluorophenyl)ethylamino]-6-(pyrazin-2-ylamino)pyridin-4-yloxy}ethanol,
(13) (S)—$N^2$-[1-(4-fluorophenyl)ethyl]-$N^4$-(pyrazin-2-yl)-6-(pyridin-3-yl)pyrimidine-2,4-diamine,
(14) (S)—$N^2$-[1-(4-fluorophenyl)ethyl]-$N^4$-(pyrazin-2-yl)-6-(pyridin-2-yl)pyrimidine-2,4-diamine,
(15) (S)—$N^2$-[1-(4-fluorophenyl)ethyl]-$N^4$-(pyrazin-2-yl)-6-(pyridin-4-yl)pyrimidine-2,4-diamine,
(16) (S)-1-{2-[1-(4-fluorophenyl)ethylamino]-6-(pyrazin-2-ylamino) pyrimidin-4-yl}pyrrolidin-2-one,
(17) (S)-4-{2-[1-(4-fluorophenyl)ethylamino]-6-(pyrazin-2-ylamino)pyrimidin-4-yl}piperazine-2,6-dione,
(18) (S)-1-{2-[1-(4-fluorophenyl)ethylamino]-6-(pyrazin-2-ylamino) pyrimidin-4-yl}tetrahydropyrimidin-2(1H)-one,
(19) (S)—$N^2$-[1-(4-fluorophenyl)ethyl]-$N^4$-(pyrazin-2-yl)-6-(pyrrolidin-1-yl)pyrimidine-2,4-diamine,
(20) (S)—$N^2$-[1-(4-fluorophenyl)ethyl]-6-morpholino-$N^4$-(pyrazin-2-yl)pyrimidine-2,4-diamine,
(21) (S)-1-{2-[1-(4-fluorophenyl)ethylamino]-6-(pyrazin-2-ylamino)pyrimidin-4-yl}imidazolidin-2-one,
(22) (S)—$N^2$-[1-(4-fluorophenyl) ethyl]-6-(oxazol-5-yl)-$N^4$-(pyrazin-2-yl)pyrimidine-2,4-diamine,
(23) (S)—$N^2$-[1-(4-fluorophenyl)ethyl]-6-(6-methoxypyridin-3-yl)-$N^4$-(pyrazin-2-yl)pyrimidine-2,4-diamine,
(24) (S)—$N^2$-[1-(4-fluorophenyl)ethyl]-$N^4$-(pyrazin-2-yl)-6-(1H-pyrazol3-yl)pyrimidine-2,4-diamine,
(25) (S)-4-{2-[1-(4-fluorophenyl)ethylamino]-6-(pyrazin-2-ylamino)pyrimidin-4-yl}pyridin-2-ol,
(26) (S)-5-{2-[1-(4-fluorophenyl)ethylamino]-6-(pyrazin-2-ylamino)pyrimidin-4-yl}pyridin-2-ol,
(27) N—((R)-1-{2-[(S)-1-(4-fluorophenyl)ethylamino]-6-(pyrazin-2-ylamino)pyrimidin-4-yl}pyrrolidin-3-yl)acetamide,
(28) (S)—$N^2$-[1-(4-fluorophenyl)ethyl]-$N^6$-(pyrazin-2-yl)-4-(1H-pyrazol-4-yl)pyridine-2,6-diamine,
(29) (S)—$N^2$-[1-(4-fluorophenyl)ethyl]-$N^6$-(pyrazin-2-yl)-4-(1H-pyrazol-3-yl)pyridine-2,6-diamine,
(30) (S)—$N^2$-[1-(4-fluorophenyl)ethyl]-6-[3-(methylsulfonyl)phenyl]-$N^4$-(pyrazin-2-yl)pyrimidine-2,4-diamine,
(31) (S)—$N^2$-[1-(4-fluorophenyl)ethyl]-4-[4-(methylsulfonyl)phenyl]-$N^6$-(pyrazin-2-yl)pyridine-2,6-diamine,
(32) (S)—$N^2$-[1-(4-fluorophenyl)ethyl]-4-(1-isopropyl-1H-pyrazol-4-yl)-$N^6$-(pyrazin-2-yl)pyridine-2,6-diamine,
(33) N-{(S)-1-[2-{[(S)-1-(4-fluorophenyl)ethyl]amino}-6-(pyrazin-2-ylamino)pyridin-4-yl]pyrrolidin-3-yl}acetamide,
(34) (S)—$N^2$-[1-(4-fluorophenyl)ethyl]-4-morpholino-$N^6$-(pyrazin-2-yl)pyridine-2,6-diamine,
(35) (S)—$N^2$-[1-(4-fluorophenyl)ethyl]-$N^6$-(pyrazin-2-yl)-4-thiomorpholinopyridine-2,6-diamine,
(36) (S)-3-{2-[1-(4-fluorophenyl)ethylamino]-6-(pyrazin-2-ylamino) pyridin-4-yl}propan-1-ol,
(37) (S)—N-(1-{2-[1-(4-fluorophenyl)ethylamino]-6-(pyrazin-2-ylamino)pyrimidin-4-yl}azetidin-3-yl)acetamide,
(38) (S)-6-(azetidin-1-yl)-$N^2$-[1-(4-fluorophenyl) ethyl]-$N^4$-(pyrazin-2-yl)pyrimidine-2,4-diamine,
(39) (S)-6-(3-fluoroazetidin-1-yl)-$N^2$-[1-(4-fluorophenyl)ethyl]-$N^4$-(pyrazin-2-yl)pyrimidine-2,4-diamine,
(40) (S)-1-{2-[1-(4-fluorophenyl)ethylamino]-6-(pyrazin-2-ylamino)pyrimidin-4-yl}azetidin-2-one,
(41) (S)-4-(1-ethyl-1H-pyrazol-4-yl)-$N^2$-[1-(4-fluoro-phenyl)ethyl]-$N^6$-(pyrazin-2-yl)pyridine-2,6-diamine,
(42) (S)—$N^2$-[1-(4-fluorophenyl)ethyl]-4-(1-methyl-1H-pyrazol-5-yl)-$N^6$-(pyrazin-2-yl)pyridine-2,6-diamine,
(43) (S)-4-[1-(cyclopropylmethyl)-1H-pyrazol-4-yl]-$N^2$-[1-(4-fluorophenyl)ethyl]-$N^6$-(pyrazin-2-yl)pyridine-2,6-diamine,
(44) (S)—$N^2$-[1-(4-fluorophenyl)ethyl]-$N^4$-(pyrazin-2-yl)-6-(thiazol-5-yl)pyrimidine-2,4-diamine,
(45) 1-{2-[(S)-1-(4-fluorophenyl)ethylamino]-6-(pyrazin-2-ylamino) pyrimidin-4-yl}pyrrolidin-3-ol,
(46) (S)—$N^2$-[1-(4-fluorophenyl)ethyl]-$N^4$-(5-methylthiazol-2-yl)-$N^6$-(pyrazin-2-yl)pyrimidine-2,4,6-triamine,
(47) (S)—$N^2$-[1-(4-fluorophenyl)ethyl]-$N^6$-(pyrazin-2-yl)-4,5'-bipyrimidine-2,6-diamine,
(48) (S)—$N^2$-[1-(4-fluorophenyl)ethyl]-6-(2-methoxythiazol-5-yl)-$N^4$-(pyrazin-2-yl)pyrimidine-2,4-diamine,
(49) (S)—$N^2$-[1-(4-fluorophenyl)ethyl]-$N^4$-(pyrazin-2-yl)-6-(thiazol-2-yl)pyrimidine-2,4-diamine,
(50) (S)-5-{2-[1-(4-fluorophenyl)ethylamino]-6-(pyrazin-2-ylamino)pyrimidin-4-yl}picolinonitrile,
(51) (S)-1-{2-[1-(4-fluorophenyl)ethylamino]-6-(pyrazin-2-ylamino)pyrimidin-4-yl}piperidine-4-carboxamide,
(52) (S)-5-{2-[1-(4-fluorophenyl)ethylamino]-6-(pyrazin-2-ylamino)pyrimidin-4-yl}picolinamide,
(53) 4-{2-[(S-1-(4-fluorophenyl)ethylamino]-6-(pyrazin-2-ylamino)pyrimidin-4-yl}piperazine-2-carboxamide,
(54) 6-(3-aminopyrrolidin-1-yl)-$N^2$-[(S)-1-(4-fluorophenyl)ethyl]-$N^4$-(pyrazin-2-yl)pyrimidine-2,4-diamine,
(55) N-(1-{2-[(S)-1-(4-fluorophenyl)ethylamino]-6-(pyrazin-2-ylamino)pyrimidin-4-yl}pyrrolidin-3-yl)methanesulfonamide,
(56) (S)-2-({2-[1-(4-fluorophenyl)ethylamino]-6-(pyrazin-2-ylamino)pyrimidin-4-yl}(2-hydroxyethyl)amino)ethan-1-ol,
(57) (S)—$N^4$-[2-(dimethylamino)ethyl]-$N^2$-[1-(4-fluorophenyl)ethyl]-$N^6$-(pyrazin-2-yl)pyrimidine-2,4,6-triamine,
(58) 1-{2-[(S)-1-(4-fluorophenyl)ethylamino]-6-(pyrazin-2-ylamino) pyrimidin-4-yl}piperidine-3-carboxamide,
(59) (S)-1-{2-[(S)-1-(4-fluorophenyl)ethylamino]-6-(pyrazin-2-ylamino)pyrimidin-4-yl}pyrrolidine-2-carboxamide,
(60) (S)—$N^2$-[1-(4-fluorophenyl)ethyl]-6-[4-(methylsulfonyl)piperazin-1-yl]-$N^4$-(pyrazin-2-yl)pyrimidine-2,4-diamine,
(61) (S)—$N^2$-[1-(4-fluorophenyl)ethyl]-$N^4$-(pyrazin-2-yl)-6-(1H-pyrrol-3-yl)pyrimidine-2,4-diamine,

(62) (R)-1-{2-[(S)-1-(4-fluorophenyl)ethylamino]-6-(pyrazin-2-ylamino)pyrimidin-4-yl}-4-hydroxypyrrolidin-2-one,
(63) $N^2$-[(S)-1-(4-fluorophenyl)ethyl]-$N^4$-(pyrazin-2-yl)-$N^6$-[(tetrahydrofuran-2-yl)methyl]pyrimidine-2,4,6-triamine,
(64) ((S)-1-{2-[(S)-1-(4-fluorophenyl)ethylamino]-6-(pyrazin-2-ylamino)pyrimidin-4-yl}pyrrolidin-2-yl)methanol,
(65) ((R)-1-{2-[(S)-1-(4-fluorophenyl)ethylamino]-6-(pyrazin-2-ylamino)pyrimidin-4-yl}pyrrolidin-2-yl)methanol,
(66) (S)-1-{2-[1-(4-fluorophenyl)ethylamino]-6-(pyrazin-2-ylamino)pyrimidin-4-yl}piperidin-4-ol,
(67) (S)-1-{2-[1-(4-fluorophenyl)ethylamino]-6-(pyrazin-2-ylamino)pyrimidin-4-yl}azetidin-3-ol,
(68) 1-{2-[(S)-1-(4-fluorophenyl)ethylamino]-6-(pyrazin-2-ylamino)pyrimidin-4-yl}piperidin-3-ol,
(69) (S)-5-{2-[1-(4-fluorophenyl)ethylamino]-6-(pyrazin-2-ylamino)pyrimidin-4-yl}nicotinonitrile,
(70) (S)—$N^2$-[1-(4-fluorophenyl)ethyl]-$N^4$-(pyrazin-2-yl)-6-(2H-tetrazol-5-yl)pyrimidine-2,4-diamine,
(71) (S)—$N^4$-(2-aminoethyl)-$N^2$-[1-(4-fluorophenyl)ethyl]-$N^6$-(pyrazin-2-yl)pyrimidine-2,4,6-triamine,
(72) (S)—N-(2-{2-[1-(4-fluorophenyl)ethylamino]-6-(pyrazin-2-ylamino)pyrimidin-4-ylamino}ethyl)methanesulfonamide,
(73) (S)—N-(2-{2-[1-(4-fluorophenyl)ethylamino]-6-(pyrazin-2-ylamino)pyrimidin-4-ylamino}ethyl)acetamide,
(74) (S)-2-{2-[1-(4-fluorophenyl)ethylamino]-6-(pyrazin-2-ylamino)pyrimidin-4-ylamino}acetamide,
(75) (S)-4-{2-[1-(4-fluorophenyl)ethylamino]-6-(pyrazin-2-ylamino)pyrimidin-4-yl}benzamide,
(76) (S)-3-{2-[1-(4-fluorophenyl)ethylamino]-6-(pyrazin-2-ylamino)pyrimidin-4-yl}benzonitrile,
(77) (S)—$N^2$-[1-(4-fluorophenyl)ethyl]-6-(furan-3-yl)-$N^4$-(pyrazin-2-yl)pyrimidine-2,4-diamine,
(78) ethyl (S)-1-{2-[1-(4-fluorophenyl)ethylamino]-6-(pyrazin-2-ylamino)pyrimidin-4-yl}piperidine-4-carboxylate,
(79) (S)-5-{2-[1-(4-fluorophenyl)ethylamino]-6-(pyrazin-2-ylamino)pyrimidin-4-yl}nicotinamide,
(80) (S)-1-{2-[1-(4-fluorophenyl)ethylamino]-6-(pyrazin-2-ylamino)pyrimidin-4-yl}piperidine-4-carboxylic acid,
(81) (S)-2-{2-[(S)-1-(4-fluorophenyl)ethylamino]-6-(pyrazin-2-ylamino)pyrimidin-4-ylamino}-2-phenylethanol,
(82) (S)-2-{2-[(S)-1-(4-fluorophenyl)ethylamino]-6-(pyrazin-2-ylamino)pyrimidin-4-ylamino}-3-phenylpropan-1-ol,
(83) (R)-2-{2-[(S)-1-(4-fluorophenyl)ethylamino]-6-(pyrazin-2-ylamino)pyrimidin-4-ylamino}-4-methylpentan-1-ol,
(84) (S)-6-[2-(dimethylamino)ethoxy]-$N^2$-[1-(4-fluorophenyl)ethyl]-$N^4$-(pyrazin-2-yl)pyrimidine-2,4-diamine,
(85) (S)-1-{2-[1-(4-fluorophenyl)ethylamino]-6-(pyrazin-2-ylamino)pyrimidin-4-yl}-1H-pyrazole-4-carboxylic acid,
(86) (S)-3-{2-[1-(4-fluorophenyl)ethylamino]-6-(pyrazin-2-ylamino)pyrimidin-4-yl}benzamide,
(87) (S)-6-(benzo[d]1,3-dioxol-5-yl)-$N^2$-[1-(4-fluorophenyl)ethyl]-$N^4$-(pyrazin-2-yl)pyrimidine-2,4-diamine,
(88) (S)—$N^2$-[1-(4-fluorophenyl)ethyl]-6-(2-fluoropyridin-4-yl)-$N^4$-(pyrazin-2-yl)pyrimidine-2,4-diamine,
(89) $N^2$-[(S)-1-(4-fluorophenyl)ethyl]-$N^4$-(pyrazin-2-yl)-6-[(tetrahydrofuran-2-yl)methoxy]pyrimidine-2,4-diamine,
(90) (S)-2-{2-[1-(4-fluorophenyl)ethylamino]-6-(pyrazin-2-ylamino)pyrimidin-4-yloxy}ethanol,
(91) (S)—$N^2$-[1-(4-fluorophenyl)ethyl]-$N^4$-(pyrazin-2-yl)-$N^6$-[2-(pyrrolidin-1-yl)ethyl]pyrimidine-2,4,6-triamine,
(92) (S)-3-{2-[1-(4-fluorophenyl)ethylamino]-6-(pyrazin-2-ylamino) pyrimidin-4-yl}isonicotinamide,
(93) (S)-3-{2-[1-(4-fluorophenyl)ethylamino]-6-(pyrazin-2-ylamino)pyrimidin-4-yl}isonicotinonitrile,
(94) (S)-2-{2-[(S)-1-(4-fluorophenyl)ethylamino]-6-(pyrazin-2-ylamino)pyrimidin-4-ylamino}-3-methylbutan-1-ol,
(95) (S)—$N^2$-[1-(4-chlorophenyl)ethyl]-6-[4-(methylsulfonyl)piperazin-1-yl]-$N^4$-(pyrazin-2-yl)pyrimidine-2,4-diamine,
(96) (1S,2S)-2-{2-[(S)-1-(4-fluorophenyl)ethylamino]-6-(pyrazin-2-ylamino)pyrimidin-4-yloxy}cyclohexanol,
(97) (S)—$N^2$-[1-(4-fluorophenyl)ethyl]-$N^4$-[(5-methylpyrazin-2-yl)methyl]-$N^6$-(pyrazin-2-yl)pyrimidine-2,4,6-triamine,
(98) (S)—$N^2$-[1-(4-fluorophenyl)ethyl]-$N^4$-(furan-2-ylmethyl)-$N^6$-(pyrazin-2-yl)pyrimidine-2,4,6-triamine,
(99) (S)—$N^2$-[1-(4-fluorophenyl)ethyl]-$N^4$-(pyrazin-2-yl)-$N^6$-[1-(pyridin-3-yl)ethyl]pyrimidine-2,4,6-triamine,
(100) (S)-1-{2-[1-(4-fluorophenyl)ethylamino]-6-(pyrazin-2-ylamino) pyrimidin-4-yl}-4-(hydroxymethyl)piperidin-4-ol,
(101) (S)—$N^2$-[1-(4-fluorophenyl)ethyl]-$N^4$-(pyrazin-2-yl)-(pyridin-2-ylmethyl)pyrimidine-2,4,6-triamine,
(102) (S)—$N^2$-[1-(4-fluorophenyl)ethyl]-$N^4$-(pyrazin-2-yl)-$N^6$-(pyridin-3-ylmethyl)pyrimidine-2,4,6-triamine,
(103) (S)—$N^2$-[1-(4-fluorophenyl)ethyl]-$N^4$-(pyrazin-2-yl)-$N^6$-(pyridin-4-ylmethyl)pyrimidine-2,4,6-triamine,
(104) (S)-2-{2-[(S)-1-(4-fluorophenyl)ethylamino]-6-(pyrazin-2-ylamino)pyrimidin-4-ylamino}-3-hydroxypropanamide,
(105) (3S,4S)-1-{2-[(S)-1-(4-fluorophenyl)ethylamino]-6-(pyrazin-2-ylamino)pyrimidin-4-yl}pyrrolidine-3,4-diol,
(106) $N^2$-[(S)-1-(4-fluorophenyl)ethyl]-$N^4$-(pyrazin-2-yl)-6-(1,4-di oxa-8-azaspiro[4.5]decan-8-yl)pyrimidine-2,4-diamine,
(107) (S)-8-{2-[1-(4-fluorophenyl)ethylamino]-6-(pyrazin-2-ylamino)pyrimidin-4-yl}-1,3-dioxo-8-azaspiro[4.5]decan-2-one,
(108) (S)-4-(1-benzyl-1H-pyrazol-4-yl)-$N^2$-[1-(4-fluorophenyl)ethyl]-$N^6$-(pyrazin-2-yl)pyridine-2,6-diamine,
(109) (S)—$N^2$-[1-(4-fluorophenyl)ethyl]-6-[4-(phenylsulfonyl)piperazin-1-yl]-$N^4$-(pyrazin-2-yl)pyrimidine-2,4-diamine,
(110) (S)-4-{2-[1-(4-fluorophenyl)ethylamino]-6-(pyrazin-2-ylamino)pyridin-4-yl}benzamide,
(111) (S)—$N^2$-[1-(4-fluorophenyl)ethyl]-$N^6$-(pyrazin-2-yl)-4-(1H-pyrrol-3-yl)pyridine-2,6-diamine,
(112) (S)—$N^2$-[1-(4-fluorophenyl)ethyl]-$N^6$-(pyrazin-2-yl)-pyridine-2,6-diamine,
(113) (S)—$N^2$-[1-(4-fluorophenyl)ethyl]-6-(4-methyl-1H-imidazol-1-yl)-$N^4$-(pyrazin-2-yl)pyrimidine-2,4-diamine,
(114) (S)—$N^2$-[1-(4-fluorophenyl)ethyl]-4-(4-methoxyphenyl)-$N^6$-(pyrazin-2-yl)pyridine-2,6-diamine,
(115) (S)-4-(4-fluorophenyl)-$N^2$-[1-(4-fluorophenyl)ethyl]-$N^6$-(pyrazin-2-yl)pyridine-2,6-diamine,
(116) (S)—$N^2$-[1-(4-fluorophenyl)ethyl]-4-methyl-$N^6$-(pyrazin-2-yl)pyridine-2,6-diamine,
(117) (S)-1-{2-[1-(4-fluorophenyl)ethylamino]-6-(pyrazin-2-ylamino)pyrimidin-4-yl}-N-(methylsulfonyl)piperidine-4-carboxamide,
(118) (S)—$N^2$-[1-(4-fluorophenyl)ethyl]-4-(furan-3-yl)-$N^6$-(pyrazin-2-yl)pyridine-2,6-diamine, (119) (S)—N²-[1-(4-fluorophenyl)ethyl]-4-[4-(methylsulfonyl)piperazin-1-yl]-N⁶-(pyrazin-2-yl)pyridine-2,6-diamine,
(120) (S)-1-{2-[1-(4-fluorophenyl)ethylamino]-6-(pyrazin-2-ylamino)pyridin-4-yl}-4-(hydroxymethyl)piperidin-4-ol,
(121) (S)-4-{2-[1-(4-fluorophenyl)ethylamino]-6-(pyrazin-2-ylamino)pyridin-4-yl}benzenesulfonamide,
(122) (S)—N²-[1-(4-fluorophenyl)ethyl]-4-methoxy-N⁶-(pyrazin-2-yl)pyridine-2,6-diamine,
(123) 4-{2-[(1S)-1-(4-fluorophenyl)ethylamino]-6-(pyrazin-2-ylamino)pyridin-4-yl]-1λ⁶,4-thiomorpholin-1,1-dione,
(124) (S)-1-{2-[1-(4-fluorophenyl)ethylamino]-6-(pyrazin-2-ylamino)pyridin-4-yl}piperidin-4-ol,
(125) (S)-1-(4-{2-[1-(4-fluorophenyl)ethylamino]-6-(pyrazin-2-ylamino)pyridin-4-yl}-1,4-diazepan-1-yl)ethanone,
(126) (S)—N²-[1-(4-fluorophenyl)ethyl]-N⁶-(pyrazin-2-yl)-N⁴-(pyrimidin-2-yl)pyridine-2,4,6-triamine,
(127) (S)—N²-[1-(4-fluorophenyl)ethyl]-N⁶-(pyrazin-2-yl)-N⁴-(pyridin-2-yl)pyridine-2,4,6-triamine,
(128) N²-[(S)-1-(4-fluorophenyl)ethyl]-N⁶-(pyrazin-2-yl)-4-(1,4-dioxa-8-azaspiro[4.5]decan-8-yl)pyridine-2,6-diamine,
(129) methyl (S)-2-[1-(4-fluorophenyl)ethylamino]-6-(pyrazin-2-ylamino)isonicotinate,
(130) (S)-4-{2-[1-(4-fluorophenyl)ethylamino]-6-(pyrazin-2-ylamino)pyrimidin-4-yl}-N-methylbenzenesulfonamide,
(131) (S)—N²-[1-(4-fluorophenyl)ethyl]-4-(4-methyl-1H-imidazol-1-yl)-N⁶-(pyrazin-2-yl)pyridine-2,6-diamine,
(132) (S)—N²-[1-(4-fluorophenyl)ethyl]-N⁴,N⁶-di(pyrazin-2-yl)pyridine-2,4,6-triamine,
(133) (S)-4-(cyclopropylmethoxy)-N²-[1-(4-fluorophenyl)ethyl]-N⁶-(pyrazin-2-yl)pyridine-2,6-diamine,
(134) (S)—N²-[1-(4-fluorophenyl)ethyl]-N²-methyl-4-(1-methyl-1H-pyrazol-4-yl)-N⁶-(pyrazin-2-yl)pyridine-2,6-diamine,
(135) (S)-{2-[1-(4-fluorophenyl)ethylamino]-6-(pyrazin-2-ylamino)pyridin-4-yl}methanol,
(136) (S)-2-[1-(4-fluorophenyl)ethylamino]-6-(pyrazin-2-ylamino)isonicotinic acid,
(137) (S)—N²-[1-(4-fluorophenyl)ethyl]-4-(2-methoxyethoxy)-N⁶-(pyrazin-2-yl)pyridine-2,6-diamine,
(138) (S)-2-[1-(4-fluorophenyl)ethylamino]-6-(pyrazin-2-ylamino)pyrimidine-4-carbonitrile,
(139) (S)-2-[1-(4-fluorophenyl)ethylamino]-6-(pyrazin-2-ylamino)isonicotinonitrile,
(140) (S)-2-[1-(4-fluorophenyl)ethylamino]-6-(pyrazin-2-ylamino)isonicotinamide,
(141) (S)—N²-[1-(4-fluorophenyl)ethyl]-6-(1,2,4-oxadiazol-3-yl)-N⁴-(pyrazin-2-yl)pyrimidine-2,4-diamine,
(142) (S)—N²-[1-(4-fluorophenyl)ethyl]-4-(1,2,4-oxadiazol-3-yl)-N⁶-(pyrazin-2-yl)pyridine-2,6-diamine,
(143) methyl (S)-2-[1-(4-fluorophenyl)ethylamino]-6-(pyrazin-2-ylamino) nicotinate,
(144) (S)-2-[1-(4-fluorophenyl)ethylamino]-N,N-dimethyl-6-(pyrazin-2-ylamino) isonicotinamide,
(145) (S)—N-[2-(dimethylamino)ethyl]-2-[1-(4-fluorophenyl)ethylamino]-6-(pyrazin-2-ylamino)isonicotinamide,
(146) (S)—N-t-butyl-2-[1-(4-fluorophenyl)ethylamino]-6-(pyrazin-2-ylamino) isonicotinamide,
(147) (S)—N-ethyl-2-[1-(4-fluorophenyl)ethylamino]-6-(pyrazin-2-yl amino) isonicotinamide,
(148) (S)-{2-[1-(4-fluorophenyl)ethylamino]-6-(pyrazin-2-ylamino)pyridin-4-yl}[4-(methanesulfonyl)piperazin-1-yl]methanone,
(149) (S)-{2-[1-(4-fluorophenyl)ethylamino]-6-(pyrazin-2-ylamino)pyridin-4-yl}(pyrrolidin-1-yl)methanone,
(150) (S)-2-[1-(4-fluorophenyl)ethylamino]-N-isopropyl-6-(pyrazin-2-ylamino)isonicotinamide,
(151) (S)-1-{2-[(S)-1-(4-fluorophenyl)ethylamino]-6-(pyrazin-2-ylamino)pyrimidin-4-yl}azetidine-2-carboxamide,
(152) (S)—N²-[1-(4-fluorophenyl)ethyl]-N⁶-(pyrazin-2-yl)-4-(tetrahydro-2H-pyran-4-yloxy)pyridine-2,6-diamine,
(153) (S)-1-{2-[1-(4-fluorophenyl)ethylamino]-6-(pyrazin-2-ylamino)pyrimidin-4-yl}azetidine-3-carboxamide,
(154) (S)-2-[1-(4-fluorophenyl) ethylamino]-N-(2-hydroxyethyl)-6-(pyrazin-2-ylamino)isonicotinamide,
(155) (S)-2-[1-(4-fluorophenyl)ethylamino]-N-methyl-6-(pyrazin-2-ylamino)isonicotinamide,
(156) (S)-{2-[1-(4-fluorophenyl)ethylamino]-6-(pyrazin-2-ylamino)pyridin-4-yl}(morpholino)methanone,
(157) (S)—N-benzyl-2-[1-(4-fluorophenyl)ethylamino]-6-(pyrazin-2-ylamino)isonicotinamide,
(158) (S)—N-cyclopropyl-2-[1-(4-fluorophenyl)ethylamino]-6-(pyrazin-2-ylamino)isonicotinamide,
(159) (S)-{2-[1-(4-fluorophenyl)ethylamino]-6-(pyrazin-2-ylamino)pyridin-4-yl}(4-methylpiperazin-1-yl)methanone,
(160) (S)-2-[1-(4-fluorophenyl)ethylamino]-N-(2-methoxyethyl)-6-(pyrazin-2-ylamino)isonicotinamide,
(161) (S)-2-[1-(4-fluorophenyl)ethylamino]-N-propyl-6-(pyrazin-2-ylamino)isonicotinamide,
(162) (S)—N-cyclopropylmethyl-2-[1-(4-fluorophenyl)ethylamino]-6-(pyrazin-2-yl amino) isonicotinamide,
(163) (S)—N-cyclobutyl-2-[1-(4-fluorophenyl)ethylamino]-6-(pyrazin-2-ylamino)isonicotinamide,
(164) (S)—N-butyl-2-[1-(4-fluorophenyl)ethylamino]-6-(pyrazin-2-ylamino) isonicotinamide,
(165) (S)-2-[1-(4-fluorophenyl)ethylamino]-N-isobutyl-6-(pyrazin-2-ylamino)isonicotinamide,
(166) (S)-2-[1-(4-fluorophenyl)ethylamino]-6-(pyrazin-2-ylamino)-N-(2,2,2,-trifluoroethyl)isonicotinamide,
(167) (S)-2-[1-(4-fluorophenyl)ethylamino]-N-(3-hydroxypropyl)-6-(pyrazin-2-ylamino)isonicotinamide,
(168) (S)—N-(2-ethoxyethyl)-2-[1-(4-fluorophenyl)ethylamino]-6-(pyrazin-2-ylamino)isonicotinamide,
(169) (S)-1-{2-[1-(4-fluorophenyl)ethylamino]-6-(pyrazin-2-ylamino) pyrimidin-4-yl}-N-methylazetidine-3-carboxamide,
(170) (S)—N²-[1-(4-fluorophenyl)ethyl]-4-(methoxymethyl)-N⁶-(pyrazin-2-yl)pyridine-2,6-diamine,
(171) (S)-1-{2-[1-(4-fluorophenyl)ethylamino]-6-(pyrazin-2-ylamino)pyrimidin-4-yl}-N,N-dimethylazetidine-3-carboxamide,
(172) (S)—N-(1-{2-[1-(4-fluorophenyl)ethylamino]-6-(pyrazin-2-ylamino)pyrimidin-4-yl}azetidin-3-yl)methanesulfonamide,
(173) (S)-1-{2-[1-(4-fluorophenyl)ethylamino]-6-(pyrazin-2-ylamino)pyrimidin-4-yl}azetidine-3-carbonitrile,
(174) 2-(4-fluorophenyl)-2-[4-(1-methyl-1H-pyrazol-4-yl)-6-(pyrazin-2-ylamino)pyridin-2-ylamino]ethanol,
(175) (S)—N-ethyl-1-{2-[1-(4-fluorophenyl)ethylamino]-6-(pyrazin-2-ylamino)pyrimidin-4-yl}azetidine-3-carboxamide,
(176) (S)—N,N-diethyl-1-{2-[1-(4-fluorophenyl)ethylamino]-6-(pyrazin-2-ylamino)pyrimidin-4-yl}azetidine-3-carboxamide,
(177) (S)-1-{2-[1-(4-fluorophenyl)ethylamino]-6-(pyrazin-2-ylamino)pyridin-4-yl}ethanone,
(178) (S)—N²-[1-(4-fluorophenyl)ethyl]-6-(3-methoxy-azetidin-1-yl)-N⁴-(pyrazin-2-yl)pyrimidine-2,4-diamine, (179) (S)-1-{2-[1-(4-fluorophenyl)ethylamino]-6-(pyrazin-2-ylamino)pyrimidin-4-yl}-3-methylazetidin-3-ol,
(180) (S)-2-[1-(4-fluorophenyl)ethylamino]-N-methyl-6-(pyrazin-2-ylamino)nicotinamide,
(181) (S)-2-[1-(4-fluorophenyl)ethylamino]-N,N-dimethyl-6-(pyrazin-2-ylamino) nicotinamide,
(182) (S)-2-[1-(4-fluorophenyl)ethylamino]-6-(pyrazin-2-ylamino) nicotinamide,
(183) (S)-{2-[1-(4-fluorophenyl)ethylamino]-6-(pyrazin-2-ylamino)pyridin-3-yl}(morpholino)methanone,
(184) (S)—N-(cyclopropylmethyl)-2-[1-(4-fluorophenyl)ethylamino]-6-(pyrazin-2-ylamino)nicotinamide,
(185) (S)—N-(1-{2-[1-(4-fluorophenyl)ethylamino]-6-(pyrazin-2-ylamino)pyrimidin-4-yl}azetidin-3-yl)ethanesulfonamide,
(186) (S)-1-{2-[1-(4-fluorophenyl)ethylamino]-6-(pyrazin-2-ylamino)pyrimidin-4-yl}-N-isopropylazetidine-3-carboxamide,
(187) (S)-1-{2-[1-(4-fluorophenyl)ethylamino]-6-(pyrazin-2-ylamino)pyrimidin-4-yl}-3-(trifluoromethyl)azetidin-3-ol,
(188) (S)-(1-{2-[1-(4-fluorophenyl)ethylamino]-6-(pyrazin-2-ylamino)pyrimidin-4-yl}azetidin-3-yl)(pyrrolidin-1-yl)methanone,
(189) (S)-1-{2-[1-(4-fluorophenyl)ethylamino]-6-(pyrazin-2-ylamino)pyrimidin-4-yl}-N-(2-methoxyethyl)azetidine-3-carboxamide,
(190) (S)-(1-{2-[1-(4-fluorophenyl)ethylamino]-6-(pyrazin-2-ylamino)pyrimidin-4-yl}azetidin-3-yl)(piperidin-1-yl)methanone,
(191) (S)-(1-{2-[1-(4-fluorophenyl)ethylamino]-6-(pyrazin-2-ylamino)pyrimidin-4-yl}azetidin-3-yl)(morpholino)methanone,
(192) (S)—N-(cyclopropyl)-1-{2-[1-(4-fluorophenyl)ethylamino]-6-(pyrazin-2-ylamino)pyrimidin-4-yl}azetidine-3-carboxamide,
(193) (S)—N-(cyclopropylmethyl)-1-{2-[1-(4-fluorophenyl)ethylamino]-6-(pyrazin-2-ylamino)pyrimidin-4-yl}azetidine-3-carboxamide,
(194) (S)-1-{2-[1-(4-fluorophenyl)ethylamino]-6-(pyrazin-2-ylamino)pyrimidin-4-yl}-N-(2-hydroxyethyl)azetidine-3-carboxamide,
(195) (S)-3-cyclopropyl-1-{2-[1-(4-fluorophenyl)ethylamino]-6-(pyrazin-2-ylamino)pyrimidin-4-yl}azetidin-3-ol,
(196) (S)-1-{2-[1-(4-fluorophenyl)ethylamino]-6-(pyrazin-2-ylamino)pyrimidin-4-yl}-3-isopropylazetidin-3-ol,
(197) (S)-1-{2-[1-(4-fluorophenyl)ethylamino]-6-(pyrazin-2-ylamino)pyridin-4-yl}azetidin-3-ol,
(198) (S)-3-cyclopropyl-1-{2-[1-(4-fluorophenyl)ethylamino]-6-(pyrazin-2-ylamino)pyridin-4-yl}azetidin-3-ol,
(199) (S)-1-{2-[1-(4-fluorophenyl)ethylamino]-6-(pyrazin-2-ylamino)pyridin-4-yl}-3-isopropylazetidin-3-ol,
(200) (S)-1-{2-[1-(4-fluorophenyl)ethylamino]-6-(pyrazin-2-ylamino)pyridin-4-yl}-3-methylazetidin-3-ol,
(201) (S)-1-{2-[1-(4-fluorophenyl)ethylamino]-6-(pyrazin-2-ylamino)pyridin-4-yl}-3-(trifluoromethyl)azetidin-3-ol,
(202) (S)-4-(3,3-difluoroazetidin-1-yl)-$N^2$-[1-(4-fluorophenyl)ethyl]-$N^6$-(pyrazin-2-yl)pyridine-2,6-diamine,
(203) (S)—N-{2-[1-(4-fluorophenyl)ethylamino]-6-(pyrazin-2-ylamino) pyridin-4-yl}acetamide,
(204) (S)—N-{2-[1-(4-fluorophenyl)ethylamino]-6-(pyrazin-2-ylamino)pyridin-4-yl}methanesulfonamide,
(205) (S)-1-{2-[1-(4-fluorophenyl)ethylamino]-6-(pyrazin-2-ylamino)pyridin-4-yl}urea,
(206) (S)-4-(3-cyclopropyl-3-methoxyazetidin-1-yl)-$N^2$-[1-(4-fluorophenyl)ethyl]-$N^6$-(pyrazin-2-yl)pyridine-2,6-diamine,
(207) (S)—$N^2$-[1-(4-fluorophenyl)ethyl]-4-(3-isopropyl-3-methoxyazetidin-1-yl)-$N^6$-(pyrazin-2-yl)pyridine-2,6-diamine,
(208) (S)—$N^2$-[1-(4-fluorophenyl)ethyl]-4-(3-methoxy-3-methylazetidin-1-yl)-$N^6$-(pyrazin-2-yl)pyridine-2,6-diamine,
(209) (S)—$N^2$-[1-(4-fluorophenyl)ethyl]-4-(1-methyl-1H-pyrazol-4-yl)-$N^6$-(5-methylpyrazin-2-yl)pyridine-2,6-diamine,
(210) (S)—$N^2$-[1-(4-fluorophenyl)ethyl]-4-[1-(methanesulfonyl)piperidin-4-yl]-$N^6$-(pyrazin-2-yl)pyridine-2,6-diamine,
(211) (S)—N-{2-[1-(4-fluorophenyl)ethylamino]-6-(pyrazin-2-ylamino)pyridin-4-yl}propionamide,
(212) (S)—$N^2$-[1-(4-fluorophenyl)ethyl]-4-[1-(2-methoxyethyl)-1H-pyrazol-4-yl]-$N^6$-(pyrazin-2-yl)pyridine-2,6-diamine,
(213) (S)-4-(1-cyclopropyl-1H-pyrazol-4-yl)-$N^2$-[1-(4-fluorophenyl)ethyl]-$N^6$-(pyrazin-2-yl)pyridine-2,6-diamine,
(214) (S)—$N^2$-[1-(4-fluorophenyl)ethyl]-4-[1-(methoxymethyl)-1H-pyrazol-4-yl]-$N^6$-(pyrazin-2-yl)pyridine-2,6-diamine,
(215) (S)-6-[3-(dimethylamino)azetidin-1-yl]-$N^2$-[1-(4-fluorophenyl)ethyl]-$N^4$-(pyrazin-2-yl)pyrimidine-2,4-diamine,
(216) (S)—$N^2$-[1-(4-fluorophenyl)ethyl]-6-[3-(methylamino)azetidin-1-yl]-$N^4$-(pyrazin-2-yl)pyrimidine-2,4-diamine,
(217) (S)—$N^2$-[1-(4-fluorophenyl)ethyl]-$N^4$-(pyrazin-2-yl)-6-[3-(pyrrolidin-1-yl)azetidin-1-yl]pyrimidine-2,4-diamine,
(218) (S)—$N^2$-[1-(4-fluorophenyl)ethyl]-6-(3-morpholinoazetidin-1-yl)-$N^4$-(pyrazin-2-yl)pyrimidine-2,4-diamine,
(219) (S)—$N^2$-[1-(4-fluorophenyl)ethyl]-6-[3-(4-methylpiperazin-1-yl)azetidin-1-yl]-$N^4$-(pyrazin-2-yl)pyrimidine-2,4-diamine,
(220) (S)-(1-{1-[2-(4-fluorophenyl)ethylamino]-6-(pyrazin-2-ylamino)pyrimidin-4-yl}azetidin-3-yl)piperidin-4-ol,
(221) 4-[2-[(1S)-1-(4-fluorophenyl)ethylamino]-6-(pyrazin-2-ylamino)pyrimidin-4-yl]-1$\lambda^6$,4-thiomorpholin-1,1-dione,
(222) (S)-1-(1-{2-[1-(4-fluorophenyl)ethylamino]-6-(pyrazin-2-ylamino)pyrimidin-4-yl}azetidin-3-yl)urea,
(223) (S)-(1-{2-[1-(4-fluorophenyl)ethylamino]-6-(pyrazin-2-ylamino)pyrimidin-4-yl}azetidin-3-yl)methanol,
(224) t-butyl (S)-(1-{2-[1-(4-fluorophenyl)ethylamino]-6-(pyrazin-2-ylamino)pyrimidin-4-yl}azetidin-3-yl)methylcarbamate,
(225) (S)-6-[3-(aminomethyl)azetidin-1-yl]-$N^2$-[1-(4-fluorophenyl)ethyl]-$N^4$-(pyrazin-2-yl)pyrimidine-2,4-diamine,
(226) (S)—N-[(1-{2-[1-(4-fluorophenyl)ethylamino]-6-(pyrazin-2-ylamino)pyrimidin-4-yl}azetidin-3-yl)methyl]ethanesulfonamide,
(227) (S)—N-[(1-{2-[1-(4-fluorophenyl)ethylamino]-6-(pyrazin-2-ylamino)pyrimidin-4-yl}azetidin-3-yl)methyl]acetamide,
(228) (S)—$N^2$-[1-(4-fluorophenyl)ethyl]-4-[3-morpholinoazetidin-1-yl]-$N^6$-(pyrazin-2-yl)pyridine-2,6-diamine, and
(229) (S)-1-(1-{2-[1-(4-fluorophenyl)ethylamino]-6-(pyrazin-2-ylamino)pyrimidin-4-yl}azetidin-3-yl)piperidin-4-ol.

The compounds of the invention or their pharmaceutically acceptable salts are useful as medicaments.

The following will describe in detail each term concerned in the invention.

"Halogen" includes, for example, fluorine, chlorine, bromine and iodine.

"Alkyl" means, for example, a straight or branched chain alkyl having 1 to 8 carbons, specifically including methyl, ethyl, n-propyl, isopropyl, n-butyl, isobutyl, sec-butyl, tert-butyl, n-pentyl, isopentyl, n-hexyl, isohexyl, n-heptyl, isoheptyl, and n-octyl. In particular, those of 1 to 6 carbons are preferred, and those of 1 to 3 carbons more preferred.

The alkyl moiety of "alkylsulfonyl", "alkylcarbonylamino", "hydroxyalkyl", "(cycloalkyl)alkyl", "alkoxyalkyl", "alkylamino", "(hydroxyalkyl)amino", "(alkoxyalkyl)amino", "dialkylamino", dialkylaminoalkyl", "(cycloalkyl)alkylamino", "alkylcarbonyl", "alkylcarbonylamino", "alkylsulfonyl", "alkylsulfonylamino", and "monoalkylaminosulfonyl" can be exemplified by the same ones as the above-described "alkyl".

"Haloalkyl" means, for example, a straight or branched chain alkyl of 1 to 8 carbons on which one or more of halogen atoms are substituted at any replaceable optional position(s). The alkyl and halogen moieties of "haloalkyl" can be exemplified by the same ones as the above "alkyl" and "halogen", respectively.

"Cycloalkyl" means, for example, those having 3 to 8 carbons, specifically including cyclopropyl, cyclobutyl, cyclopentyl, cyclohexyl, cycloheptyl, cyclooctyl, and the like.

The cycloalkyl moiety of "(cycloalkyl)alkyl", "cycloalkylamino" and "(cycloalkyl)alkylamino" can be exemplified by the same ones as the above "cycloalkyl".

"Alkoxy" means, for example, a straight or branched chain alkoxy having 1 to 8 carbons, specifically including methoxy, ethoxy, n-propoxy, isopropoxy, n-butoxy, isobutoxy, sec-butoxy, t-butoxy, n-pentyloxy, n-hexyloxy, n-heptyloxy, and n-octyloxy.

The alkoxy moiety of "alkoxyalkyl" and "(alkoxyalkyl) amino" is exemplified by the same ones as the above "alkoxy".

"Aryl" means those having 6 to 10 carbons, including for example phenyl, 1-naphthyl, and 2-naphthyl. In particular, phenyl is preferred.

"Aralkyl" means, for example, a straight or branched chain alkyl of 1 to 8 carbons on which an aryl of 6 to 10 carbons is substituted at any replaceable optional position, including for example benzyl, phenylethyl (e.g. 1-phenylethyl, 2-phenylethyl), phenylpropyl (1-phenylpropyl, 2-phenylpropyl, 3-phenylpropyl, etc.), and naphthylmethyl (e.g. 1-naphthylmethyl, 2-naphthylmethyl, etc.).

"Saturated cyclic amino group" means, for example, a 4- to 7-membered saturated cyclic amino group which may contain one of O or S with one or two of N as ring-constituting atoms, specifically including 1-azetidinyl, 1-pyrrolidinyl, 1-imidazolidinyl, piperidino, 1-piperazinyl, 1-tetrahydropyrimidinyl, morpholino, thiomorpholino, and 1-homopiperazinyl.

"N-containing saturated heterocyclic group" means, for example, a 5- or 6-membered saturated heterocyclic group containing one of N as a ring-constituting atom, specifically including for example 2-pyrrolidinyl, 3-pyrrolidinyl, 2-piperidinyl, 3-piperidinyl, and 4-piperidinyl.

"Optionally O-containing saturated cyclic group" means, for example, a 5- or 6-membered saturated cyclic group which may contain one of O as a ring-constituting atom, specifically including for example cyclopentyl, cyclohexyl, tetrahydrofuranyl, and tetrahydropyranyl.

"Heteroaryl" means, for example, 5- or 6-membered heteroaryl containing 1 to 4 of N, O and S as (a) ring-constituting atom (s), specifically including for example furyl (e.g. 2-furyl, 3-furyl), theinyl (e.g. 2-thienyl, 3-thienyl), pyrrolyl (e.g. 1-pyrrolyl, 2-pyrrolyl, 3-pyrrolyl), imidazolyl (e.g. 1-imidazolyl, 2-imidazolyl, 4-imidazolyl), pyrazolyl (e.g. 1-pyrazolyl, 3-pyrazolyl, 4-pyrazolyl), triazolyl (e.g. 1,2,4-triazol-1-yl, 1,2,4-triazol-3-yl, 1,2,4-triazolyl-4-yl), tetrazolyl (e.g. 1-tetrazolyl, 2-tetrazolyl, 5-tetrazolyl), oxazolyl (e.g. 2-oxazolyl, 4-oxazolyl, 5-oxazolyl), isoxazolyl (e.g. 3-isoxazolyl, 4-isoxazolyl, 5-isoxazolyl), oxadiazolyl (e.g. 1,3,4-oxadiazol-2-yl), thiazolyl (e.g. 2-thiazolyl, 4-thiazolyl, 5-thiazolyl), thiadiazolyl, isothiazolyl (e.g. 3-isothiazolyl, 4-isothiazolyl, 5-isothiazolyl), pyridyl (e.g. 2-pyridiyl, 3-pyridyl, 4-pyridyl), pyridazinyl (e.g. 3-pyridazinyl, 4-pyridazinyl), pyrimidinyl (e.g. 2-pyrimidinyl, 4-pyrimidinyl, 5-pyrimidinyl), and pyrazinyl (e.g. 2-pyrazinyl).

"Tetrahydrofuranyl" includes, for example, 2-tetrahydrofuranyl and 3-tetrahydrofuranyl.

"Tetrahydropyranyl" includes, for example, 2-tetrahydropyranyl, 3-tetrahydropyranyl, and 4-tetrahydropyranyl.

DETAILED DESCRIPTION OF THE INVENTION

The compounds of the invention can be produced from known compounds or from readily synthesizable intermediates, for example, according to the following processes. In producing the compounds of the invention, when the starting material has a substituent influencing the reaction, the reaction is usually carried out after preliminary protection of the starting material with a suitable protecting group according to a known method. The protecting group may be removed after the reaction completion according to a known method.

Process 1: In the case of $R^2$ being halogen

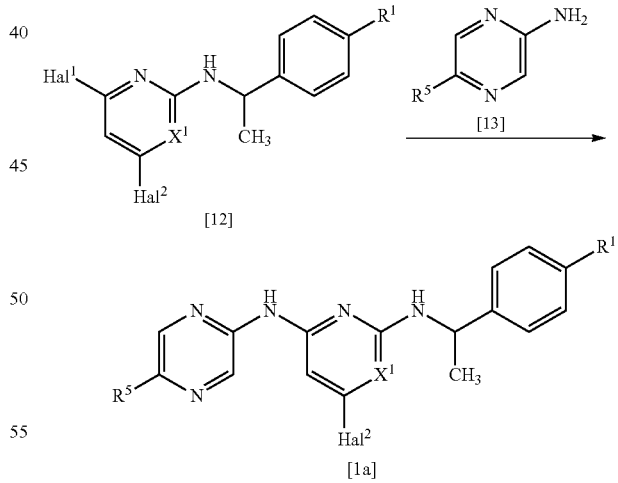

(wherein $R^1$ and $R^5$ have the same meanings as described above; $X^1$ represents CH or N; and $Hal^1$ and $Hal^2$ are the same or different, and each represents halogen.)

The reaction is a condensation reaction of Compound [12] with Compound [13] using a palladium catalyst and thus may be carried out per se according to a known method. The usable solvent includes, for example, hydrocarbons such as toluene, xylene; ethers such as 1,4-dioxane, tetrahydrofuran; amides such as N,N-dimethylformamide, N,N-dimethylacetamide, N-methyl-2-pyrrolidone; or a mixture of them, but there is no particular limitation as long as they have no influence on the reaction. The reaction is carried out at a temperature of 20° C. to 200° C. in the presence of a base. The usable palladium catalyst includes, for example, tris(dibenzylideneacetone)(chloroform)dipalladium(0), tris(dibenzylideneacetone)dipalladium (0), and palladium(II)acetate. The amount of the palladium catalyst to be used is preferably within the range of 0.001-0.1 mole for 1 mole of the aryl halide. The usable ligand for the palladium catalyst includes, for example, 1,1'-bis-(diphenylphosphino)ferrocene, 4,5-bis(diphenylphosphino)-9,9'-dimethylxanthene, 2-dicyclohexylphosphino-2',4',6'-triisopropylbiphenyl, (±)-2,2'-bis(diphenylphosphino)-1,1'-binaphthyl, 2-(di-t-butylphosphino)biphenyl, bis[2-(diphenylphosphino)phenyl]ether, and tri-t-butylphosphine. The usable base includes, for example, sodium t-butoxide, tripotassium phosphate, and cesium carbonate. The reaction time depends on the kind of the starting material used and the reaction temperature, and is usually in the range of 10 minutes to 24 hours.

Compound [12] as a starting material may be produced according to a known method (Bioorg. Med. Chem. Lett., 14, 2004, 4249-4252; Org. Lett., 6, 2004, 3671-3674).

Process 2: In the case of $R^2$ being —$OR^P$ (wherein $R^P$ has the same Meaning as described above.)

Process 2-1

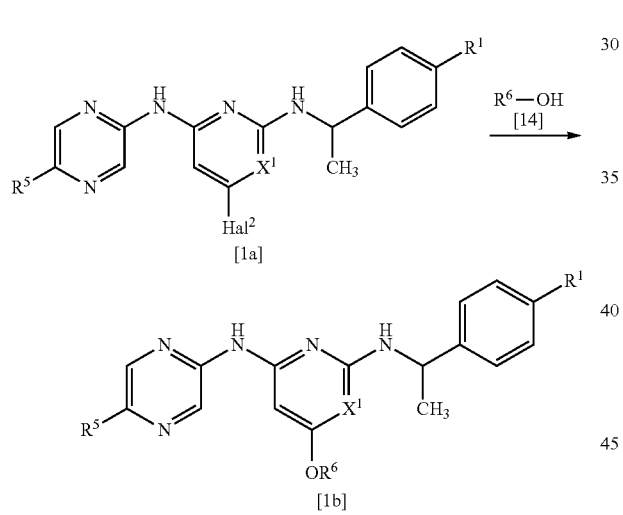

(wherein $X^1$, $R^1$, $R^5$, and $Hal^2$ have the same meanings as described above; and $R^6$ represents an alkyl optionally substituted by a group selected from the group consisting of hydroxy, dialkylamino, alkoxy, tetrahydrofuranyl and cycloalkyl, or an optionally O-containing saturated cyclic group.)

The reaction is carried out by condensing Compound [1a] with an alcohol compound [14] using a palladium catalyst. The usable solvent includes, for example, hydrocarbons such as toluene, xylene; ethers such as 1,4-dioxane, tetrahydrofuran; amides such as N,N-dimethylformamide, N,N-dimethylacetamide, N-methyl-2-pyrrolidone; or a mixture of them, but there is no particular limitation as long as they have no influence on the reaction. The reaction is carried out at a temperature of 20° C. to 200° C. in the presence of a base. The usable palladium catalyst includes, for example, tris(dibenzylideneacetone)(chloroform)dipalladium(0), tris(dibenzylideneacetone)dipalladium(0), and palladium(II)acetate. The amount of the palladium catalyst to be used is preferably within the range of 0.001-0.1 mole for 1 mole of the aryl halide. The usable ligand for the palladium catalyst includes, for example, 4,5-bis(diphenylphosphino)-9,9'-dimethylxanthene, 2-dicyclohexylphosphino-2',4',6'-triisopropylbiphenyl, (±)-2,2'-bis(diphenylphosphino)-1,1'-binaphthyl, 2-(di-t-butylphosphino)biphenyl, and bis[2-(diphenylphosphino)phenyl]ether. The usable base includes, for example, sodium t-butoxide and tripotassium phosphate. The reaction time depends on the kind of the starting material used and the reaction temperature, and is usually in the range of 10 minutes to 24 hours.

Process 2-2

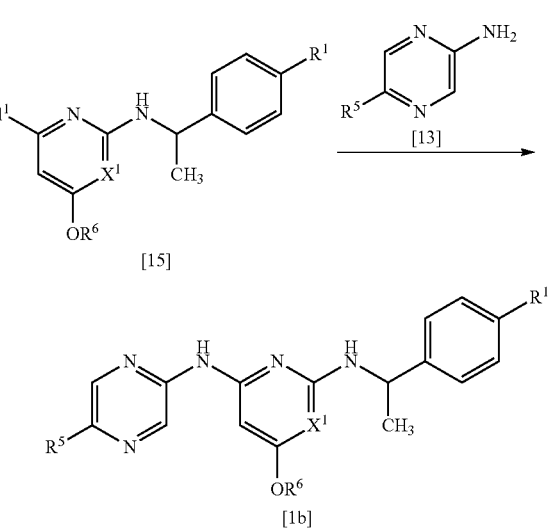

(wherein $X^1$, $R^1$, $R^5$, $R^6$ and $Hal^1$ have the same meanings as described above.)

The reaction is a condensation reaction of Compound [15] with Compound [13] using a palladium catalyst and thus may be carried out in the same manner as in Process 1 as mentioned above.

Compound [15] as a starting compound may be produced, for example, according to the following method.

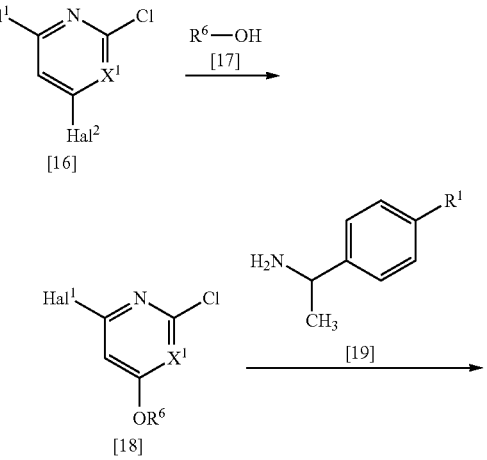

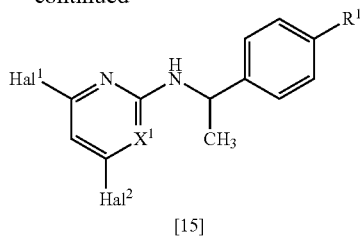

[15]

(wherein $X^1$, $R^1$, $R^6$, $Hal^1$ and $Hal^2$ have the same meanings as described above.)

Step 1

Compound [18] may be produced by reacting Compound [16] with an alcohol compound [17] in a suitable solvent in the presence of a base at a temperature of $-20°$ C. to $100°$ C. The usable base includes, for example, sodium hydride, sodium hydroxide, and the like. The usable solvent includes, for example, hydrocarbons such as toluene, xylene; ethers such as 1,4-dioxane, tetrahydrofuran; amides such as N,N-dimethylformamide, N,N-dimethylacetamide, N-methyl-2-pyrrolidone; water; or a mixture of them, but there is no particular limitation as long as they have no influence on the reaction. The reaction time depends on the kind of the starting material used and the reaction temperature, and is usually in the range of 30 minutes to 24 hours.

Step 2

The reaction is a condensation reaction of Compound [18] with Compound [19] using a palladium catalyst and thus may be carried out per se according to a known method. The usable solvent includes, for example, hydrocarbons such as toluene, xylene; ethers such as 1,4-dioxane, tetrahydrofuran; amides such as N,N-dimethylformamide, N,N-dimethylacetamide, N-methyl-2-pyrrolidone; or a mixture of them, but there is no particular limitation as long as they have no influence on the reaction. The reaction is carried out at a temperature of $20°$ C. to $200°$ C. in the presence of a base. The usable palladium catalyst includes, for example, tris(dibenzylideneacetone)(chloroform)dipalladium(0), tris(dibenzylideneacetone)dipalladium(0), and palladium(II)acetate. The amount of the palladium catalyst to be used is preferably within the range of 0.001-0.1 mole for 1 mole of the aryl halide. The usable ligand for the palladium catalyst includes, for example, 4,5-bis(diphenylphosphino)-9,9'-dimethylxanthene, (±)-2,2'-bis(diphenylphosphino)-1,1'-binaphthyl, 2-(di-t-butylphosphino)biphenyl, bis[2-(diphenylphosphino)phenyl]ether, and tri-t-butylphosphine. The usable base includes, for example, sodium t-butoxide, tripotassium phosphate, and cesium carbonate. The reaction time depends on the kind of the starting material used and the reaction temperature, and is usually in the range of 10 minutes to 24 hours.

Process 3: In the case of $R^2$ being represented by the following general formula [9]:

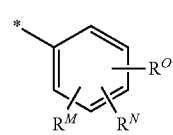

[9]

(wherein $R^M$, $R^N$, $R^O$ and * have the same meanings as described above), or in the case of $R^2$ being a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl (but the bonding site is limited to C.)

Process 3-1

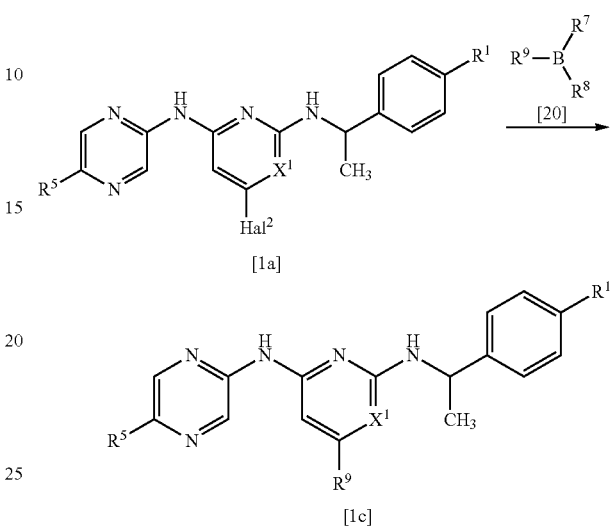

[1a]

[1c]

(wherein $X^1$, $R^1$, $R^5$ and $Hal^2$ have the same meanings as described above; and $R^7$ and $R^8$ each represent hydroxy, or $R^7$ and $R^8$ are taken together to represent $-O-C(CH_3)_2-C(CH_3)_2-O-$, $-O-(CH_2)_3-O-$, or $-O-CH_2-C(CH_3)_2-CH_2-O-$; and $R^9$ represents a group represented by the following general formula [9]:

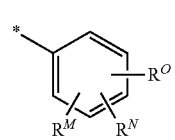

[9]

(wherein $R^M$, $R^N$, $R^O$ and * have the same meanings as described above), or a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl (but the bonding site is limited to C).)

The reaction is a cross-coupling reaction using Compound [1a] and an organoborane compound [20], and thus may be carried out per se according to a known method. The reaction may be carried out, for example, in the presence of a palladium catalyst and a base in a suitable solvent at $20$-$200°$ C. The usable palladium catalyst includes, for example, tetrakis(triphenylphosphine)palladium, dichlorobis(triphenylphosphine)palladium, and 1,1'-bis(diphenylphosphino)ferrocene-palladium(II) dichloride-dichloromethane complex. The amount of the palladium catalyst to be used is preferably within the range of 0.001-0.1 mole for 1 mole of the aryl halide. The usable solvent includes, for example, ethers such as tetrahydrofuran, 1,4-dioxane, 1,2-dimethoxyethane; alcohols such as methanol, ethanol; amides such as N,N-dimethylformamide, N,N-dimethylacetamide; hydrocarbons such as benzene, toluene; water; or a mixture of them, but there is no particular limitation as long as they have no influence on the reaction. The usable base includes, for example, sodium hydroxide, potassium carbonate, and sodium carbonate. The reaction time depends on the kind of the starting material used and the reaction temperature, and is usually in the range of 30 minutes to 24 hours.
Process 3-2

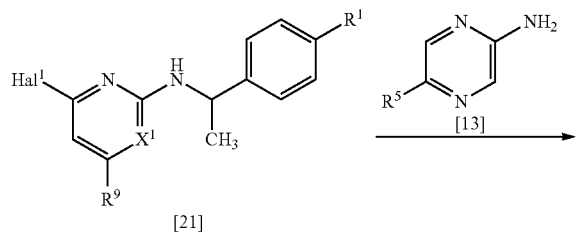

(wherein $X^1$, $R^1$, $R^5$, $R^9$ and $Hal^1$ have the same meanings as described above.)

The reaction is a condensation reaction of Compound [21] with Compound [13] using a palladium catalyst and thus may be carried out per se according to a known method. The usable solvent includes, for example, hydrocarbons such as toluene, xylene; ethers such as 1,4-dioxane, tetrahydrofuran; amides such as N,N-dimethylformamide, N,N-dimethylacetamide, N-methyl-2-pyrrolidone; or a mixture of them, but there is no particular limitation as long as they have no influence on the reaction. The reaction is carried out at a temperature of 20° C. to 200° C. in the presence of a base. The usable palladium catalyst includes, for example, tris(dibenzylideneacetone) (chloroform)dipalladium(0), tris(dibenzylideneacetone)dipalladium(0), and palladium(II)acetate. The amount of the palladium catalyst to be used is preferably within the range of 0.001-0.1 mole for 1 mole of the aryl halide. The usable ligand for the palladium catalyst includes, for example, 1,1'-bis(diphenylphosphino)ferrocene, 4,5-bis(diphenylphosphino)-9,9'-dimethylxanthene, 2-dicyclohexylphosphino-2',4',6'-triisopropylbiphenyl, (±)-2,2'-bis(diphenylphosphino)-1,1'-binaphthyl, 2-(di-t-butylphosphino)biphenyl, bis[2-(diphenylphosphino)phenyl]ether, and tri-t-butylphosphine. The usable base includes, for example, sodium t-butoxide, tripotassium phosphate, and cesium carbonate. The reaction time depends on the kind of the starting material used and the reaction temperature, and is usually in the range of 10 minutes to 24 hours.

Compound [21] as a starting compound may be produced, for example, according to the following 3 processes.
Process A

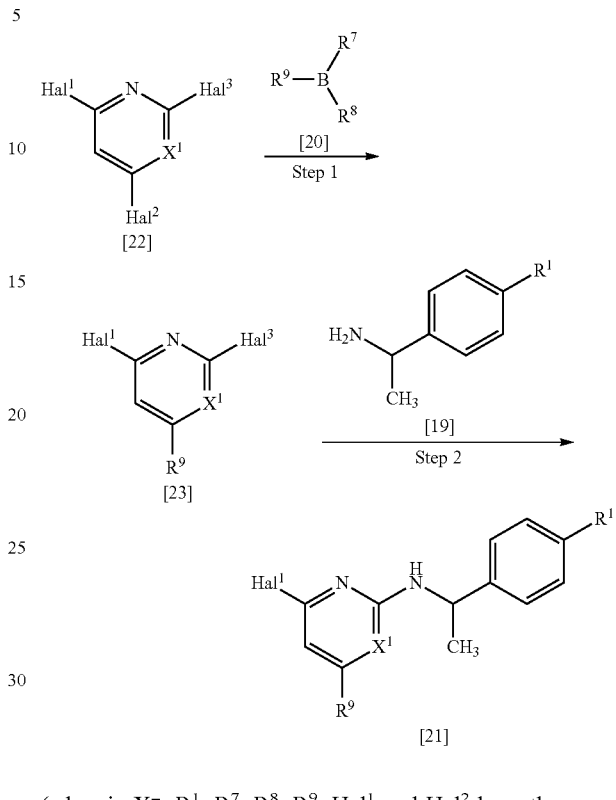

(wherein $X^-$, $R^1$, $R^7$, $R^8$, $R^9$, $Hal^1$ and $Hal^2$ have the same meanings as described above; and $Hal^3$ represents a halogen.)
Step 1

The reaction is a cross-coupling reaction using Compound [22] and an organoborane compound [20], and thus may be carried out per se according to a known method. The reaction may be carried out, for example, in the presence of a palladium catalyst and a base in a suitable solvent at a temperature of 20-200° C. The usable palladium catalyst includes, for example, tetrakis(triphenylphosphine)palladium, dichlorobis (triphenylphosphine)palladium, and 1,1'-bis(diphenylphosphino) ferrocene-palladium(II) dichloride-dichloromethane complex. The amount of the palladium catalyst to be used is preferably within the range of 0.001-0.1 mole for 1 mole of the aryl halide. The usable solvent includes, for example, ethers such as tetrahydrofuran, 1,4-dioxane, 1,2-dimethoxyethane; alcohols such as methanol, ethanol; amides such as N,N-dimethylformamide, N,N-dimethylacetamide; hydrocarbons such as benzene, toluene; water; or a mixture of them, but there is no particular limitation as long as they have no influence on the reaction. The usable base includes, for example, sodium hydroxide, potassium carbonate, and sodium carbonate. The reaction time depends on the kind of the starting material used and the reaction temperature, and is usually in the range of 30 minutes to 24 hours.
Step 2

The reaction is a condensation reaction of Compound [23] with Compound [19] using a palladium catalyst and thus may be carried out per se according to a known method. The usable solvent includes, for example, hydrocarbons such as toluene, xylene; ethers such as 1,4-dioxane, tetrahydrofuran; amides such as N,N-dimethylformamide, N,N-dimethylacetamide, N-methyl-2-pyrrolidone; or a mixture of them, but there is no particular limitation as long as they have no influence on the reaction. The reaction is carried out at a temperature of 20° C. to 200° C. in the presence of a base. The usable palladium catalyst includes, for example, tris(dibenzylideneacetone)(chloroform)dipalladium(0), tris(dibenzylideneacetone)dipalladium (0), and palladium(II)acetate. The amount of the palladium catalyst to be used is preferably within the range of 0.001-0.1 mole for 1 mole of the aryl halide. The usable ligand for the palladium catalyst includes, for example, 4,5-bis(diphenylphosphino)-9,9'-dimethylxanthene, (±)-2,2'-bis(diphenylphosphino)-1,1'-binaphthyl, 2-(di-t-butylphosphino)biphenyl, bis[2-(diphenylphosphino)phenyl]ether, and tri-t-butylphosphine. The usable base includes, for example, sodium t-butoxide, tripotassium phosphate, and cesium carbonate. The reaction time depends on the kind of the starting material used and the reaction temperature, and is usually in the range of 10 minutes to 24 hours.

Process B

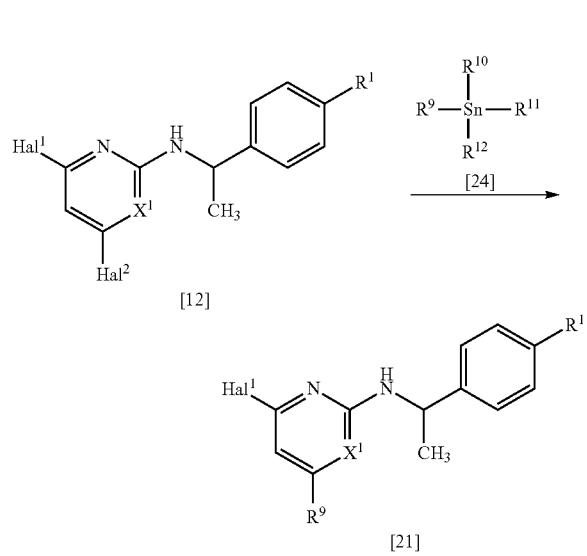

(wherein $X^1$, $R^1$, $R^9$, $Hal^1$ and $Hal^2$ have the same meanings as described above; and $R^{10}$, $R^{11}$ and $R^{12}$ are the same or different and each represents alkyl.)

The reaction is a cross-coupling reaction using Compound [12] and an organotin compound [24], and thus may be carried out per se according to a known method. The reaction may be carried out, for example, in the presence of a palladium catalyst in a suitable solvent at 20-200° C. The usable palladium catalyst includes, for example, tetrakis(triphenylphosphine)palladium, dichlorobis(triphenylphosphine)palladium, 1,1'-bis(diphenylphosphino)ferrocene-palladium (II) dichloride-dichloromethane complex, and palladium acetate. The amount of the palladium catalyst to be used is preferably within the range of 0.001-0.1 mole for 1 mole of the aryl halide. The usable solvent includes, for example, ethers such as tetrahydrofuran, 1,4-dioxane, 1,2-dimethoxyethane; amides such as N,N-dimethylformamide, N,N-dimethylacetamide; hydrocarbons such as benzene, toluene; or a mixture of them, but there is no particular limitation as long as they have no influence on the reaction. It is also possible to add an additive such as copper oxide or silver oxide. The reaction time depends on the kind of the starting material used and the reaction temperature, and is usually in the range of 1 to 24 hours.

Process C

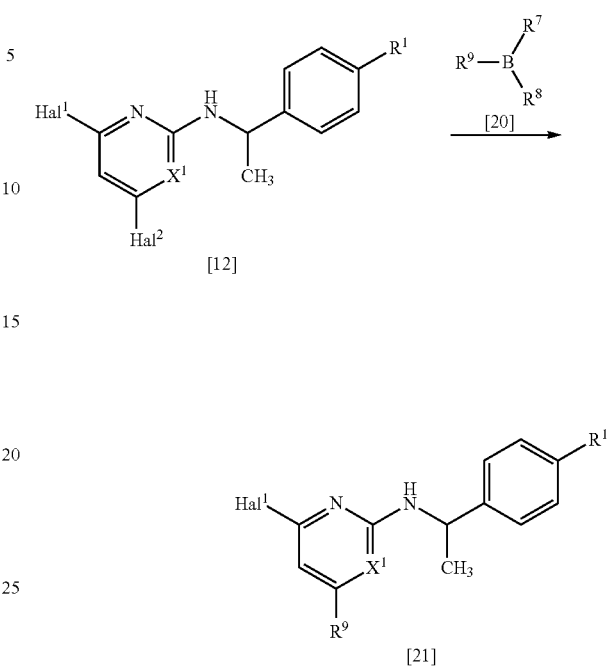

(wherein X, $R^1$, $R^7$, $R^8$, $R^9$, $Hal^1$ and $Hal^2$ have the same meanings as described above.)

The reaction is a cross-coupling reaction using Compound [12] and an organoborane compound [20], and thus may be carried out per se according to a known method. The reaction may be carried out, for example, in the presence of a palladium catalyst and a base in a suitable solvent at a temperature of 20-200° C. The usable palladium catalyst includes, for example, tetrakis(triphenylphosphine)palladium, dichlorobis(triphenylphosphine)palladium, and 1,1'-bis(diphenylphosphino)ferrocene-palladium(II) dichloride-dichloromethane complex. The amount of the palladium catalyst to be used is preferably within the range of 0.001-0.1 mole for 1 mole of the aryl halide. The usable reaction solvent includes, for example, ethers such as tetrahydrofuran, 1,4-dioxane, 1,2-dimethoxyethane; alcohols such as methanol, ethanol; amides such as N, N-dimethylformamide, N, N-dimethylacetamide; hydrocarbons such as benzene, toluene; water; or a mixture of them, but there is no particular limitation as long as they have no influence on the reaction. The usable base includes, for example, sodium hydroxide, potassium carbonate, and sodium carbonate. The reaction time depends on the kind of the starting material used and the reaction temperature, and is usually in the range of 30 minutes to 24 hours.

Process 4: In the case of $R^2$ being represented by the following general formula [3]:

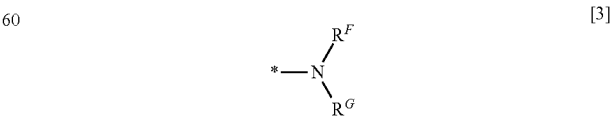

(wherein $R^F$ and $R^G$ each have the same meanings as described above.)

Process 4-1

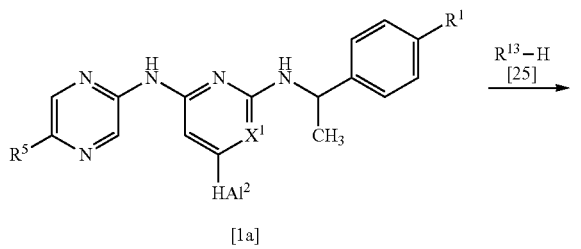

[1a]

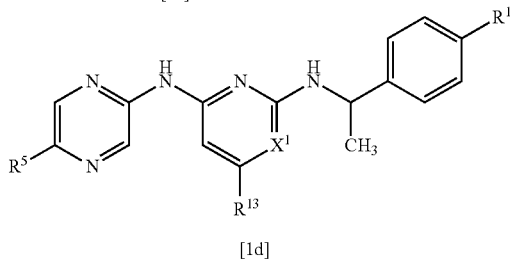

[1d]

(wherein $X^1$, $R^1$, $R^5$ and $Hal^2$ each have the same meanings as described above; and $R^{13}$ is a group represented by the following general formula [3]:

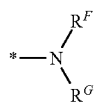

[3]

(wherein $R^F$ and $R^G$ each have the same meanings as described above).)

The reaction is a cross-coupling reaction using Compound [1a] and Compound [25], and thus may be carried out per se according to a known method. The usable solvent includes, for example, hydrocarbons such as toluene, xylene; ethers such as 1,4-dioxane, tetrahydrofuran; amides such as N,N-dimethylformamide, N,N-dimethylacetamide, N-methyl-2-pyrrolidone; or a mixture of them, but there is no particular limitation as long as they have no influence on the reaction. The reaction may be carried out, for example, in the presence of a palladium catalyst and a base in a suitable solvent at a temperature of 20-200° C. The usable palladium catalyst includes, for example, tris(dibenzylideneacetone)(chloroform)dipalladium(0), tris(dibenzylideneacetone)dipalladium(0), and palladium(II)acetate. The amount of the palladium catalyst to be used is preferably within the range of 0.001-0.1 mole for 1 mole of the aryl halide. The usable ligand for the palladium catalyst includes, for example, 1,1'-bis-(diphenylphosphino)ferrocene, 4,5-bis(diphenylphosphino)-9,9'-dimethylxanthene, 2-dicyclohexylphosphino-2',4',6'-triisopropylbiphenyl, (±)-2,2'-bis(diphenylphosphino)-1,1'-binaphthyl, 2-(di-t-butylphosphino)biphenyl, bis[2-(diphenylphosphino)phenyl]ether, and tri-t-butylphosphine. The usable base includes, for example, sodium t-butoxide, tripotassium phosphate, and cesium carbonate. The reaction time depends on the kind of the starting material used and the reaction temperature, and is usually in the range of 30 minutes to 24 hours.

Process 4-2

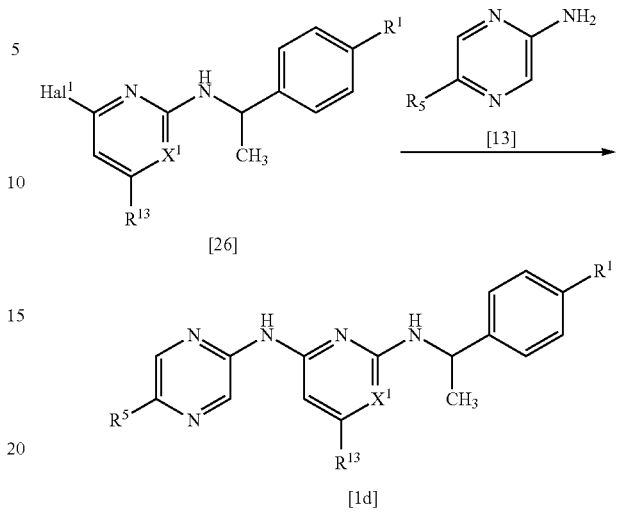

[26]

[1d]

(wherein $X^1$, $R^1$, $R^5$, $R^{13}$ and $Hal^1$ each have the same meanings as described above.)

The reaction is a condensation reaction of Compound [26] with Compound [13] using a palladium catalyst and thus may be carried out per se according to a known method. The usable solvent includes, for example, hydrocarbons such as toluene, xylene; ethers such as 1,4-dioxane, tetrahydrofuran; amides such as N,N-dimethylformamide, N,N-dimethylacetamide, N-methyl-2-pyrrolidone; or a mixture of them, but there is no particular limitation as long as they have no influence on the reaction. The reaction is carried out at a temperature of 20° C. to 200° C. in the presence of a base. The usable palladium catalyst includes, for example, tris(dibenzylideneacetone)(chloroform)dipalladium(0), tris(dibenzylideneacetone)dipalladium(0), and palladium(II)acetate. The amount of the palladium catalyst to be used is preferably within the range of 0.001-0.1 mole for 1 mole of the aryl halide. The usable ligand for the palladium catalyst includes, for example, 1,1'-bis-(diphenylphosphino)ferrocene, 4,5-bis(diphenylphosphino)-9,9'-dimethylxanthene, 2-dicyclohexylphosphino-2',4',6'-triisopropylbiphenyl, (±)-2,2'-bis(diphenylphosphino)-1,1'-binaphthyl, 2-(di-t-butylphosphino)biphenyl, bis[2-(diphenylphosphino)phenyl]ether, and tri-t-butylphosphine. The usable base includes, for example, sodium t-butoxide, tripotassium phosphate, and cesium carbonate. The reaction time depends on the kind of the starting material used and the reaction temperature, and is usually in the range of 10 minutes to 24 hours.

Compound [26] as a starting compound may be produced, for example, according to the following 2 processes.

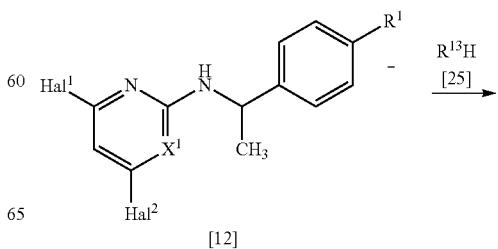

[12]

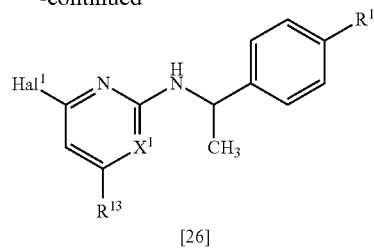

[26]

(wherein $X^1$, $R^1$, $R^{13}$, $Hal^1$ and $Hal^2$ each have the same meanings as described above.)

Process a

Compound [26] may be produced by reacting Compound [12] with Compound [25] in a suitable solvent in the presence of a base at a temperature of 20° C. to 200° C. The usable base includes, for example, pyridine, triethylamine, N,N-diisopropylethylamine, potassium carbonate, and sodium bicarbonate. The usable solvent includes alcohols such as 1-butanol, 2-methoxyethanol; ethers such as tetrahydrofuran, 1,4-dioxane; amides such as N, N-dimethylformamide, N,N-dimethylacetamide; hydrocarbons such as benzene, toluene; acetonitrile; or a mixture of them, but there is no particular limitation as long as they have no influence on the reaction. The reaction time depends on the kind of the starting material used and the reaction temperature, and in general it is preferably in the range of 1 to 24 hours.

Process b

Compound [26] can be produced by condensation reaction of Compound [12] with Compound [25] using a palladium catalyst per se according to a known method. The usable solvent includes, for example, hydrocarbons such as toluene, xylene; ethers such as 1,4-dioxane, tetrahydrofuran; or a mixture of them, but there is no particular limitation as long as they have no influence on the reaction. The reaction may be carried out in the presence of a base at a temperature of 20° C. to 200° C. The usable palladium catalyst includes, for example, tris(dibenzylideneacetone)(chloroform)dipalladium(0), tris(dibenzylideneacetone)dipalladium(0), and palladium(II)acetate. The amount of the palladium catalyst to be used is preferably within the range of 0.001-0.1 mole for 1 mole of the aryl halide. The usable ligand for the palladium catalyst includes, for example, 1,1'-bis-(diphenylphosphino)ferrocene, 4,5-bis(diphenylphosphino)-9,9'-dimethylxanthene, 2-dicyclohexylphosphino-2',4',6'-triisopropylbiphenyl, (±)-2,2'-bis(diphenylphosphino)-1,1'-binaphthyl, 2-(di-t-butylphosphino)biphenyl, bis[2-(diphenylphosphino)phenyl]ether, and tri-t-butylphosphine. The usable base includes, for example, sodium t-butoxide, tripotassium phosphate, and cesium carbonate. The reaction time depends on the kind of the starting material used and the reaction temperature, and is usually in the range of 10 minutes to 24 hours.

Process 5: In the Case of $R^2$ being a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl (but the bonding site is limited to N.)

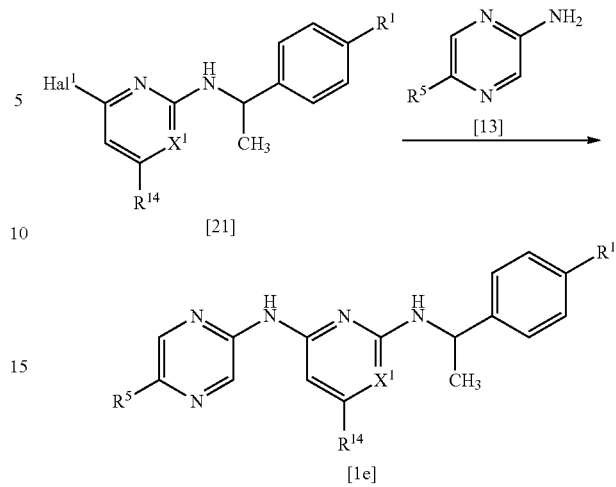

(wherein $X^1$, $R^1$, $R^5$ and $Hal^1$ each have the same meanings as described above; and $R^{14}$ is a heteroaryl optionally substituted by one or two groups selected from the group consisting of cyano, halogen, hydroxy, alkoxy, alkylcarbonyl, carbamoyl, alkyl, cycloalkyl, (cycloalkyl)alkyl, aralkyl, hydroxycarbonyl and alkoxyalkyl (but the bonding site is limited to N).)

The reaction is a condensation reaction of Compound [27] with Compound [13] using a palladium catalyst, and may be carried out in the same manner as in Process 4-2 as mentioned above.

Compound [27] as a starting compound may be produced according to the following method.

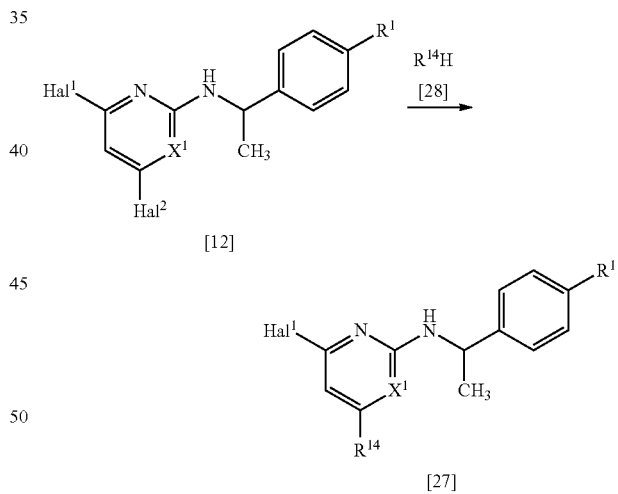

(wherein $X^1$, $R^1$, $R^{14}$, $Hal^1$ and $Hal^2$ each have the same meanings as described above.)

The reaction is a cross-coupling reaction using Compound [12] and Compound [28], and may be carried out per se according to a known method. The reaction may be carried out, for example, in the presence or absence of a copper catalyst in a proper solvent at a temperature of 20 to 200° C. The usable copper catalyst includes, for example, copper iodide and copper acetate. The amount of the copper catalyst to be used is preferably in the range of 0.01 to 0.2 mole for 1 mole of the aryl halide. The ligand for copper such as trans-N,N'-dimethylcyclohexane-1,2-diamine, trans-1,2-cyclohexanediamine, 1,10-phenanthroline, etc. may be used. The usable reaction solvent includes, for example, ethers such as tetrahydrofuran, 1,4-dioxane, 1,2-dimethoxyethane; alcohols such as methanol, ethanol; amides such as N,N-dimethylformamide, N,N-dimethylacetamide; hydrocarbons such as benzene, toluene; or a mixture of them, but there is no particular limitation as long as they have no influence on the reaction. The usable base includes, for example, tripotassium phosphate, potassium carbonate, sodium carbonate, and cesium carbonate. The reaction time depends on the kind of the starting material used and the reaction temperature, and in general it is preferably in the range of 30 minutes to 24 hours.

Process 6: In the case of $R^2$ being alkoxycarbonyl

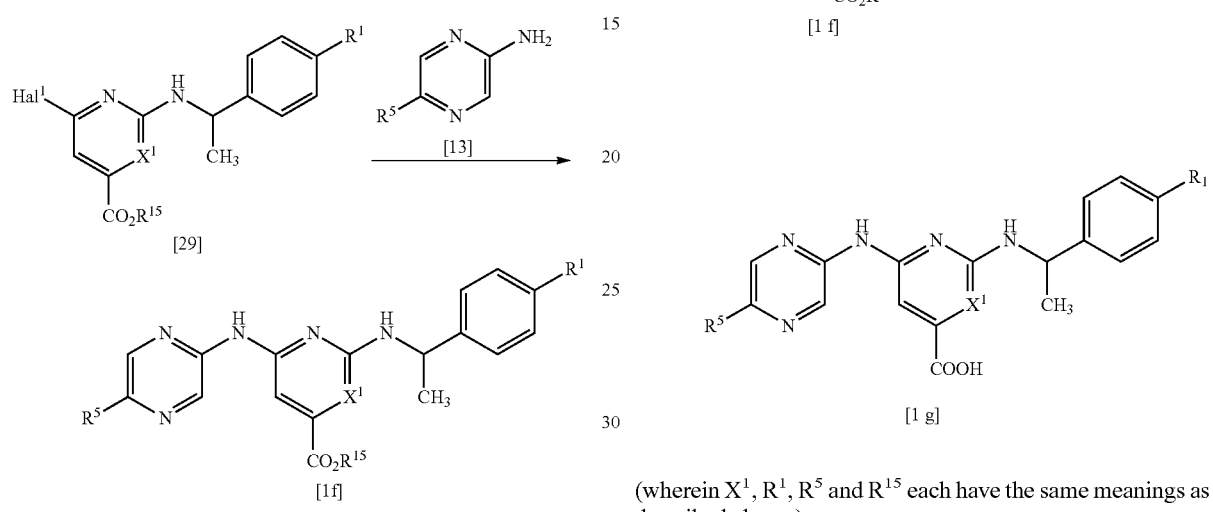

(wherein $X^1$, $R^1$, $R^5$ and $Hal^1$ each have the same meanings as described above; and $R^{15}$ represents an alkyl.)

The reaction is a condensation reaction of Compound [29] with Compound [13] using a palladium catalyst, and may be carried out in the same manner as in Process 4-2 as mentioned above.

Compound [29] as a starting compound may be produced according to the following method.

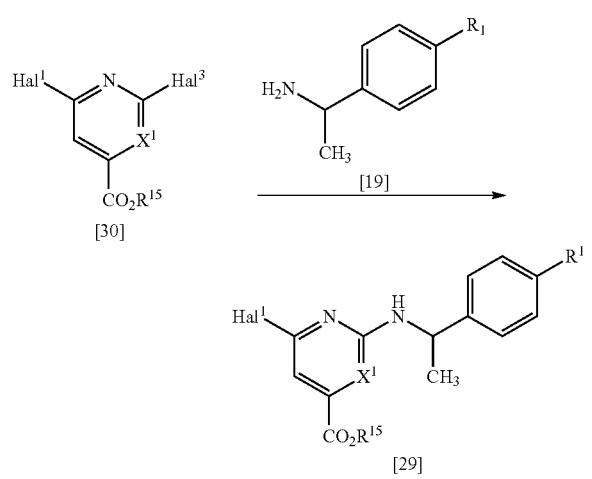

(wherein $X^1$, $R^1$, $R^{15}$, $Hal^1$ and $Hal^3$ each have the same meanings as described above.)

The reaction is a condensation reaction of Compound [30] with Compound [19] using a palladium catalyst, and may be carried out in the same manner as in Step 2 in the process for producing Compound [15] as a starting compound as mentioned above.

Process 7: In the case of $R^2$ being hydroxycarbonyl

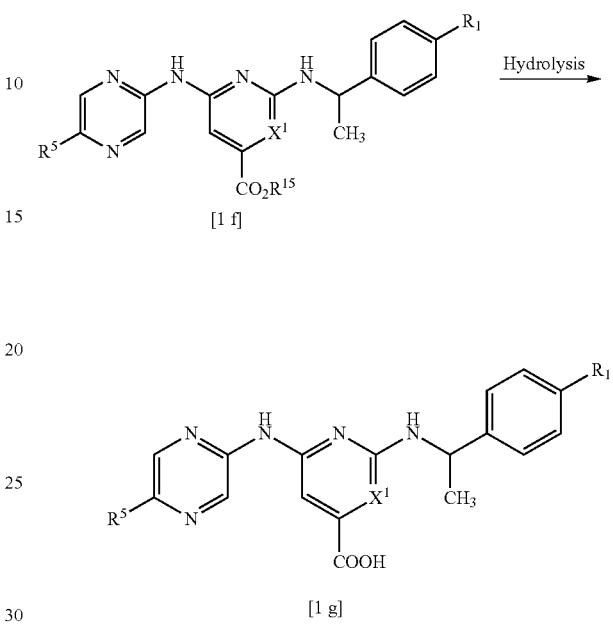

(wherein $X^1$, $R^1$, $R^5$ and $R^{15}$ each have the same meanings as described above.)

The reaction is a hydrolysis reaction of Compound [1f] and may be carried out per se according to a known method. In general, the reaction can be carried out by hydrolyzing Compound [1f] in the presence of an acid or base to yield Compound [1g]. The acid used in the reaction includes, for example, inorganic acids such as hydrochloric acid and sulfuric acid; the base includes, for example, inorganic bases such as sodium hydroxide and potassium hydroxide. The solvent usable in the reaction includes, for example, alcohols such as methanol, ethanol; ethers such as tetrahydrofuran, 1,4-dioxane; water; or a mixture of them. The reaction is conducted at a temperature of 0° C. to 100° C., usually for a period of 30 minutes to 24 hours.

Process 8: In the case of $R^2$ being (a) a saturated cyclic amino group optionally substituted by alkyl or alkylsulfonyl; or (b) an aminocarbonyl optionally substituted by one or two groups selected from the group consisting of alkyl, cycloalkyl, (cycloalkyl)alkyl, aralkyl, haloalkyl, dialkylaminoalkyl, alkoxyalkyl, and hydroxyalkyl

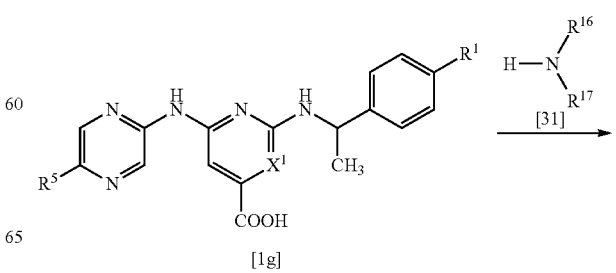

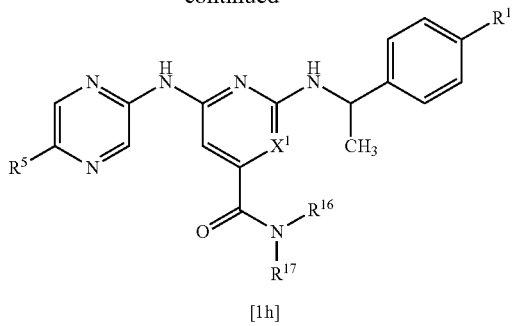

[1h]

(wherein $X^1$, $R^1$ and $R^5$ each have the same meanings as described above; $R^{16}$ and $R^{17}$ are the same or different and each represents H, alkyl, cycloalkyl, (cycloalkyl)alkyl, aralkyl, haloalkyl, dialkylaminoalkyl, alkoxyalkyl, or hydroxyalkyl, or they are taken together with the adjacent N to represent a saturated cyclic amino group; said saturated cyclic amino group may optionally be substituted by alkyl or alkylsulfonyl.)

The reaction is a condensation reaction of Compound [1g] with Compound [31], and can be carried out per se according to a known method. Compound [1h] can be synthesized by reacting Compound [1g] as a carboxylic acid or a reactive derivative thereof with Compound [31]. The reactive derivative of Compound [1g] includes those conventionally used in the amide condensation reaction, for example, acid halides (e.g. acid chloride, acid bromide), mixed acid anhydrides, imidazolides, active amide, and the like. In case of using Compound [1g], the reaction is carried out in the presence or absence of a base using a condensing agent at a temperature of −20 to 100° C. The condensing agent usable in the reaction includes, for example, 1,1'-oxalyldiimidazole, 1-ethyl-3-(3-dimethylaminopropyl)carbodiimide, dicyclohexylcarbodiimide, diethyl cyanophosphate, O-(benzotriazol-1-yl)-N,N,N',N'-tetramethyluronium hexafluorophospate, and 1H-benzotriazol-1-yloxytripyrrolidinophosphonium hexafluorophosphate. The base usable in the reaction includes organic base, for example, triethylamine, N,N-diisopropylethylamine, N,N-dimethylanline, pyridine, and 1,8-diazabicyclo[5.4.0]-7-undecene. The usable solvent includes, for example, ethers such as tetrahydrofuran, 1,4-dioxane, diethyl ether; amides such as N,N-dimethylformamide, N,N-dimethylacetamide; nitriles such as acetonitrile, propionitrile; hydrocarbons such as benzene, toluene; halogenated hydrocarbons such as chloroform, methylene chloride; or a mixture of them, but there is no particular limitation as long as they have no influence on the reaction. If required, an additive may be used. The usable additive includes, for example, 1-hydroxybenzotriazole and 1-hydroxy-7-azabenzotriazole. The reaction time depends on the kind of the starting material used and the reaction temperature, and in general it is preferably in the range of 10 minutes to 24 hours. The amount of Compound [31] and the condensing agent is preferably, for example, in the range of 1 equimolar to 3 equimolar amount for 1 mole of Compound [1g].

Process 9: In the case of $R^2$ being H, alkylcarboyl, an N-containing saturated heterocyclic group optionally substituted by alkylsulfonyl or an alkyl optionally substituted by hydroxy or alkoxy

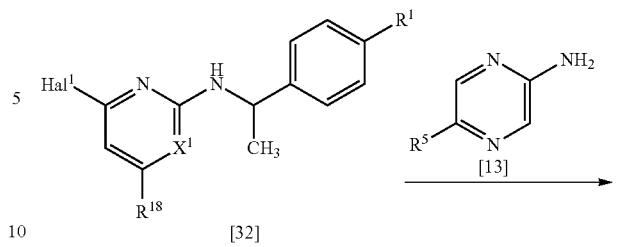

[32]

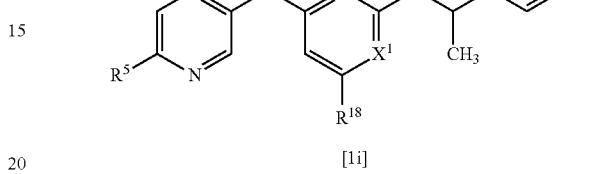

[1i]

(wherein $X^1$, $R^1$, $R^5$ and $Hal^1$ each have the same meanings as described above; and $R^{18}$ represents H or alkyl optionally substituted by alkoxy.)

The reaction is a condensation reaction of Compound [32] with Compound [13] using a palladium catalyst, and can be carried out in the same manner as in Process 1 as mentioned above.

Process 10: In the case of $R^2$ being cyano

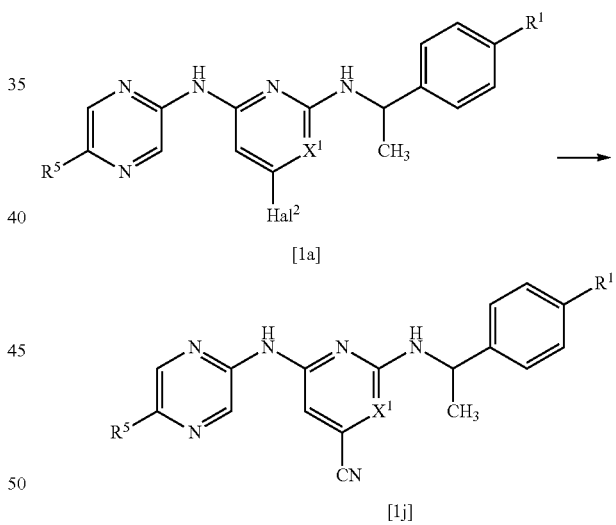

(wherein $X^1$, $R^1$, $R^5$ and $Hal^2$ each have the same meanings as described above.)

The reaction is a cyanation reaction of Compound [1a], and can be carried out per se according to a known method. The reaction may be carried out using a cyano compound, for example, in the presence or absence of a palladium catalyst at a temperature of 20 to 200° C., if required under microwave. The usable palladium catalyst includes, for example, tetrakis(triphenylphosphine)palladium, 1,1'-bis(diphenylphosphino)ferrocene-palladium(II)dichloride-dichloromethane complex, and tris(dibenzylideneacetone)dipalladium(0). The amount of the palladium catalyst to be used is preferably within the range of 0.001-0.1 mole for 1 mole of the aryl halide. If required, a palladium ligand such as 4,5-bis(diphenylphosphino)-9,9'-dimethylxanthene, 2-dicyclohexylphosphino-2',4',6'-triisopropylbiphenyl, 2-dicyclohexylphosphino-2',6'-dimethoxybiphenyl, and the like may be used. The usable cyano compound includes copper(I) cyanide, zinc (II) cyanide, potassium cyanide, and sodium cyanide. The usable solvent includes, for example, ethers such as tetrahydrofuran, 1,4-dioxane; alcohols such as methanol, ethanol; amides such as N,N-dimethylformamide, N,N-dimethylacetamide, N-methyl-2-pyrrolidone; hydrocarbons such as benzene, toluene; dimethylsulfoxide; water; or a mixture of them, but there is no particular limitation as long as they have no influence on the reaction. The reaction time depends on the kind of the starting material used and the reaction temperature, and in general it is preferably in the range of 30 minutes to 24 hours.

Process 11: In the case of X being —$CR^A$, and $R^A$ being alkoxycarbonyl

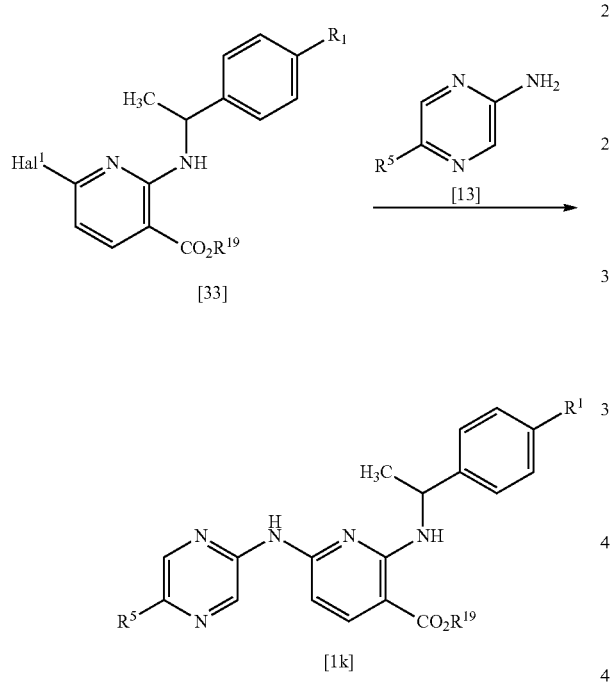

(wherein $R^1$, $R^5$ and $Hal^1$ each have the same meanings as described above; and $R^{19}$ represents an alkyl.)

The reaction is a condensation reaction of Compound [33] with Compound [13] using a palladium catalyst, and can be carried out in the same manner as in Process 4-2 as mentioned above.

Compound [33] as a starting compound may be produced according to the following method.

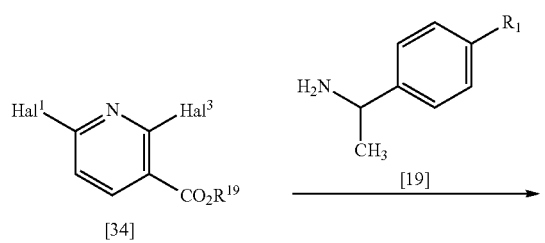

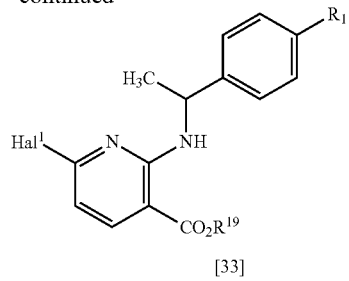

(wherein $R^1$, $R^{19}$, $Hal^1$ and $Hal^3$ each have the same meanings as described above.)

The reaction is a condensation reaction of Compound [34] with Compound [19] using a palladium catalyst, and can be carried out in the same manner as in Step 2 of Process A, Process 3-2 as mentioned above.

Process 12: In the case of X being —$CR^A$, and $R^A$ being hydroxycarbonyl

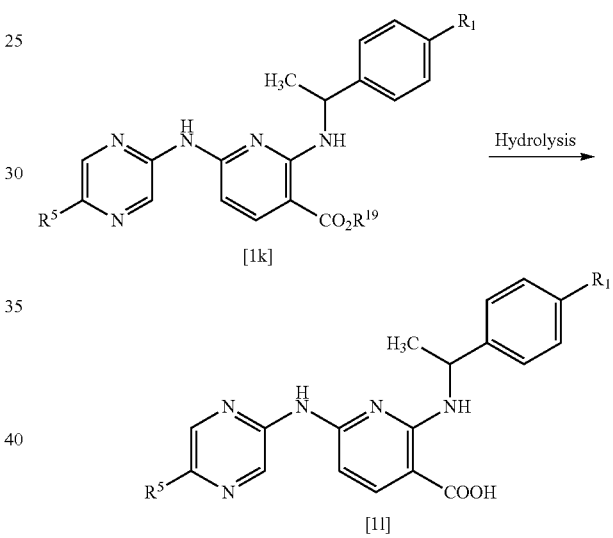

(wherein $R^1$, $R^5$ and $R^{19}$ each have the same meanings as described above.)

The reaction is a hydrolytic reaction of Compound [1k] and can be carried out in the same manner as in Process 7 as mentioned above.

Process 13: In the case of X being —$CR^A$; and $R^A$ being a group as represented by the general formula [35]:

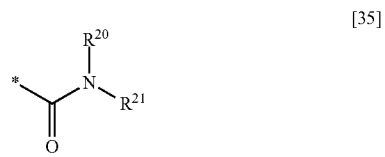

(wherein * has the same meaning as described above; $R^{20}$ and $R^{21}$ are the same or different, and each represents H, alkyl, cycloalkyl, (cycloalkyl)alkyl, or alkoxyalkyl, or they are taken together with the adjacent N to represent a saturated cyclic amino group.)

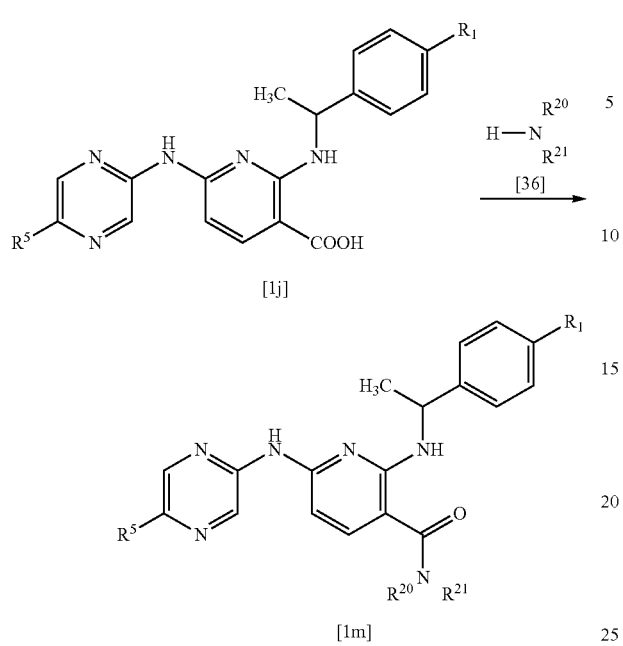

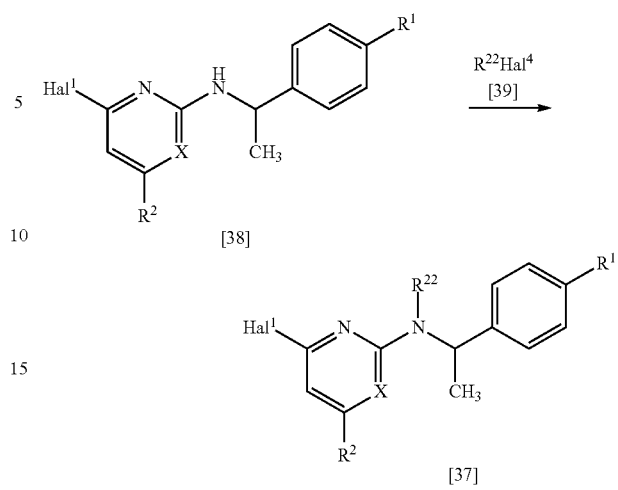

(wherein $R^1$, $R^5$, $R^{20}$ and $R^{21}$ each have the same meanings as described above.)

The reaction is a condensation reaction of Compound [1j] with Compound [36], and can be carried out in the same manner as in Process 8 as mentioned above.

Process 14: In the case of $R^4$ being alkyl

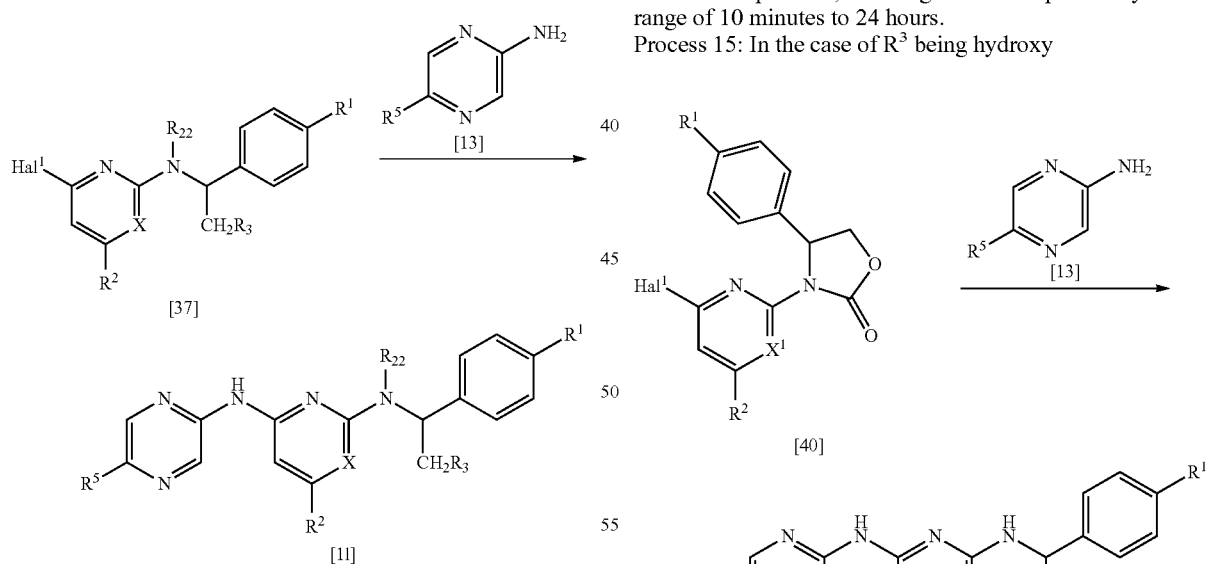

(wherein X, $R^1$, $R^2$, $R^3$, $R^5$ and $Hal^1$ each have the same meanings as described above; and $R^{22}$ represents an alkyl.)

The reaction is a condensation reaction of Compound [37] with Compound [13] using a palladium catalyst, and can be carried out in the same manner as in Process 4-2 as mentioned above.

Compound [37] as a starting compound may be produced according to the following method.

(wherein X, $R^1$, $R^2$, $R^{22}$ and $Hal^1$ each have the same meanings as described above; and $Hal^4$ represents a halogen.)

In this step, Compound [38] is allowed to react with Compound [39] in a suitable solvent in the presence of a base at 20° C. to 200° C., if required under a microwave. The usable base includes, for example, sodium hydride, lithium diisopropylamide, and n-butyllithium. The usable solvent includes, for example, ethers such as tetrahydrofuran, 1,4-dioxane; amides such as N,N-dimethylformamide, N,N-dimethylacetamide; hydrocarbons such as benzene, toluene; acetonitrile; or a mixture of them, but there is no particular limitation as long as they have no influence on the reaction. The reaction time depends on the kind of the starting material used and the reaction temperature, and in general it is preferably in the range of 10 minutes to 24 hours.

Process 15: In the case of $R^3$ being hydroxy

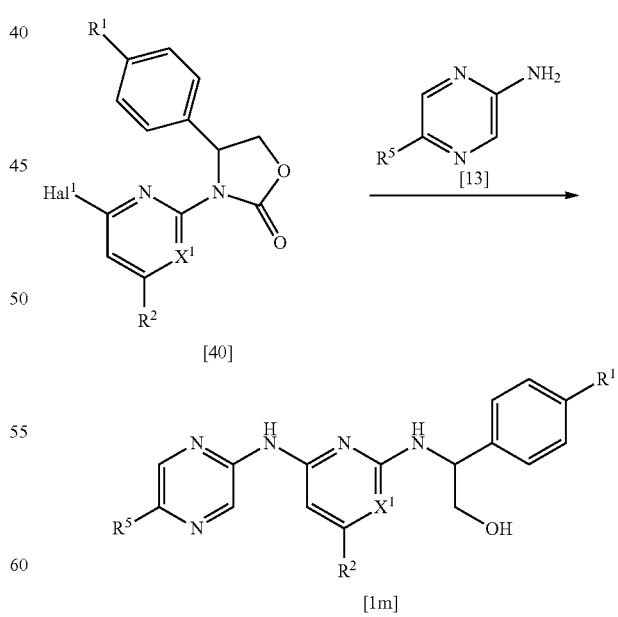

(wherein $X^1$, $R^1$, $R^2$, $R^5$ and $Hal^1$ each have the same meanings as described above.)

The reaction is a condensation reaction of Compound [40] with Compound [13] using a palladium catalyst, and can be carried out in the same manner as in Process 1 as mentioned above. As for the base usable in this reaction, sodium t-butoxide is appropriate.

Compound [40] as a starting compound may be produced according to the following method.

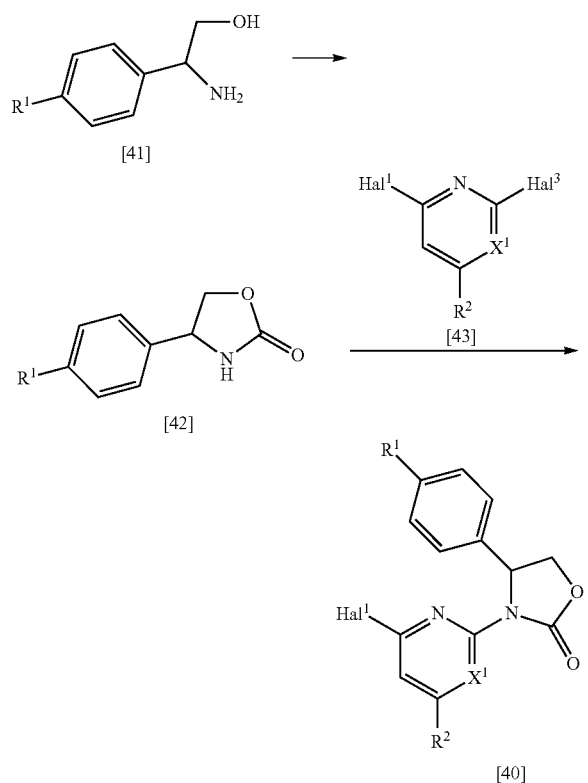

(wherein $X^1$, $R^1$, $R^2$, $Hal^1$ and $Hal^3$ each have the same meanings as described above.)

Step 1

Compound [42] can be produced according to a known method (J. Org. Chem., 65, 2000, 9059-9068).

Step 2

In this step, Compound [42] is subjected to the condensation reaction with Compound [43] using a palladium catalyst, and the reaction can be carried out in the same manner as in Process 1 as mentioned above.

Though the compounds of the invention can be utilized as such as medicaments, they may also be used in a form of pharmaceutically acceptable salts according to a known method. Such salts include those with mineral acids, e.g. hydrochloric acid, hydrobromic acid, sulfuric acid, phosphoric acid, or with organic acids, e.g. acetic acid, citric acid, tartaric acid, maleic acid, succinic acid, fumaric acid, p-toluenesulfonic acid, benzenesulfonic acid, methanesulfonic acid, etc.

For example, the hydrochlorides of the compounds of the invention can be produced by dissolving the compounds of the invention in a solution of hydrogen chloride in an alcohol or ethyl acetate or diethyl ether.

Since some of the compounds of the invention have an asymmetric carbon, all of the optical isomers and their mixtures are encompassed in the invention. The optical isomers can be obtained by optical resolution of the racemates prepared as mentioned above with an optically active acid (tartaric acid, dibenzoyltartaric acid, mandelic acid, 10-camphor- sulfonic acid, etc.) utilizing their basicity according to a known method, or alternatively the optical isomers may be obtained from optically active starting compounds prepared in advance. Otherwise, they may be produced by optical resolution with a chiral column or by asymmetric synthesis.

When the compounds of the invention exist in a form of geometrical isomers or tautomers, not only one of the isomers but also their mixtures are encompassed in the invention.

The compounds of the invention or pharmaceutically acceptable salts thereof are useful as medicaments. The pharmaceutical compositions containing the compounds of the invention or pharmaceutically acceptable salts thereof as active ingredients can be used as preventives or therapeutics for cancers (e.g. hematic cancers (e.g. polycythemiavera, essential thrombocythemia, myeloidproliferative neoplasms such as idiopathic myelofibrosis (chronic myeloid proliferative diseases), osteomyelodysplasia syndrome, acute lymphocytic leukemia, acute myeloid leukemia, chronic myeloid leukemia, multiple myeloma), solid cancers (e.g. prostatic cancer, breast cancer)), inflammatory diseases (e.g. rheumatoid arthritis, inflammatory bowel disease, osteoporosis, multiple sclerosis), and angiopathy (e.g., pulmonary hypertension, arteriosclerosis, aneurysm, varicose vein).

When the compounds of the invention or pharmaceutically acceptable salts thereof are administered as medicaments, they may be administered as such or as a pharmaceutical compositions containing, for example, 0.001% to 99.5%, preferably 0.1% to 90% of the active ingredient in (a) pharmaceutically acceptable nontoxic and inactive carrier(s) to mammals including humans.

As for the carrier, one or more members of solid, semi-solid, or liquid excipients, fillers, and other auxiliaries for pharmaceutical formulation may be used. The pharmaceutical compositions of the invention may desirably be administered in a unit dosage form. The pharmaceutical composition may be administered through tissue, orally, intravenously, locally (percutaneously, eye drops, etc.) or rectally. The composition may naturally be administered in a dosage form suitable for these administration methods.

The dose as medicament is desirably determined depending on the state of a patient, such as age, weight, the kind and condition of a disease, and administration route, and in general it is appropriate to administer in the range of 0.1 mg-5 g/day, preferably 1 mg-500 mg/day for an adult as the compound of the invention or a pharmaceutically acceptable salt thereof as an active ingredient in oral administration. In some cases, the dose may be lower than the above range or if required, may be higher. In general, it may be administered in a single or divided doses or intravenously continuously over 1 to 24 hours.

EXAMPLE

The present invention will now be described in more detail by way of Reference Examples, Examples, Test Examples and Formulation Examples of the compound of the present invention, to which, however, the present invention is not limited.

Reference Example 1

(S)-4,6-Dichloro-N-[1-(4-fluorophenyl)ethyl]pyrimidin-2-amine 2.4 g of 2,4,6-trichloropyrimidine was dissolved in 24 ml of tetrahydrofuran, and 2.0 ml of triethylamine was added at room temperature, and a solution of 2.0 g of (S)-(−)-1-(4- fluorophenyl)ethylamine in 12 mL of tetrahydrofuran was added dropwise, and then the mixture was stirred at room temperature for 9.5 hours. The reaction mixture was filtrated to remove precipitates, and then the filtrate was concentrated under reduced pressure. The residue was purified with silica gel column chromatography to obtain 1.77 g of the objective compound.

MS (ESI) m/z 286 (M+H)$^+$

Reference Example 2

(S)-4-Chloro-N$^2$-[1-(4-fluorophenyl)ethyl]-N$^6$-(pyrazin-2-yl)pyridine-2,6-diamine Step 1.
(S)-4,6-Dichloro-N-[1-(4-fluorophenyl)ethyl]pyridin-2-amine 7.2 g of 2,4,6-trichloropyridine and 2.74 g of (S)-(−)-1-(4-fluorophenyl)ethylamine were dissolved in 25 ml of 1-butanol, and 13.7 ml of N,N-diisopropylethylamine was added thereto, and the mixture was stirred at 120° C. for 42 hours. The reaction solution was air-cooled to room temperature, and then diluted with ethyl acetate. The solution was washed with water and then dried over magnesium sulfate. The solvent was distilled off under reduced pressure, and then the obtained residue was purified by silica gel column chromatography to obtain 2.57 g of the objective compound as yellow oil.

MS (ESI) m/z 285 (M+H)$^+$

Step 2.
(S)-4-Chloro-N$^2$-[1-(4-fluorophenyl)ethyl]-N$^6$-(pyrazin-2-yl)pyridine-2,6-diamine To 734 mg of (S)-4,6-dichloro-N-[1-(4-fluorophenyl)ethyl]pyridine-2-amine, 343 mg of 2-aminopyrazine, 1.39 g of tripotassium phosphate, 190 mg of 4,5-bis(diphenylphosphino)-9,9'-dimethylxanthene and 170 mg of tris(dibenzylideneacetone)(chloroform)dipalladium was added 17 ml of 1,4-dioxane, the mixture was subjected to degassing and was substituted with argon, and was stirred at 100° C. for 19 hours. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 654 mg of the objective compound as brown powder.

MS (ESI) m/z 344 (M+H)$^+$

Example 1

(S)-4-{2-[1-(4-Fluorophenyl)ethylamino]-6-(pyrazin-2-ylamino) pyrimidin-4-yl}piperazin-2-one Step 1.
(S)-4-{6-Chloro-2-[1-(4-fluorophenyl)ethylamino]pyrimidin-4-yl}piperazin-2-one To a solution of 150 mg of (S)-4,6-dichloro-N-[1-(4-fluorophenyl)ethyl]pyrimidine-2-amine and 58 mg of piperazin-2-one in 1.5 ml of 1-butanol was added 183 μl of N,N-diisopropylethylamine, and the mixture was stirred at 60° C. for 20 hours. The reaction solution was air-cooled to room temperature, and then diluted with ethyl acetate. The solution was washed in turn with water and brine and then dried over magnesium sulfate. The solvent was distilled off under reduced pressure to obtain 196 mg of the objective compound as white powder.

MS (ESI) m/z 355 (M+H)$^+$

Step 2.
(S)-4-{2-[1-(4-Fluorophenyl)ethylamino]-6-(pyrazin-2-ylamino)pyrimidin-4-yl}piperazin-2-one 196 mg of (S)-4-{6-chloro-2-[1-(4-fluorophenyl)ethylamino]pyrimidin-4-yl}piperazin-2-one, 55 mg of 2-aminopyrazine, 50 mg of 2-dicyclohexylphosphino-2',4',6'-triisopropylbiphenyl, 101 mg of sodium t-butoxide and 27 mg of tris(dibenzylideneacetone)(chloroform)dipalladium were added in turn to 6 ml of degassed toluene, and the mixture was stirred at 100° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 196 mg of the objective compound as pale brown powder.

MS (ESI) m/z 409 (M+H)$^+$

Example 2

N-{(S)-1-[2-{[(S)-1-(4-Fluorophenyl)ethyl]amino-}-6-(pyrazin-2-ylamino)pyrimidin-4-yl]pyrrolidin-3-yl}acetamide hydrochloride N-{(S)-1-[2-{[(S)-1-(4-Fluorophenyl)ethyl]amino}-6-(pyrazin-2-ylamino)pyrimidin-4-yl]pyrrolidin-3-yl}acetamide was obtained by the same process as in Example 1 using (S)—N-(pyrrolidin-3-yl)acetamide instead of piperazin-2-one. The obtained compound was dissolved in methanol, and an equivalent of 1N hydrochloric acid was added thereto, and then the solvent was removed to obtain the objective compound as white powder.

MS (ESI) m/z 437 (M+H)$^+$

Example 3

(S)-6-(3,3-Difluoroazetidin-1-yl)-N$^2$-[1-(4-fluorophenyl)ethyl]-N$^4$-(pyrazin-2-yl)pyrimidine-2,4-diamine hydrochloride (S)-6-(3,3-Difluoroazetidin-1-yl)-N$^2$-[1-(4-fluorophenyl)ethyl]-N$^4$-(pyrazin-2-yl)pyrimidine-2,4-diamine was obtained by the same process as in Example 1 using 3,3-difluoroazetidine hydrochloride instead of piperazin-2-one. The obtained compound was dissolved in methanol, and an equivalent of 1N hydrochloric acid was added thereto, and then the solvent was removed to obtain the objective compound as white powder.

MS (ESI) m/z 402 (M+H)$^+$

Example 4

(S)—N$^2$-[1-(4-Fluorophenyl)ethyl]-4-(1-methyl-1H-pyrazol-4-yl)-N$^6$-(pyrazin-2-yl)pyridine-2,6-diamine hydrochloride Step 1.
2,6-Dichloro-4-(1-methyl-1H-pyrazol-4-yl)pyridine 500 mg of 2,6-dichloro-4-iodopyridine, 379 mg of 1-methyl-4-(4,4,5,5-tetramethyl-1,3,2-dioxaborolan-2-yl)-1H-pyrazole, 753 mg of potassium carbonate and 74 mg of 1,1'-bis(diphenylphosphino)ferrocene-palladium(II)dichloride-dichloromethane complex were added in turn to a degassed mixed solvent of 7.5 ml of 1,4-dioxane and 2.5 ml of water, and the mixture was stirred at 90° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 257 mg of the objective compound.

MS (ESI) m/z 228 (M+H)$^+$

Step 2.

(S)-6-Chloro-N-[1-(4-fluorophenyl)ethyl]-4-(1-methyl-1H-pyrazol-4-yl)pyridine-2-amine 257 mg of 2,6-dichloro-4-(1-methyl-1H-pyrazol-4-yl)pyridine obtained by Step 1, 164 mg of (S)-(−)-1-(4-fluorophenyl)ethylamine, 66 mg of 2-(di-t-butylphosphino)biphenyl, 271 mg of sodium t-butoxide and 25 mg of palladium acetate were added in turn to 6 ml of degassed toluene, and the mixture was stirred at 85° C. for 2 hours under argon atmosphere. The reaction solution was purified by silica gel column chromatography to obtain 240 mg of the objective compound as pale yellow powder.

MS (ESI) m/z 331 (M+H)$^+$

Step 3.

(S)—N$^2$-[1-(4-Fluorophenyl)ethyl]-4-(1-methyl-1H-pyrazol-4-yl)-N$^6$-(pyrazin-2-yl)pyridine-2,6-diamine hydrochloride 235 mg of (S)-6-chloro-N-[1-(4-fluorophenyl)ethyl]-4-(1-methyl-1H-pyrazol-4-yl)pyridine-2-amine, 74 mg of 2-aminopyrazine, 68 mg of 2-dicyclohexylphosphino-2',4',6'-triisopropylbiphenyl, 95 mg of sodium t-butoxide and 37 mg of tris(dibenzylideneacetone)(chloroform)dipalladium were added in turn to 6 ml of degassed toluene, and the mixture was stirred at 100° C. for 1.5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 204 mg of (S)—N$^2$-[1-(4-fluorophenyl)ethyl]-4-(1-methyl-1H-pyrazol-4-yl)-N$^6$-(pyrazin-2-yl)pyridine-2,6-diamine as pale yellow powder. The obtained compound was dissolved in ethanol, and an equivalent of 1N hydrochloric acid was added thereto, and then the solvent was removed to obtain the objective compound as pale yellow powder.

MS (ESI) m/z 390 (M+H)$^+$

Example 5

(S)—N$^{2'}$-[1-(4-Fluorophenyl)ethyl]-N$^{6'}$-(pyrazin-2-yl)-3,4'-bipyridine-2',6'-diamine hydrochloride (S)—N$^{2'}$-[1-(4-Fluorophenyl)ethyl]-N$^{6'}$-(pyrazin-2-yl)-3,4'-bipyridine-2',6'-diamine was obtained by the same process as in Example 4 using 3-(1,3,2-dioxaborinan-2-yl)pyridine instead of 1-methyl-4-(4,4,5,5-tetramethyl-1,3,2-dioxaborolan-2-yl)-1H-pyrazole. The obtained compound was dissolved in ethanol, and an equivalent of 1N hydrochloric acid was added thereto, and then the solvent was removed to obtain the objective compound as yellow powder.

MS (ESI) m/z 387 (M+H)$^+$

Example 6

(S)—N$^{2'}$-[1-(4-Fluorophenyl)ethyl]-6-methoxy-N$^{6'}$-(pyrazin-2-yl)-3,4'-bipyridine-2',6'-diamine The objective compound was obtained as pale yellow powder by the same process as in Example 4 using 2-methoxy-5-pyridine boronic acid instead of 1-methyl-4-(4,4,5,5-tetramethyl-1,3,2-dioxaborolan-2-yl)-1H-pyrazole.

MS (ESI) m/z 417 (M+H)$^+$

Example 7

(S)-2'-[1-(4-Fluorophenyl)ethylamino]-6'-(pyrazin-2-ylamino)-3,4'-bipyridin-6-ol hydrochloride 108 mg of (S)—N$^{2'}$-[1-(4-fluorophenyl)ethyl]-6-methoxy-N$^{6'}$-(pyrazin-2-yl)-3,4'-bipyridine-2',6'-diamine was dissolved in 3 ml of acetonitrile, 116 mg of sodium iodide and 99 μl of trimethylsilyl chloride were added, and the mixture was stirred at 70° C. for 3.5 hours under argon atmosphere. The reaction solution was diluted with ethyl acetate and water, and the pH of the mixture was adjusted to 9 by using saturated sodium bicarbonate aqueous solution. The organic layer was washed with brine, and then dried over magnesium sulfate. The solvent was distilled off under reduced pressure, and the obtained residue was purified by silica gel column chromatography to obtain 78 mg of (S)-2'-[1-(4-fluorophenyl)ethylamino]-6'-(pyrazin-2-ylamino)-3,4'-bipyridin-6-ol as pale yellow powder. The obtained compound was dissolved in methanol, and an equivalent of 1N hydrochloric acid was added thereto, and then the solvent was removed to obtain the objective compound as pale yellow powder.

MS (ESI) m/z 403 (M+H)$^+$

Example 8

(S)—N$^2$-[1-(4-Fluorophenyl)ethyl]-4-(oxazol-5-yl)-N$^6$-(pyrazin-2-yl)pyridine-2,6-diamine Step 1.

5-(2,6-Dichloropyridin-4-yl)oxazole 528 mg of 2,6-dichloroisonicotinaldehyde (this compound was prepared by the method described in J. Chem. Soc., Chem. Commun., 1998, 1567-1568) was dissolved in 10 ml of methanol, and 586 mg of p-toluenesulfonyl methyl isocyanide and 415 mg of potassium carbonate ware added, and the mixture was stirred at 50° C. for 30 minutes. The reaction solution was concentrated, and then diluted with ethyl acetate, and the organic layer was washed with a saturated aqueous solution of sodium bicarbonate and brine, and then dried over magnesium sulfate. The solvent was distilled off under reduced pressure to obtain 630 mg of the objective compound as white powder.

MS (ESI) m/z 215 (M+H)$^+$

Step 2.

(S)—N$^2$-[1-(4-Fluorophenyl)ethyl]-4-(oxazol-5-yl)-N$^6$-(pyrazin-2-yl)pyridine-2,6-diamine 630 mg of 5-(2,6-dichloropyridin-4-yl) oxazole obtained by Step 1, 408 mg of (S)-(−)-1-(4-fluorophenyl)ethylamine, 182 mg of 2,2'-bis(diphenylphosphino)-1,1'-binaphthyl, 1.9 g of cesium carbonate and 66 mg of palladium acetate were added in turn to 30 ml of degassed toluene, and the mixture was stirred at 100° C. for 1.5 hours under argon atmosphere. The reaction solution was purified by silica gel column chromatography to obtain 600 mg of (S)-6-chloro-N-[1-(4-fluorophenyl)ethyl]-4-(oxazol-5-yl)pyridine-2-amine as pale yellow powder. 10 ml of degassed toluene was added to the obtained powder, and 180 mg of 2-aminopyrazine, 180 mg of 2-dicyclohexylphosphino-2',4',6'-triisopropyl biphenyl, 254 mg of sodium t-butoxide and 98 mg of tris(dibenzylideneacetone)dipalladium were added in turn, and the mixture was stirred at 100° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 390 mg of the objective compound as pale yellow powder.

MS (ESI) m/z 377 (M+H)$^+$

Example 9

(S)-6-Chloro-$N^2$-[1-(4-fluorophenyl)ethyl]-$N^4$-(pyrazin-2-yl)pyrimidine-2,4-diamine To 1.37 g of (S)-4,6-dichloro-N-[1-(4-fluorophenyl)ethyl] pyrimidine-2-amine (Reference Example 1), 460 mg of 2-aminopyrazine, 277 mg of 4,5-bis(diphenylphosphino)-9,9'-dimethylxanthene, 2.04 g of tripotassium phosphate and 248 mg of tris(dibenzylideneacetone)(chloroform)dipalladium, was added 30 ml of 1,4-dioxane, and the mixture was subjected to degassing and was substituted with argon gas, and then was stirred at 100° C. for 2 hours. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 960 mg of the objective compound as pale yellow powder.

MS (ESI) m/z 345 (M+H)$^+$

Example 10

(S)—$N^2$-[1-(4-Fluorophenyl)ethyl]-6-[4-(methylsulfonyl)phenyl]-$N^4$-(pyrazin-2-yl)pyrimidine-2,4-diamine hydrochloride 100 mg of (S)-6-chloro-$N^2$-[1-(4-fluorophenyl)ethyl]-$N^4$-(pyrazin-2-yl)pyrimidine-2,4-diamine, 145 mg of 4-(methylsulfonyl)phenylboronic acid, 123 mg of sodium carbonate and 17 mg of tetrakis(triphenylphosphine)palladium were added in turn to a degassed mixed solvent of 3 ml of 1,4-dioxane and 1.2 ml of water, and the mixture was stirred at 100° C. for 3 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 124 mg of (S)—$N^2$-[1-(4-fluorophenyl)ethyl]-6-[4-(methylsulfonyl)phenyl]-$N^4$-(pyrazin-2-yl)pyrimidine-2,4-diamine as white powder. The obtained compound was dissolved in methanol, and an equivalent of 1N hydrochloric acid was added thereto, and then the solvent was removed to obtain the objective compound as white powder.

MS (ESI) m/z 465 (M+H)$^+$

Example 11

(S)—$N^2$-[1-(4-Fluorophenyl)ethyl]-$N^4$-(pyrazin-2-yl)-6-(1H-pyrazol-4-yl)pyrimidine-2,4-diamine hydrochloride (S)—$N^2$-[1-(4-Fluorophenyl)ethyl]-$N^4$-(pyrazin-2-yl)-6-(1 H-pyrazol-4-yl)pyrimidine-2,4-diamine was obtained by the same process as in Example 10 using t-butyl 4-(4,4,5,5-tetramethyl-1,3,2-dioxaboran-2-yl)-1H-pyrazol-1-carbamate instead of 4-(methylsulfonyl)phenylboronic acid.

Furthermore, the obtained compound was subjected to hydrochlorination using a conventional method to obtain the objective compound as white powder.

MS (ESI) m/z 377 (M+H)$^+$

Example 12

(S)-2-{2-[1-(4-Fluorophenyl)ethylamino]-6-(pyrazin-2-ylamino)pyridin-4-yloxy}ethanol hydrochloride To 150 mg of (S)-4-chloro-$N^2$-[1-(4-fluorophenyl)ethyl]-$N^6$-(pyrazin-2-yl)pyridine-2,6-diamine, 187 mg of tripotassium phosphate, 84 mg of 2-dicyclohexylphosphino-2',4',6'-triisopropylbiphenyl and 46 mg of tris (dibenzylideneacetone)(chloroform)dipalladium were added 3 ml of ethylene glycol and 1.5 ml of 1,4-dioxane, and the mixture was degassed, and substituted by argon gas, and the mixture was stirred at 100° C. for 13 hours. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 62 mg of (S)-2-{2-[1-(4-fluorophenyl)ethylamino]-6-(pyrazin-2-ylamino) pyridin-4-yloxy}ethanol as pale brown powder. Furthermore, the obtained compound was subjected to hydrochlorination using a conventional method to obtain 52 mg of the objective compound as yellow powder.

MS (ESI) m/z 370 (M+H)$^+$

Example 13

(S)—$N^2$-[1-(4-Fluorophenyl)ethyl]-$N^4$-(pyrazin-2-yl)-6-(pyridin-3-yl)pyrimidine-2,4-diamine Step 1.
(S)-4-Chloro-N-[1-(4-fluorophenyl)ethyl]-6-(pyridin-3-yl) pyrimidine-2-amine 500 mg of (S)-4,6-dichloro-N-[1-(4-fluorophenyl)ethyl] pyrimidine-2-amine (Reference Example 1), 314 mg of 3-(1,3,2-dioxaborinan-2-yl)pyridine, 927 mg of sodium carbonate and 202 mg of tetrakis(triphenylphosphine)palladium were added in turn to a degassed mixed solvent of 15 ml of toluene, 7 ml of ethanol and 10 ml of water, and the mixture was stirred at 110° C. for 3 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 218 mg of the objective compound as white powder.
Step 2.
(S)—$N^2$-[1-(4-Fluorophenyl)ethyl]-$N^4$-(pyrazin-2-yl)-6-(pyridin-3-yl)pyrimidine-2,4-diamine To 100 mg of (S)-4-chloro-N-[1-(4-fluorophenyl)ethyl]-6-(pyridin-3-yl)pyrimidine-2-amine, 35 mg of 2-aminopyrazine, 18 mg of 4,5-bis(diphenylphosphino)-9,9'-dimethylxanthene, 129 mg of tripotassium phosphate and 16 mg of tris(dibenzylideneacetone)(chloroform)dipalladium, was added ml of 1,4-dioxane, and the mixture was degassed, and substituted by argon gas, and then was stirred at 100° C. for 1 hour. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 54 mg of the objective compound as white powder.

MS (ESI) m/z 388 (M+H)$^+$
Specific rotation $[\alpha]^D_{20}$=−29.60° (c=0.5, methanol)

Example 14

(S)—N$^2$-[1-(4-Fluorophenyl)ethyl]-N$^4$-(pyrazin-2-yl)-6-(pyridin-2-yl)pyrimidine-2,4-diamine Step 1.
(S)-4-Chloro-N-[1-(4-fluorophenyl)ethyl]-6-(pyridin-2-yl)pyrimidine-2-amine 200 mg of (S)-4,6-dichloro-N-[1-(4-fluorophenyl)ethyl]pyrimidine-2-amine (Reference Example 1), 0.22 ml of 2-(tributylstannyl)pyridine, mg of copper oxide and 81 mg of tetrakis(triphenylphosphine)palladium were added in turn to degassed toluene, and the mixture was stirred at 110° C. for 4 hours under argon atmosphere. The reaction solution was purified by silica gel column chromatography to obtain 63 mg of the objective compound as colorless oil.
Step 2.
(S)—N$^2$-[1-(4-Fluorophenyl)ethyl]-N$^4$-(pyrazin-2-yl)-6-(pyridin-2-yl)pyrimidine-2,4-diamine To 62 mg of (S)-4-chloro-N-[1-(4-fluorophenyl)ethyl]-6-(pyridin-2-yl)pyrimidine-2-amine, 22 mg of 2-aminopyrazine, 22 mg of 4,5-bis(diphenylphosphino)-9,9'-dimethylxanthene, 80 mg of tripotassium phosphate and 20 mg of tris(dibenzylideneacetone)(chloroform)dipalladium, was added 2 ml of 1,4-dioxane, and the mixture was degassed, and substituted by argon gas, and then was stirred at 100° C. for 2 hours. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 25 mg of the objective compound as white powder.

MS (ESI) m/z 388 (M+H)$^+$
Specific rotation $[\alpha]^D_{20}$=−61.20° (c=0.5, methanol)

Example 15

(S)—N$^2$-[1-(4-Fluorophenyl)ethyl]-N$^4$-(pyrazin-2-yl)-6-(pyridin-4-yl)pyrimidine-2,4-diamine The objective compound was obtained as pale yellow powder by the same process as in Example 14 using 4-(tributylstannyl)pyridine instead of 2-(tributylstannyl)pyridine.

MS (ESI) m/z 388 (M+H)$^+$

Example 16

(S)-1-{2-[1-(4-Fluorophenyl)ethylamino]-6-(pyrazin-2-ylamino)pyrimidin-4-yl}pyrrolidin-2-one Step 1.
(S)-1-{6-Chloro-2-[1-(4-fluorophenyl)ethylamino]pyrimidin-4-yl}pyrrolidin-2-one 100 mg of (S)-4,6-dichloro-N-[1-(4-fluorophenyl)ethyl]pyrimidine-2-amine (Reference Example 1), 33 mg of 2-pyrrolidone, 20 mg of 4,5-bis(diphenylphosphino)-9,9'-dimethylxanthene, 149 mg of tripotassium phosphate and 19 mg of tris(dibenzylideneacetone)(chloroform)dipalladium were added in turn to 3 ml of degassed 1,4-dioxane, and the mixture was stirred at 100° C. for 3 hours under argon atmosphere. The reaction solution was filtrated to remove precipitates, and the solvent was distilled off under reduced pressure, and then the obtained residue was purified by silica gel column chromatography to obtain 106 mg of the objective compound as yellow oil.
Step 2.
(S)-1-{2-[1-(4-Fluorophenyl)ethylamino]-6-(pyrazin-2-ylamino)pyrimidin-4-yl}pyrrolidin-2-one 104 mg of (S)-1-{6-chloro-2-[1-(4-fluorophenyl)ethylamino]pyrimidin-4-yl}pyrrolidin-2-one, 33 mg of 2-aminopyrazine, 18 mg of 4,5-bis(diphenylphosphino)-9,9'-dimethylxanthene, 132 mg of tripotassium phosphate and 17 mg of tris(dibenzylideneacetone)(chloroform)dipalladium were added in turn to 3 ml of degassed 1,4-dioxane, and then the mixture was stirred at 100° C. for 11 hours under argon atmosphere. The solvent was distilled off under reduced pressure, and then the obtained residue was purified by silica gel column chromatography to obtain 74 mg of the objective compound as pale brown powder.

MS (ESI) m/z 394 (M+H)$^+$
Specific rotation $[\alpha]^D_{20}$=−19.60° (c=0.5, methanol)

Example 17

(S)-4-{2-[1-(4-Fluorophenyl)ethylamino]-6-(pyrazin-2-ylamino) pyrimidin-4-yl}piperazine-2,6-dione Step 1.
(S)-4-{6-Chloro-2-[1-(4-fluorophenyl)ethylamino]pyrimidin-4-yl}piperazine-2,6-dione 182 mg of (S)-4,6-dichloro-N-[1-(4-fluorophenyl)ethyl]pyrimidine-2-amine (Reference Example 1) and 80 mg of piperazine-2,6-dione were dissolved in 2 ml of tetrahydrofuran and 2 ml of N,N-dimethylformamide, and 122 μl of N,N-diisopropylethylamine was added thereto, and the mixture was stirred at 80° C. for 32 hours. The reaction solution was air-cooled to room temperature, and then diluted with ethyl acetate. The solution was washed with water and then dried over magnesium sulfate. The solvent was distilled off under reduced pressure to obtain 136 mg of the objective compound as white powder.
Step 2.
(S)-4-{2-[1-(4-Fluorophenyl)ethylamino]-6-(pyrazin-2-ylamino) pyrimidin-4-yl}piperazine-2,6-dione 119 mg of (S)-4-{6-chloro-2-[1-(4-fluorophenyl)ethylamino]pyrimidin-4-yl}piperazine-2,6-dione, 34 mg of 2-aminopyrazine, 19 mg of 4,5-bis(diphenylphosphino)-9,9'-dimethylxanthene, 139 mg of tripotassium phosphate and 17 mg of tris(dibenzylideneacetone)(chloroform)dipalladium were added to 2.5 ml of degassed 1,4-dioxane, and then the mixture was stirred at 100° C. for 2 hours under argon atmosphere. The reaction solution was diluted with ethyl acetate. The solution was washed with water, and then dried over magnesium sulfate. The solvent was distilled off under reduced pressure, and then the obtained residue was purified by silica gel column chromatography to obtain 26 mg of the objective compound as pale yellow powder.

MS (ESI) m/z 423 (M+H)$^+$

Example 18

(S)-1-{2-[1-(4-Fluorophenyl)ethylamino]-6-(pyrazin-2-ylamino)pyrimidin-4-yl}tetrahydropyrimidin-2(1H)-one The objective compound was obtained as pale yellow powder by the same process as in Example 16 using tetrahydro-2-pyrimidinone instead of 2-pyrrolidone MS (ESI) m/z 409 (M+H)$^+$

Example 19

(S)—N²-[1-(4-Fluorophenyl)ethyl]-N⁴-(pyrazin-2-yl)-6-(pyrrolidin-1-yl)pyrimidine-2,4-diamine The objective compound was obtained as a pale yellow amorphous solid by the same process as in Example 1 using pyrrolidine instead of piperazin-2-one.

MS (ESI) m/z 380 (M+H)⁺

Example 20

(S)—N²-[1-(4-Fluorophenyl)ethyl]-6-morpholino-N⁴-(pyrazin-2-yl)pyrimidine-2,4-diamine The objective compound was obtained as a pale yellow amorphous solid by the same process as in Example 1 using morpholine instead of piperazin-2-one.

MS (ESI) m/z 396 (M+H)⁺

Specific rotation $[\alpha]^D_{20} = -25.19°$ (c=0.5, methanol)

Example 21

(S)-1-{2-[1-(4-Fluorophenyl)ethylamino]-6-(pyrazin-2-ylamino) pyrimidin-4-yl}imidazolidin-2-one hydrochloride 150 mg of (S)-6-chloro-N²-[1-(4-fluorophenyl)ethyl]-N⁴-(pyrazin-2-yl)pyrimidine-2,4-diamine (Example 9), 224 mg of 2-imidazolidinone, 26 mg of 4,5-bis(diphenylphosphino)-9,9'-dimethylxanthene, 185 mg of tripotassium phosphate and 23 mg of tris(dibenzylideneacetone)(chloroform)dipalladium were added in turn to 5 ml of degassed 1,4-dioxane, and then the mixture was stirred at 100° C. for 2 hours under argon atmosphere. The reaction solution was diluted with ethyl acetate. The solution was washed with water, and then dried over magnesium sulfate. The solvent was distilled off under reduced pressure, and then the obtained residue was purified by silica gel column chromatography to obtain 80 mg of (S)-1-{2-[1-(4-fluorophenyl)ethylamino]-6-(pyrazin-2-ylamino) pyrimidin-4-yl}imidazolidin-2-one as white powder. Furthermore, the obtained compound was subjected to hydrochlorination using a conventional method to obtain 56 mg of the objective compound as pale yellow powder.

MS (ESI) m/z 395 (M+H)⁺

Elemental analysis value (as $C_{19}H_{19}FN_8O \cdot HCl + 0.5H_2O + 0.1C_2H_5OH$)

Calculated value (%) C, 51.88; H, 4.90; N, 25.21

Found value (%) C, 51.71; H, 4.77; N, 24.87

Example 22

(S)—N²-[1-(4-Fluorophenyl)ethyl]-6-(oxazol-5-yl)-N⁴-(pyrazin-2-yl)pyrimidine-2,4-diamine hydrochloride Step 1.
(S)—N²-[1-(4-Fluorophenyl)ethyl]-N⁴-(pyrazin-2-yl)-6-[2-(triisopropylsilyl)oxazol-5-yl]pyrimidine-2,4-diamine 150 mg of (S)-6-chloro-N²-[1-(4-fluorophenyl)ethyl]-N⁴-(pyrazin-2-yl)pyrimidine-2,4-diamine (Example 9), 246 mg of 5-(tributylstannyl)-2-(triisopropylsilyl) oxazole (synthesized according to the method described in WO2007/17096), and 25 mg of tetrakis(triphenylphosphine) palladium were added in turn to 5 ml of degassed dimethylformamide, and then the mixture was stirred at 100° C. for 2.5 hours under argon atmosphere. 246 mg of 5-(tributylstannyl)-2-(triisopropylsilyl) oxazole was added thereto, and the mixture was further stirred for four hours. The reaction solution was diluted with water, and then subjected to extraction with ethyl acetate. The organic layer was washed in turn with water and brine, and then dried over magnesium sulfate. The solvent was distilled off under reduced pressure, and then the obtained residue was purified by silica gel column chromatography to obtain 153 mg of (S)—N²-[1-(4-fluorophenyl)ethyl]-N⁴-(pyrazin-2-yl)-6-[2-(tri isopropylsilyl) oxazol-5-yl]pyrimidine-2,4-diamine as pale orange oil.

Step 2.
(S)—N²-[1-(4-Fluorophenyl)ethyl]-6-(oxazol-5-yl)-N⁴-(pyrazin-2-yl)pyrimidine-2,4-diamine hydrochloride 122 mg of (S)—N²-[1-(4-fluorophenyl)ethyl]-N⁴-(pyrazin-2-yl)-6-[2-(tri isopropylsilyl)oxazol-5-yl]pyrimidine-2,4-diamine was dissolved in 1.2 ml of tetrahydrofuran, and 0.5 ml of 1 M tetrabutylammonium fluoride tetrahydrofuran solution was added. The reaction solution was stirred at room temperature for 20 min, and then diluted with ethyl acetate. The solution was washed in turn with water and brine and then dried over magnesium sulfate. The solvent was distilled off under reduced pressure, and then the obtained residue was purified by silica gel column chromatography to obtain 60 mg of (S)—N²-[1-(4-fluorophenyl)ethyl]-6-(oxazol-5-yl)-N⁴-(pyrazin-2-yl)pyrimidine-2,4-diamine as white powder. The obtained compound was subjected to hydrochlorination using a conventional method to obtain 45 mg of the objective compound as pale orange powder.

MS (ESI) m/z 378 (M+H)⁺

Elemental analysis value (as $C_{19}H_{16}FN_7O \cdot HCl$)

Calculated value (%) C, 55.14; H, 4.14; N, 23.69

Found value (%) C, 54.94; H, 3.92; N, 23.81

Example 23

(S)—N²-[1-(4-Fluorophenyl)ethyl]-6-(6-methoxypyridin-3-yl)-N⁴-(pyrazin-2-yl)pyrimidine-2,4-diamine hydrochloride (S)—N²-[1-(4-Fluorophenyl)ethyl]-6-(6-methoxypyridin-3-yl)-N⁴-(pyrazin-2-yl)pyrimidine-2,4-diamine was obtained by the same process as in Example 10 using 2-methoxy-5-pyridine boronic acid instead of 4-(methylsulfonyl)phenylboronic acid. Furthermore, the obtained compound was subjected to hydrochlorination using a conventional method to obtain the objective compound as pale yellow powder.

MS (ESI) m/z 418 (M+H)⁺

Elemental analysis value (as $C_{22}H_{20}FN_7O \cdot HCl$)

Calculated value (%) C, 58.21; H, 4.66; N, 21.60

Found value (%) C, 57.80; H, 4.48; N, 21.54

Specific rotation $[\alpha]^D_{20} = -24.80°$ (c=0.5, methanol)

Example 24

(S)—N²-[1-(4-Fluorophenyl)ethyl]-N⁴-(pyrazin-2-yl)-6-(1H-pyrazol-3-yl)pyrimidine-2,4-diamine hydrochloride (S)—N²-[1-(4-Fluorophenyl)ethyl]-N⁴-(pyrazin-2-yl)-6-(1H-pyrazol-3-yl)pyrimidine-2,4-diamine was obtained by the same process as in Example 10 using 1H-pyrazol-3-boronic acid instead of 4-(methylsulfonyl)phenylboronic acid.

Furthermore, the obtained compound was subjected to hydrochlorination using a conventional method to obtain the objective compound as pale yellow powder.

MS (ESI) m/z 377 (M+H)+
Elemental analysis value (as $C_{19}H_{17}FN_8$ HCl+0.8$H_2O$)
Calculated value (%) C, 53.41; H, 4.62; N, 26.23
Found value (%) C, 53.21; H, 4.31; N, 26.25
Specific rotation $[\alpha]^D_{20}$=−86.40° (c=0.5, methanol)

Example 25

(S)-4-{2-[1-(4-Fluorophenyl)ethylamino]-6-(pyrazin-2-ylamino) pyrimidin-4-yl}pyridin-2-ol Step 1.
(S)—$N^2$-[1-(4-Fluorophenyl)ethyl]-6-(2-fluoropyridin-4-yl)-$N^4$-(pyrazin-2-yl)pyrimidine-2,4-diamine The objective compound was obtained by the same process as in Example 10 using 2-fluoropyridine-4-boronic acid instead of 4-(methylsulfonyl)phenylboronic acid.

Step 2.
(S)-4-{2-[1-(4-Fluorophenyl)ethylamino]-6-(pyrazin-2-ylamino)pyrimidin-4-yl}pyridin-2-ol 1 ml of 1,2-dimethoxyethane and 10% hydrochloric acid were added to 80 mg of (S)—$N^2$-[1-(4-fluorophenyl)ethyl]-6-(2-fluoropyridin-4-yl)-$N^4$-(pyrazin-2-yl)pyrimidine-2,4-diamine, and the mixture was stirred at 85° C. for 2 hours. 0.5 ml of 10% hydrochloric acid was added thereto, and the mixture was further stirred for 2 hours. The reaction solution was diluted with ethyl acetate and alkalified with a saturated aqueous solution of sodium bicarbonate. The mixture was subjected to extraction, and the obtained organic layer was dried over magnesium sulfate. The solvent was distilled off under reduced pressure, and then the obtained solid was washed with diethyl ether and filtrated, and then dried under reduced pressure to obtain 54 mg of the objective compound as white powder.

MS (ESI) m/z 404 (M+H)

Example 26

(S)-5-{2-[1-(4-Fluorophenyl)ethylamino]-6-(pyrazin-2-ylamino)pyrimidin-4-yl}pyridin-2-ol The objective compound was obtained as pale brown powder by the same process as in Example 7 using (S)—$N^2$-[1-(4-fluorophenyl)ethyl]-6-(6-methoxypyridin-3-yl)-$N^4$-(pyrazin-2-yl)pyrimidine-2,4-diamine (Example 23) instead of (S)-1e-[1-(4-fluorophenyl)ethyl]-6-methoxy-$N^{6'}$-(pyrazin-2-yl)-3,4'-bipyridine-2',6'-diamine.

MS (ESI) m/z 404 (M+H)+
Specific rotation $[\alpha]^D_{20}$=−39.60° (c=0.5, methanol)

Example 27

N—((R)-1-{2-[(S)-1-(4-Fluorophenyl)ethylamino]-6-(pyrazin-2-ylamino)pyrimidin-4-}pyrrolidin-3-yl)acetamide hydrochloride N—((R)-1-{2-[(S)-1-(4-Fluorophenyl)ethylamino]-6-(pyrazin-2-ylamino)pyrimidin-4-yl}pyrrolidin-3-yl)acetamide was obtained as in Example 1 using (R)—N-(pyrrolidin-3-yl)acetamide instead of piperazin-2-one. The obtained compound was subjected to hydrochlorination using a conventional method to obtain the objective compound as white powder.

MS (ESI) m/z 437 (M+H)+
Elemental analysis value (as $C_{22}H_{25}FN_8O$ HCl)
Calculated value (%) C, 55.87; H, 5.54; N, 23.69
Found value (%) C, 55.49; H, 5.21; N, 23.59
Specific rotation $[\alpha]^D_{20}$=113.59° (c=0.5, methanol)

Example 28

(S)—$N^2$-[1-(4-Fluorophenyl)ethyl]-$N^6$-(pyrazin-2-yl)-4-(1H-pyrazol-4-yl)pyridine-2,6-diamine Step 1.
2,6-Dichloro-4-(1H-pyrazol-4-yl)pyridine 188 mg of 2,6-dichloro-4-iodopyridine, 201 mg of t-butyl 4-(4,4,5,5-tetramethyl-1,3,2-dioxaboran-2-yl)-1H-pyrazol-1-carbamate, 284 mg of potassium carbonate and 56 mg of 1,1'-bis(diphenylphosphino)ferrocene-palladium(II)dichloride-dichloromethane complex were added in turn to a degassed mixed solution of 3 ml of 1,4-dioxane and 1 ml of water, and then the mixture was stirred at 90° C. for 5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 90 mg of the objective compound.

Step 2.
2,6-Dichloro-4-(1-{[2-(trimethylsilyl)ethoxy)methyl}-1H-pyrazol-4-yl)pyridine Under argon atmosphere, 90 mg of 2,6-dichloro-4-(1H-pyrazol-4-yl)pyridine was dissolved in 2 ml of tetrahydrofuran, and 20 mg of 60% sodium hydride was added at 0° C., and the mixture was stirred at 0° C. for 15 minutes. Subsequently, 82 µl of (2-chloromethoxy)ethyl trimethylsilane was added to the mixture, and the mixture was allowed to warm to room temperature and stirred for 2 hours. The reaction solution was added with water and was subjected to extraction with ethyl acetate. The organic layer was washed with brine, and then dried over magnesium sulfate. The solvent was distilled off under reduced pressure, and then the obtained residue was purified by silica gel column chromatography to obtain 106 mg of the objective compound.

Step 3.
(S)-6-Chloro-N-[1-(4-fluorophenyl)ethyl]-4-(1-{[2-(trimethyl silyl)ethoxy]methyl}-1H-pyrazol-4-yl)pyridine-2-amine 100 mg of 2,6-dichloro-4-(1-{[2-(trimethylsilyl)ethoxy]methyl}-1H-pyrazol-4-yl)pyridine obtained by Step 2, 44 mg of (S)-(−)-1-(4-fluorophenyl)ethylamine, 17 mg of 2-(di-t-butylphosphino)biphenyl, 70 mg of sodium t-butoxide and 6 mg of palladium acetate were added in turn to 3 ml of degassed toluene, and then the mixture was stirred at 85° C. for 1.5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 70 mg of the objective compound as colorless oil.

Step 4.

(S)—$N^2$-[1-(4-Fluorophenyl)ethyl]-$N^6$-(pyrazin-2-yl)-4-(1-{[2-(trimethylsilyl)ethoxy]methyl}-1H-pyrazol-4-yl)pyridine-2,6-diamine 68 mg of (S)-6-chloro-N-[1-(4-fluorophenyl)ethyl]-4-(1-{[2-(trimethyl silyl)ethoxy]methyl}-1H-pyrazol-4-yl)pyridine-2-amine obtained by Step 3, 17 mg of 2-aminopyrazine, 15 mg of 2-dicyclohexylphosphino-2',4',6'-triisopropylbiphenyl, 21 mg of sodium t-butoxide and 8 mg of tris(dibenzylideneacetone)(chloroform)dipalladium were added in turn, and the mixture was stirred at 100° C. for 1 hour under argon atmosphere. The reaction solution was purified by silica gel column chromatography to obtain 70 mg of the objective compound as colorless oil.

Step 5.
(S)—$N^2$-[1-(4-Fluorophenyl)ethyl]-$N^6$-(pyrazin-2-yl)-4-(1H-pyrazol-4-yl)pyridine-2,6-diamine To 53 mg of (S)—$N^2$-[1-(4-fluorophenyl)ethyl]-$N^6$-(pyrazin-2-yl)-4-(1-{[2-(trimethylsilyl)ethoxy]methyl}-1H-pyrazol-4-yl)pyridine-2,6-diamine obtained by Step 4, was added a mixed solvent of 1 ml of trifluoroacetic acid and 0.1 ml of water, and the mixture was stirred at room temperature for 3 hours. The solvent was distilled off under reduced pressure, and then the obtained residue was diluted with water and alkalified with a saturated aqueous solution of sodium bicarbonate. The reaction solution was subjected to extraction with ethyl acetate, and the organic layer was washed with water and then dried over magnesium sulfate. The solvent was distilled off, and then the obtained residue was purified by silica gel column chromatography to obtain 15 mg of the objective compound as a pale yellow amorphous solid.

MS (ESI) m/z 376 (M+H)$^+$

Specific rotation $[\alpha]^D_{20}$=−103.59° (c=0.5, methanol)

Example 29

(S)—$N^2$-[1-(4-Fluorophenyl)ethyl]-$N^6$-(pyrazin-2-yl)-4-(1H-pyrazol-3-yl)pyridine-2,6-diamine Step 1.
2,6-Dichloro-N-methoxy-N-methylisonicotinamide 586 mg of 2,6-dichloroisonicotinic acid was dissolved in ml of dimethylformamide, and 690 mg of 1-ethyl-3-(3-dimethylaminopropyl)carbodiimide hydrochloride, 490 mg of 1-hydroxybenzotriazole, 440 mg of N,O-dimethylhydroxyamine hydrochloride and 1.67 ml of triethylamine were added, and the mixture was stirred at room temperature for 17 hours. To the reaction solution was added a saturated aqueous solution of sodium bicarbonate, and the mixture was diluted with ethyl acetate. The mixture was washed with brine, and then dried over magnesium sulfate. The solvent was distilled off under reduced pressure, and then the obtained residue was purified by silica gel column chromatography to obtain 500 mg of the objective compound.

Step 2.
1-(2,6-Dichloropyridin-4-yl)ethanone 490 mg of 2,6-dichloro-N-methoxy-N-methyl isonicotinamide was dissolved in tetrahydrofuran, 2.1 ml of 3M methyl magnesium bromide tetrahydrofuran solution was added dropwise at 0° C., and the mixture was stirred at 0° C. for 1 hour. To the reaction solution was added ammonium chloride aqueous solution, and the mixture was diluted with ethyl acetate. The mixture was washed with brine, and then dried over magnesium sulfate. The solvent was distilled off under reduced pressure to obtain 325 mg of the objective compound.

Step 3.
2,6-Dichloro-4-(1H-pyrazol-3-yl)pyridine 5 ml of N,N-dimethylformamide diethyl acetal was added to 325 mg of 1-(2,6-dichloropyridin-4-yl)ethanone, and the mixture was heated at reflux for 30 minutes. N,N-Dimethylformamide diethyl acetal was distilled off under reduced pressure, and to the obtained residue, 5 ml of ethanol and 91 μl of hydrazine monohydrate were added, and the mixture was heated at reflux for 1 hour. The solvent was distilled off under reduced pressure, and then the obtained residue was purified by silica gel column chromatography to obtain 320 mg of the objective compound.

Step 4.
2,6-Dichloro-4-(1-{[2-(trimethylsilyl)ethoxy)methyl}-1H-pyrazol-3-yl)pyridine Under argon atmosphere, 250 mg of 2,6-dichloro-4-(1H-pyrazol-3-yl)pyridine was dissolved in 6 ml of tetrahydrofuran, and 56 mg of 60% sodium hydride was added by small portions at 0° C., and the mixture was stirred at 0° C. for 30 minutes. Subsequently, 0.25 ml of (2-chloromethoxy)ethyl trimethylsilane was added to the mixture, and the mixture was allowed to warm to room temperature and stirred for 2 hours. The reaction solution was added with water. The solution was subjected to extraction with ethyl acetate. The organic layer was washed with brine and then dried over magnesium sulfate. The solvent was distilled off under reduced pressure to obtain 440 mg of the objective compound.

Step 5.
(S)-6-Chloro-N-[1-(4-fluorophenyl)ethyl]-6-(1-{[2-(trimethyl silyl)ethoxy]methyl}-1H-pyrazol-3-yl)pyridine-2-amine 100 mg of 2,6-dichloro-4-(1-{[2-(trimethylsilyl)ethoxy]methyl}-1H-pyrazol-3-yl)pyridine obtained by Step 4, 45 mg of (S)-(−)-1-(4-fluorophenyl)ethylamine, 17 mg of 2-(di-t-butylphosphino)biphenyl, 70 mg of sodium t-butoxide and 7 mg of palladium acetate were added in turn to 3 ml of degassed toluene, and then the mixture was stirred at 85° C. for 1 hour under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 130 mg of the objective compound as brown oil.

Step 6.
(S)—$N^2$-[1-(4-Fluorophenyl)ethyl]-$N^6$-(pyrazin-2-yl)-4-(1-{[2-(trimethylsilyl)ethoxy]methyl}-1H-pyrazol-3-yl)pyridine-2,6-diamine 130 mg of (S)-6-chloro-N-[1-(4-fluorophenyl)ethyl]-6-(1-{[2-(trimethyl silyl)ethoxy]methyl}-1H-pyrazol-3-yl)pyridine-2-amine obtained by Step 5, 35 mg of 2-aminopyrazine, 30 mg of 2-dicyclohexylphosphino-2',4',6'-triisopropylbiphenyl, 42 mg of sodium t-butoxide and 18 mg of tris(dibenzylideneacetone)(chloroform)dipalladium were added in turn, and the mixture was stirred at 100° C. for 1 hour under argon atmosphere. The reaction solution was purified by silica gel column chromatography to obtain 95 mg of the objective compound as brown oil.

Step 7.
(S)—$N^2$-[1-(4-Fluorophenyl)ethyl]-$N^6$-(pyrazin-2-yl)-4-(1H-pyrazol-3-yl)pyridine-2,6-diamine A mixed solvent of 3 ml of trifluoroacetic acid and 0.3 ml of water was added to 95 mg of (S)—$N^2$-[1-(4-fluorophenyl)ethyl]-$N^6$-(pyrazin-2-yl)-4-(1-{[2-(trimethylsilyl)ethoxy]methyl}-1H-pyrazol-3-yl)pyridine-2,6-diamine obtained by Step 6, and the mixture was stirred at 60° C. for 1 hour. The solvent was distilled off under reduced pressure, and then the obtained residue was diluted with water and alkalified with a saturated aqueous solution of sodium bicarbonate. The reaction solution was subjected to extraction with ethyl acetate, and the organic layer was washed with water and then dried over magnesium sulfate. The solvent was distilled off under reduced pressure to obtain 20 mg of the objective compound as pale yellow powder.

MS (ESI) m/z 376 (M+H)$^+$

Example 30

(S)—$N^2$-[1-(4-Fluorophenyl)ethyl]-4-(1-methyl-1H-pyrazol-4-yl)-$N^6$-(pyrazin-2-yl)pyridine-2,6-diamine maleate 1.34 g of (S)-6-chloro-N-[1-(4-fluorophenyl)ethyl]-4-(1-methyl-1H-pyrazol-4-yl)pyridine-2-amine synthesized by the same method as in Steps 1 and 2 of Example 4, 423 mg of 2-aminopyrazine, 154 mg of 2-dicyclohexylphosphino-2',4',6'-triisopropylbiphenyl, 544 mg of sodium t-butoxide and 74 mg of tris(dibenzylideneacetone)dipalladium were added in turn to 13 ml of degassed toluene, and the mixture was stirred at 100° C. for 1 hour under argon atmosphere. The reaction solution was diluted with ethyl acetate. The solution was washed with water and then dried over magnesium sulfate. The solvent was distilled off under reduced pressure, and the obtained residue was purified by silica gel column chromatography to obtain 1.26 g of (S)—$N^2$-[1-(4-fluorophenyl)ethyl]-4-(1-methyl-1H-pyrazol-4-yl)-$N^6$-(pyrazin-2-yl)pyridine-2,6-diamine as pale yellow powder. Subsequently, 1.0 g of the obtained (S)—$N^2$-[1-(4-fluorophenyl)ethyl]-4-(1-methyl-1H-pyrazol-4-yl)-$N^6$-(pyrazin-2-yl)pyridine-2,6-diamine was dissolved in 1 ml of methanol, and 300 mg of maleic acid was added. The reaction solution was added with 6 ml of ethyl acetate, and stirred at room temperature for 2 hours. The precipitated solid was filtered to obtain 1.1 g of the objective compound as white powder.

MS (ESI) m/z 390 (M+H)$^+$
Elemental analysis value (as $C_{25}H_{24}FN_7O_4$)
Calculated value (%) C, 59.40; H, 4.79; N, 19.40
Found value (%) C, 59.19; H, 4.58; N, 19.36
Specific rotation $[\alpha]^D_{20}$=68.40° (c=0.5, methanol)

Example 31

(S)—$N^2$-[1-(4-Fluorophenyl)ethyl]-6-morpholino-$N^4$-(pyrazin-2-yl)pyrimidine-2,4-diamine maleate (S)—$N^2$-[1-(4-Fluorophenyl)ethyl]-6-morpholino-$N^4$-(pyrazin-2-yl)pyrimidine-2,4-diamine synthesized in Example 20 was converted to maleate by the same method as in Example 30.

MS (ESI) m/z 396 (M+H)$^+$
Elemental analysis value (as $C_{24}H_{26}FN_7O_5$)
Calculated value (%) C, 56.35; H, 5.12; N, 19.17
Found value (%) C, 56.42; H, 5.07; N, 19.41
Specific rotation $[\alpha]^D_{20}$=81.20° (c=0.5, methanol)

Example 32

(S)—$N^2$-[1-(4-Fluorophenyl)ethyl]-$N^4$-(pyrazin-2-yl)-6-(pyridin-3-yl)pyrimidine-2,4-diamine ½ maleate (S)—$N^2$-([1-(4-Fluorophenyl)ethyl]-$N^4$-(pyrazin-2-yl)-6-(pyridin-3-yl)pyrimidine-2,4-diamine synthesized in Example 13 was converted to maleate by the same method as in Example 30.

MS (ESI) m/z 388 (M+H)$^+$
Elemental analysis value (as $C_{23}H_{20}FN_7O_2$)
Calculated value (%) C, 62.02; H, 4.53; N, 22.01
Found value (%) C, 61.79; H, 4.50; N, 22.14
Specific rotation $[\alpha]^D_{20}$=−42.00° (c=0.5, methanol)

Example 33

N-{(S)-1-[2-{[(S)-1-(4-Fluorophenyl)ethyl]amino}-6-(pyrazin-2-ylamino)pyrimidin-4-yl]pyrrolidin-3-yl}acetamide maleate N-{(S)-1-[2-{[(S)-1-(4-Fluorophenyl)ethyl]amino}-6-(pyrazin-2-ylamino)pyrimidin-4-yl]pyrrolidin-3-yl}acetamide synthesized in Example 2 was converted to maleate by the same method as in Example 30.

MS (ESI) m/z 437 (M+H)$^+$
Elemental analysis value (as $C_{26}H_{29}FN_8O_5$)
Calculated value (%) C, 56.52; H, 5.29; N, 20.28
Found value (%) C, 56.49; H, 5.24; N, 20.45
Specific rotation $[\alpha]^D_{20}$=26.39° (c=0.5, methanol)

Example 34

(S)—$N^2$-[1-(4-Fluorophenyl)ethyl]-$N^4$-(pyrazin-2-yl)-6-(1H-pyrazol-4-yl)pyrimidine-2,4-diamine maleate (S)—$N^2$-([1-(4-Fluorophenyl)ethyl]-$N^4$-(pyrazin-2-yl)-6-(1H-pyrazol-4-yl)pyrimidine-2,4-diamine synthesized in Example 11 was converted to maleate by the same method as in Example 30.

MS (ESI) m/z 377 (M+H)$^+$
Elemental analysis value (as $C_{23}H_{21}FN_8O_4+0.2H_2O$)
Calculated value (%) C, 55.69; H, 4.35; N, 22.59
Found value (%) C, 55.32; H, 4.33; N, 22.61
Specific rotation $[\alpha]^D_{20}$=−51.60° (c=0.5, methanol)

Example 35

(S)—$N^2$-[1-(4-Fluorophenyl)ethyl]-6-[3-(methylsulfonyl)phenyl]-$N^4$-(pyrazin-2-yl) yrimidine-2,4-diamine hydrochloride (S)—$N^2$-[1-(4-Fluorophenyl)ethyl]-6-[3-(methylsulfonyl)phenyl]-$N^4$-(pyrazin-2-yl)pyrimidine-2,4-diamine was obtained by the same process as in Example 10 using 3-(methylsulfonyl)phenylboronic acid instead of 4-(methylsulfonyl)phenylboronic acid. Furthermore, the obtained compound was subjected to hydrochlorination using a conventional method to obtain the objective compound as white powder.

MS (ESI) m/z 465 (M+H)$^+$
Elemental analysis value (as $C_{23}H_{21}FN_6O_2S$ HCl+0.5$H_2O$)
Calculated value (%) C, 54.17; H, 4.55; N, 16.48
Found value (%) C, 54.04; H, 4.35; N, 16.10
Specific rotation $[\alpha]^D_{20}$=−12.40° (c=0.5, methanol)

Example 36

(S)—$N^2$-[1-(4-Fluorophenyl)ethyl]-4-[4-(methylsulfonyl)phenyl]-$N^6$-(pyrazin-2-yl)pyridine-2,6-diamine hydrochloride (S)—$N^2$-[1-(4-Fluorophenyl)ethyl]-4-[4-(methylsulfonyl)phenyl]-$N^6$-(pyrazin-2-yl)pyridine-2,6-diamine was obtained by the same process as in Example 4 using 4-(methylsulfonyl)phenylboronic acid instead of 1-methyl-4-(4,4,5,5-tetramethyl-1,3,2-dioxaboran-2-yl)-1H-pyrazole. The obtained compound was subjected to hydrochlorination using a conventional method to obtain the objective compound as yellow powder.

MS (ESI) m/z 464 (M+H)$^+$

Elemental analysis value (as $C_{24}H_{22}FN_5O_2S$ HCl+ 0.2H$_2$O)

Calculated value (%) C, 57.24; H, 4.68; N, 13.91
Found value (%) C, 56.97; H, 4.35; N, 13.71
Specific rotation $[\alpha]^D_{20}$=74.00° (c=0.5, methanol)

Example 37

(S)—N$^2$-[1-(4-Fluorophenyl)ethyl]-4-(1-isopropyl-1H-pyrazol-4-yl)-N$^6$-(pyrazin-2-yl)pyridine-2,6-diamine hydrochloride Step 1.
4-Iodo-1-isopropyl-1H-pyrazole Under argon atmosphere, 96 mg of 60% sodium hydride was suspended in 6 ml of N,N-dimethylformamide, and 388 mg of 4-iodo-1H-pyrazol was added at 0° C., and the mixture was stirred at 0° C. for 30 minutes. Subsequently, 0.21 ml of 2-bromopropane was added and the reaction mixture was stirred at 100° C. for 2 hours. The reaction solution was added with water. The solution was subjected to extraction with ethyl acetate. The organic layer was washed with brine and then dried over magnesium sulfate. The solvent was distilled off under reduced pressure, and then the obtained residue was purified by silica gel column chromatography to obtain 328 mg of the objective compound.

Step 2.
2,6-Dichloro-4-(1-isopropyl-1H-pyrazol-4-yl)pyridine 251 mg of 2,6-dichloro-4-(4,4,5,5-tetramethyl-1,3,2-dioxaboran-2-yl)pyridine (synthesized by a method described in J. Am. Chem. Soc., 2003, 125, 7792-7793), 325 mg of 4-iodo-1-isopropyl-1H-pyrazole, 381 mg of potassium carbonate and 22 mg of 1,1'-bis(diphenylphosphino)ferrocene-palladium(II)dichloride-dichloromethane complex were added in turn to a degassed mixed solvent of 6 ml of 1,4-dioxane and 2 ml of water, and the mixture was stirred at 90° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 145 mg of the objective compound.

Step 3.
(S)-6-Chloro-N-[1-(4-fluorophenyl)ethyl]-4-(1-isopropyl-1H-pyrazol-4-yl)pyridine-2-amine 145 mg of 2,6-dichloro-4-(1-isopropyl-1H-pyrazol-4-yl)pyridine obtained by Step 2, 87 mg of (S)-(−)-1-(4-fluorophenyl)ethylamine, 34 mg of 2-(di-t-butylphosphino)biphenyl, 109 mg of sodium t-butoxide and 13 mg of palladium acetate were added in turn to 6 ml of degassed toluene, and then the mixture was stirred at 85° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 59 mg of the objective compound as pale yellow powder.

Step 4.
(S)—N$^2$-[1-(4-Fluorophenyl)ethyl]-4-(1-isopropyl-1H-pyrazol-4-yl)-N$^6$-(pyrazin-2-yl)pyridine-2,6-diamine hydrochloride 59 mg of (S)-6-chloro-N-[1-(4-fluorophenyl)ethyl]-4-(1-isopropyl-1H-pyrazol-4-yl)pyridine-2-amine, 19 mg of 2-aminopyrazine, 16 mg of 2-dicyclohexylphosphino-2',4',6'-triisopropylbiphenyl, 22 mg of sodium t-butoxide and 9 mg of tris(dibenzylideneacetone)(chloroform)dipalladium were added in turn to 5 ml of degassed toluene, and the mixture was stirred at 85° C. for 1.5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 40 mg of (S)—N$^2$-[1-(4-fluorophenyl)ethyl]-4-(1-isopropyl-1H-pyrazol-4-yl)-N$^6$-(pyrazin-2-yl)pyridine-2,6-diamine as pale yellow powder. The obtained compound was subjected to hydrochlorination using a conventional method to obtain 30 mg of the objective compound as brown powder.

MS (ESI) m/z 418 (M+H)$^+$
Specific rotation $[\alpha]^D_{20}$=76.40° (c=0.5, methanol)

Example 38

N-{(S)-1-[2-{[(S)-1-(4-Fluorophenyl)ethyl]amino}-6-(pyrazin-2-ylamino)pyridin-4-yl]pyrrolidin-3-yl}acetamide hydrochloride 100 mg of (S)-4-chloro-N$^2$-[1-(4-fluorophenyl)ethyl]-N$^6$-(pyrazin-2-yl)pyridine-2,6-diamine (Reference Example 2), 112 mg of (S)—N-(pyrrolidin-3-yl)acetamide, 69 mg of 2-dicyclohexylphosphino-2',4',6'-triisopropylbiphenyl, 92 mg of sodium t-butoxide and 30 mg of tris(dibenzylideneacetone)(chloroform)dipalladium were added in turn to 6 ml of degassed toluene, and the mixture was stirred at 100° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 115 mg of N-{(S)-1-[2-{[(S)-1-(4-fluorophenyl)ethyl]amino}-6-(pyrazin-2-ylamino)pyridin-4-yl]pyrrolidin-3-yl}acetamide as pale brown powder. The obtained compound was subjected to hydrochlorination using a conventional method to obtain 67 mg of the objective compound as brown powder.

MS (ESI) m/z 436 (M+H)$^+$
Specific rotation $[\alpha]^D_{20}$=63.20° (c=0.5, methanol)

Example 39

(S)—N$^2$-[1-(4-Fluorophenyl)ethyl]-4-morpholine-N$^6$-(pyrazin-2-yl)pyridine-2,6-diamine The objective compound was obtained as brown powder by the same process as in Example 38 using morpholine instead of (S)—N-(pyrrolidin-3-yl)acetamide.

MS (ESI) m/z 395 (M+H)$^+$
Specific rotation $[\alpha]^D_{20}$=−38.80° (c=0.5, methanol)

Example 40

(S)—N$^2$-[1-(4-Fluorophenyl)ethyl]-N$^6$-(pyrazin-2-yl)-4-thiomorpholinopyridine-2,6-diamine The objective compound was obtained as brown powder by the same process as in Example 38 using thiomorpholine instead of (S)—N-(pyrrolidin-3-yl)acetamide.

MS (ESI) m/z 411 (M+H)$^+$

Example 41

(S)-3-{2-[1-(4-Fluorophenyl)ethylamino]-6-(pyrazin-2-ylamino)pyridin-4-yl}propan-1-ol hydrochloride The objective compound was obtained as yellow powder by the same process as in Example 12 using 1,3-propanediol instead of ethylene glycol.

MS (ESI) m/z 384 (M+H)$^+$

Example 42

(S)—N-(1-{2-[1-(4-Fluorophenyl)ethylamino]-6-(pyrazin-2-ylamino)pyrimidin-4-yl}azetidin-3-yl)acetamide 100 mg of t-butyl azetidin-3-ylcarbamate was dissolved in ml of methylene chloride, and 225 mg of N,N-diisopropylethylamine was added. Under ice-cooling, the reaction mixture was added with 68 mg of acetyl chloride, and stirred at room temperature for 2 days. The reaction solution was diluted with ethyl acetate, and the organic layer was washed with 5% citric acid aqueous solution and brine in turn, and dried over magnesium sulfate. The solvent was distilled off under reduced pressure to obtain 146 mg of a brown oily matter. The obtained residue was dissolved in 2.5 ml of methylene chloride, and 1 ml of trifluoroacetic acid was added thereto, and the mixture was stirred at room temperature overnight. The solvent was distilled off under reduced pressure, and then 66 mg of N-(azetidin-3-yl)acetamide trifluoroacetate was obtained. Subsequently, 33 mg of N-(azetidin-3-yl)acetamide trifluoroacetate, 148 mg of triethylamine, 100 mg of (S)-6-chloro-N$^2$-[1-(4-fluorophenyl)ethyl]-N$^4$-(pyrazin-2-yl)pyrimidine-2,4-diamine, 28 mg of 2-dicyclohexylphosphino-2',4',6'-triisopropylbiphenyl, 56 mg of sodium t-butoxide and 30 mg of tris(dibenzylideneacetone)(chloroform)dipalladium were added in turn to 3 ml of degassed 1,4-dioxane, and the mixture was stirred at 90° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 17 mg of the objective compound as bright golden yellow powder.

MS (ESI) m/z 423 (M+H)$^+$

Example 43

(S)-6-(Azetidin-1-yl)-N$^2$-[1-(4-fluorophenyl)ethyl]-N$^4$-(pyrazin-2-yl)pyrimidine-2,4-diamine The objective compound was obtained as a white amorphous solid by the same process as in Example 1 using azetidine hydrochloride instead of piperazin-2-one.

MS (ESI) m/z 366 (M+H)$^+$

Example 44

(S)-6-(3-Fluoroazetidin-1-yl)-N$^2$-[1-(4-fluorophenyl)ethyl]-N$^4$-(pyrazin-2-yl)pyrimidine-2,4-diamine The objective compound was obtained as a pale yellow amorphous solid by the same process as in Example 1 using 3-fluoroazetidine hydrochloride instead of piperazin-2-one.

MS (ESI) m/z 384 (M+H)$^+$

Specific rotation $[\alpha]^D_{20}$=84.00° (c=0.5, methanol)

Example 45

(S)-1-{2-[1-(4-Fluorophenyl)ethylamino]-6-(pyrazin-2-ylamino)pyrimidin-4-yl}azetidin-2-one 100 mg of (S)-6-chloro-N$^2$-[1-(4-fluorophenyl)ethyl]-N$^4$-(pyrazin-2-yl)pyrimidine-2,4-diamine (Example 9), 41 mg of 2-azetidinone, 34 mg of 4,5-bis(diphenylphosphino)-9,9'-dimethylxanthene, 123 mg of tripotassium phosphate and 30 mg of tris(dibenzylideneacetone)(chloroform)dipalladium were added in turn to 3 ml of degassed 1,4-dioxane, and the mixture was stirred at 90° C. for 5 hours under argon atmosphere. The reaction mixture was filtrated to remove precipitates, and the solvent was distilled off under reduced pressure, and then the obtained residue was purified by silica gel column chromatography to obtain 58 mg of the objective compound as white powder.

MS (ESI) m/z 380 (M+H)$^+$

Specific rotation $[\alpha]^D_{20}$=−62.40° (c=0.5, methanol)

Example 46

(S)-4-(1-Ethyl-1H-pyrazol-4-yl)-N$^2$-[1-(4-fluorophenyl)ethyl]-N$^6$-(pyrazin-2-yl)pyridine-2,6-diamine The objective compound was obtained as pale yellow powder by the same process as in Example 37 using iodoethane instead of 2-bromopropane.

MS (ESI) m/z 404 (M+H)$^+$

Specific rotation $[\alpha]^D_{20}$=−83.60° (c=0.5, methanol)

Example 47

(S)—N$^2$-[1-(4-Fluorophenyl)ethyl]-4-(1-methyl-1H-pyrazol-5-yl)-N$^6$-(pyrazin-2-yl)pyridine-2,6-diamine The objective compound was obtained as white powder by the same process as in Example 4 using 1-methyl-5-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole.

MS (ESI) m/z 390 (M+H)$^+$

Example 48

(S)-4-[1-(Cyclopropylmethyl)-1H-pyrazol-4-yl]-N$^2$-[1-(4-fluorophenyl)ethyl]-N$^6$-(pyrazin-2-yl)pyridine-2,6-diamine The objective compound was obtained as yellow ocher powder by the same process as in Example 37 using (bromomethyl)cyclopropane instead of 2-bromopropane.

MS (ESI) m/z 430 (M+H)$^+$

Example 49

(S)—N²-[1-(4-Fluorophenyl)ethyl]-N⁴-(pyrazin-2-yl)-6-(thiazol-5-yl)pyrimidine-2,4-diamine Step 1.
(S)-4-Chloro-N-[1-(4-fluorophenyl)ethyl]-6-(thiazol-5-yl)pyrimidine-2-amine 286 mg of (S)-4,6-dichloro-N-[1-(4-fluorophenyl)ethyl]pyrimidine-2-amine (Reference Example 1), 411 mg of 5-(tributylstannyl)thiazole and 115 mg of tetrakis(triphenylphosphine)palladium were added in turn to degassed dimethylformamide, and then the mixture was stirred at 100° C. for 5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 175 mg of (S)-4-chloro-N-[1-(4-fluorophenyl)ethyl]-6-(thiazol-5-yl)pyrimidine-2-amine as a white solid.

Step 2.
(S)—N²-[1-(4-Fluorophenyl)ethyl]-N⁴-(pyrazin-2-yl)-6-(thiazol-5-yl)pyrimidine-2,4-diamine To 155 mg of (S)-4-chloro-N-[1-(4-fluorophenyl)ethyl]-6-(thiazol-5-yl)pyrimidine-2-amine, 53 mg of 2-aminopyrazine, 72 mg of 4,5-bis(diphenylphosphino)-9,9'-dimethylxanthene, 196 mg of tripotassium phosphate and 81 mg of tris(dibenzylideneacetone)(chloroform)dipalladium, was added 4 ml of 1,4-dioxane, and the mixture was subjected to degassing, and substituted by argon gas, and then was stirred at 100° C. for 5 hours. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 105 mg of the objective compound as pale yellow powder.

MS (ESI) m/z 394 (M+H)⁺

Example 50

1-{2-[(S)-1-(4-Fluorophenyl)ethylamino]-6-(pyrazin-2-ylamino)pyrimidin-4-yl}pyrrolidin-3-ol hydrochloride Step 1.
1-{6-Chloro-2-[(S)-1-(4-fluorophenyl)ethylamino]pyrimidin-4-yl}pyrrolidin-3-ol The objective compound was obtained as a white powder by the same process as in Example 1, Step 1 using DL-3-pyrrolidinol instead of piperazin-2-one.

Step 2.
1-{2-[(S)-1-(4-Fluorophenyl)ethylamino]-6-(pyrazin-2-ylamino) pyrimidin-4-yl}pyrrolidin-3-ol hydrochloride 119 mg of 1-{6-chloro-2-[(S)-1-(4-fluorophenyl)ethylamino]pyrimidin-4-yl}pyrrolidin-3-ol, 40 mg of 2-aminopyrazine, 20 mg of 4,5-bis(diphenylphosphino)-9,9'-dimethylxanthene, 150 mg of tripotassium phosphate and 19 mg of tris(dibenzylideneacetone)dipalladium were added in turn to 3 ml of degassed 1,4-dioxane, and the mixture was stirred at 100° C. for 2.5 hours under argon atmosphere. The reaction mixture was filtrated to remove precipitates, and the filtrate was concentrated under reduced pressure, and the obtained residue was purified by silica gel column chromatography to obtain 47 mg of 1-{2-[(S)-1-(4-fluorophenyl)ethylamino]-6-(pyrazin-2-ylamino)pyrimidin-4-yl}pyrrolidine-3-ol. Furthermore, the obtained compound was subjected to hydrochlorination using a conventional method to obtain 32 mg of the objective compound as pale yellow powder.

MS (ESI) m/z 396 (M+H)⁺

Elemental analysis value (as $C_{20}H_{22}FN_7O$ HCl+0.25H₂O)

Calculated value (%) C, 55.04; H, 5.43; N, 22.47

Found value (%) C, 55.06; H, 5.12; N, 22.50

Example 51

(S)—N²-[1-(4-Fluorophenyl)ethyl]-N⁴-(5-methylthiazol-2-yl)-N⁶-(pyrazin-2-yl)pyrimidine-2,4,6-triamine The objective compound was obtained as pale yellow powder by the same process as in Example 16 using 2-amino-5-methylthiazole instead of 2-pyrrolidone.

MS (ESI) m/z 423 (M+H)⁺

Example 52

(S)—N²-[1-(4-Fluorophenyl)ethyl]-N⁶-(pyrazin-2-yl)-4,5'-bipyrimidine-2,6-diamine Step 1.
(S)-6-Chloro-N-[1-(4-fluorophenyl)ethyl]-4,5'-bipyrimidine-2-amine 210 mg of (S)-4,6-dichloro-N-[1-(4-fluorophenyl)ethyl]pyrimidine-2-amine (Reference Example 1), 91 mg of pyrimidine-5-boronic acid, 304 mg of potassium carbonate and 60 mg of 1,1'-bis(diphenylphosphino)ferrocene-palladium (II)dichloride-dichloromethane complex were added in turn to a degassed mixed solution of 3 ml of 1,4-dioxane and 1 ml of water, and the mixture was stirred at 90° C. for 6 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 73 mg of (S)-6-chloro-N-[1-(4-fluorophenyl)ethyl]-4,5'-bipyrimidine-2-amine as a white amorphous solid.

Step 2.
(S)—N²-[1-(4-Fluorophenyl)ethyl]-N⁶-(pyrazin-2-yl)-4,5'-bipyrimidine-2,6-diamine To 90 mg of (S)-6-chloro-N-[1-(4-fluorophenyl)ethyl]-4,5'-bipyrimidine-2-amine, 31 mg of 2-aminopyrazine, 31 mg of 4,5-bis(diphenylphosphino)-9,9'-dimethylxanthene, 116 mg of tripotassium phosphate and 28 mg of tris(dibenzylideneacetone)(chloroform)dipalladium, was added 2 ml of 1,4-dioxane, and the mixture was subjected to degassing, and substituted by argon gas, and then was stirred at 100° C. for 3 hours. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 30 mg of the objective compound as pale yellow powder.

MS (ESI) m/z 389 (M+H)⁺

Example 53

(S)—N²-[1-(4-Fluorophenyl)ethyl]-6-(2-methoxythiazol-5-yl)-N⁴-(pyrazin-2-yl)pyrimidine-2,4-diamine The objective compound was obtained as pale orange powder by the same process as in Example 49 using 2-methoxy-5-(tributylstannyl)thiazole instead of 5-(tributylstannyl)thiazole.

MS (ESI) m/z 424 (M+H)⁺

Example 54

(S)—N²-[1-(4-Fluorophenyl)ethyl]-N⁴-(pyrazin-2-yl)-6-(thiazol-2-yl)pyrimidine-2,4-diamine Step 1.
t-Butyl ((S)-4,6-dichloropyrimidin-2-yl)[1-(4-fluorophenyl)ethyl]carbamate 300 mg of (S)-4,6-dichloro-N-[1-(4-fluorophenyl)ethyl]pyrimidine-2-amine was dissolved in 7 ml of tetrahydrofuran, and 0.70 ml of di-t-butyldicarbonate and 58 mg of 4-dimethylaminopyridine were added, and then the reaction mixture was stirred at room temperature overnight. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 285 mg of the objective compound as colorless oil.

Step 2.
t-Butyl (S)-4-chloro-6-(thiazol-2-yl)pyrimidin-2-yl-[1-(4-fluorophenyl)ethyl]carbamate 270 mg of t-butyl ((S)-4,6-dichloropyrimidin-2-yl)[1-(4-fluorophenyl)ethyl] carbamate, 314 mg of 2-(tributylstannyl)thiazole and 81 mg of tetrakis(triphenylphosphine) palladium were added in turn to 5 ml of degassed toluene, and the mixture was stirred at 100° C. for 3 hours under argon atmosphere. The solvent of the reaction solution was distilled off under reduced pressure, and then the obtained residue was purified by silica gel column chromatography to obtain 150 mg of the objective compound as pale yellow oil.

Step 3.
(S)—N²-[1-(4-Fluorophenyl)ethyl]-N⁴-(pyrazin-2-yl)-6-(thiazol-2-yl)pyrimidine-2,4-diamine 130 mg of t-butyl (S)-4-chloro-6-(thiazol-2-yl)pyrimidin-2-yl[1-(4-fluorophenyl)ethyl]carbamate, 34 mg of 2-aminopyrazine, 35 mg of 4,5-bis (diphenylphosphino)-9,9'-dimethylxanthene, 127 mg of tripotassium phosphate and 31 mg of tris(dibenzylideneacetone)(chloroform)dipalladium were added in turn to 4 ml of degassed 1,4-dioxane, and the mixture was stirred at 100° C. for 3 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 90 mg of pale yellow oil. To the obtained oil, 2 ml of trifluoroacetic acid was added, and stirred at room temperature for 2 hours. Trifluoroacetic acid was distilled off under reduced pressure, and then the obtained residue was diluted with water and alkalified with a saturated aqueous solution of sodium bicarbonate. The reaction solution was subjected to extraction with ethyl acetate, and the organic layer was washed with water and brine in turn, and then dried over magnesium sulfate. The solvent was distilled off under reduced pressure, and then the obtained residue was purified by silica gel column chromatography to obtain 25 mg of the objective compound as white powder.

MS (ESI) m/z 394 (M+H)⁺

Example 55

(S)-5-{2-[1-(4-Fluorophenyl)ethylamino]-6-(pyrazin-2-ylamino)pyrimidin-4-yl}picolinonitrile The objective compound was obtained as pale yellow powder by the same process as in Example 52 using 2-cyanopyridine-5-boronic acid pinacol ester instead of pyrimidine-5-boronic acid.

MS (ESI) m/z 413 (M+H)⁺

Example 56

(S)-1-{2-[1-(4-Fluorophenyl)ethylamino]-6-(pyrazin-2-ylamino) pyrimidin-4-yl}piperidine-4-carboxamide hydrochloride The objective compound was obtained by the same process as in Example 1 using isonipecotamide instead of piperazin-2-one. Furthermore, the obtained compound was subjected to hydrochlorination using a conventional method to obtain the objective compound as a white powder.

MS (ESI) m/z 437 (M+H)⁺

Example 57

(S)-5-{2-[1-(4-Fluorophenyl)ethylamino]-6-(pyrazin-2-ylamino)pyrimidin-4-yl}picolinamide To 38 mg of (S)-5-{2-[1-(4-fluorophenyl)ethylamino]-6-(pyrazin-2-ylamino) pyrimidin-4-yl}picolinonitrile, was added t-butanol, and 60 mg of potassium fluoride supported on activated alumina was added thereto, and the mixture was stirred at 90° C. for 4 hours. The reaction solution was filtrated to remove precipitates, and then the filtrate was concentrated under reduced pressure. The obtained residue was purified by silica gel column chromatography to obtain 25 mg of the objective compound as an amorphous solid.

MS (ESI) m/z 431 (M+H)⁺

Example 58

4-{2-[(S)-1-(4-Fluorophenyl)ethylamino]-6-(pyrazin-2-ylamino) pyrimidin-4-yl}piperazin-2-carboxamide The objective compound was obtained as a pale yellow amorphous solid by the same process as in Example 1 using piperazine-2-carboxamide instead of piperazin-2-one.

MS (ESI) m/z 438 (M+H)⁺

Example 59

6-(3-Aminopyrrolidin-1-yl)-N²-[(S)-1-(4-fluorophenyl)ethyl]-N⁴-(pyrazin-2-yl)pyrimidine-2,4-diamine t-Butyl 1-{2-[(S)-1-(4-fluorophenyl)ethylamino]-6-(pyrazin-2-ylamino) pyrimidin-4-yl}pyrrolidin-3-yl carbamate was obtained by the same process as in Example 1 using 3-(t-butoxycarbonylamino)pyrrolidine instead of piperazin-2-one. 2 ml of trifluoroacetic acid was added to the obtained compound, and the mixture was stirred at room temperature for 1 hour. Trifluoroacetic acid was distilled off, and then the obtained residue was diluted with water and alkalified with a saturated aqueous solution of sodium bicarbonate. The reaction solution was subjected to extraction with ethyl acetate, and the organic layer was washed with water and then dried over magnesium sulfate. The solvent was distilled off under reduced pressure to obtain the objective compound as pale yellow powder.

MS (ESI) m/z 395 (M+H)$^+$

Example 60

N-(1-{2-[(S)-1-(4-Fluorophenyl)ethylamino]-6-(pyrazin-2-ylamino)pyrimidin-4-yl}pyrrolidin-3-yl)methanesulfonamide hydrochloride 110 mg of 6-(3-aminopyrrolidin-1-yl)-$N^2$-[(S)-1-(4-fluorophenyl)ethyl]-$N^4$-(pyrazin-2-yl)pyrimidine-2,4-diamine (Example 59) was dissolved in 3 ml of tetrahydrofuran, and 91 μl of N,N-diisopropylethylamine and 21 μl of methanesulfonyl chloride were added at 0° C., and the mixture was stirred at 0° C. for 1 hour. Water was added to the reaction solution, and then the reaction solution was subjected to extraction with ethyl acetate, and the organic layer was washed with water and brine in turn, and then dried over magnesium sulfate. The solvent was distilled off under reduced pressure, and the obtained residue was purified by silica gel column chromatography to obtain 92 mg of N-(1-{2-[(S)-1-(4-fluorophenyl)ethylamino]-6-(pyrazin-2-ylamino)pyrimidin-4-yl}pyrrolidin-3-yl)methanesulfonamide as a pale yellow amorphous solid. The obtained compound was subjected to hydrochlorination using a conventional method to obtain 70 mg of the objective compound as pale yellow powder.

MS (ESI) m/z 473 (M+H)$^+$

Elemental analysis value (as $C_{21}H_{25}FN_8O_2S$ HCl+0.5$H_2O$+0.2$CH_3CO_2C_2H_5$)

Calculated value (%) C, 48.88; H, 5.38; N, 20.92
Found value (%) C, 48.64; H, 5.17; N, 20.73

Example 61

(S)-2-({2-[1-(4-Fluorophenyl)ethylamino]-6-(pyrazin-2-ylamino)pyrimidin-4-yl}(2-hydroxyethyl)amino)ethan-1-ol hydrochloride (S)-2-({2-[1-(4-Fluorophenyl)ethylamino]-6-(pyrazin-2-ylamino)pyrimidin-4-yl}(2-hydroxyethyl)amino)ethan-1-ol was obtained by the same process as in Example 1 using diethanolamine instead of piperazin-2-one. Furthermore, the obtained compound was subjected to hydrochlorination using a conventional method to obtain the objective compound as white powder.

MS (ESI) m/z 414 (M+H)$^+$
Elemental analysis value (as $C_{20}H_{24}FN_7O_2$ HCl+$H_2O$)
Calculated value (%) C, 52.97; H, 5.65; N, 21.62
Found value (%) C, 52.91; H, 5.45; N, 21.37

Example 62

(S)—$N^4$-[2-(Dimethylamino)ethyl]-$N^2$-[1-(4-fluorophenyl)ethyl]-$N^6$-(pyrazin-2-yl)pyrimidine-2,4,6-triamine dihydrochloride (S)—$N^4$-[2-(Dimethylamino) ethyl]-$N^2$-[1-(4-fluorophenyl)ethyl]-$N^6$-(pyrazin-2-yl)pyrimidine-2,4,6-triamine was obtained by the same process as in Example 1 using N,N-dimethylethylenediamine instead of piperazin-2-one. Furthermore, the obtained compound was subjected to hydrochlorination using a conventional method to obtain the objective compound as pale brown powder.

MS (ESI) m/z 397 (M+H)$^+$
Elemental analysis value (as $C_{20}H_{25}FN_8$ 2HCl+1.5$H_2O$)
Calculated value (%) C, 48.39; H, 6.09; N, 22.57
Found value (%) C, 48.30; H, 5.81; N, 22.45

Example 63

1-{2-[(S)-1-(4-Fluorophenyl)ethylamino]-6-(pyrazin-2-ylamino)pyrimidin-4-yl}piperidin-3-carboxamide hydrochloride 1-{2-[(S)-1-(4-Fluorophenyl)ethylamino]-6-(pyrazin-2-ylamino)pyrimidin-4-yl}piperidin-3-carboxamide was obtained by the same process as in Example 1 using nipecotamide instead of piperazin-2-one. Furthermore, the obtained compound was subjected to hydrochlorination using a conventional method to obtain the objective compound as white powder.

MS (ESI) m/z 437 (M+H)$^+$

Example 64

(S)-1-{2-[(S)-1-(4-Fluorophenyl)ethylamino]-6-(pyrazin-2-ylamino)pyrimidin-4-yl}pyrrolidin-2-carboxamide hydrochloride (S)-1-{2-[(S)-1-(4-Fluorophenyl)ethylamino]-6-(pyrazin-2-ylamino)pyrimidin-4-yl}pyrrolidin-2-carboxamide was obtained by the same process as in Example 1 using L-prolinamide instead of piperazin-2-one. Furthermore, the obtained compound was subjected to hydrochlorination using a conventional method to obtain the objective compound as yellow powder.

MS (ESI) m/z 423 (M+H)$^+$
Elemental analysis value (as $C_{21}H_{23}FN_8O$ HCl+1.5$H_2O$)
Calculated value (%) C, 51.90; H, 5.60; N, 23.06
Found value (%) C, 51.89; H, 5.26; N, 22.97

Example 65

(S)—$N^2$-[1-(4-Fluorophenyl)ethyl]-6-[4-(methylsulfonyl)piperazin-1-yl]-$N^4$-(pyrazin-2-yl)pyrimidine-2,4-diamine hydrochloride (S)—$N^2$-[1-(4-Fluorophenyl)ethyl]-6-[4-(methylsulfonyl)piperazin-1-yl]-$N^4$-(pyrazin-2-yl)pyrimidine-2,4-diamine was obtained by the same process as in Example 1 using 1-methanesulfonylpiperazine instead of piperazin-2-one. Furthermore, the obtained compound was subjected to hydrochlorination using a conventional method to obtain the objective compound as white powder.

MS (ESI) m/z 473 (M+H)$^+$
Elemental analysis value (as $C_{21}H_{25}FN_8O_2S$ HCl+1.6$H_2O$)
Calculated value (%) C, 46.90; H, 5.47; N, 20.83
Found value (%) C, 46.52; H, 5.09; N, 20.69

Example 66

(S)—N²-[1-(4-Fluorophenyl)ethyl]-N⁴-(pyrazin-2-yl)-6-(1H-pyrrol-3-yl)pyrimidine-2,4-diamine Step 1.
(S)—N²-[1-(4-Fluorophenyl)ethyl]-N⁴-(pyrazin-2-yl)-6-[1-(tri isopropylsilyl)-1H-pyrrol-3-yl]pyrimidine-2,4-diamine The objective compound was obtained by the same process as in Example 52 using 1-(triisopropylsilyl)-1H-pyrrole-3-boronic acid instead of a pyrimidine-5-boronic acid.

Step 2.
(S)—N²-[1-(4-Fluorophenyl)ethyl]-N⁴-(pyrazin-2-yl)-6-(1H-pyrrol-3-yl)pyrimidine-2,4-diamine 305 mg of (S)—N²-[1-(4-fluorophenyl)ethyl]-N⁴-(pyrazin-2-yl)-6-[1-(triisopropylsilyl)-1H-pyrrol-3-yl]pyrimidine-2,4-diamine was dissolved in 3 ml of tetrahydrofuran, and 0.86 ml of 1M tetrabutylammoniumfluoride/tetrahydrofuran solution was added under ice water cooling, and the mixture was stirred at room temperature for 15 minutes. The reaction solution was added with water. The solution was subjected to extraction with ethyl acetate. The organic layer was washed in turn with water and brine, and then dried over magnesium sulfate. The solvent was distilled off under reduced pressure, and then the obtained residue was purified by silica gel column chromatography to obtain 199 mg of the objective compound as pale brown powder.

MS (ESI) m/z 376 (M+H)⁺

Example 67

(R)-1-{2-[(S)-1-(4-Fluorophenyl)ethylamino]-6-(pyrazin-2-ylamino)pyrimidin-4-yl}-4-hydroxypyrrolidin-2-one The objective compound was obtained as a pale yellow amorphous solid by the same process as in Example 16 using (R)-(+)-4-hydroxy-2-pyrrolidinone instead of 2-pyrrolidone.

MS (ESI) m/z 410 (M+H)⁺

Example 68

N²-[(S)-1-(4-Fluorophenyl)ethyl]-N⁴-(pyrazin-2-yl)-N⁶-[(tetra hydrofuran-2-yl)methyl]pyrimidine-2,4,6-triamine The objective compound was obtained as an amorphous solid by the same process as in Example 1 using tetrahydrofurfurylamine instead of piperazin-2-one.

MS (ESI) m/z 410 (M+H)⁺

Example 69

HS)-1-{2-[(S)-1-(4-Fluorophenyl)ethylamino]-6-(pyrazin-2-ylamino)pyrimidin-4-yl}pyrrolidin-2-yl)methanol hydrochloride ((S)-1-{2-[(S)-1-(4-Fluorophenyl)ethylamino]-6-(pyrazin-2-ylamino)pyrimidin-4-yl}pyrrolidin-2-yl)methanol was obtained by the same process as in Example 1 using L-prolinol instead of piperazin-2-one. Furthermore, the obtained compound was subjected to hydrochlorination using a conventional method to obtain the objective compound as brown powder.

MS (ESI) m/z 410 (M+H)⁺
Elemental analysis value (as $C_{21}H_{24}FN_7O$ HCl+0.4H$_2$O+0.5CH$_3$OH)
Calculated value (%) C, 55.04; H, 5.97; N, 20.90
Found value (%) C, 55.05; H, 5.75; N, 20.57

Example 70

((R)-1-{2-[(S)-1-(4-Fluorophenyl)ethylamino]-6-(pyrazin-2-yl amino)pyrimidin-4-yl}pyrrolidin-2-yl)methanol hydrochloride ((R)-1-{2-[(S)-1-(4-Fluorophenyl)ethylamino]-6-(pyrazin-2-ylamino)pyrimidin-4-yl}pyrrolidin-2-yl)methanol was obtained by the same process as in Example 1 using D-prolinol instead of piperazin-2-one. Furthermore, the obtained compound was subjected to hydrochlorination using a conventional method to obtain the objective compound as brown powder.

MS (ESI) m/z 410 (M+H)⁺
Elemental analysis value (as $C_{21}H_{24}FN_7O$ HCl+0.4H$_2$O+0.5CH$_3$OH)
Calculated value (%) C, 55.04; H, 5.97; N, 20.90
Found value (%) C, 54.74; H, 5.70; N, 20.70

Example 71

(S)-1-{2-[1-(4-Fluorophenyl)ethylamino]-6-(pyrazin-2-ylamino)pyrimidin-4-yl}piperidin-4-ol hydrochloride (S)-1-{2-[1-(4-Fluorophenyl)ethylamino]-6-(pyrazin-2-ylamino)pyrimidin-4-yl}piperidin-4-ol was obtained by the same process as in Example 1 using 4-hydroxypiperidine instead of piperazin-2-one. Furthermore, the obtained compound was subjected to hydrochlorination using a conventional method to obtain the objective compound as pale yellow powder.

MS (ESI) m/z 410 (M+H)⁺
Elemental analysis value (as $C_{21}H_{24}FN_7O$ HCl)
Calculated value (%) C, 56.56; H, 5.65; N, 21.99
Found value (%) C, 56.23; H, 5.53; N, 21.99

Example 72

(S)-1-{2-[1-(4-Fluorophenyl)ethylamino]-6-(pyrazin-2-ylamino)pyrimidin-4-yl}azetidin-3-ol hydrochloride (S)-1-{2-[1-(4-Fluorophenyl)ethylamino]-6-(pyrazin-2-ylamino)pyrimidin-4-yl}azetidin-3-ol was obtained by the same process as in Example 1 using 3-hydroxyazetidine hydrochloride instead of piperazin-2-one. Furthermore, the obtained compound was subjected to hydrochlorination using a conventional method to obtain the objective compound as pale yellow powder.

MS (ESI) m/z 382 (M+H)⁺
Elemental analysis value (as $C_{19}H_{29}FN_7O$/HCl+1.2H$_2$O+0.2CH$_3$OH)
Calculated value (%) C, 51.72; H, 5.47; N, 21.99
Found value (%) C, 51.45; H, 5.14; N, 22.29

Example 73

1-{2-[(S)-1-(4-Fluorophenyl)ethylamino]-6-(pyrazin-2-ylamino)pyrimidin-4-yl}piperidin-3-ol hydrochloride 1-{2-[(S)-1-(4-Fluorophenyl)ethylamino]-6-(pyrazin-2-ylamino)pyrimidin-4-yl}piperidin-3-ol was obtained by the same process as in Example 1 using 3-hydroxypiperidine instead of piperazin-2-one. Furthermore, the obtained compound was subjected to hydrochlorination using a conventional method to obtain the objective compound as a pale yellow powder.

MS (ESI) m/z 410 (M+H)$^+$

Elemental analysis value (as $C_{21}H_{24}FN_7O$ HCl+0.9H$_2$O+0.4CH$_3$OH)

Calculated value (%) C, 54.12; H, 6.03; N, 20.64

Found value (%) C, 53.90; H, 5.78; N, 20.93

Example 74

(S)-5-{2-[1-(4-Fluorophenyl)ethylamino]-6-(pyrazin-2-ylamino)pyrimidin-4-yl}nicotinonitrile Step 1.
5-(Trimethylstannyl)nicotinonitrile 300 mg of 5-bromo-3-cyanopyridine, 750 mg of hexamethylditin and 185 mg of tetrakis(triphenylphosphine)palladium were added in turn to 5 ml of degassed 1,4-dioxane, and the mixture was stirred at 100° C. for 3 hours under argon atmosphere. The solvent of the reaction solution was distilled off under reduced pressure, and then the obtained residue was purified by silica gel column chromatography to obtain 178 mg of the objective compound as colorless oil.

Step 2.
(S)-5-{6-Chloro-2-[1-(4-fluorophenyl)ethylamino]pyrimidin-4-yl}nicotinonitrile 187 mg of (S)-4,6-dichloro-N-[1-(4-fluorophenyl)ethyl]pyrimidine-2-amine (Reference Example 1), 175 mg of 5-(trimethylstannyl)nicotinonitrile, 25 mg of copper iodide and 75 mg of tetrakis(triphenylphosphine)palladium were added in turn to 3 ml of degassed toluene, and the mixture was stirred at 110° C. for 17 hours under argon atmosphere. The reaction solution was purified by silica gel column chromatography to obtain 58 mg of (S)-5-{6-chloro-2-[1-(4-fluorophenyl)ethylamino]pyrimidin-4-yl}nicotinonitrile as colorless oil.

Step 3.
(S)-5-{2-[1-(4-Fluorophenyl)ethylamino]-6-(pyrazin-2-ylamino)pyrimidin-4-yl}nicotinonitrile 55 mg of (S)-5-{6-chloro-2-[1-(4-fluorophenyl)ethylamino]pyrimidin-4-yl}nicotinonitrile, 16 mg of 2-aminopyrazine, 15 mg of 2-dicyclohexylphosphino-2',4',6'-triisopropylbiphenyl, 21 mg of sodium t-butoxide and 8 mg of tris(dibenzylideneacetone)(chloroform)dipalladium were added in turn to 2 ml of degassed toluene, and the mixture was stirred at 100° C. for 1 hour under argon atmosphere. The reaction solution was purified by silica gel column chromatography to obtain 21 mg of the objective compound as white powder.

MS (ESI) m/z 413 (M+H)$^+$

Example 75

(S)—N$^2$-[1-(4-Fluorophenyl)ethyl]-N$^4$-(pyrazin-2-yl)-6-(2H-tetrazol-5-yl)pyrimidine-2,4-diamine Step 1.
(S)-6-[2-(Benzyloxymethyl)-2H-tetrazol-5-yl]-N$^2$-[1-(4-fluoro phenyl)ethyl]-N$^4$-(pyrazin-2-yl)pyrimidine-2,4-diamine (S)-6-[2-(Benzyloxymethyl)-2H-tetrazol-5-yl]-N$^2$-[1-(4-fluorophenyl)ethyl]-N$^4$-(pyrazin-2-yl)pyrimidine-2,4-diamine was obtained by the same process as in Example 74 using 2-(benzyloxymethyl)-5-(tributylstannyl)-2H-tetrazole (synthesized according to the method described in Tetrahedron Lett., 2000, 41, 2805-2809) instead of 5-(trimethylstannyl)nicotinonitrile.

Step 2.
(S)—N$^2$-[1-(4-Fluorophenyl)ethyl]-N$^4$-(pyrazin-2-yl)-6-(2H-tetrazol-5-yl)pyrimidine-2,4-diamine 50 mg of (S)-6-[2-(Benzyloxymethyl)-2H-tetrazol-5-yl]-N$^2$-[1-(4-fluoro phenyl)ethyl]-N$^4$-(pyrazin-2-yl)pyrimidine-2,4-diamine was dissolved in 1.5 ml of methanol, and 1.5 ml of 10% hydrochloric acid was added thereto, and the mixture was stirred at 80° C. for hours. The reaction solution was air-cooled to room temperature, and then diluted with ethyl acetate, and the pH of the mixture was adjusted to 4 by using saturated sodium bicarbonate aqueous solution. The organic layer was subjected to extraction, and washed in turn with water and brine, and then dried over magnesium sulfate. The solvent was distilled off under reduced pressure, and then the obtained residue was washed with methanol and filtered and dried under reduced pressure to obtain 15 mg of the objective compound as white powder.

MS (ESI) m/z 379 (M+H)$^+$

Example 76

(S)—N$^4$-(2-Aminoethyl)-N$^2$-[1-(4-fluorophenyl)ethyl]-N$^6$-(pyrazin-2-yl)pyrimidine-2,4,6-triamine dihydrochloride (S)—N$^4$-(2-Aminoethyl)-N$^2$-[1-(4-fluorophenyl)ethyl]-N$^6$-(pyrazin-2-yl)pyrimidine-2,4,6-triamine was obtained by the same process as in Example 59 using t-butyl N-(2-aminoethyl) carbamate instead of 3-(t-butoxycarbonylamino)pyrrolidine. Furthermore, the obtained compound was subjected to hydrochlorination using a conventional method to obtain the objective compound as a pale yellow powder.

MS (ESI) m/z 369 (M+H)$^+$

Elemental analysis value (as $C_{18}H_{21}FN_8$ 2HCl+0.5H$_2$O)

Calculated value (%) C, 48.01; H, 5.37; N, 24.88

Found value (s) C, 47.72; H, 5.51; N, 24.70

Example 77

(S)—N-(2-{2-[1-(4-Fluorophenyl)ethylamino]-6-(pyrazin-2-ylamino)pyrimidin-4-ylamino}ethyl)methanesulfonamide hydrochloride (S)—N-(2-{2-[1-(4-Fluorophenyl)ethylamino]-6-(pyrazin-2-ylamino)pyrimidin-4-ylamino}ethyl)methanesulfonamide was obtained by the same process as in Example 60 using (S)—N$^4$-(2-aminoethyl)-N$^2$-[1-(4-fluorophenyl)ethyl]-N$^6$-(pyrazin-2-yl)pyrimidine-2,4,6-triamine instead of 6-(3-aminopyrrolidin-1-yl)-N$^2$-[(S)-1-(4-fluorophenyl)ethyl]-N$^4$-(pyrazin-2-yl)pyrimidine-2,4-diamine. Furthermore, the obtained compound was subjected to hydrochlorination using a conventional method to obtain the objective compound as pale yellow powder.

MS (ESI) m/z 447 (M+H)$^+$

Elemental analysis value (as $C_{19}H_{23}FN_8O_2S$ HCl+H$_2$O)

Calculated value (%) C, 45.55; H, 5.23; N, 22.37

Found value (%) C, 45.61; H, 5.07; N, 22.24

Example 78

(S)—N-(2-{2-[1-(4-Fluorophenyl)ethylamino]-6-(pyrazin-2-ylamino)pyrimidin-4-ylamino}ethyl)acetamide hydrochloride Saturated sodium bicarbonate aqueous solution and chloroform were added to 141 mg of (S)—N$^4$-(2-aminoethyl)-N$^2$-

[1-(4-fluorophenyl)ethyl]-N⁶-(pyrazin-2-yl)pyrimidine-2,4,6-triamine dihydrochloride (Example 76), and the mixture was subjected to extraction. The organic layer washed with brine, and dried over magnesium sulfate. The solvent was distilled off under reduced pressure, and then the obtained residue was dissolved in 3 ml of tetrahydrofuran, and 223 μl of diisopropylethylamine and 23 μl of acetyl chloride were added at 0° C., and the mixture was stirred at 0° C. for 30 minutes. The reaction solution was added with water and subjected to extraction with ethyl acetate. The organic layer washed with brine, and dried over magnesium sulfate. The solvent was distilled off under reduced pressure, and then the obtained residue was purified by silica gel column chromatography to obtain 95 mg of (S)—N-(2-{2-[1-(4-fluorophenyl)ethylamino]-6-(pyrazin-2-ylamino)pyrimidin-4-ylamino}ethyl)acetamide as white powder. The obtained compound was subjected to hydrochlorination using a conventional method to obtain 74 mg of the objective compound as pale yellow powder.
MS (ESI) m/z 411 (M+H)⁺
Elemental analysis value (as $C_{20}H_{23}FN_8O$ HCl)
Calculated value (%) C, 53.75; H, 5.41; N, 25.07
Found value (%) C, 53.47; H, 5.55; N, 24.87

Example 79

(S)-2-{2-[1-(4-Fluorophenyl)ethylamino]-6-(pyrazin-2-ylamino)pyrimidin-4-ylamino}acetamide hydrochloride (S)-2-{2-[1-(4-Fluorophenyl)ethylamino]-6-(pyrazin-2-ylamino)pyrimidin-4-ylamino}acetamide was obtained by the same process as in Example 1 using 2-aminoacetamide instead of piperazin-2-one. Furthermore, the obtained compound was subjected to hydrochlorination using a conventional method to obtain the objective compound as pale brown powder.
MS (ESI) m/z 383 (M+H)⁺
Elemental analysis value (as $C_{18}H_{19}FN_8O$ HCl+1.2H₂O)
Calculated value (%) C, 49.08; H, 5.13; N, 25.44
Found value (%) C, 49.33; H, 5.45; N, 25.14

Example 80

(S)-4-{2-[1-(4-Fluorophenyl)ethylamino]-6-(pyrazin-2-ylamino) pyrimidin-4-yl}benzamide hydrochloride (S)-4-{2-[1-(4-Fluorophenyl)ethylamino]-6-(pyrazin-2-ylamino)pyrimidin-4-yl}benzamide was obtained by the same process as in Example 10 using 4-carbamoylphenylboronic acid instead of 4-(methylsulfonyl)phenylboronic acid. Furthermore, the obtained compound was subjected to hydrochlorination using a conventional method to obtain the objective compound as white powder.
MS (ESI) m/z 430 (M+H)⁺
Elemental analysis value (as $C_{23}H_{20}FN_7O$ HCl+H₂O)
Calculated value (%) C, 57.09; H, 4.79; N, 20.26
Found value (%) C, 57.16; H, 4.68; N, 20.45

Example 81

(S)-3-{2-[1-(4-Fluorophenyl)ethylamino]-6-(pyrazin-2-ylamino)pyrimidin-4-yl}benzonitrile The objective compound was obtained as a pale yellow amorphous solid by the same process as in Example 10 using 3-cyanophenylboronic acid instead of 4-(methylsulfonyl)phenylboronic acid.
MS (ESI) m/z 412 (M+H)⁺

Example 82

(S)—N²-[1-(4-Fluorophenyl)ethyl]-6-(furan-3-yl)-N⁴-(pyrazin-2-yl)pyrimidine-2,4-diamine hydrochloride (S)—N²-[1-(4-Fluorophenyl)ethyl]-6-(furan-3-yl)-N⁴-(pyrazin-2-yl)pyrimidine-2,4-diamine was obtained by the same process as in Example 10 using 3-furylboronic acid instead of 4-(methylsulfonyl)phenylboronic acid. Furthermore, the obtained compound was subjected to hydrochlorination using a conventional method to obtain the objective compound as white powder.
MS (ESI) m/z 377 (M+H)⁺
Elemental analysis value (as $C_{20}H_{17}FN_6O$ HCl)
Calculated value (%) C, 58.18; H, 4.39; N, 20.36
Found value (%) C, 57.88; H, 4.58; N, 20.24

Example 83

Ethyl (S)-1-{2-[1-(4-fluorophenyl)ethylamino]-6-(pyrazin-2-ylamino)pyrimidin-4-yl}piperidin-4-carboxylate The objective compound was obtained as a pale yellow amorphous solid by the same process as in Example 1 using ethyl isonipecotate instead of piperazin-2-one.
MS (ESI) m/z 466 (M+H)⁺

Example 84

(S)-5-{2-[1-(4-Fluorophenyl)ethylamino]-6-(pyrazin-2-ylamino) pyrimidin-4-yl}nicotinamide The objective compound was obtained as an amorphous solid by the same process as in Example 57 using (S)-5-{(2-[1-(4-fluorophenyl)ethylamino]-6-(pyrazin-2-ylamino) pyrimidin-4-yl}nicotinonitrile instead of (S)-5-{2-[1-(4-fluorophenyl)ethylamino]-6-(pyrazin-2-ylamino)pyrimidin-4-yl}picolinonitrile.
MS (ESI) m/z 431 (M+H)⁺

Example 85

(S)-1-{2-[1-(4-Fluorophenyl)ethylamino]-6-(pyrazin-2-ylamino)pyrimidin-4-yl}piperidine-4-carboxylic acid 128 mg of ethyl (S)-1-{2-[1-(4-fluorophenyl)ethylamino]-6-(pyrazin-2-ylamino) pyrimidin-4-yl}piperidine-4-carboxylate (Example 83) was dissolved in 3 ml of ethanol, 0.28 ml of 12% sodium hydroxide aqueous solution was added thereto, and the mixture was stirred at room temperature for 6 hours. Ethanol was distilled off and then the obtained residue was diluted with water and the aqueous layer was washed with diethyl ether. The aqueous layer was neutralized with a 10% hydrochloric acid to pH 7 and subjected to extraction with ethyl acetate, and the organic layer was washed with brine, and then dried over magnesium sulfate. The solvent was distilled off under reduced pressure, and then the obtained residue was washed with diethyl ether, and filtered and dried under reduced pressure to obtain 58 mg of the objective compound as white powder.
MS (ESI) m/z 438 (M+H)⁺

Example 86

(S)-2-{2-[(S)-1-(4-Fluorophenyl)ethylamino]-6-(pyrazin-2-ylamino)pyrimidin-4-ylamino}-2-phenylethanol The objective compound was obtained as brown powder by the same process as in Example 1 using (S)-(+)-2-phenylglycinol instead of piperazin-2-one, and using ethoxyethanol as a reaction solvent in Step 1, which was subjected to reaction at 135° C.

MS (ESI) m/z 446 (M+H)$^+$

Example 87

(S)-2-{2-[(S)-1-(4-Fluorophenyl)ethylamino]-6-(pyrazin-2-ylamino)pyrimidin-4-ylamino}-3-phenyl-propan-1-ol The objective compound was obtained as brown powder by the same process as in Example 1 using L-phenylalaminol instead of piperazin-2-one, and using ethoxyethanol as a reaction solvent in Step 1, which was subjected to reaction at 135° C.

MS (ESI) m/z 460 (M+H)$^+$

Example 88

(R)-2-{2-[(S)-1-(4-Fluorophenyl)ethylamino]-6-(pyrazin-2-ylamino) pyrimidin-4-ylamino}-4-methylpentan-1-ol The objective compound was obtained as brown powder by the same process as in Example 1 using D-leucinol instead of piperazin-2-one, and using ethoxyethanol as a reaction solvent in Step 1, which was subjected to reaction at 135° C.

MS (ESI) m/z 426 (M+H)$^+$

Example 89

(S)-6-[2-(Dimethylamino)ethoxy]-N$^2$-[1-(4-fluorophenyl)ethyl]-N$^4$-(pyrazin-2-yl)pyrimidine-2,4-diamine dihydrochloride To 172 mg of (S)-6-chloro-N$^2$-[1-(4-fluorophenyl)ethyl]-N$^4$-(pyrazin-2-yl)pyrimidine-2,4-diamine, 212 mg of tripotassium phosphate, 95 mg of 2-dicyclohexylphosphino-2',4',6'-triisopropylbiphenyl and 52 mg of tris(dibenzylideneacetone)(chloroform)dipalladium was added, 4 ml of 2-dimethyl aminoethanol, and the mixture was subjected to degassing, and substituted by argon gas, and then was stirred at 100° C. for 1 hour. The reaction solution was diluted with ethyl acetate. The solution was washed in turn with water and brine and then dried over magnesium sulfate. The solvent was distilled off under reduced pressure, and the obtained residue was purified by silica gel column chromatography to obtain 118 mg of (S)-6-[2-(dimethylamino)ethoxy]-N$^2$-[1-(4-fluorophenyl)ethyl]-N$^4$-(pyrazin-2-yl)pyrimidine-2,4-diamine. Furthermore, the obtained compound was subjected to hydrochlorination using a conventional method to obtain 101 mg of the objective compound as pale yellow powder.

MS (ESI) m/z 398 (M+H)$^+$
Elemental analysis value (as $C_{20}H_{24}FN_7O$ 2HCl+1.2H$_2$O)
Calculated value (%) C, 48.83; H, 5.82; N, 19.93
Found value (%) C, 48.89; H, 5.63; N, 19.86

Example 90

(S)-1-{2-[1-(4-Fluorophenyl)ethylamino]-6-(pyrazin-2-ylamino)pyrimidin-4-yl}-1H-pyrazole-4-carboxylic acid Step 1.
Ethyl (S)-1-{6-chloro-2-[1-(4-fluorophenyl)ethylamino]pyrimidin-4-yl}-1H-pyrazole-4-carboxylate
500 mg of (S)-4,6-dichloro-N-[1-(4-fluorophenyl)ethyl]pyrimidine-2-amine (Reference Example 1), 270 mg of ethyl 4-pyrazole carboxylate, 0.20 ml of trans-N,N'-dimethylcyclohexane-1,2-diamine, 780 mg of tripotassium phosphate and 100 mg of copper iodide were added in turn to 10 ml of degassed 1,4-dioxane, and the mixture was stirred at 100° C. for 6 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 51 mg of the objective compound as white powder.

MS (ESI) m/z 390 (M+H)$^+$

Step 2.
Ethyl (S)-1-{2-[1-(4-fluorophenyl)ethylamino]-6-(pyrazin-2-ylamino) pyrimidin-4-yl}-1H-pyrazole-4-carboxylate
50 mg of ethyl (S)-1-{6-chloro-2-[1-(4-fluorophenyl)ethylamino]pyrimidin-4-yl}-1H-pyrazole-4-carboxylate, 15 mg of 2-aminopyrazine, 12 mg of 2-dicyclohexylphosphino-2',4',6'-triisopropylbiphenyl, 17 mg of sodium t-butoxide and 7 mg of tris(dibenzylideneacetone)(chloroform)dipalladium were added in turn to 10 ml of degassed toluene, and the mixture was stirred at 100° C. for 2 hours under argon atmosphere. The reaction solution was purified by silica gel column chromatography to obtain 45 mg of the objective compound as white powder.

MS (ESI) m/z 449 (M+H)$^+$

Step 3.
(S)-1-{2-[1-(4-Fluorophenyl)ethylamino]-6-(pyrazin-2-ylamino)pyrimidin-4-yl}-1H-pyrazole-4-carboxylic acid
2 ml of ethanol, 1 ml of tetrahydrofuran and 80 µl of 12% sodium hydroxide aqueous solution were added to 35 mg of ethyl (S)-1-{2-[1-(4-fluorophenyl)ethylamino]-6-(pyrazin-2-ylamino)pyrimidin-4-yl}-1H-pyrazole-4-carboxylate, and the mixture was stirred at room temperature for 18 hours. 160 µl of 12% sodium hydroxide aqueous solution was added thereto, and the mixture was further stirred for 3 hours. Ethanol was distilled off. The obtained residue was diluted with ethanol, and diluted with water, and the pH of the mixture was adjusted to 7 by using 10% hydrochloric acid, the mixture was subjected to extraction with ethyl acetate, and the organic layer was washed with brine, and then dried over magnesium sulfate. The solvent was distilled off under reduced pressure to obtain 14 mg of the objective compound as white powder.

MS (ESI) m/z 421 (M+H)$^+$

Example 91

(S)-3-{(2-[1-(4-Fluorophenyl)ethylamino]-6-(pyrazin-2-ylamino)pyrimidin-4-yl}benzamide 192 mg of (S)-3-{2-[1-(4-fluorophenyl)ethylamino]-6-(pyrazin-2-ylamino) pyrimidin-4-yl}benzonitrile (Example 81) was added to 5 ml of t-butanol, and 384 mg of potassium fluoride supported on activated alumina was added thereto, and the mixture was stirred at 80° C. for 2 hours. 384 mg of potassium fluoride supported on activated alumina was added thereto, and the mixture was further stirred for 15 hours. The reaction solution was filtrated to remove precipitates, and then the filtrate was concentrated under reduced pressure, and the obtained residue was purified by silica gel column chromatography to obtain 158 mg of the objective compound as white powder.
MS (ESI) m/z 430 (M+H)$^+$ Example 92

(S)-6-(Benzo[d]1,3-dioxol-5-yl)-N$^2$-[1-(4-fluorophenyl)ethyl]-N$^4$-(pyrazin-2-yl)pyrimidine-2,4-diamine hydrochloride (S)-6-(Benzo[d]1,3-dioxol-5-yl)-N$^2$-[1-(4-fluorophenyl)ethyl]-N$^4$-(pyrazin-2-yl)pyrimidine-2,4-diamine was obtained by the same process as in Example 10 using 3,4-(methylenedioxy)phenylboronic acid instead of 4-(methylsulfonyl)phenylboronic acid. Furthermore, the obtained compound was subjected to hydrochlorination using a conventional method to obtain the objective compound as white powder.
MS (ESI) m/z 431 (M+H)$^+$
Elemental analysis value (as $C_{23}H_{19}FN_6O_2$ HCl+$H_2O$)
Calculated value (%) C, 56.97; H, 4.57; N, 17.33
Found value (%) C, 56.58; H, 4.38; N, 17.45

Example 93

(S)—N$^2$-[1-(4-Fluorophenyl)ethyl]-6-(2-fluoropyridin-4-yl)-N$^4$-(pyrazin-2-yl)pyrimidine-2,4-diamine The objective compound was obtained as white powder by the same process as in Example 10 using 2-fluoropyridine-4-boronic acid instead of 4-(methylsulfonyl)phenylboronic acid.
MS (ESI) m/z 406 (M+H)$^+$ Example 94

N$^2$-[(S)-1-(4-Fluorophenyl)ethyl]-N$^4$-(pyrazin-2-yl)-6-[(tetra hydrofuran-2-yl)methoxy]pyrimidine-2,4-diamine To 200 mg of (S)-6-chloro-N$^2$-[1-(4-fluorophenyl)ethyl]-N$^4$-(pyrazin-2-yl)pyrimidine-2,4-diamine, 246 mg of tripotassium phosphate, 111 mg of 2-dicyclohexylphosphino-2',4',6'-triisopropylbiphenyl and 60 mg of tris(dibenzylideneacetone) (chloroform)dipalladium, 4 ml of tetrahydrofurfurylalcohol and 2 ml of 1,4-dioxane were added, and the mixture was subjected to degassing, and substituted by argon gas, and then was stirred at 100° C. for 1 hour. The reaction solution was diluted with ethyl acetate and was washed in turn with water and brine and then dried over magnesium sulfate. The solvent was distilled off under reduced pressure, and then the obtained residue was purified by silica gel column chromatography to obtain 77 mg of the objective compound as pale yellow powder.
MS (ESI) m/z 411 (M+H)$^+$ Example 95

(S)-2-{2-[1-(4-Fluorophenyl)ethylamino]-6-(pyrazin-2-ylamino)pyrimidin-4-yloxy}ethanol hydrochloride (S)-2-{2-[1-(4-Fluorophenyl)ethylamino]-6-(pyrazin-2-ylamino)pyrimidin-4-yloxy}ethanol was obtained by the same process as in Example 94 using ethylene glycol instead of tetrahydrofurfurylalcohol. The obtained compound was subjected to hydrochlorination using a conventional method to obtain the objective compound as pale yellow powder.
MS (ESI) m/z 371 (M+H)
Elemental analysis value (as $C_{18}H_{19}FN_6O_2$HCl)
Calculated value (%) C, 53.14; H, 4.95; N, 20.66
Found value (%) C, 52.94; H, 4.95; N, 20.52

Example 96

(S)—N$^2$-[1-(4-Fluorophenyl)ethyl]-N$^4$-(pyrazin-2-yl)-N$^6$-[2-(pyrrolidin-1-yl)ethyl]pyrimidine-2,4,6-triamine The objective compound was obtained as brown powder by the same process as in Example 1 using 1-(2-aminoethyl)pyrrolidine instead of piperazin-2-one.
MS (ESI) m/z 423 (M+H)$^+$ Example 97

(S)-3-{2-[1-(4-Fluorophenyl)ethylamino]-6-(pyrazin-2-ylamino)pyrimidin-4-yl}isonicotinamide 150 mg of (S)-6-chloro-N$^2$-[1-(4-fluorophenyl)ethyl]-N$^4$-(pyrazin-2-yl)pyrimidine-2,4-diamine, 235 mg of 4-cyanopyridine-3-boronic acid neopentyl glycol ester, 184 mg of sodium carbonate and 25 mg of tetrakis(triphenylphosphine)palladium were added in turn to a degassed mixed solution of 3.5 ml of 1,4-dioxane and 1.5 ml of water, and the mixture was stirred at 100° C. for 5 hours under argon atmosphere. The reaction solution was diluted with ethyl acetate. The solution was washed in turn with water and brine and then dried over magnesium sulfate. The solvent was distilled off under reduced pressure, and then the obtained powder was washed with ethyl acetate, and filtered and dried under reduced pressure to obtain 31 mg of (S)-3-{2-[1-(4-fluorophenyl)ethylamino]-6-(pyrazin-2-ylamino)pyrimidin-4-yl}isonicotinamide as white powder.
MS (ESI) m/z 431 (M+H)$^+$ Example 98

(S)-3-{2-[1-(4-Fluorophenyl)ethylamino]-6-(pyrazin-2-ylamino)pyrimidin-4-yl}isonicotinonitrile The filtrate obtained in Example 97 was distilled off under reduced pressure, and the residue was purified by silica gel column chromatography to obtain 15 mg of (S)-3-{2-[1-(4-fluorophenyl)ethylamino]-6-(pyrazin-2-ylamino)pyrimidin-4-yl}isonicotinonitrile as white powder.
MS (ESI) m/z 413 (M+H)$^+$ Example 99

(S)-2-{2-[(S)-1-(4-Fluorophenyl)ethylamino]-6-(pyrazin-2-ylamino)pyrimidin-4-ylamino}-3-methylbutan-1-ol hydrochloride The objective compound was obtained as pale yellow powder by the same process as in Example 1 using L-valinol instead of piperazin-2-one.
MS (ESI) m/z 412 (M+H)$^+$
Elemental analysis value (as $C_{21}H_{26}FN_7O$ HCl+$H_2O$)
Calculated value (%) C, 54.13; H, 6.27; N, 21.04
Found value (%) C, 54.18; H, 5.91; N, 21.14

Example 100

(S)—N²-[1-(4-Chlorophenyl)ethyl]-6-[4-(methylsulfonyl)piperazin-1-yl]-N⁴-(pyrazin-2-yl)pyrimidine-2,4-diamine hydrochloride Step 1.
(S)-6-Chloro-N-[1-(4-chlorophenyl)ethyl]-4-[4-(methylsulfonyl)piperazin-1-yl]pyrimidine-2-amine 200 mg of (S)-4,6-dichloro-N-[1-(4-chlorophenyl)ethyl]pyrimidine-2-amine and 119 mg of 1-methanesulfonyl piperazine were dissolved in 3 ml of 1-butanol, and 0.23 ml of N,N-diisopropylethylamine was added thereto, and the mixture was stirred at 60° C. for 20 hours. The reaction solution was air-cooled to room temperature, and then diluted with ethyl acetate. The solution was washed in turn with water and brine and then dried over magnesium sulfate. The solvent was distilled off under reduced pressure, and then the obtained residue was purified by silica gel column chromatography to obtain 196 mg of the objective compound as white powder.

MS (ESI) m/z 430 (M+H)⁺

Step 2.
(S)—N²-[1-(4-Chlorophenyl)ethyl]-6-[4-(methylsulfonyl)piperazin-1-yl]-N⁴-(pyrazin-2-yl)pyrimidine-2,4-diamine hydrochloride 210 mg of (S)-6-chloro-N-[1-(4-chlorophenyl)ethyl]-4-[4-(methylsulfonyl)piperazin-1-yl]pyrimidine-2-amine, 56 mg of 2-aminopyrazine, mg of 2-dicyclohexylphosphino-2',4',6'-triisopropylbiphenyl, 66 mg of sodium t-butoxide and 25 mg of tris(dibenzylideneacetone)(chloroform)dipalladium were added in turn to 6 ml of degassed toluene, and the mixture was stirred at 100° C. for 4 hours under argon atmosphere. The reaction solution was purified by silica gel column chromatography to obtain 120 mg of (S)—N²-[1-(4-chlorophenyl)ethyl]-6-[4-(methylsulfonyl)piperazin-1-yl]-N⁴-(pyrazin-2-yl)pyrimidine-2,4-diamine. Furthermore, the obtained compound was subjected to hydrochlorination using a conventional method to obtain the objective compound as pale yellow powder.

MS (ESI) m/z 489 (M+H)⁺
Elemental analysis value (as $C_{21}H_{25}ClFN_8O_2S$ HCl+0.4H₂O)
Calculated value (%) C, 47.35; H, 5.07; N, 21.04
Found value (%) C, 47.24; H, 4.79; N, 20.97

Example 101

(1S,2S)-2-{2-[(S)-1-(4-Fluorophenyl)ethylamino]-6-(pyrazin-2-ylamino)pyrimidin-4-yloxy}cyclohexanol hydrochloride (1S,2S)-2-{2-[(S)-1-(4-Fluorophenyl)ethylamino]-6-(pyrazin-2-ylamino)pyrimidin-4-yloxy}cyclohexanol was obtained by the same process as in Example 94 using (1S,2S)-trans-1,2-cyclohexanediol instead of tetrahydrofurfurylalcohol. Furthermore, the obtained compound was subjected to hydrochlorination using a conventional method to obtain the objective compound as pale yellow powder.

MS (ESI) m/z 425 (M+H)⁺
Elemental analysis value (as $C_{22}H_{25}FN_6O_2$ HCl+0.2H₂O)
Calculated value (%) C, 56.88; H, 5.73; N, 18.09
Found value (%) C, 56.94; H, 5.53; N, 18.14

Example 102

(S)—N²-[1-(4-Fluorophenyl)ethyl]-N⁴-[(5-methylpyrazin-2-yl)methyl]-N⁶-(pyrazin-2-yl)pyrimidine-2,4,6-triamine hydrochloride (S)—N²-[1-(4-Fluorophenyl)ethyl]-N⁴-[(5-methylpyrazin-2-yl)methyl]-N⁶-(pyrazin-2-yl)pyrimidine-2,4,6-triamine was obtained by the same process as in Example 1 using 2-(aminomethyl)-5-methylpyrazine instead of piperazin-2-one. Furthermore, the obtained compound was subjected to hydrochlorination using a conventional method to obtain the objective compound as pale yellow powder.

MS (ESI) m/z 432 (M+H)⁺
Elemental analysis value (as $C_{22}H_{22}FN_9$ HCl+H₂O+0.5CH₃OH)
Calculated value (%) C, 53.84; H, 5.42; N, 25.11
Found value (%) C, 53.44; H, 5.05; N, 25.40

Example 103

(S)—N²-[1-(4-Fluorophenyl)ethyl]-N⁴-(furan-2-ylmethyl)-N⁶-(pyrazin-2-yl)pyrimidine-2,4,6-triamine hydrochloride (S)—N²-[1-(4-Fluorophenyl)ethyl]-N⁴-(furan-2-ylmethyl)-N⁶-(pyrazin-2-yl)pyrimidine-2,4,6-triamine was obtained by the same process as in Example 1 using furfurylamine instead of piperazin-2-one. Furthermore, the obtained compound was subjected to hydrochlorination using a conventional method to obtain the objective compound as pale yellow powder.

MS (ESI) m/z 406 (M+H)⁺
Elemental analysis value (as $C_{21}H_{20}FN_7O$ HCl+1.5H₂O)
Calculated value (%) C, 53.79; H, 5.16; N, 20.91
Found value (%) C, 53.85; H, 4.84; N, 20.85

Example 104

(S)—N²-[1-(4-Fluorophenyl)ethyl]-N⁴-(pyrazin-2-yl)-N⁶-[1-(pyridin-3-yl)ethyl]pyrimidine-2,4,6-triamine The objective compound was obtained as brown powder by the same process as in Example 1 using 1-(3-pyridyl)ethylamine instead of piperazin-2-one and using ethoxyethanol as a reaction solvent in Step 1, which was subjected to reaction at 135° C.

MS (ESI) m/z 431 (M+H)⁺

Example 105

(S)-1-{2-[1-(4-Fluorophenyl)ethylamino]-6-(pyrazin-2-ylamino)pyrimidin-4-yl}-4-(hydroxymethyl)piperidin-4-ol Step 1.
4-(Hydroxymethyl)piperidin-4-ol hydrochloride 500 mg of 1-benzyl-4-(hydroxymethyl)piperidin-4-ol (synthesized according to the method described in J. Med. Chem., 1988, 486-491) was dissolved in 10 ml of ethanol, 300 mg of 10% palladium carbon and 0.38 ml of concentrated hydrochloric acid were added thereto, and the mixture was subjected to hydrogenation at room temperature overnight. The reaction mixture was filtrated to remove precipitates, the precipitates were washed with ethanol and water, and the filtrate was concentrated under reduced pressure. The obtained residue was turned into powder by adding diethylether to obtain 374 mg of the objective compound as a white powder.

Step 2.

(S)-1-{6-Chloro-2-[1-(4-fluorophenyl)ethylamino]pyrimidin-4-yl}-4-(hydroxymethyl)piperidin-4-ol 150 mg of (S)-4,6-dichloro-N-[1-(4-fluorophenyl)ethyl]pyrimidine-2-amine and 97 mg of 4-(hydroxymethyl)piperidin-4-ol hydrochloride were dissolved in 3 ml of 2-ethoxyethanol, and 274 μl of N,N-diisopropylethylamine was added thereto, and the mixture was stirred at 135° C. for 20 hours. The reaction solution was air-cooled to room temperature, and then diluted with ethyl acetate. The solution was washed in turn with water and brine and then dried over magnesium sulfate. The solvent was distilled off under reduced pressure to obtain 194 mg of the objective compound as brown oil.

Step 3.

(S)-1-{2-[1-(4-Fluorophenyl)ethylamino]-6-(pyrazin-2-ylamino)pyrimidin-4-yl}-4-(hydroxymethyl)piperidin-4-ol 100 mg of (S)-1-{6-chloro-2-[1-(4-fluorophenyl)ethylamino]pyrimidin-4-yl}-4-(hydroxymethyl)piperidin-4-ol, 32 mg of 2-aminopyrazine, mg of 2-dicyclohexylphosphino-2',4',6'-triisopropylbiphenyl, 38 mg of sodium t-butoxide and 27 mg of tris(dibenzylideneacetone)(chloroform)palladium were added in turn to a degassed mixed solution of 3 ml of toluene and 2 ml of 1,4-dioxane, and the mixture was stirred at 100° C. for 1 hour under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 80 mg of the objective compound as brown powder.

MS (ESI) m/z 440 (M+H)+

Example 106

(S)—$N^2$-[1-(4-Fluorophenyl)ethyl]-$N^4$-(pyrazin-2-yl)-$N^6$-(pyridin-2-ylmethyl)pyrimidine-2,4,6-triamine The objective compound was obtained as brown powder by the same process as in Example 1 using 2-(aminomethyl)pyridine instead of piperazin-2-one, and using ethoxyethanol as a reaction solvent in Step 1, which was subjected to reaction at 135° C.

MS (ESI) m/z 417 (M+H)+

Example 107

(S)—$N^2$-[1-(4-Fluorophenyl)ethyl]-$N^4$-(pyrazin-2-yl)-$N^6$-(pyridin-3-ylmethyl)pyrimidine-2,4,6-triamine The objective compound was obtained as brown powder by the same process as in Example 1 using 3-(aminomethyl)pyridine instead of piperazin-2-one, and using ethoxyethanol as a reaction solvent in Step 1, which was subjected to reaction at 135° C.

MS (ESI) m/z 417 (M+H)+

Example 108

(S)—$N^2$-[1-(4-Fluorophenyl)ethyl]-$N^4$-(pyrazin-2-yl)-$N^6$-(pyridin-4-ylmethyl)pyrimidine-2,4,6-triamine The objective compound was obtained as brown powder by the same process as in Example 1 using 4-(aminomethyl)pyridine instead of piperazin-2-one, and using ethoxyethanol as a reaction solvent in Step 1, which was subjected to reaction at 135° C.

MS (ESI) m/z 417 (M+H)+

Example 109

(S)-2-{2-[(S)-1-(4-Fluorophenyl)ethylamino]-6-(pyrazin-2-ylamino)pyrimidin-4-ylamino}-3-hydroxypropanamide The objective compound was obtained as white powder by the same process as in Example 1 using L-serinamide instead of piperazin-2-one, and using ethoxyethanol as a reaction solvent in Step 1, which was subjected to reaction at 135° C.

MS (ESI) m/z 413 (M+H)+

Example 110

(3S,4S)-1-{2-[(S)-1-(4-Fluorophenyl)ethylamino]-6-(pyrazin-2-ylamino)pyrimidin-4-yl}pyrrolidin-3,4-diol The objective compound was obtained as yellow powder by the same process as in Example 1 using (3S,4S)-3,4-pyrrolidinol instead of piperazin-2-one.

MS (ESI) m/z 412 (M+H)+

Example 111

$N^2$-[(S)-1-(4-Fluorophenyl)ethyl]-$N^4$-(pyrazin-2-yl)-6-(1,4-dioxa-8-azaspiro[4.5]decan-8-yl)pyrimidine-2,4-diamine The objective compound was obtained as brown powder by the same process as in Example 1 using 1,4-dioxa-8-azaspiro[4.5]decane instead of piperazin-2-one, and using ethoxyethanol as a reaction solvent in Step 1, which was subjected to reaction at 135° C.

MS (ESI) m/z 452 (M+H)+

Example 112

(S)-8-{2-[1-(4-Fluorophenyl)ethylamino]-6-(pyrazin-2-ylamino)pyrimidin-4-yl}-1,3-dioxo-8-azaspiro[4.5]decan-2-one 50 mg of (S)-1-{2-[1-(4-Fluorophenyl)ethylamino]-6-(pyrazin-2-ylamino)pyrimidin-4-yl}-4-(hydroxymethyl)piperidin-4-ol (Example 105) and 24 mg of N,N'-carbonyldiimidazole were dissolved in 2 ml of methylene chloride, and the mixture was stirred at room temperature for 15 minutes. The reaction solution was purified by silica gel column chromatography to obtain 52 mg of the objective compound as pale brown powder.

MS (ESI) m/z 466 (M+H)+

Example 113

(S)-4-(1-Benzyl-1H-pyrazol-4-yl)-$N^2$-[1-(4-fluorophenyl)ethyl]-$N^6$-(pyrazin-2-yl)pyridine-2,6-diamine The objective compound was obtained as pale yellow powder by the same process as in Example 4 using 1-benzyl-4-

(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole.

MS (ESI) m/z 466 (M+H)$^+$

Example 114

(S)—N$^2$-[1-(4-Fluorophenyl)ethyl]-6-[4-(phenylsulfonyl)piperazin-1-yl]-N$^4$-(pyrazin-2-yl)pyrimidine-2,4-diamine hydrochloride (S)—N$^2$-[1-(4-Fluorophenyl)ethyl]-6-[4-(phenylsulfonyl)piperazin-1-yl]-N$^4$-(pyrazin-2-yl)pyrimidine-2,4-diamine was obtained by the same process as in Example 50 using 1-phenylsulfonylpiperazine instead of DL-3-pyrrolidinol. The obtained compound was subjected to hydrochlorination using a conventional method to obtain the objective compound as white powder.

MS (ESI) m/z 535 (M+H)$^+$

Elemental analysis value (as $C_{26}H_{27}FN_8O_2S$ HCl+1.3H$_2$O)

Calculated value (%) C, 52.53; H, 5.19; N, 18.85

Found value (%) C, 52.65; H, 5.02; N, 18.54

Example 115

(S)-4-{2-[1-(4-Fluorophenyl)ethylamino]-6-(pyrazin-2-ylamino)pyridin-4-yl}benzamide dihydrochloride 150 mg of (S)-4-chloro-N$^2$-[1-(4-fluorophenyl)ethyl]-N$^6$-(pyrazin-2-yl)pyridine-2,6-diamine (Reference Example 2), 108 mg of 4-carbamoylphenylboronic acid, 567 mg of cesium carbonate, 21 mg of 2-dicyclohexylphosphino-2',6'-dimethoxybiphenyl and 13 mg of tris(dibenzylideneacetone)dipalladium were added in turn to a degassed mixed solution of 3 ml of 1,4-dioxane and 0.6 ml of water, and the mixture was stirred at 100° C. for 17 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 39 mg of (S)-4-{2-[1-(4-fluorophenyl)ethylamino]-6-(pyrazin-2-ylamino)pyridin-4-yl}benzamide. Furthermore, the obtained compound was subjected to hydrochlorination using a conventional method to obtain 31 mg of the objective compound as orange powder.

MS (ESI) m/z 429 (M+H)$^+$

Elemental analysis value (as $C_{24}H_{21}FN_6O$ 2HCl+H$_2$O)

Calculated value (%) C, 55.50; H, 4.85; N, 16.18

Found value (%) C, 55.57; H, 4.70; N, 16.25

Example 116

(S)—N$^2$-[1-(4-Fluorophenyl)ethyl]-N$^6$-(pyrazin-2-yl)-4-(1H-pyrrol-3-yl)pyridine-2,6-diamine dihydrochloride (S)—N$^2$-[1-(4-Fluorophenyl)ethyl]-N$^6$-(pyrazin-2-yl)-4-(1H-pyrrol-3-yl)pyridine-2,6-diamine was obtained by the same process as in Example 115 using 1-(triisopropylsilyl)-1H-pyrrole-3-boronic acid instead of 4-carbamoylphenylboronic acid. The obtained compound was subjected to hydrochlorination using a conventional method to obtain the objective compound as orange powder.

MS (ESI) m/z 375 (M+H)$^+$

Elemental analysis value (as $C_{21}H_{19}FN_6$ 2HCl+0.4H$_2$O)

Calculated value (%) C, 55.49; H, 4.83; N, 18.49

Found value (%) C, 55.70; H, 4.80; N, 18.11

Example 117

(S)—N$^2$-[1-(4-Fluorophenyl)ethyl]-N$^6$-(pyrazin-2-yl)pyridine-2,6-diamine dihydrochloride Step 1.
(S)-6-Chloro-N-[1-(4-fluorophenyl)ethyl]pyridine-2-amine 300 mg of 2,6-dichloropyridine, 296 mg of (S)-(−)-1-(4-fluorophenyl)ethylamine, 119 mg of 2-(di-t-butylphosphino)biphenyl, 487 mg of sodium t-butoxide and 45 mg of palladium acetate were added in turn to 6 ml of degassed toluene, and the mixture was stirred at 85° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 210 mg of the objective compound as pale yellow oil.

Step 2.
(S)—N$^2$-[1-(4-Fluorophenyl)ethyl]-N$^6$-(pyrazin-2-yl)pyridine-2,6-diamine dihydrochloride 207 mg of (S)-6-chloro-N-[1-(4-fluorophenyl)ethyl]pyridine-2-amine, 86 mg of 2-aminopyrazine, 79 mg of 2-dicyclohexylphosphino-2',4',6'-triisopropylbiphenyl, 111 mg of sodium t-butoxide and 43 mg of tris(dibenzylideneacetone)(chloroform)dipalladium were added in turn to 4 ml of degassed toluene, and the mixture was stirred at 100° C. for 1 hour under argon atmosphere. The reaction solution was purified by silica gel column chromatography to obtain 202 mg of (S)—N$^2$-[1-(4-fluorophenyl)ethyl]-N$^6$-(pyrazin-2-yl)pyridine-2,6-diamine as pale yellow powder. Furthermore, the obtained compound was subjected to hydrochlorination using a conventional method to obtain 128 mg of the objective compound as pale orange powder.

MS (ESI) m/z 310 (M+H)$^+$

Example 118

(S)—N$^2$-[1-(4-Fluorophenyl)ethyl]-6-(4-methyl-1H-imidazol-1-yl)-N$^4$-(pyrazin-2-yl)pyrimidine-2,4-diamine hydrochloride Step 1.
(S)-4-Chloro-N-[1-(4-fluorophenyl)ethyl]-6-(4-methyl-1H-imidazol-1-yl)pyrimidine-2-amine 200 mg of (S)-4,6-dichloro-N-[1-(4-fluorophenyl)ethyl]pyrimidine-2-amine and 63 mg of 4-methylimidazole were dissolved in 2 ml of dimethylformamide, and 193 mg of potassium carbonate was added thereto, and the mixture was stirred at 100° C. for 17 hours. The reaction solution was diluted with water, and then subjected to extraction with ethyl acetate. The organic layer was washed in turn with water and brine, and then dried over magnesium sulfate. The solvent was distilled off under reduced pressure, and then the obtained residue was purified by silica gel column chromatography to obtain 62 mg of the objective compound as a white solid.

Step 2.

(S)—N²-[1-(4-Fluorophenyl)ethyl]-6-(4-methyl-1H-imidazol-1-yl)-N⁴-(pyrazin-2-yl)pyrimidine-2,4-diamine hydrochloride 60 mg of (S)-4-chloro-N-[1-(4-fluorophenyl)ethyl]-6-(4-methyl-1H-imidazol-1-yl)pyrimidine-2-amine, 19 mg of 2-aminopyrazine, 17 mg of 2-dicyclohexylphosphino-2',4',6'-triisopropylbiphenyl, 35 mg of sodium t-butoxide and 9 mg of tris(dibenzylideneacetone)dipalladium were added in turn to 2 ml of degassed toluene, and the mixture was stirred at 100° C. for 2 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 69 mg of (S)—N²-[1-(4-fluorophenyl)ethyl]-6-(4-methyl-1H-imidazol-1-yl)-N⁴-(pyrazin-2-yl)pyrimidine-2,4-diamine. Furthermore, the obtained compound was subjected to hydrochlorination using a conventional method to obtain 48 mg of the objective compound as pale yellow powder.

MS (ESI) m/z 391 (M+H)⁺

Example 119

(S)—N²-[1-(4-Fluorophenyl)ethyl]-4-(4-methoxyphenyl)-N⁶-(pyrazin-2-yl)pyridine-2,6-diamine hydrochloride (S)—N²-[1-(4-Fluorophenyl)ethyl]-4-(4-methoxyphenyl)-N⁶-(pyrazin-2-yl)pyridine-2,6-diamine was obtained by the same process as in Example 37 using 4-bromoanisole instead of 4-iodo-1-isopropyl-1H-pyrazole. The obtained compound was subjected to hydrochlorination using a conventional method to obtain the objective compound as brown powder.

MS (ESI) m/z 416 (M+H)⁺
Elemental analysis value (as $C_{24}H_{22}FN_5O$ HCl+1.5$H_2O$)
Calculated value (%) C, 60.19; H, 5.47; N, 14.62
Found value (%) C, 60.37; H, 5.08; N, 14.71

Example 120

(S)-4-(4-Fluorophenyl)-N²-[1-(4-fluorophenyl)ethyl]-N⁶-(pyrazin-2-yl)pyridine-2,6-diamine hydrochloride (S)-4-(4-Fluorophenyl)-N²-[1-(4-fluorophenyl)ethyl]-N⁶-(pyrazin-2-yl)pyridine-2,6-diamine was obtained by the same process as in Example 37 using 4-bromofluorobenzene instead of 4-iodo-1-isopropyl-1H-pyrazole. The obtained compound was subjected to hydrochlorination using a conventional method to obtain the objective compound as brown powder.

MS (ESI) m/z 404 (M+H)⁺

Example 121

(S)—N²-[1-(4-Fluorophenyl)ethyl]-4-methyl-N⁶-(pyrazin-2-yl)pyridine-2,6-diamine hydrochloride Step 1.
(S)-6-Chloro-N-[1-(4-fluorophenyl)ethyl]-4-methylpyridine-2-amine 500 mg of 2,6-dichloro-4-iodopyridine, 0.51 ml of trimethylboroxine, 1.0 g of potassium carbonate and 208 mg of tetrakis(triphenylphosphine)palladium were added in turn to 6 ml of degassed dimethylformamide, and the mixture was stirred at 110° C. for 3 hours under argon atmosphere. The reaction solution was diluted with ethyl acetate. The solution was washed in turn with water and brine and then dried over magnesium sulfate. The solvent was distilled off under reduced pressure, and the obtained residue was purified by silica gel column chromatography to obtain 330 mg of a pale yellow solid. The obtained solid was dissolved in 6 ml of degassed toluene, 253 mg of (S)-(−)-1-(4-fluorophenyl)ethylamine, 147 mg of bis[2-(diphenylphosphino)phenyl]ether, 244 mg of sodium t-butoxide and 40 mg of palladium acetate were added in turn thereto, and the mixture was stirred at 80° C. for 1 hour under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 100 mg of the objective compound as colorless oil.

Step 2.
(S)—N²-[1-(4-Fluorophenyl)ethyl]-4-methyl-N⁶-(pyrazin-2-yl)pyridine-2,6-diamine hydrochloride 95 mg of (S)-6-chloro-N-[1-(4-fluorophenyl)ethyl]-4-methylpyridine-2-amine, 40 mg of 2-aminopyrazine, 34 mg of 2-dicyclohexylphosphino-2',4',6'-triisopropylbiphenyl, 48 mg of sodium t-butoxide and 19 mg of tris(dibenzylideneacetone)(chloroform)dipalladium were added in turn to 6 ml of degassed toluene, and the mixture was stirred at 100° C. for 1 hour under argon atmosphere. The reaction solution was purified by silica gel column chromatography to obtain 85 mg of (S)—N²-[1-(4-fluorophenyl)ethyl]-4-methyl-N⁶-(pyrazin-2-yl)pyridine-2,6-diamine. Furthermore, the obtained compound was subjected to hydrochlorination using a conventional method to obtain 38 mg of the objective compound as yellow powder.

MS (ESI) m/z 324 (M+H)⁺
Elemental analysis value (as $C_{18}H_{18}FN_5$ HCl+0.5$H_2O$)
Calculated value (%) C, 58.62; H, 5.47; N, 18.99
Found value (%) C, 58.86; H, 5.68; N, 18.61

Example 122

(S)-1-{2-[1-(4-Fluorophenyl)ethylamino]-6-(pyrazin-2-ylamino)pyrimidin-4-yl}-N-(methylsulfonyl)piperidine-4-carboxamide Under argon atmosphere, 92 mg of (S)-1-{2-[1-(4-fluorophenyl)ethylamino]-6-(pyrazin-2-ylamino) pyrimidin-4-yl}piperidine-4-carboxylic acid (Example 85) was dissolved in 2 ml of tetrahydrofuran, and 41 mg of N,N'-carbonyldiimidazole was added thereto, and the mixture was stirred at 70° C. for 1 hour. The reaction solution was air-cooled to room temperature, and 80 mg of methanesulfonamide and 63 μl of 1,8-diazabicyclo[5,4,0]-7-undecene were added thereto, and the mixture was stirred at room temperature for 4 hours. The reaction solution was diluted with water, and the pH of the mixture was adjusted to 4 by using acetic acid. The reaction solution was subjected to extraction with ethyl acetate, and the organic layer was washed in turn with water and brine, and then dried over magnesium sulfate. The solvent was distilled off under reduced pressure to obtain 42 mg of the objective compound as white powder.

MS (ESI) m/z 515 (M+H)⁺

Example 123

(S)—N²-[1-(4-Fluorophenyl)ethyl]-4-(furan-3-yl)-N⁶-(pyrazin-2-yl)pyridine-2,6-diamine The objective compound was obtained as pale yellow powder by the same process as in Example 37 using 3-bromofuran instead of 4-iodo-1-isopropyl-1H-pyrazole.

MS (ESI) m/z 376 (M+H)⁺

Example 124

(S)—N$^2$-[1-(4-Fluorophenyl)ethyl]-4-[4-(methylsulfonyl)piperazin-1-yl]-N$^6$-(pyrazin-2-yl)pyridine-2,6-diamine hydrochloride (S)—N$^2$-[1-(4-Fluorophenyl)ethyl]-4-[4-(methylsulfonyl)piperazin-1-yl]-N$^6$-(pyrazin-2-yl)pyridine-2,6-diamine was obtained by the same process as in Example 38 using 1-methanesulfonylpiperazine instead of (S)—N-(pyrrolidin-3-yl)acetamide, and using 1,4-dioxane as a reaction solvent. Furthermore, the obtained compound was subjected to hydrochlorination using a conventional method to obtain the objective compound as brown powder.

MS (ESI) m/z 472 (M+H)$^+$

Example 125

(S)-1-{2-[1-(4-Fluorophenyl)ethylamino]-6-(pyrazin-2-ylamino) pyridin-4-yl}-4-(hydroxymethyl)piperidin-4-ol (S)-4-(2,2-Dimethyl-1,3-dioxa-8-azaspiro [4.5]decan-8-yl)-N$^2$-[1-(4-fluorophenyl)ethyl]-N$^6$-(pyrazin-2-yl)pyridine-2,6-diamine was obtained by the same process as in Example 38 using 2,2-dimethyl-1,3-dioxa-8-azaspiro[4.5]decane instead of (S)—N-(pyrrolidin-3-yl)acetamide, and using 1,4-dioxane as a reaction solvent. 46 mg of the obtained compound was dissolved in 1 ml of chloroform, and 0.5 ml of 50% trifluoroacetic acid aqueous solution was added at 0° C. thereto, and the mixture was stirred. The solvent was distilled off under reduced pressure, and then the obtained residue was purified by silica gel column chromatography to obtain 21 mg of the objective compound as brown powder.

MS (ESI) m/z 439 (M+H)$^+$

Example 126

(S)-4-{2-[1-(4-Fluorophenyl)ethylamino]-6-(pyrazin-2-ylamino)pyridin-4-yl}benzenesulfonamide The objective compound was obtained as brown powder by the same process as in Example 37 using 4-bromobenzene sulfonamide instead of 4-iodo-1-isopropyl-1H-pyrazole.

MS (ESI) m/z 465 (M+H)$^+$

Example 127

(S)—N$^2$-[1-(4-Fluorophenyl)ethyl]-4-methoxy-N$^6$-(pyrazin-2-yl)pyridine-2,6-diamine The objective compound was obtained as white powder by the same process as in Example 4 using 2,6-dichloro-4-methoxypyridine (synthesized according to the method described in WO2007/21710A1) instead of 2,6-dichloro-4-(1-methyl-1H-pyrazol-4-yl) pyridine.

MS (ESI) m/z 340 (M+H)$^+$

Example 128

4-{2-[(1S)-1-(4-Fluorophenyl)ethylamino]-6-(pyrazin-2-ylamino)pyridin-4-yl}-1λ$^6$, 4-thiomorpholin-1,1-dione The objective compound was obtained as brown powder by the same process as in Example 38 using thiomorpholin-1,1-dioxide instead of (S)—N-(pyrrolidin-3-yl)acetamide, and using 1,4-dioxane as a reaction solvent.

MS (ESI) m/z 443 (M+H)$^+$

Example 129

(S)-1-{2-[1-(4-Fluorophenyl)ethylamino]-6-(pyrazin-2-ylamino)pyridin-4-yl}piperidin-4-ol The objective compound was obtained as brown powder by the same process as in Example 38 using 4-hydroxypiperidine instead of (S)—N-(pyrrolidin-3-yl)acetamide, and using 1,4-dioxane as a reaction solvent.

MS (ESI) m/z 409 (M+H)$^+$

Example 130

(S)-1-(4-{2-[1-(4-fluorophenyl)ethylamino]-6-(pyrazin-2-ylamino)pyridin-4-yl}-1,4-diazepan-1-yl)ethanone The objective compound was obtained as brown powder by the same process as in Example 38 using N-acetylhomopiperazine instead of (S)—N-(pyrrolidin-3-yl)acetamide.

MS (ESI) m/z 450 (M+H)$^+$

Example 131

(S)—N$^2$-[1-(4-Fluorophenyl)ethyl]-N$^6$-(pyrazin-2-yl)-N$^4$-(pyrimidin-2-yl)pyridine-2,4,6-triamine The objective compound was obtained as brown powder by the same process as in Example 38 using 2-aminopyrimidine instead of (S)—N-(pyrrolidin-3-yl)acetamide, and using 1,4-dioxane as a reaction solvent.

MS (ESI) m/z 403 (M+H)$^+$

Example 132

(S)—N$^2$-[1-(4-Fluorophenyl)ethyl]-N$^6$-(pyrazin-2-yl)-N$^4$-(pyridin-2-yl)pyridine-2,4,6-triamine The objective compound was obtained as brown powder by the same process as in Example 38 using 2-aminopyridine instead of (S)—N-(pyrrolidin-3-yl)acetamide, and using 1,4-dioxane as a reaction solvent.

MS (ESI) m/z 402 (M+H)$^+$

Example 133

N$^2$-[(S)-1-(4-Fluorophenyl)ethyl]-N$^6$-(pyrazin-2-yl)-4-(1,4-dioxa-8-azaspiro[4.5]decan-8-yl)pyridine-2,6-diamine The objective compound was obtained as brown powder by the same process as in Example 38 using 1,4-dioxa-8-azaspiro[4.5]decane instead of (S)—N-(pyrrolidin-3-yl)acetamide, and using 1,4-dioxane as a reaction solvent.

MS (ESI) m/z 451 (M+H)$^+$

Example 134

Methyl (S)-2-[1-(4-fluorophenyl)ethylamino]-6-(pyrazin-2-ylamino)isonicotinate

Step 1.
Methyl (S)-2-chloro-6-[1-(4-fluorophenyl)ethylamino]isonicotinate 8.3 g of methyl 2,6-dichloroisonicotinate, 6.1 ml of (S)-(−)-1-(4-fluorophenyl)ethylamine, 20.5 g of cesium carbonate, 2.1 g of (±)-2,2'-bis(diphenylphosphino)-1,1'-binaphthyl and 505 mg of palladium acetate were added in turn to 100 ml of degassed 1,4-dioxane, and the mixture was stirred at 70° C. for 7 hours under argon atmosphere. The reaction mixture was purified by silica gel column chromatography to obtain 4.4 g of the objective compound as pale yellow powder.
Step 2.
Methyl (S)-2-[1-(4-fluorophenyl)ethylamino]-6-(pyrazin-2-ylamino)isonicotinate 4.4 g of methyl (S)-2-chloro-6-[1-(4-fluorophenyl)ethylamino]isonicotinate, 1.3 g of 2-aminopyrazine, 2.67 g of 2-dicyclohexylphosphino-2',4',6'-triisopropylbiphenyl, 5.0 g of tripotassium phosphate and 1.28 g of tris(dibenzylideneacetone)dipalladium were added in turn to 100 ml of degassed toluene, and the mixture was stirred at 100° C. for 24 hours under argon atmosphere. The reaction mixture was filtrated by celite, and the filtrate was concentrated under reduced pressure, and the obtained residue was purified by silica gel column chromatography to obtain 4.9 g of the objective compound as white powder.
MS (ESI) m/z 368 (M+H)$^+$

Example 135

(S)-4-{2-[1-(4-Fluorophenyl)ethylamino]-6-(pyrazin-2-ylamino) pyrimidin-4-yl}-N-methylbenzenesulfonamide hydrochloride (S)-4-{2-[1-(4-Fluorophenyl)ethylamino]-6-(pyrazin-2-ylamino)pyrimidin-4-yl}-N-methylbenzenesulfonamide was obtained by the same process as in Example 10 using 4-(N-methylsulfamoyl)phenylboronic acid pinacol ester instead of 4-(methylsulfonyl)phenylboronic acid. Furthermore, the obtained compound was subjected to hydrochlorination using a conventional method to obtain the objective compound as white powder.
MS (ESI) m/z 480 (M+H)$^+$
Elemental analysis value (as $C_{23}H_{22}FN_7O_2S$ HCl+ 0.2H$_2$O)
Calculated value (%) C, 53.17; H, 4.54; N, 18.87
Found value (%) C, 52.98; H, 4.34; N, 18.84

Example 136

(S)—N$^2$-[1-(4-Fluorophenyl)ethyl]-4-(4-methyl-1H-imidazol-1-yl)-N$^6$-(pyrazin-2-yl)pyridine-2,6-diamine dihydrochloride 1.10 g of 2,6-dichloro-4-(4,4,5,5,-tetramethyl-1,3,2-dioxaboran-2-yl)pyridine, 164 mg of 4-methylimidazole, 0.56 ml of triethylamine and 0.32 ml of pyridine were dissolved in 4 ml of methylene chloride, and 545 mg of copper acetate was added thereto, and the mixture was stirred at room temperature for 24 hours. The reaction solution was diluted with water, and chloroform and concentrated ammonia aqueous solution were added thereto, and the mixture was subjected to extraction. The aqueous layer was further subjected to extraction with chloroform, and the obtained organic layers were combined, and dried over magnesium sulfate. The solvent was distilled off under reduced pressure, and then the obtained residue was purified by silica gel column chromatography to obtain 117 mg of 2,6-dichloro-4-(4-methyl-1H-imidazol-1-yl)pyridine. Subsequently, (S)—N$^2$-[1-(4-fluorophenyl)ethyl]-4-(4-methyl-1H-imidazol-1-yl)-N$^6$-(pyrazin-2-yl)pyridine-2,6-diamine was obtained by the same process as in Steps 2 and 3 of Example 4 using 2,6-dichloro-4-(4-methyl-1H-imidazol-1-yl)pyridine instead of 2,6-dichloro-4-(1-methyl-1H-pyrazol-4-yl)pyridine. The obtained compound was subjected to hydrochlorination using a conventional method to obtain the objective compound as yellow powder.
MS (ESI) m/z 390 (M+H)$^+$

Example 137

(S)—N$^2$-[1-(4-Fluorophenyl)ethyl]-N$^4$,N$^6$-di(pyrazin-2-yl)pyridine-2,4,6-triamine The objective compound was obtained as brown powder by the same process as in Example 38 using 2-aminopyrazine instead of (S)—N-(pyrrolidin-3-yl)acetamide.
MS (ESI) m/z 403 (M+H)$^+$

Example 138

(S)-4-(Cyclopropylmethoxy)-N$^2$-[1-(4-fluorophenyl)ethyl]-N$^6$-(pyrazin-2-yl)pyridine-2,6-diamine Step 1.
2,6-Dichloro-4-(cyclopropylmethoxy)pyridine 109 mg of cyclopropylcarbinol was dissolved in 2 ml of dimethylformamide, and 60 mg of 60% sodium hydride was added thereto under ice water cooling, and the mixture was stirred at room temperature for 20 minutes. To the reaction solution was added 400 mg of 2,4,6-trichloropyridine, and stirred at room temperature for 30 minutes. The reaction solution was added with water and subjected to extraction with ethyl acetate. The organic layer was washed with brine, and then dried over magnesium sulfate. The solvent was distilled off under reduced pressure, and then the obtained residue was purified by silica gel column chromatography to obtain 133 mg of the objective compound as colorless oil.
Step 2.
(S)-6-Chloro-4-(cyclopropylmethoxy)-N-[1-(4-fluorophenyl)ethyl]pyridine-2-amine 130 mg of 2,6-dichloro-4-(cyclopropylmethoxy)pyridine, mg of (S)-(−)-1-(4-fluorophenyl)ethylamine, 36 mg 2-(di-t-butylphosphino)biphenyl, 144 mg of sodium t-butoxide and 14 mg of palladium acetate were added in turn to 2 ml of degassed toluene, and the mixture was stirred at 80° C. for 15 minutes under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 122 mg of the objective compound as colorless oil.
Step 3.
(S)-4-(Cyclopropylmethoxy)-N$^2$-[1-(4-fluorophenyl)ethyl]-N$^6$-(pyrazin-2-yl)pyridine-2,6-diamine 112 mg of (S)-6-chloro-4-(cyclopropylmethoxy)-N-[1-(4-fluorophenyl)ethyl]pyridine-2-amine, 43 mg of 2-aminopyrazine, 67 mg of 2-dicyclohexylphosphino-2',4',6'-triisopropylbiphenyl, 51 mg of sodium t-butoxide and 36 mg of tris (dibenzylideneacetone)(chloroform)dipalladium were added in turn to 2 ml of degassed 1,4-dioxane, and the mixture was stirred at 100° C. for 1.5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 103 mg of the objective compound as brown powder.

MS (ESI) m/z 380 (M+H)$^+$

Example 139

(S)—$N^2$-[1-(4-Fluorophenyl)ethyl]-$N^2$-methyl-4-(1-methyl-1H-pyrazol-4-yl)-$N^6$-(pyrazin-2-yl)pyridine-2,6-diamine hydrochloride Step 1.
(S)-6-Chloro-N-[1-(4-fluorophenyl)ethyl]-N-methyl-4-(1-methy 1-1H-pyrazol-4-yl)pyridine-2-amine 92 mg of (S)-6-chloro-N-[1-(4-fluorophenyl)ethyl]-4-(1-methyl-1H-pyrazol-4-yl)pyridine-2-amine was dissolved in 1.5 ml of tetrahydrofuran, and 17 mg of 60% sodium hydride was added thereto, and the mixture was stirred at room temperature for 10 minutes. 26 μl of methyl iodide was added thereto, and the reaction solution was subjected to microwave irradiation at 100° C. for 5 minutes. 8 mg of 60% sodium hydride and 26 μl of methyl iodide were added to the reaction solution, and the reaction solution was stirred at 130° C. for 10 minutes, and furthermore 17 mg of 60% sodium hydride and 26 μl of methyl iodide were added, and the mixture was stirred at 130° C. for 10 minutes. The reaction solution was added with water and subjected to extraction with ethyl acetate. The organic layer was washed in turn with water and brine, and then dried over magnesium sulfate. The solvent was distilled off under reduced pressure, and then the obtained residue was purified by silica gel column chromatography to obtain 62 mg of the objective compound as pale yellow oil.

Step 2.
(S)—$N^2$-[1-(4-Fluorophenyl)ethyl]-$N^2$-methyl-4-(1-methyl-1H-pyrazol-4-yl)-$N^6$-(pyrazin-2-yl)pyridine-2,6-diamine hydrochloride 60 mg of (S)-6-chloro-N-[1-(4-fluorophenyl)ethyl]-N-methyl-4-(1-methy 1-1H-pyrazol-4-yl)pyridine-2-amine, 18 mg of 2-aminopyrazine, 16 mg of 2-dicyclohexylphosphino-2',4',6'-triisopropylbiphenyl, 24 mg of sodium t-butoxide and 9 mg of tris(dibenzylideneacetone)(chloroform)dipalladium were added in turn to 2 ml of degassed toluene, and the mixture was stirred at 100° C. for 1 hour under argon atmosphere. The reaction solution was purified by silica gel column chromatography to obtain 60 mg of (S)—$N^2$-[1-(4-fluorophenyl)ethyl]-$N^2$-methyl-4-(1-methyl-1H-pyrazol-4-yl)-$N^6$-(pyrazin-2-yl)pyridine-2,6-diamine as pale yellow oil. Furthermore, the obtained compound was subjected to hydrochlorination using a conventional method to obtain 29 mg of the objective compound as pale yellow powder.

MS (ESI) m/z 404 (M+H)$^+$
Elemental analysis value (as $C_{22}H_{22}FN_7$ HCl+2.2$H_2O$)
Calculated value (%) C, 55.10; H, 5.76; N, 20.45
Found value (%) C, 55.27; H, 5.44; N, 20.09

Example 140

(S)-{2-[1-(4-Fluorophenyl)ethylamino]-6-(pyrazin-2-ylamino)pyridin-4-yl}methanol 100 mg of methyl (S)-2-[1-(4-fluorophenyl)ethylamino]-6-(pyrazin-2-ylamino)isonicotinate was dissolved in 1 ml of tetrahydrofuran, 20 mg of lithium aluminum hydride was added by small portions, and the mixture was stirred at room temperature for 6 hours. The reaction solution was diluted with tetrahydrofuran, and then cooled to 0° C., and 25 μl of water, 25 μl of 2N sodium hydroxide aqueous solution, and further 75 μl of water were added, and the reaction mixture was dried over magnesium sulfate. The solvent was distilled off under reduced pressure, and then the obtained residue was purified by silica gel column chromatography to obtain 60 mg of the objective compound as pale yellow powder.

MS (ESI) m/z 340 (M+H)$^+$

Example 141

(S)-2-[1-(4-Fluorophenyl)ethylamino]-6-(pyrazin-2-ylamino)isonicotinic acid

To 500 mg of methyl (S)-2-[1-(4-fluorophenyl)ethylamino](pyrazin-2-ylamino) isonicotinate (Example 134), was added 5 ml of methanol, and 2.7 ml of 2N sodium hydroxide aqueous solution was added subsequently, and the mixture was stirred at room temperature for 6 hours. The reaction solution was diluted with ethyl acetate and water, and subjected to extraction, and 2N hydrochloric acid was added to the aqueous layer. The precipitated solid was filtered, and dried under reduced pressure to obtain 160 mg of the objective compound as white powder.

MS (ESI) m/z 354 (M+H)$^+$

Example 142

(S)—$N^2$-[1-(4-Fluorophenyl)ethyl]-4-(2-methoxyethoxy)-$N^6$-(pyrazin-2-yl)pyridine-2,6-diamine hydrochloride (S)—$N^2$-[1-(4-Fluorophenyl)ethyl]-4-(2-methoxyethoxy)-$N^6$-(pyrazin-2-yl)pyridine-2,6-diamine was obtained by the same process as in Example 12 using 2-methoxyethanol instead of ethylene glycol. Furthermore, the obtained compound was subjected to hydrochlorination using a conventional method to obtain the objective compound as brown powder.

MS (ESI) m/z 384 (M+H)$^+$

Example 143

(S)-2-[1-(4-Fluorophenyl)ethylamino]-6-(pyrazin-2-ylamino)pyrimidine-4-carbonitrile To 500 mg of (S)-6-chloro-$N^2$-[1-(4-fluorophenyl)ethyl]-$N^4$-(pyrazin-2-yl)pyrimidine-2,4-diamine (Example 9), 197 mg of zinc cyanide, 66 mg of 2-dicyclohexylphosphino-2',6'-dimethoxybiphenyl and 66 mg of tris(dibenzylideneacetone) dipalladium was added a mixed solution of dimethylformamide and water (99/1), and the solution was bubbled with argon gas for three minutes, and subjected to microwave irradiation at 150° C. for 15 minutes. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 323 mg of the objective compound as pale yellow powder.

MS (ESI) m/z 336 (M+H)$^+$

Example 144

(S)-2-[1-(4-Fluorophenyl)ethylamino]-6-(pyrazin-2-ylamino)isonicotinonitrile

The objective compound was obtained as pale yellow powder by the same process as in Example 143 using (S)-4-chloro-$N^2$-[1-(4-fluorophenyl)ethyl]-$N^6$-(pyrazin-2-yl)pyridine-2,6-diamine instead of (S)-6-chloro-$N^2$-[1-(4-fluorophenyl)ethyl]-$N^4$-(pyrazin-2-yl)pyrimidine-2,4-diamine (Example 9).

MS (ESI) m/z 335 (M+H)$^+$

Example 145

(S)-2-[1-(4-Fluorophenyl)ethylamino]-6-(pyrazin-2-ylamino)isonicotinamide

To 500 mg of (S)-2-[1-(4-fluorophenyl)ethylamino]-6-(pyrazin-2-ylamino)_isonicotinatic acid (Example 141), was added 15 ml of 7N ammonia/methanol solution and the mixture was stirred at 100° C. for 3 days in a sealed tube. The solvent of the reaction solution was distilled off under reduced pressure, and then the obtained residue was purified by silica gel column chromatography to obtain 310 mg of the objective compound as pale yellow powder.

MS (ESI) m/z 353 (M+H)$^+$

Example 146

(S)—$N^2$-[1-(4-Fluorophenyl)ethyl]-6-(1,2,4-oxadiazol-3-yl)-$N^4$-(pyrazin-2-yl)pyrimidine-2,4-diamine hydrochloride 150 mg of (S)-2-[1-(4-fluorophenyl)ethylamino]-6-(pyrazin-2-ylamino)pyrimidine-4-carbonitrile (Example 143) was dissolved in 5 ml of anhydrous ethanol, and 156 mg of hydroxyamine hydrochloride and 309 µl of triethylamine were added, and the mixture was refluxed for 2 hours. The reaction solution was diluted with water, and the mixture was subjected to extraction with ethyl acetate, and the organic layer was washed in turn with water and brine, and then dried over magnesium sulfate. The solvent was distilled off under reduced pressure, and the obtained residue was purified by silica gel column chromatography to obtain 140 mg of a brown amorphous solid. To the reaction solution, 5 ml of triethyl orthoformate and 7 mg of p-toluenesulfonic acid were added, and the mixture was stirred at 60° C. for 4 hours. The reaction solution was poured into a saturated aqueous solution of sodium bicarbonate, and the mixture was subjected to extraction with ethyl acetate. The organic layer was washed in turn with water and brine, and then dried over magnesium sulfate. The solvent was distilled off under reduced pressure, and the obtained residue was purified by silica gel column chromatography to obtain 141 mg of (S)—$N^2$-[1-(4-fluorophenyl)ethyl]-6-(1,2,4-oxadiazol-3-yl)-$N^4$-(pyrazin-2-yl)pyrimidine-2,4-diamine. The obtained compound was subjected to hydrochlorination using a conventional method to obtain 67 mg of the objective compound as yellow powder.

MS (ESI) m/z 379 (M+H)$^+$

Elemental analysis value (as $C_{18}H_{15}FN_8O$ HCl)

Calculated value (%) C, 52.12; H, 3.89; N, 27.01

Found value (%) C, 52.33; H, 3.97; N, 26.90

Example 147

(S)—$N^2$-[1-(4-Fluorophenyl)ethyl]-4-(1,2,4-oxadiazol-3-yl)-$N^6$-(pyrazin-2-yl)pyridine-2,6-diamine hydrochloride (S)—$N^2$-[1-(4-Fluorophenyl)ethyl]-4-(1,2,4-oxadiazol-3-yl)-$N^6$-(pyrazin-2-yl)pyridine-2,6-diamine was obtained by the same process as in Example 146 using (S)-2-[1-(4-fluorophenyl)ethylamino]-6-(pyrazin-2-ylamino)isonicotinonitrile instead of(S)-2-[1-(4-fluorophenyl)ethylamino]-6-(pyrazin-2-ylamino) pyrimidine-4-carbonitrile. Furthermore, the obtained compound was subjected to hydrochlorination using a conventional method to obtain the objective compound as white powder.

MS (ESI) m/z 378 (M+H)$^+$

Example 148

Methyl (S)-2-[1-(4-fluorophenyl)ethylamino]-6-(pyrazin-2-ylamino)nicotinate

Step 1.

Methyl (S)-6-chloro-2-[1-(4-fluorophenyl)ethylamino]nicotinate 5.0 g of methyl 2,6-dichloronicotinate was dissolved in ml of dimethylformamide, and 4.39 g of (S)-(–)-1-(4-fluorophenyl)ethylamine, 6.27 g of diisopropylethylamine and 150 mg of 4-dimethylaminopyridine were added thereto, and the mixture was stirred at 60° C. for 24 hours. The reaction solution was cooled, and then diluted with ethyl acetate, and washed in turn with water and brine, and the organic layer was dried over magnesium sulfate. The solvent was distilled off under reduced pressure, and then the obtained residue was purified by silica gel column chromatography to obtain 2.83 g of the objective compound as white powder.

Step 2.

Methyl (S)-2-[1-(4-fluorophenyl)ethylamino]-6-(pyrazin-2-ylamino)nicotinate 2.83 g of methyl (S)-6-chloro-2-[1-(4-fluorophenyl)ethylamino]nicotinate, 870 mg of 2-aminopyrazine, 1.06 g of 2-dicyclohexylphosphino-2',4',6'-triisopropylbiphenyl, 4.09 g of tripotassium phosphate and 475 mg of tris(dibenzylideneacetone)(chloroform)dipalladium were added in turn to 15 ml of degassed 1,4-dioxane, and the mixture was stirred at 100° C. for 1 hour under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 3.14 g of the objective compound as orange powder.

MS (ESI) m/z 368 (M+H)$^+$

Example 149

(S)-2-[1-(4-Fluorophenyl)ethylamino]-N,N-dimethyl-6-(pyrazin-2-ylamino)isonicotinamide 70 mg of (S)-2-[1-(4-fluorophenyl)ethylamino]-6-(pyrazin-2-ylamino)isonicotinic acid (Example 141) was dissolved in 0.5 ml of dimethylformamide, 81 mg of dimethylamine hydrochloride, 37 mg of 1-ethyl-3-(3-dimethylaminopropyl)carbodiimide hydrochloride, 32 mg of 1-hydroxy-7-azabenzotriazole, and 0.18 ml of diisopropylethylamine were added thereto, and the mixture was stirred at room temperature for 4 hours. The reaction solution was diluted with ethyl acetate, and the organic layer was washed in turn with water and brine, and then dried over magnesium sulfate. The solvent was distilled off, and then the obtained residue was purified by silica gel column chromatography to obtain 45 mg of the objective compound as pale yellow powder.

MS (ESI) m/z 381 (M+H)$^+$

Example 150

(S)—N-[2-(Dimethylamino)ethyl]-2-[1-(4-fluorophenyl)ethylamino]-6-(pyrazin-2-ylamino)isonicotinamide The objective compound was obtained as pale yellow powder by the same process as in Example 149 using N,N-dimethylethylenediamine instead of dimethylamine hydrochloride.

MS (ESI) m/z 424 (M+H)$^+$

Example 151

(S)—N-t-Butyl-2-[1-(4-fluorophenyl)ethylamino]-6-(pyrazin-2-ylamino)isonicotinamide The objective compound was obtained as white powder by the same process as in Example 149 using t-butylamine instead of dimethylamine hydrochloride.

MS (ESI) m/z 409 (M+H)$^+$

Example 152

(S)—N-Ethyl-2-[1-(4-fluorophenyl)ethylamino]-6-(pyrazin-2-yl amino) isonicotinamide To a dimethylformamide solution of 450 mg of (S)-2-[1-(4-fluorophenyl)ethylamino]-6-(pyrazin-2-ylamino)isonicotinic acid (Example 141) and 2.2 ml of diisopropylamine was added, 1.32 g of 1H-benzotriazol-1-yloxy tripyrrolidinophosphonium hexafluorophosphate, and the mixture was stirred for 15 minutes. 520 mg of ethylamine hydrochloride was added thereto, and the mixture was stirred for 2 days. The reaction solution was diluted with ethyl acetate, and the organic layer was washed in turn with water and brine, and then dried over magnesium sulfate. The solvent was distilled off, and then the obtained residue was purified by silica gel column chromatography to obtain 390 mg of the objective compound as a pale yellow powder.

MS (ESI) m/z 381 (M+H)$^+$

Example 153

(S)-{2-[1-(4-Fluorophenyl)ethylamino]-6-(pyrazin-2-ylamino)pyridin-4-yl}[4-(methanesulfonyl)piperazin-1-yl]methanone The objective compound was obtained as pale yellow powder by the same process as in Example 152 using 1-methanesulfonylpiperazine instead of ethylamine hydrochloride.

MS (ESI) m/z 500 (M+H)$^+$

Example 154

(S)-{2-[1-(4-Fluorophenyl)ethylamino]-6-(pyrazin-2-ylamino)pyridin-4-yl}(pyrrolidin-1-yl)methanone As a by-product of Example 153, (S)-{2-[1-(4-fluorophenyl)ethylamino]-6-(pyrazin-2-ylamino)pyridin-4-yl}(pyrrolidin-1-yl)methanone was obtained as pale yellow powder.

MS (ESI) m/z 407 (M+H)$^+$

Example 155

(S)-2-[1-(4-Fluorophenyl)ethylamino]-N-isopropyl-6-(pyrazin-2-ylamino)isonicotinamide The objective compound was obtained as pale yellow powder by the same process as in Example 149 using isopropylamine instead of dimethylamine hydrochloride.

MS (ESI) m/z 395 (M+H)$^+$

Example 156

(S)-1-{2-[(S)-1-(4-Fluorophenyl)ethylamino]-6-(pyrazin-2-ylamino)pyrimidin-4-yl}azetidine-2-carboxamide The objective compound was obtained as brown powder by the same process as in Example 1 using (S)-azetidine-2-carboxamide (synthesized according to the method described in Chem. Pharm. Bull., 1998, 787-796) instead of piperazin-2-one, and using 1,4-dioxane as a reaction solvent in Step 2.

MS (ESI) m/z 409 (M+H)$^+$

Example 157

(S)—N$^2$-[1-(4-Fluorophenyl)ethyl]-N$^6$-(pyrazin-2-yl)-4-(tetrahydro-2H-pyran-4-yloxy)pyridine-2,6-diamine hydrochloride (S)—N$^2$-([1-(4-fluorophenyl)ethyl]-N$^6$-(pyrazin-2-yl)-4-(tetrahydro-2H-pyran-4-yloxy)pyridine-2,6-diamine was obtained by the same process as in Example 138 using tetrahydro-2H-pyran-4-ol instead of cyclopropylcarbinol. Furthermore, the obtained compound was subjected to hydrochlorination using a conventional method to obtain the objective compound as pale yellow powder.

MS (ESI) m/z 410 (M+H)$^+$

Example 158

(S)-1-{2-[1-(4-Fluorophenyl)ethylamino]-6-(pyrazin-2-ylamino)pyrimidin-4-yl}azetidine-3-carboxamide The objective compound was obtained as brown powder by the same process as in Example 1 using 3-azetidine carboxamide instead of piperazin-2-one, and using 1,4-dioxane as a reaction solvent in Step 2.

MS (ESI) m/z 409 (M+H)$^+$

Example 159

(S)-2-[1-(4-Fluorophenyl)ethylamino]-N-(2-hydroxyethyl)-6-(pyrazin-2-ylamino)isonicotinamide The objective compound was obtained as a red-brown powder by the same process as in Example 149 using 2-hydroxyethylamine instead of dimethylamine hydrochloride.

MS (ESI) m/z 397 (M+H)$^+$

Example 160

(S)-2-[1-(4-Fluorophenyl)ethylamino]-N-methyl-6-(pyrazin-2-ylamino)isonicotinamide The objective compound was obtained as pale yellow powder by the same process as in Example 149 using methylamine hydrochloride instead of dimethylamine hydrochloride.
MS (ESI) m/z 367 (M+H)$^+$

Example 161

(S)-{2-[1-(4-Fluorophenyl)ethylamino]-6-(pyrazin-2-ylamino)pyridin-4-yl}(morpholino)methanone The objective compound was obtained as pale yellow powder by the same process as in Example 149 using morpholine instead of dimethylamine hydrochloride.
MS (ESI) m/z 423 (M+H)$^+$

Example 162

(S)—N-Benzyl-2-[1-(4-fluorophenyl)ethylamino]-6-(pyrazin-2-ylamino)isonicotinamide hydrochloride (S)—N-Benzyl-2-[1-(4-fluorophenyl)ethylamino]-6-(pyrazin-2-ylamino)isonicotinamide was obtained by the same process as in Example 152 using benzylamine instead of ethylamine hydrochloride. Furthermore, the obtained compound was subjected to hydrochlorination using a conventional method to obtain the objective compound as yellow powder.
MS (ESI) m/z 443 (M+H)$^+$

Example 163

(S)—N-Cyclopropyl-2-[1-(4-fluorophenyl)ethylamino]-6-(pyrazin-2-ylamino)isonicotinamide The objective compound was obtained as pale yellow powder by the same process as in Example 149 using cyclopropylamine instead of dimethylamine hydrochloride.
MS (ESI) m/z 393 (M+H)$^+$

Example 164

(S)-{2-[1-(4-Fluorophenyl)ethylamino]-6-(pyrazin-2-ylamino)pyridin-4-yl}(4-methylpiperazin-1-yl)methanone hydrochloride (S)-{2-[1-(4-Fluorophenyl)ethylamino]-6-(pyrazin-2-ylamino)pyridin-4-yl}(4-methylpiperazin-1-yl)methanone was obtained by the same process as in Example 152 using 1-methylpiperazine instead of ethylamine hydrochloride. Furthermore, the obtained compound was subjected to hydrochlorination using a conventional method to obtain the objective compound as yellow powder.
MS (ESI) m/z 436 (M+H)$^+$

Example 165

(S)-2-[1-(4-Fluorophenyl)ethylamino]-N-(2-methoxyethyl)-6-(pyrazin-2-ylamino)isonicotinamide The objective compound was obtained as yellow powder by the same process as in Example 152 using methoxyethylamine instead of ethylamine hydrochloride.
MS (ESI) m/z 411 (M+H)$^+$

Example 166

(S)-2-[1-(4-Fluorophenyl)ethylamino]-N-propyl-6-(pyrazin-2-ylamino)isonicotinamide The objective compound was obtained as pink powder by the same process as in Example 152 using 1-propylamine instead of ethylamine hydrochloride.
MS (ESI) m/z 395 (M+H)$^+$

Example 167

(S)—N-Cyclopropylmethyl-2-[1-(4-fluorophenyl)ethylamino]-6-(pyrazin-2-ylamino) isonicotinamide The objective compound was obtained as pale yellow powder by the same process as in Example 152 using cyclopropylmethylamine instead of ethylamine hydrochloride.
MS (ESI) m/z 407 (M+H)$^+$

Example 168

(S)—N-Cyclobutyl-2-[1-(4-fluorophenyl)ethylamino]-6-(pyrazin-2-ylamino)isonicotinamide The objective compound was obtained as red-brown powder by the same process as in Example 152 using cyclobutylamine instead of ethylamine hydrochloride.
MS (ESI) m/z 407 (M+H)$^+$

Example 169

(S)—N-Butyl-2-[1-(4-fluorophenyl)ethylamino]-6-(pyrazin-2-yl amino) isonicotinamide The objective compound was obtained as yellow powder by the same process as in Example 152 using n-butylamine instead of ethylamine hydrochloride.
MS (ESI) m/z 409 (M+H)$^+$

Example 170

(S)-2-[1-(4-Fluorophenyl)ethylamino]-N-isobutyl-6-(pyrazin-2-ylamino) isonicotinamide The objective compound was obtained as pale yellow powder by the same process as in Example 152 using isobutylamine instead of ethylamine hydrochloride.
MS (ESI) m/z 409 (M+H)$^+$

Example 171

(S)-2-[1-(4-Fluorophenyl)ethylamino]-6-(pyrazin-2-ylamino)-N-(2,2,2-trifluoroethyl) isonicotinamide The objective compound was obtained as pale yellow powder by the same process as in Example 152 using 2,2,2-trifluoroethylamine instead of ethylamine hydrochloride.
MS (ESI) m/z 435 (M+H)$^+$

Example 172

(S)-2-[1-(4-Fluorophenyl)ethylamino]-N-(3-hydroxypropyl)-6-(pyrazin-2-ylamino)isonicotinamide The objective compound was obtained as yellow powder by the same process as in Example 152 using 3-hydroxy propylamine instead of ethylamine hydrochloride.
MS (ESI) m/z 411 (M+H)$^+$

Example 173

(S)—N-(2-Ethoxyethyl)-2-[1-(4-fluorophenyl)ethylamino]-6-(pyrazin-2-ylamino)isonicotinamide The objective compound was obtained as yellow powder by the same process as in Example 152 using 2-ethoxyethylamine instead of ethylamine hydrochloride.
MS (ESI) m/z 425 (M+H)$^+$

Example 174

(S)-1-{(2-[1-(4-Fluorophenyl)ethylamino]-6-(pyrazin-2-ylamino)pyrimidin-4-yl}-N-methylazetidin-3-carboxamide Step 1.
1-Benzhydryl-N-methylazetidine-3-carboxamide
400 mg of 1-benzhydrylazetidin-3-carboxylic acid (synthesized according to the method described in WO2005/49602) was dissolved in 4 ml of dimethylformamide, and 683 mg of triethylamine, 122 mg of methylamine hydrochloride, 304 mg of 1-hydroxybenzotriazole and 431 mg of 1-ethyl-3-(3-dimethylaminopropyl)carbodiimide hydrochloride were added thereto, and the mixture was stirred at room temperature overnight. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 158 mg of the objective compound.
Step 2.
(S)-1-{2-[1-(4-Fluorophenyl)ethylamino]-6-(pyrazin-2-ylamino) pyrimidin-4-yl}-N-methylazetidine-3-carboxamide
150 mg of 1-benzhydryl-N-methylazetidin-3-carboxamide was dissolved in 6 ml of methanol, 535 µl of 4N hydrogen chloride ethyl acetate solution and 150 mg of 20% palladium hydroxide were added thereto, and the mixture was subjected to hydrogenation under 4 atmospheric pressures at room temperature overnight. Palladium hydroxide was filtered off, and the filtrate was concentrated under reduced pressure to obtain 150 mg of pale yellow oil. 81 mg of the obtained compound was dissolved in 5 ml of degassed 1,4-dioxane, and 81 mg of triethylamine, 184 mg of (S)-6-chloro-N$^2$-[1-(4-fluorophenyl)ethyl]-N$^4$-(pyrazin-2-yl)pyrimidine-2,4-diamine, 51 mg of 2-dicyclohexylphosphino-2',4',6'-triisopropylbiphenyl, 103 mg of sodium t-butoxide and 55 mg of tris(dibenzylideneacetone)(chloroform)dipalladium were added in turn thereto, and the mixture was stirred at 90° C. for 3.5 hours under argon atmosphere. The reaction solution was diluted with ethyl acetate, and was washed in turn with water and brine and then dried over magnesium sulfate. The solvent was distilled off under reduced pressure, and then the obtained residue was purified by silica gel column chromatography to obtain 24 mg of (S)-1-{2-[1-(4-fluorophenyl)ethylamino]-6-(pyrazin-2-ylamino)pyrimidin-4-yl}-N-methylazetidine-3-carboxamide as yellow powder.
MS (ESI) m/z 423 (M+H)$^+$

Example 175

(S)—N$^2$-[1-(4-Fluorophenyl)ethyl]-4-(methoxymethyl)-N$^6$-(pyrazin-2-yl)pyridine-2,6-diamine 20 mg of (S)-{2-[1-(4-fluorophenyl)ethylamino]-6-(pyrazin-2-ylamino)pyridin-4-yl}methanol (Example 140) was dissolved in methylene chloride, and 59 mg of carbon tetrabromide and 47 mg of triphenylphosphine were added under ice-cooling, and the mixture was stirred for 30 minutes. Subsequently, 90 µl of 9.8 M sodium methoxide/methanol solution was added thereto, and the mixture was stirred overnight. The reaction solution was diluted with ethyl acetate and was washed in turn with water and brine and then dried over magnesium sulfate. The solvent was distilled off under reduced pressure, and then the obtained residue was purified by silica gel column chromatography to obtain 7 mg of the objective compound as yellow powder.
MS (ESI) m/z 354 (M+H)$^+$

Example 176

(S)-1-{2-[1-(4-Fluorophenyl)ethylamino]-6-(pyrazin-2-ylamino)pyrimidin-4-yl}-N,N-dimethylazetidin-3-carboxamide The objective compound was obtained as white powder by the same process as in Example 174 using dimethylamine hydrochloride instead of methylamine hydrochloride.
MS (ESI) m/z 437 (M+H)$^+$

Example 177

(S)—N-(1-{2-[1-(4-Fluorophenyl)ethylamino]-6-(pyrazin-2-ylamino)pyrimidin-4-yl}azetidin-3-yl)methanesulfonamide 100 mg of 1-(t-butoxycarbonyl)-3-aminoazetidine was dissolved in 5 ml of methylene chloride, and 225 mg of diisopropylethylamine was added thereto. Subsequently, 100 mg of methanesulfonyl chloride was added under ice-cooling, and the mixture was allowed to warm to room temperature and stirred overnight. The reaction solution was diluted with ethyl acetate. The solution was washed in turn with 5% citric acid aqueous solution and brine, and then dried over magnesium sulfate. The solvent was distilled off under reduced pressure to obtain 199 mg of colorless oil. The obtained oil was dissolved in 2.5 ml of methylene chloride, and 1 ml of trifluoroacetic acid was added thereto, and the mixture was stirred at room temperature overnight. The solvent was distilled off under reduced pressure to obtain yellow oil. The obtained oil was dissolved in 6 ml of degassed 1,4-dioxane, and 200 mg of (S)-6-chloro-N$^2$-[1-(4-fluorophenyl)ethyl]-N$^4$-(pyrazin-2-yl)pyrimidine-2,4-diamine, 55 mg of 2-dicyclohexylphosphino-2',4',6'-triisopropylbiphenyl, 111 mg of sodium t-butoxide, 294 mg of triethylamine and 60 mg of tris(dibenzylideneacetone)(chloroform)dipalladium were added in turn, and the mixture was stirred at 90° C. for 3 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 12 mg of the objective compound as pale yellow powder.
MS (ESI) m/z 459 (M+H)$^+$

Example 178

(S)-1-{2-[1-(4-Fluorophenyl)ethylamino]-6-(pyrazin-2-ylamino)pyrimidin-4-yl}azetidine-3-carbonitrile 216 mg of 1-(t-butoxycarbonyl)-3-cyanoazetidine was dissolved in 2.5 ml of methylene chloride, and 1 ml of trifluoroacetic acid was added thereto, and the mixture was stirred at room temperature overnight. The solvent was distilled off under reduced pressure to obtain brown oil. The obtained oil was dissolved in 4 ml of degassed 1,4-dioxane, and 302 mg of triethylamine, 205 mg of (S)-6-chloro-$N^2$-[1-(4-fluorophenyl)ethyl]-$N^4$-(pyrazin-2-yl)pyrimidine-2,4-diamine, 57 mg of 2-dicyclohexylphosphino-2',4',6'-triisopropylbiphenyl, 229 mg of sodium t-butoxide and 62 mg of tris(dibenzylideneacetone)(chloroform)dipalladium were added in turn, and the mixture was stirred at 90° C. for 3 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 58 mg of the objective compound as pale yellow powder.

MS (ESI) m/z 391 (M+H)$^+$

Example 179

2-(4-Fluorophenyl)-2-[4-(1-methyl-1H-pyrazol-4-yl)-6-(pyrazin-2-ylamino)pyridin-2-ylamino]ethanol Step 1.
4-(4-Fluorophenyl)oxazolidin-2-one 600 mg of 2-amino-2-(4-fluorophenyl)ethan-1-ol and 80 mg of potassium carbonate were suspended in 914 mg of diethyl carbonate, and the mixture was stirred at 130° C. for 2.5 hours, and further stirred at 100° C. for 2.5 hours while removing the ethanol that was generated. The reaction solution was diluted with ethyl acetate. The solution was washed in turn with water and brine and then dried over magnesium sulfate. The solvent was distilled off under reduced pressure to obtain 610 mg of the objective compound as pale yellow oil.

Step 2.
3-[6-Chloro-4-(1-methyl-1H-pyrazol-4-yl)pyridin-2-yl]-4-(4-fluorophenyl)oxazolidin-2-one 379 mg of 2,6-dichloro-4-(1-methyl-1H-pyrazol-4-yl)pyridine, 300 mg of 4-(4-fluorophenyl)oxazolidin-2-one, 192 mg of 4,5-bis(diphenylphosphino)-9,9'-dimethylxanthene, 705 mg of tripotassium phosphate and 172 mg of tris(dibenzylideneacetone)(chloroform)dipalladium were added in turn to 10 ml of degassed 1,4-dioxane, and the mixture was stirred at 90° C. for 5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 212 mg of the objective compound as yellow powder.

Step 3.
2-(4-Fluorophenyl)-2-[4-(1-methyl-1H-pyrazol-4-yl)-6-(pyrazin-2-ylamino)pyridin-2-ylamino]ethanol 80 mg of 3-[6-chloro-4-(1-methyl-1H-pyrazol-4-yl)pyridin-2-yl]-4-(4-fluorophenyl)oxazolidin-2-one, 20 mg of 2-aminopyrazine, 20 mg of 2-dicyclohexylphosphino-2',4',6'-triisopropylbiphenyl, 41 mg of sodium t-butoxide and 22 mg of tris(dibenzylideneacetone)(chloroform)dipalladium were added in turn to 2.5 ml of degassed 1,4-dioxane, and the mixture was stirred at 90° C. for 1 hour under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 34 mg of the objective compound as white powder.

MS (ESI) m/z 406 (M+H)$^+$

Example 180

(S)—N-Ethyl-1-{2-[1-(4-fluorophenyl)ethylamino]-6-(pyrazin-2-ylamino)pyrimidin-4-yl}azetidine-3-carboxamide The objective compound was obtained as pale yellow powder by the same process as in Example 174 using ethylamine hydrochloride instead of methylamine hydrochloride.

MS (ESI) m/z 437 (M+H)$^+$

Example 181

(S)—N,N-Diethyl-1-{2-[1-(4-fluorophenyl)ethylamino]-6-(pyrazin-2-ylamino)pyrimidin-4-yl}azetidine-3-carboxamide The objective compound was obtained as white powder by the same process as in Example 174 using diethylamine instead of methylamine hydrochloride.

MS (ESI) m/z 465 (M+H)$^+$

Example 182

(S)-1-{2-[1-(4-Fluorophenyl)ethylamino]-6-(pyrazin-2-ylamino)pyridin-4-yl}ethanone hydrochloride Step 1.
(S)-1-{2-Chloro-6-[1-(4-fluorophenyl)ethylamino]pyridin-4-yl}ethanone 535 mg of 1-(2,6-dichloropyridin-4-yl)ethanone (Steps 1 and 2 of Example 29), 391 mg of (S)-(−)-1-(4-fluorophenyl)ethylamine, 262 mg of (±)-2,2'-bis(diphenylphosphino)-1,1'-binaphthyl, 1.28 g of cesium carbonate and 63 mg of palladium acetate were added in turn to 10 ml of degassed toluene, and the mixture was stirred at 100° C. for 3 hours under argon atmosphere. The reaction solution was purified by silica gel column chromatography to obtain 132 mg of the objective compound as pale yellow powder.

MS (ESI) m/z 293 (M+H)$^+$

Step 2.
(S)-1-{2-[1-(4-Fluorophenyl)ethylamino]-6-(pyrazin-2-ylamino)pyridin-4-yl}ethanone hydrochloride 150 mg of (S)-1-{2-chloro-6-[1-(4-fluorophenyl)ethylamino]pyridin-4-yl}ethanone, mg of 2-aminopyrazine, 49 mg of 2-dicyclohexylphosphino-2',4',6'-triisopropylbiphenyl, 59 mg of sodium t-butoxide and 23 mg of tris(dibenzylideneacetone)dipalladium were added in turn to 6 ml of degassed toluene, and the mixture was stirred at 100° C. for 20 minutes under argon atmosphere. The reaction solution was purified by silica gel column chromatography to obtain 77 mg of (S)-1-{2-[1-(4-fluorophenyl)ethylamino]-6-(pyrazin-2-ylamino) pyridin-4-yl}ethanone. The obtained compound was subjected to hydrochlorination using a conventional method to obtain the objective compound as yellow powder.

MS (ESI) m/z 352 (M+H)$^+$
Elemental analysis value (as $C_{19}H_{18}FN_5O$ HCl+0.8$H_2O$)
Calculated value (%) C, 56.73. H, 5.16; N, 17.41
Found value (%) C, 57.06; H, 5.20; N, 17.02

Example 183

(S)—N²-[1-(4-Fluorophenyl)ethyl]-6-(3-methoxyazetidin-1-yl)-N⁴-(pyrazin-2-yl)pyrimidine-2,4-diamine hydrochloride (S)—N²-[1-(4-Fluorophenyl)ethyl]-6-(3-methoxyazetidin-1-yl)-N⁴-(pyrazin-2-yl)pyrimidine-2,4-diamine was obtained by the same process as in Example 1 using 3-methoxyazetidine hydrochloride instead of piperazin-2-one. The obtained compound was subjected to hydrochlorination using a conventional method to obtain the objective compound as a pale yellow powder.
MS (ESI) m/z 396 (M+H)⁺
Elemental analysis value (as $C_{20}H_{22}FN_7O$ HCl+0.3H$_2$O)
Calculated value (%) C, 54.93; H, 5.44; N, 22.42
Found value (%) C, 55.14; H, 5.44; N, 22.16

Example 184

(S)-1-{2-[1-(4-Fluorophenyl)ethylamino]-6-(pyrazin-2-ylamino)pyrimidin-4-yl}-3-methylazetidin-3-ol hydrochloride (S)-1-{2-[1-(4-Fluorophenyl)ethylamino]-6-(pyrazin-2-ylamino)pyrimidin-4-yl}-3-methylazetidin-3-ol was obtained by the same process as in Example 1 using 3-methylazetidin-3-ol hydrochloride instead of piperazin-2-one. The obtained compound was subjected to hydrochlorination using a conventional method to obtain the objective compound as white powder.
MS (ESI) m/z 396 (M+H)⁺

Example 185

(S)-2-[1-(4-Fluorophenyl)ethylamino]-N-methyl-6-(pyrazin-2-ylamino)nicotinamide

Step 1.
(S)-2-[1-(4-Fluorophenyl)ethylamino]-6-(pyrazin-2-ylamino)nicotinic acid 1.0 g of methyl (S)-2-[1-(4-fluorophenyl)ethylamino]-6-(pyrazin-2-ylamino)nicotinate was dissolved in 60 ml of methanol, and 20 ml of 10% sodium hydroxide aqueous solution was added thereto, and the reaction solution was heated at reflux for 4 hour. The reaction solution was distilled off under reduced pressure to remove methanol. The obtained aqueous layer was washed with diethyl ether, and the pH of the mixture was adjusted to 3 by 10% hydrochloric acid. The precipitated solid was filtered, and washed with water. The obtained solid was dried under reduced pressure to obtain 880 mg of the objective compound as pale yellow powder.
Step 2.
(S)-2-[1-(4-Fluorophenyl)ethylamino]-N-methyl-6-(pyrazin-2-ylamino)nicotinamide 80 mg of (S)-2-[1-(4-Fluorophenyl)ethylamino]-6-(pyrazin-2-ylamino)nicotinic acid was dissolved in 1 ml of tetrahydrofuran, 86 mg of O-(benzotriazol-1-yl)-N,N,N',N'-tetramethyluronium hexafluorophosphate salt (HBTU) and 59 mg of triethylamine were added thereto. The mixture was stirred at room temperature for 30 minutes, and then 119 μl of 2M methylamine/tetrahydrofuran solution was added thereto, and the mixture was stirred for 5 hours. The reaction solution was purified by silica gel column chromatography to obtain 45 mg of the objective compound as white powder.
MS (ESI) m/z 367 (M+H)⁺

Example 186

(S)-2-[1-(4-Fluorophenyl)ethylamino]-N,N-dimethyl-6-(pyrazin-2-ylamino) nicotinamide The objective compound was obtained as white powder by the same process as in Example 185 using dimethylamine hydrochloride instead of 2M methylamine/tetrahydrofuran solution.
MS (ESI) m/z 381 (M+H)⁺

Example 187

(S)-2-[1-(4-Fluorophenyl)ethylamino]-6-(pyrazin-2-ylamino) nicotinamide 2 ml of oxalyl chloride was added to 82 mg of (S)-2-[1-(4-fluorophenyl)ethylamino]-6-(pyrazin-2-ylamino)nicotinic acid (Step 1 of Example 185), and the mixture was heated at reflux for 30 minutes. The reaction solution was concentrated under reduced pressure, and 5 ml of concentrated ammonia aqueous solution was added to the obtained residue, and the mixture was stirred at 100° C. for 30 minutes. The reaction solution was air-cooled to room temperature, and then diluted with ethyl acetate. The solution was washed with water and then dried over magnesium sulfate. The solvent was distilled off under reduced pressure, and then the obtained residue was purified by silica gel column chromatography to obtain 13 mg of the objective compound as brown powder.
MS (ESI) m/z 353 (M+H)⁺

Example 188

(S)-{2-[1-(4-Fluorophenyl)ethylamino]-6-(pyrazin-2-ylamino)pyridin-3-yl}(morpholino)methanone dihydrochloride (S)-{2-[1-(4-Fluorophenyl)ethylamino]-6-(pyrazin-2-ylamino)pyridin-3-yl}(morpholino)methanone was obtained by the same process as in Example 185 using morpholine instead of 2M methylamine/tetrahydrofuran solution. Furthermore, the obtained compound was subjected to hydrochlorination using a conventional method to obtain the objective compound as white powder.
MS (ESI) m/z 423 (M+H)⁺
Elemental analysis value (as $C_{22}H_{23}FN_6O_2$ 2HCl)
Calculated value (%) C, 53.34; H, 5.09; N, 16.96
Found value (%) C, 53.18; H, 4.86; N, 16.99

Example 189

(S)—N-(Cyclopropylmethyl)-2-[1-(4-fluorophenyl)ethylamino]-6-(pyrazin-2-ylamino)nicotinamide The objective compound was obtained as white powder by the same process as in Example 185 using cyclopropylmethylamine instead of 2M methylamine/tetrahydrofuran solution.
MS (ESI) m/z 407 (M+H)⁺

Example 190

(S)—N-(1-{2-[1-(4-Fluorophenyl)ethylamino]-6-(pyrazin-2-ylamino)pyrimidin-4-yl}azetidin-3-yl)ethanesulfonamide The objective compound was obtained as pale orange powder by the same process as in Example 177 using ethanesulfonyl chloride instead of methanesulfonyl chloride.
MS (ESI) m/z 473 (M+H)⁺

Example 191

(S)-1-{2-[1-(4-Fluorophenyl)ethylamino]-6-(pyrazin-2-ylamino)pyrimidin-4-yl}-N-isopropylazetidine-3-carboxamide The objective compound was obtained as pale yellow powder by the same process as in Example 174 using isopropylamine instead of methylamine hydrochloride.
MS (ESI) m/z 451 (M+H)$^+$

Example 192

(S)-1-{2-[1-(4-Fluorophenyl)ethylamino]-6-(pyrazin-2-ylamino)pyrimidin-4-yl}-3-(trifluoromethyl)azetidin-3-ol hydrochloride (S)-1-{2-[1-(4-Fluorophenyl)ethylamino]-6-(pyrazin-2-ylamino)pyrimidin-4-yl}-3-(trifluoromethyl)azetidin-3-ol was obtained by the same process as in Example 1 using 3-(trifluoromethyl)azetidin-3-ol hydrochloride (synthesized according to the method described in US2007/275930) instead of piperazin-2-one. The obtained compound was subjected to hydrochlorination using a conventional method to obtain the objective compound as pale yellow powder.
MS (ESI) m/z 450 (M+H)$^+$
Elemental analysis value (as $C_{20}H_{19}F_4N_7O$ HCl+$H_2O$)
Calculated value (%) C, 47.67; H, 4.40; N, 19.46
Found value (%) C, 48.05; H, 4.11; N, 19.23

Example 193

(S)-(1-{2-[1-(4-Fluorophenyl)ethylamino]-6-(pyrazin-2-ylamino)pyrimidin-4-yl}azetidin-3-yl)(pyrrolidin-1-yl)methanone The objective compound was obtained as white powder by the same process as in Example 174 using pyrrolidine instead of methylamine hydrochloride.
MS (ESI) m/z 463 (M+H)$^+$

Example 194

(S)-1-{2-[1-(4-Fluorophenyl)ethylamino]-6-(pyrazin-2-ylamino)pyrimidin-4-yl}-N-(2-methoxyethyl) azetidine-3-carboxamide The objective compound was obtained as white powder by the same process as in Example 174 using 2-methoxyethylamine instead of methylamine hydrochloride.
MS (ESI) m/z 467 (M+H)$^+$

Example 195

(S)-(1-{2-[1-(4-Fluorophenyl)ethylamino]-6-(pyrazin-2-ylamino)pyrimidin-4-yl}azetidin-3-yl)(piperidin-1-yl)methanone The objective compound was obtained as white powder by the same process as in Example 174 using piperidine instead of methylamine hydrochloride.
MS (ESI) m/z 477 (M+H)$^+$

Example 196

(S)-(1-{2-[1-(4-Fluorophenyl)ethylamino]-6-(pyrazin-2-ylamino)pyrimidin-4-yl}azetidin-3-yl) (morpholino) methanone The objective compound was obtained as white powder by the same process as in Example 174 using morpholine instead of methylamine hydrochloride.
MS (ESI) m/z 479 (M+H)$^+$

Example 197

(S)—N-(Cyclopropyl)-1-{2-[1-(4-fluorophenyl)ethylamino]-6-(pyrazin-2-ylamino)pyrimidin-4-yl}azetidine-3-carboxamide The objective compound was obtained as white powder by the same process as in Example 174 using cyclopropylamine instead of methylamine hydrochloride.
MS (ESI) m/z 449 (M+H)$^+$

Example 198

(S)—N-(Cyclopropylmethyl)-1-{2-[1-(4-fluorophenyl)ethylamino]-6-(pyrazin-2-ylamino)pyrimidin-4-yl}azetidine-3-carboxamide The objective compound was obtained as white powder by the same process as in Example 174 using cyclopropylmethylamine instead of methylamine hydrochloride.
MS (ESI) m/z 463 (M+H)$^+$

Example 199

(S)-1-{2-[1-(4-Fluorophenyl)ethylamino]-6-(pyrazin-2-ylamino)pyrimidin-4-yl}-N-(2-hydroxyethyl)azetidine-3-carboxamide The objective compound was obtained as pale yellow powder by the same process as in Example 174 using 2-hydroxy ethyl amine instead of methylamine hydrochloride.
MS (ESI) m/z 453 (M+H)$^+$

Example 200

(S)-3-Cyclopropyl-1-{2-[1-(4-fluorophenyl)ethylamino]-6-(pyrazin-2-ylamino)pyrimidin-4-yl}azetidin-3-ol hydrochloride (S)-3-Cyclopropyl-1-{2-[1-(4-fluorophenyl)ethylamino]-6-(pyrazin-2-ylamino)pyrimidin-4-yl}azetidin-3-ol was obtained by the same process as in Example 1 using 3-cyclopropylazetidin-3-ol hydrochloride (synthesized according to the method described in US2007/275930) instead of piperazin-2-one. The obtained compound was subjected to hydrochlorination using a conventional method to obtain the objective compound as brown powder.
MS (ESI) m/z 422 (M+H)$^+$
Elemental analysis value (as $C_{22}H_{24}FN_7O$ HCl+0.5$H_2O$)
Calculated value CO C, 56.59; H, 5.61; N, 21.00
Found value (%) C, 56.35; H, 5.24; N, 20.97

Example 201

(S)-1-{2-[1-(4-Fluorophenyl)ethylamino]-6-(pyrazin-2-ylamino) pyrimidin-4-yl}-3-isopropylazetidin-3-ol hydrochloride (S)-1-{2-[1-(4-Fluorophenyl)ethylamino]-6-(pyrazin-2-ylamino)pyrimidin-4-yl}-3-isopropylazetidin-3-ol was obtained by the same process as in Example 1 using 3-isopropylazetidin-3-ol hydrochloride (synthesized according to

Example 202

(S)-1-{2-[1-(4-Fluorophenyl)ethylamino]-6-(pyrazin-2-ylamino)pyridin-4-yl}azetidin-3-ol hydrochloride 100 mg of 3-hydroxyazetidine hydrochloride was dissolved in 2 ml of methanol, and 43 mg of sodium t-butoxide was added thereto, and the solvent was distilled off under reduced pressure. 4 ml of degassed 1,4-dioxane was added to the obtained residue, and subsequently 105 mg of (S)-4-chloro-$N^2$-[1-(4-fluorophenyl)ethyl]-N-6-(pyrazin-2-yl)pyridine-2,6-diamine (Reference Example 2), 57 mg of 2-dicyclohexylphosphino-2',4',6'-triisopropylbiphenyl, 96 mg of sodium t-butoxide and 32 mg of tris(dibenzylideneacetone)(chloroform)dipalladium were added in turn, and the mixture was stirred at 100° C. for 1 hour under argon atmosphere. The reaction solution was diluted with ethyl acetate. The solution was washed in turn with a saturated aqueous solution of ammonium chloride and brine, and then dried over magnesium sulfate. The solvent was distilled off under reduced pressure, and then the obtained residue was purified by silica gel column chromatography to obtain 78 mg of (S)-1-{2-[1-(4-fluorophenyl)ethylamino]-6-(pyrazin-2-ylamino)pyridin-4-yl}azetidin-3-ol. Furthermore, the obtained compound was subjected to hydrochlorination using a conventional method to obtain 60 mg of the objective compound as brown powder.

MS (ESI) m/z 381 (M+H)⁺

Example 203

(S)-3-Cyclopropyl-1-{2-[1-(4-fluorophenyl)ethylamino]-6-(pyrazin-2-ylamino)pyridin-4-yl}azetidin-3-ol hydrochloride (S)-3-Cyclopropyl-1-{2-[1-(4-fluorophenyl)ethylamino]-6-(pyrazin-2-ylamino)pyridin-4-yl}azetidin-3-ol was obtained by the same process as in Example 202 using 3-cyclopropylazetidin-3-ol hydrochloride instead of 3-hydroxyazetidine hydrochloride. The obtained compound was subjected to hydrochlorination using a conventional method to obtain the objective compound as brown powder.

MS (ESI) m/z 421 (M+H)⁺

Example 204

(S)-1-{2-[1-(4-Fluorophenyl)ethylamino]-6-(pyrazin-2-ylamino)pyridin-4-yl}-3-isopropylazetidin-3-ol hydrochloride (S)-1-{2-[1-(4-Fluorophenyl)ethylamino]-6-(pyrazin-2-ylamino)pyridin-4-yl}-3-isopropylazetidin-3-ol was obtained by the same process as in Example 202 using 3-isopropylazetidin-3-ol hydrochloride instead of 3-hydroxyazetidine hydrochloride, and using toluene instead of 1,4-dioxane as a solvent. The obtained compound was subjected to hydrochlorination using a conventional method to obtain the objective compound as brown powder.

MS (ESI) m/z 423 (M+H)⁺ the method described in US2007/275930) instead of piperazin-2-one. The obtained compound was subjected to hydrochlorination using a conventional method to obtain the objective compound as brown powder.

MS (ESI) m/z 424 (M+H)⁺
Elemental analysis value (as $C_{22}H_{26}FN_7O$ HCl+0.4H$_2$O)
Calculated value (%) C, 56.56; H, 6.00; N, 20.99
Found value (%) C, 56.81; H, 5.82; N, 20.94

Example 205

(S)-1-{2-[1-(4-Fluorophenyl)ethylamino]-6-(pyrazin-2-ylamino)pyridin-4-yl}-3-methylazetidin-3-ol hydrochloride (S)-1-{2-[1-(4-Fluorophenyl)ethylamino]-6-(pyrazin-2-ylamino)pyridin-4-yl}-3-methylazetidin-3-ol was obtained by the same process as in Example 202 using 3-methylazetidin-3-ol hydrochloride instead of 3-hydroxyazetidine hydrochloride, and using toluene instead of 1,4-dioxane as a solvent. The obtained compound was subjected to hydrochlorination using a conventional method to obtain the objective compound as brown powder.

MS (ESI) m/z 395 (M+H)⁺

Example 206

(S)-1-{2-[1-(4-Fluorophenyl)ethylamino]-6-(pyrazin-2-ylamino)pyridin-4-yl}-3-(trifluoromethyl)azetidin-3-ol hydrochloride (S)-1-{2-[1-(4-fluorophenyl)ethylamino]-6-(pyrazin-2-ylamino)pyridin-4-yl}-3-(trifluoromethyl)azetidin-3-ol was obtained by the same process as in Example 202 using 3-(trifluoromethyl)azetidin-3-ol hydrochloride instead of 3-hydroxyazetidine hydrochloride, and using toluene instead of 1,4-dioxane as a solvent. The obtained compound was subjected to hydrochlorination using a conventional method to obtain the objective compound as brown powder.

MS (ESI) m/z 449 (M+H)⁺

Example 207

(S)-4-(3,3-Difluoroazetidin-1-yl)-$N^2$-[1-(4-fluorophenyl)ethyl]-$N^6$-(pyrazin-2-yl)pyridine-2,6-diamine hydrochloride (S)-4-(3,3-Difluoroazetidin-1-yl)-$N^2$-[1-(4-fluorophenyl)ethyl]-$N^6$-(pyrazin-2-yl)pyridine-2,6-diamine was obtained by the same process as in Example 202 using 3,3-difluoroazetidine hydrochloride instead of 3-hydroxyazetidine hydrochloride, and using toluene instead of 1,4-dioxane as a solvent. The obtained compound was subjected to hydrochlorination using a conventional method to obtain the objective compound as brown powder.

MS (ESI) m/z 401 (M+H)⁺

Example 208

(S)—N-{2-[1-(4-Fluorophenyl)ethylamino]-6-(pyrazin-2-ylamino)pyridin-4-yl}acetamide Step 1.
t-Butyl 2,6-dichloropyridin-4-yl carbamate 1.0 g of 2,6-dichloroisonicotinic acid was dissolved in 20 ml of t-butylalcohol, and 0.87 ml of triethylamine and 1.2 ml of diphenylphosphorylazide were added thereto, and the mixture was heated at reflux overnight. The solvent of the reaction mixture was distilled off under reduced pressure, and the obtained residue was purified by silica gel column chromatography to obtain 969 mg of the objective compound as white powder.

Step 2.

t-Butyl (S)-2-chloro-6-[1-(4-fluorophenyl)ethylamino]pyridin-4-yl carbamate 390 mg of t-butyl 2,6-dichloropyridin-4-yl carbamate, 220 μl of (S)-(−)-1-(4-fluorophenyl)ethylamine, 243 mg of bis[2-(diphenylphosphino)phenyl]ethyl ether, 199 mg of sodium t-butoxide and 67 mg of palladium acetate were added in turn to 10 ml of degassed 1,4-dioxane, and the mixture was stirred at 100° C. for 10 hours under argon atmosphere. 118 μl of acetic acid was added to the reaction solution, and then the mixture was diluted with ethyl acetate. The reaction mixture was filtrated by celite to remove precipitates, and the filtrate was concentrated under reduced pressure, and the obtained residue was purified by silica gel column chromatography to obtain 210 mg of the objective compound as a white amorphous solid.

Step 3.

t-Butyl (S)-2-[1-(4-fluorophenyl)ethylamino]-6-(pyrazin-2-ylamino)pyridin-4-yl carbamate 195 mg of t-butyl (S)-2-chloro-6-[1-(4-fluorophenyl)ethylamino]pyridin-4-yl carbamate, 61 mg of 2-aminopyrazine, 152 mg of 2-dicyclohexylphosphino-2',4',6'-triisopropylbiphenyl, 71 mg of sodium t-butoxide and 73 mg of tris(dibenzylideneacetone)(chloroform)dipalladium were added in turn to 10 ml of degassed toluene, and the mixture was stirred at 100° C. overnight under argon atmosphere. 43 μl of acetic acid was added to the reaction solution, and then the mixture was diluted with ethyl acetate. The reaction mixture was filtrated by celite to remove precipitates, and the filtrate was concentrated under reduced pressure, and the obtained residue was purified by silica gel column chromatography to obtain 203 mg of the objective compound as a pale yellow amorphous solid.

Step 4.

(S)—$N^2$-[1-(4-Fluorophenyl)ethyl]-$N^6$-(pyrazin-2-yl)pyridine-2,4,6-triamine 210 mg of t-butyl (S)-2-[1-(4-fluorophenyl)ethylamino]-6-(pyrazin-2-ylamino)pyridin-4-yl carbamate was dissolved in 3 ml of methylene chloride, and 1 ml of trifluoroacetic acid was added thereto, and the mixture was stirred at room temperature for 5 hours. The reaction solution was poured into an ice-cooled saturated aqueous solution of sodium bicarbonate, and the mixture was subjected to extraction with ethyl acetate. The organic layer was washed in turn with water and brine, and then dried over magnesium sulfate. The solvent was distilled off under reduced pressure, and then the obtained residue was purified by silica gel column chromatography to obtain 151 mg of the objective compound as a pale yellow amorphous solid.

Step 5.

(S)—N-{2-[1-(4-Fluorophenyl)ethylamino]-6-(pyrazin-2-ylamino)pyridin-4-yl}acetamide 50 mg of (S)—$N^2$-[1-(4-fluorophenyl)ethyl]-$N^6$-(pyrazin-2-yl)pyridine-2,4,6-triamine was dissolved in 1 ml of methylene chloride, and 43 μl of triethylamine, 22 μl of acetic anhydride and 1 mg of 4-dimethylaminopyridine were added thereto, and the mixture was stirred at room temperature overnight. The reaction solution was diluted with water. The solution was subjected to extraction with ethyl acetate, and the organic layer was washed in turn with water and brine, and then dried over magnesium sulfate. The solvent was distilled off under reduced pressure, and then the obtained residue was purified by silica gel column chromatography to obtain 32 mg of the objective compound as yellow powder.

MS (ESI) m/z 367 (M+H)$^+$

Example 209

(S)—N-{2-[1-(4-Fluorophenyl)ethylamino]-6-(pyrazin-2-ylamino)pyridin-4-yl}methanesulfonamide hydrochloride (S)—N-{2-[1-(4-fluorophenyl)ethylamino]-6-(pyrazin-2-ylamino)pyridin-4-yl}methanesulfonamide was obtained by the same process as in Step 5 of Example 208, using methanesulfonic anhydride instead of acetic anhydride. The obtained compound was subjected to hydrochlorination using a conventional method to obtain the objective compound as yellow powder.

MS (ESI) m/z 403 (M+H)$^+$

Example 210

(S)-1-[2-[1-(4-Fluorophenyl)ethylamino]-6-(pyrazin-2-ylamino)pyridin-4-yl]urea 50 mg of (S)—$N^2$-[1-(4-fluorophenyl)ethyl]-$N^6$-(pyrazin-2-yl)pyridine-2,4,6-triamine was dissolved in 2 ml of methylene chloride, and 49 mg of N,N'-carbonyldiimidazole was added thereto, and the mixture was stirred at room temperature overnight. A saturated ammonia methanol solution was added to the reaction mixture, and the mixture was stirred at room temperature overnight. The solvent of the reaction solution was distilled off under reduced pressure, and the obtained residue was purified by silica gel column chromatography to obtain 23 mg of the objective compound as pale yellow powder.

MS (ESI) m/z 368 (M+H)$^+$

Example 211

(S)-4-(3-Cyclopropyl-3-methoxyazetidin-1-yl)-$N^2$-[1-(4-fluorophenyl)ethyl]-$N^6$-(pyrazin-2-yl)pyridine-2,6-diamine hydrochloride Step 1.

1-Benzhydryl-3-cyclopropylazetidin-3-ol 300 mg of 1-benzhydrylazetidin-3-one dissolved in 3.8 ml of tetrahydrofuran was added to 2 ml of 1M cyclopropyl magnesium bromide/tetrahydrofuran solution under ice water cooling, and the mixture was allowed to warm to room temperature and stirred for 30 minutes. The reaction solution was poured into a saturated aqueous solution of sodium carbonate and the mixture was subjected to extraction with diethyl ether, and dried over magnesium sulfate. The solvent was distilled off under reduced pressure, and then the obtained residue was purified by silica gel column chromatography to obtain 334 mg of the objective compound.

Step 2.

1-Benzhydryl-3-cyclopropyl-3-methoxyazetidine 334 mg of 1-benzhydryl-3-cyclopropylazetidin-3-ol was dissolved in dimethylformamide, and 72 mg of 60% sodium hydride was added thereto, and the mixture was stirred at room temperature for 30 minutes. 112 μl of methyl iodide was added thereto, and the mixture was further stirred at room temperature for 2 hours. To the reaction solution was added water and the mixture was subjected to extraction with diethyl ether, and dried over magnesium sulfate. The solvent was distilled off under reduced pressure, and then the obtained residue was purified by silica gel column chromatography to obtain 280 mg of the objective compound.

Step 3.
(S)-4-(3-Cyclopropyl-3-methoxyazetidin-1-yl)-N$^2$-[1-(4-fluorophenyl)ethyl]-N$^6$-(pyrazin-2-yl)pyridine-2,6-diamine hydrochloride 275 mg of 1-benzhydryl-3-cyclopropyl-3-methoxyazetidine was dissolved in 15 ml of methanol, and 0.70 ml of 2N hydrochloric acid and 150 mg of 20% palladium hydroxide were added thereto, and the mixture was stirred at room temperature overnight under hydrogen pressure of 3.5 kgf/cm$^2$. The reaction mixture was filtrated to remove precipitates, and then the filtrate was concentrated under reduced pressure to obtain 146 mg of white powder. 62 mg of the obtained compound was dissolved in 2 ml of methanol, and 41 mg of sodium t-butoxide was added thereto, and the solvent was distilled off under reduced pressure. 4 ml of degassed toluene was added to the residue, and then 100 mg of (S)-4-chloro-N$^2$-[1-(4-fluorophenyl)ethyl]-N$^6$-(pyrazin-2-yl)pyridine-2,6-diamine (Reference Example 2), 55 mg of 2-dicyclohexylphosphino-2',4',6'-triisopropylbiphenyl, 41 mg of sodium t-butoxide and 27 mg of tris(dibenzylideneacetone)dipalladium were added in turn, and the mixture was stirred at 100° C. for 1 hour under argon atmosphere. The reaction solution was diluted with ethyl acetate. The solution was washed in turn with a saturated aqueous solution of ammonium chloride and brine, and then dried over magnesium sulfate. The solvent was distilled off under reduced pressure, and the obtained residue was purified by silica gel column chromatography to obtain 47 mg of (S)-4-(3-cyclopropyl-3-methoxyazetidin-1-yl)-N$^2$-[1-(4-fluoro phenyl) ethyl]-N$^6$-(pyrazin-2-yl)pyridine-2,6-diamine. Furthermore, the obtained compound was subjected to hydrochlorination using a conventional method to obtain the objective compound as brown powder.

MS (ESI) m/z 435 (M+H)$^+$

Example 212

(S)—N$^2$-[1-(4-Fluorophenyl)ethyl]-4-(3-isopropyl-3-methoxyazetidin-1-yl)-N$^6$-(pyrazin-2-yl)pyridine-2,6-diamine hydrochloride (S)—N$^2$-[1-(4-Fluorophenyl)ethyl]-4-(3-isopropyl-3-methoxyazetidin-1-yl)-N$^6$-(pyrazin-2-yl)pyridine-2,6-diamine was obtained by the same process as in Example 211, using 0.79M isopropyl magnesium bromide/tetrahydrofuran solution instead of 1M cyclopropyl magnesium bromide/tetrahydrofuran solution. Furthermore, the obtained compound was subjected to hydrochlorination using a conventional method to obtain the objective compound as brown powder.

MS (ESI) m/z 437 (M+H)$^+$

Example 213

(S)—N$^2$-[1-(4-Fluorophenyl)ethyl]-4-(3-methoxy-3-methylazetidin-1-yl)-N$^6$-(pyrazin-2-yl)pyridine-2,6-diamine hydrochloride (S)—N$^2$-[1-(4-Fluorophenyl)ethyl]-4-(3-methoxy-3-methylazetidin-1-yl)-N$^{6-}$(pyrazin-2-yl)pyridine-2,6-diamine was obtained by the same process as in Example 211, using 3M methyl magnesium bromide/tetrahydrofuran solution instead of 1M cyclopropyl magnesium bromide/tetrahydrofuran solution. Furthermore, the obtained compound was subjected to hydrochlorination using a conventional method to obtain the objective compound as brown powder.

MS (ESI) m/z 409 (M+H)$^+$

Example 214

(S)—N$^2$-[1-(4-Fluorophenyl)ethyl]-4-(1-methyl-1H-pyrazol-4-yl)-N$^6$-(5-methylpyrazin-2-yl)pyridine-2,6-diamine 250 mg of 2-amino-5-bromopyrazine, 0.40 ml of trimethylboroxine, 794 mg of potassium carbonate and 166 mg of tetrakis(triphenylphosphine)palladium were added in turn to 4 ml of degassed dimethylformamide, and the mixture was stirred at 110° C. under argon atmosphere overnight. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 100 mg of pale yellow oil. The obtained residue was dissolved in 6 ml of degassed toluene, and 100 mg of (S)-6-chloro-N-[1-(4-fluorophenyl)ethyl]-4-(1-methyl-1H-pyrazol-4-yl)pyridine-2-amine, 29 mg of 2-dicyclohexylphosphino-2',4',6'-triisopropylbiphenyl, 41 mg of sodium t-butoxide and 14 mg of tris(dibenzylideneacetone)dipalladium were added in turn, and the mixture was stirred at 100° C. for 1 hour under argon atmosphere. The reaction solution was purified by silica gel column chromatography to obtain 90 mg of the objective compound as pale yellow powder.

MS (ESI) m/z 404 (M+H)$^+$

Example 215

(S)—N$^2$-[1-(4-Fluorophenyl)ethyl]-4-[1-(methanesulfonyl)piperidin-4-yl]-N$^6$-(pyrazin-2-yl)pyridine-2,6-diamine Step 1.
t-Butyl 4-(2,6-dichloropyridin-4-yl)-5,6-dihydropyridine-1(2H)-carba mate 874 mg of 2,6-dichloro-4-(4,4,5,5,-tetramethyl-1,3,2-dioxaboran-2-yl)pyridine, 1.06 g of t-butyl 4-(trifluoromethylsulfonyl oxy)-5,6-dihydropyridine-1(2H)-carbamate, 1.33 g of potassium carbonate and 26 mg of 1,1'-bis(diphenylphosphino)ferrocene-palladium(II) dichloride-dichloromethane complex were added in turn to 16 ml of degassed dimethylformamide, and the mixture was stirred at 80° C. for 1.5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 631 mg of the objective compound.
Step 2.
2,6-Dichloro-4-[1-(methylsulfonyl)-1,2,3,6-tetrahydropyridin-4-yl]pyridine 327 mg of t-butyl 4-(2,6-dichloropyridin-4-yl)-5,6-dihydropyridine-1(2H)-carba mate was dissolved in 4 ml of methylene chloride, and 2 ml of trifluoroacetic acid was added thereto, and the mixture was stirred at room temperature for 1 hour. The reaction solution was poured into 2N sodium hydroxide aqueous solution, and the mixture was subjected to extraction with ethyl acetate. The organic layer was washed in turn with water and brine, and then dried over magnesium sulfate. The solvent was distilled off under reduced pressure to obtain 221 mg of a brown solid. The obtained solid was dissolved in 10 ml of methylene chloride, and 270 µl of triethylamine, 251 mg of methanesulfonic anhydride and 1 mg of 4-dimethylaminopyridine were added thereto, and the mixture was stirred at room temperature for 1 hour. To the reaction solution was added a saturated aqueous solution of sodium bicarbonate, and then the mixture was subjected to extraction with ethyl acetate, and the organic layer was washed in turn with water and brine, and then dried over magnesium sulfate. The solvent was distilled off under reduced pressure, and then the obtained residue was purified by silica gel column chromatography to obtain 236 mg of the objective compound as pale brown powder.

Step 3.

(S)-6-Chloro-N-[1-(4-fluorophenyl)ethyl]-4-[1-(methylsulfonyl)-1,2,3,6-tetrahydropyridin-4-yl]pyridine-2-amine 225 mg of 2,6-dichloro-4-[1-(methylsulfonyl)-1,2,3,6-tetrahydropyridin-4-yl]pyridine, 104 μl of (S)-(−)-1-(4-fluorophenyl)ethylamine, 68 mg of (±)-2,2'-bis(diphenylphosphino)-1,1'-binaphthyl, 359 mg of cesium carbonate and 17 mg of palladium acetate were added in turn to 5 ml of degassed tetrahydrofuran, and the mixture was stirred at 60° C. for 10 hours under argon atmosphere. The reaction solution was diluted with ethyl acetate, and filtrated to remove precipitates, and then the filtrate was concentrated under reduced pressure, and the obtained residue was purified by silica gel column chromatography to obtain 118 mg of the objective compound as pale yellow powder.

Step 4.

(S)—$N^2$-[1-(4-Fluorophenyl)ethyl]-4-[1-(methylsulfonyl)-1,2,3,6-tetrahydropyridin-4-yl]-$N^6$-(pyrazin-2-yl)pyridine-2,6-diamine 115 mg of (S)-6-chloro-N-[1-(4-fluorophenyl)ethyl]-4-[1-(methylsulfonyl)-1,2,3,6-tetrahydropyridin-4-yl]pyridine-2-amine, 40 mg of 2-aminopyrazine, 53 mg of 2-dicyclohexylphosphino-2',4',6'-triisopropylbiphenyl, 40 mg of sodium t-butoxide and 26 mg of tris(dibenzylideneacetone)dipalladium were added in turn to 5 ml of degassed toluene, and the mixture was stirred at 100° C. for 5 hours under argon atmosphere. The reaction solution was diluted with ethyl acetate. The solution was washed in turn with water and brine and then dried over magnesium sulfate. The solvent was distilled off under reduced pressure, and then the obtained residue was purified by silica gel column chromatography to obtain 89 mg of the objective compound as pale brown powder.

Step 5.

(S)—$N^2$-[1-(4-Fluorophenyl)ethyl]-4-[1-(methanesulfonyl)piperidin-4-yl]-$N^6$-(pyrazin-2-yl)pyridine-2,6-diamine 88 mg of (S)—$N^2$-[1-(4-fluorophenyl)ethyl]-4-[1-(methylsulfonyl)-1,2,3,6-tetrahydropyridin-4-yl]-$N^6$-(pyrazin-2-yl)pyridine-2,6-diamine was dissolved in 5 ml of methanol, and 599 mg of ammonium formate and 18 mg of palladium hydroxide 20% on carbon were added thereto, and the mixture was heated at reflux for 3 hours. 599 mg of ammonium formate and 18 mg of palladium hydroxide 20% on carbon were added to the reaction solution, and the reaction solution was further heated at reflux for 2 hours. The reaction solution was filtrated to remove precipitates, and then the filtrate was concentrated under reduced pressure. The obtained residue was diluted with ethyl acetate. The solution was washed in turn with water and brine, and then dried over magnesium sulfate. The solvent was distilled off under reduced pressure, and then the obtained residue was purified by silica gel column chromatography to obtain 34 mg of the objective compound as pale yellow powder.

MS (ESI) m/z 471 (M+H)$^+$

Example 216

(S)—N-{2-[1-(4-Fluorophenyl)ethylamino]-6-(pyrazin-2-ylamino)pyridin-4-yl}propionamide The objective compound was obtained as a yellow amorphous solid by the same process as in Step 5 of Example 208, using propionic anhydride instead of acetic anhydride.

MS (ESI) m/z 381 (M+H)$^+$

Example 217

(S)—$N^2$-[1-(4-Fluorophenyl)ethyl]-4-[1-(2-methoxyethyl)-1H-pyrazol-4-yl]-$N^6$-(pyrazin-2-yl)pyridine-2,6-diamine The objective compound was obtained as pale yellow powder by the same process as in Example 37 using 2-bromoethyl methyl ether instead of 2-bromopropane.

MS (ESI) m/z 434 (M+H)$^+$

Example 218

(S)-4-(1-Cyclopropyl-1H-pyrazol-4-yl)-$N^2$-[1-(4-fluorophenyl)ethyl]-$N^6$-(pyrazin-2-yl)pyridine-2,6-diamine Step 1.
1-Cyclopropyl-4-iodo-1H-pyrazole 100 mg of pyrazole, 253 mg of cyclopropylboronic acid, and 312 mg of sodium carbonate were added to 2.5 ml of 1,2-dichloroethane, and 5 ml of 1,2-dichloroethane suspension including 267 mg of copper acetate and 230 mg of 2,2-bipyridine, was added dropwise thereto, and the mixture was stirred at 70° C. for 4 hours. The reaction solution was diluted with ethyl acetate. The solution was washed in turn with a saturated aqueous solution of ammonium chloride, water and brine, and then dried over magnesium sulfate. The solvent was distilled off under reduced pressure to obtain 148 mg of yellow oil. The obtained oil was dissolved in 3 ml of acetonitrile, 209 mg of iodine and 451 mg of diammonium cerium(IV) nitrate were added thereto under ice water cooling, and the mixture was stirred at room temperature for 5 hours. 6 ml of 5% sodium hydrogensulfite aqueous solution was added thereto, and the mixture was stirred at room temperature for 10 minutes. The reaction solution was diluted with ethyl acetate. The solution was washed in turn with water and brine, and then dried over magnesium sulfate. The solvent was distilled off under reduced pressure, and then the obtained residue was purified by silica gel column chromatography to obtain 167 mg of the objective compound as pale yellow oil.

Step 2.
(S)-4-(1-Cyclopropyl-1H-pyrazol-4-yl)-$N^2$-[1-(4-fluorophenyl)ethyl]-$N^6$-(pyrazin-2-yl)pyridine-2,6-diamine The objective compound was obtained as pale yellow powder by the same process as in Example 37 using 1-cyclopropyl-4-iodo-1H-pyrazole instead of 4-iodo-1-isopropyl-1H-pyrazole.

MS (ESI) m/z 416 (M+H)$^+$

Example 219

(S)—$N^2$-[1-(4-Fluorophenyl)ethyl]-4-[1-(methoxymethyl)-1H-pyrazol-4-yl]-$N^6$-(pyrazin-2-yl)pyridine-2,6-diamine The objective compound was obtained as brown powder by the same process as in Example 37 using bromomethyl methyl ether instead of 2-bromopropane.

MS (ESI) m/z 420 (M+H)$^+$

Example 220

(S)-6-[3-(Dimethylamino)azetidin-1-yl]-$N^2$-[1-(4-fluorophenyl)ethyl]-$N^4$-(pyrazin-2-yl)pyrimidine-2,4-diamine Step 1.
(S)-1-{2-[1-(4-Fluorophenyl)ethylamino]-6-(pyrazin-2-ylamino)pyrimidin-4-yl}azetidin-3-one 156 mg of (S)-1-{2-[1-(4-fluorophenyl)ethylamino]-6-(pyrazin-2-ylamino) pyrimidin-4-yl}azetidin-3-ol (Example 72) was dissolved in 1 ml of dimethyl sulfoxide, and 571 µl of triethylamine was added thereto and cooled to 15° C. 0.5 ml of dimethyl sulfoxide suspension including 388 mg of pyridine-trisulfur oxide complex was added thereto, and the mixture was stirred at room temperature overnight. Ice and saturated ammonium chloride aqueous solution were added to the reaction solution, and the mixture was stirred for 15 minutes, and diluted with ethyl acetate, and the organic layer was washed with saturated ammonium chloride aqueous solution and water in turn, and dried over sodium sulfate. The solvent was distilled off under reduced pressure, and then the obtained residue was purified by silica gel column chromatography to obtain 50 mg of the objective compound as a brown amorphous solid.

MS (ESI) m/z 380 (M+H)$^+$

Step 2.
(S)-6-[3-(Dimethylamino)azetidin-1-yl]-$N^2$-[1-(4-fluorophenyl)ethyl]-$N^4$-(pyrazin-2-yl)pyrimidine-2,4-diamine 300 mg of (S)-1-{2-[1-(4-fluorophenyl)ethylamino]-6-(pyrazin-2-ylamino) pyrimidin-4-yl}azetidin-3-one was dissolved in 5 ml of 1,2-dichloroethane, and 12 ml of 2M dimethylamine/tetrahydrofuran solution and 290 of acetic acid were added thereto, and the mixture was stirred at room temperature for 30 minutes. 340 mg of sodium triacetoxyborohydride was added thereto, and the mixture was stirred at room temperature overnight. The reaction solution was diluted with ethyl acetate. The solution was washed in turn with a saturated aqueous solution of sodium bicarbonate and brine, and then dried over sodium sulfate. The solvent was distilled off under reduced pressure, and then the obtained residue was purified by silica gel column chromatography to obtain 187 mg of the objective compound as brown powder.

MS (ESI) m/z 409 (M+H)$^+$

Example 221

(S)—$N^2$-[1-(4-Fluorophenyl)ethyl]-6-[3-(methylamino)azetidin-1-yl]-$N^4$-(pyrazin-2-yl)pyrimidine-2,4-diamine The objective compound was obtained as white powder by the same process as in Example 220 using 2 M methylamine/tetrahydrofuran solution instead of 2 dimethylamine/tetrahydrofuran solution.

MS (ESI) m/z 395 (M+H)$^+$

Example 222

(S)—$N^2$-[1-(4-Fluorophenyl)ethyl]-$N^4$-(pyrazin-2-yl)-6-[3-(pyrrolidin-1-yl) azetidin-1-yl]pyrimidine-2,4-diamine The objective compound was obtained as white powder by the same process as in Example 220 using pyrrolidine instead of 2 M dimethylamine/tetrahydrofuran solution.

MS (ESI) m/z 435 (M+H)$^+$

Example 223

(S)—$N^2$-[1-(4-Fluorophenyl)ethyl]-6-(3-morpholinoazetidin-1-yl)-$N^4$-(pyrazin-2-yl)pyrimidine-2,4-diamine The objective compound was obtained as white powder by the same process as in Example 220 using morpholine instead of 2 M dimethylamine/tetrahydrofuran solution.

MS (ESI) m/z 451 (M+H)$^+$

Example 224

(S)—$N^2$-[1-(4-Fluorophenyl)ethyl]-6-[3-(4-methylpiperazin-1-yl)azetidin-1-yl]-$N^4$-(pyrazin-2-yl)pyrimidine-2,4-diamine The objective compound was obtained as brown powder by the same process as in Example 220 using N-methylpiperazine instead of 2 M dimethylamine/tetrahydrofuran solution.

MS (ESI) m/z 464 (M+H)$^+$

Example 225

(S)-(1-{1-[2-(4-Fluorophenyl)ethylamino]-6-(pyrazin-2-ylamino)pyrimidin-4-yl}azetidin-3-yl)piperidin-4-ol The objective compound was obtained as white powder by the same process as in Example 220 using 4-hydroxypiperidine instead of 2 M dimethylamine/tetrahydrofuran solution.

MS (ESI) m/z 465 (M+H)$^+$

Example 226

4-{2-[(1S)-1-(4-Fluorophenyl)ethylamino]-6-(pyrazin-2-ylamino)pyrimidin-4-yl}-1$\lambda^6$,4-thiomorpholin-1,1-dione Step 1.
4-{6-Chloro-2-[(1S)-1-(4-fluorophenyl)ethylamino]pyrimidin-4-yl}-1$\lambda^6$,4-thiomorpholin-1,1-dione The objective compound was obtained as a colorless amorphous solid by the same process as in Step 1 of Example 1 using thiomorpholin-1,1-dioxide instead of piperazin-2-one.

MS (ESI) m/z 385 (M+H)$^+$

Step 2.
4-{2-[(1S)-1-(4-Fluorophenyl)ethylamino]-6-(pyrazin-2-ylamino)pyrimidin-4-yl}-1$\lambda^6$,4-thiomorpholin-1,1-dione The objective compound was obtained as a brown amorphous solid by the same process as in Step 2 of Example 1 using 4-{6-chloro-2-[(1S)-1-(4-fluorophenyl)ethylamino]pyrimidin-4-yl}-1$\lambda^6$,4-thiomorpholin-1,1-dione as a starting material, and using a mixed solvent of toluene/1,4-dioxane instead of toluene as a reaction solvent.

MS (ESI) m/z 444 (M+H)$^F$

Example 227

(S)-1-(1-{2-[1-(4-Fluorophenyl)ethylamino]-6-(pyrazin-2-ylamino)pyrimidin-4-yl}azetidin-3-yl) urea Step 1.
(S)-1-(1-{6-Chloro-2-[1-(4-fluorophenyl)ethylamino]pyrimidin-4-yl}azetidin-3-yl)urea 105 mg of t-butyl 3-(carbamoylamino)azetidin-1-carboxylate was dissolved in 2 ml of methylene chloride, and 0.5 ml of trifluoroacetic acid was added thereto, and the mixture solution was stirred at room temperature for 30 min. The solvent was distilled off under reduced pressure and then the obtained residue was dissolved in 3 ml of 1-butanol. 108 mg of (S)-4,6-dichloro-N-[1-(4-fluorophenyl)ethyl]pyrimidine-2-amine and 331 μl of N,N-diisopropylethylamine were added to the mixture, and the mixture was stirred at 60° C. for 20 hours. The reaction solution was air-cooled to room temperature, and then diluted with ethyl acetate. The solution was washed in turn with water and brine and then dried over magnesium sulfate. The solvent was distilled off under reduced pressure to obtain 89 mg of the objective compound as white powder.

Step 2.
(S)-1-(1-{2-[1-(4-Fluorophenyl)ethylamino]-6-(pyrazin-2-ylamino)pyrimidin-4-yl}azetidin-3-yl)urea 73 mg of (S)-1-(1-{6-chloro-2-[1-(4-fluorophenyl)ethylamino]pyrimidin-4-yl}azetidin-3-yl)urea, 25 mg of 2-aminopyrazine, 38 mg of 2-dicyclohexylphosphino-2',4',6'-triisopropylbiphenyl, 29 mg of sodium t-butoxide and 18 mg of tris(dibenzylideneacetone)dipalladium were added in turn to 3 ml of a degassed mixed solvent of toluene/1,4-dioxane (1/1), and the mixture was stirred at 90° C. for 1 hour under argon atmosphere. The reaction solution was diluted with ethyl acetate. The solution was washed in turn with a saturated aqueous solution of ammonium chloride and brine, and then dried over magnesium sulfate. The solvent was distilled off under reduced pressure, and then the obtained residue was purified by silica gel column chromatography to obtain 31 mg of the objective compound as brown powder.

MS (ESI) m/z 424 (M+H)$^+$

Example 228

(S)-(1-{2-[1-(4-Fluorophenyl)ethylamino]-6-(pyrazin-2-ylamino)pyrimidin-4-yl}azetidin-3-yl) methanol Step 1.
(S)-(1-{6-Chloro-2-[1-(4-fluorophenyl)ethylamino]pyrimidin-4-yl}azetidin-3-yl)methanol The objective compound was obtained as white powder by the same process as in Step 1 of Example 1 using azetidin-3-yl-methanol instead of piperazin-2-one.

MS (ESI) m/z 323 (M+H)$^+$

Step 2.
(S)-(1-{2-[1-(4-Fluorophenyl)ethylamino]-6-(pyrazin-2-ylamino)pyrimidin-4-yl}azetidin-3-yl)methanol The objective compound was obtained as a brown amorphous solid by the same process as in Step 2 of Example 1 using (S)-(1-{6-chloro-2-[1-(4-fluorophenyl)ethylamino]pyrimidin-4-yl}azetidin-3-yl)methanol as a starting material, and using 1,4-dioxane instead of toluene as a reaction solvent.

MS (ESI) m/z 396 (M+H)$^+$

Example 229 t-Butyl (S)-(1-{2-[1-(4-fluorophenyl)ethylamino]-6-(pyrazin-2-ylamino)pyrimidin-4-yl}azetidin-3-yl) methyl carbamate The objective compound was obtained as a brown amorphous solid by the same process as in Example 1 using t-butyl azetidin-3-ylmethyl carbamate instead of piperazin-2-one.

MS (ESI) m/z 495 (M+H)$^+$

Example 230

(S)-6-[3-(Aminomethyl)azetidin-1-yl]-N$^2$-[1-(4-fluorophenyl)ethyl]-N$^4$-(pyrazin-2-yl)pyrimidine-2,4-diamine 80 mg of t-butyl (S)-(1-{2-[1-(4-fluorophenyl)ethylamino]-6-(pyrazin-2-ylamino)pyrimidin-4-yl}azetidin-3-yl)methylcarbamate was dissolved in 4 ml of dichloromethane, and 0.8 ml of trifluoroacetic acid was added thereto, and the mixture solution was stirred at room temperature for 1 hour. The solvent was distilled off under reduced pressure, and then the obtained residue was purified by silica gel column chromatography to obtain 63 mg of the objective compound as a brown amorphous solid.

MS (ESI) m/z 395 (M+H)$^+$

Example 231

(S)—N-[(1-{2-[1-(4-Fluorophenyl)ethylamino]-6-(pyrazin-2-ylamino)pyrimidin-4-yl}azetidin-3-yl) methyl]ethane sulfonamide 23 mg of (S)-6-[3-(aminomethyl)azetidin-1-yl]-N$^2$-[1-(4-fluorophenyl)ethyl]-N$^4$-(pyrazin-2-yl)pyrimidine-2,4-diamine was dissolved in 2 ml of 1,2-dichloroethane, and 8.1 mg of ethanesulfonyl chloride and 22 μl of N,N-diisopropylethylamine were added thereto, and the mixture was stirred at room temperature overnight. The solvent was distilled off under reduced pressure, and then the obtained residue was purified by silica gel column chromatography to obtain 15 mg of the objective compound as a brown amorphous solid.

MS (ESI) m/z 487 (M+H)$^+$

Example 232

(S)—N-[(1-{2-[1-(4-Fluorophenyl)ethylamino]-6-(pyrazin-2-ylamino)pyrimidin-4-yl}azetidin-3-yl) methyl]acetamide 23 mg of (S)-6-[3-(aminomethyl) azetidin-1-yl]-N$^2$-[1-(4-fluorophenyl)ethyl]-N$^4$-(pyrazin-2-yl)pyrimidine-2,4-diamine was dissolved in 2 ml of 1,2-dichloroethane, and 7 μl of acetic anhydride and 11 μl of pyridine were added thereto, and the mixture was stirred at room temperature overnight. The solvent was distilled off under reduced pressure, and then the obtained residue was purified by silica gel column chromatography to obtain 20 mg of the objective compound as a brown amorphous solid.

MS (ESI) m/z 437 (M+H)$^+$

Example 233

(S)—N²-[1-(4-Fluorophenyl)ethyl]-4-[3-morpholinoazetidin-1-yl]-N⁶-(pyrazin-2-yl)pyridine-2,6-diamine The objective compound was obtained as brown powder by the same process as in Example 38 using 4-(azetidin-3-yl)morpholine dihydrochloride instead of (S)—N-(pyrrolidin-3-yl)acetamide.

MS (ESI) m/z 450 (M+H)⁺

Example 234

(S)-1-(1-{2-[1-(4-Fluorophenyl)ethylamino]-6-(pyrazin-2-ylamino)pyridin-4-yl}azetidin-3-yl)piperidin-4-ol The objective compound was obtained as brown powder by the same process as in Example 38 using 1-(3-azetidinyl)-4-piperidinol dihydrochloride instead of (S)—N-(pyrrolidin-3-yl)acetamide.

MS (ESI) m/z 464 (M+H)⁺

The formula of Example 1 to Example 234 is shown in Table 1 to Table 12.

TABLE 1

| Example | Structural formula |
|---|---|
| 1 | |
| 2 | |
| 3 | 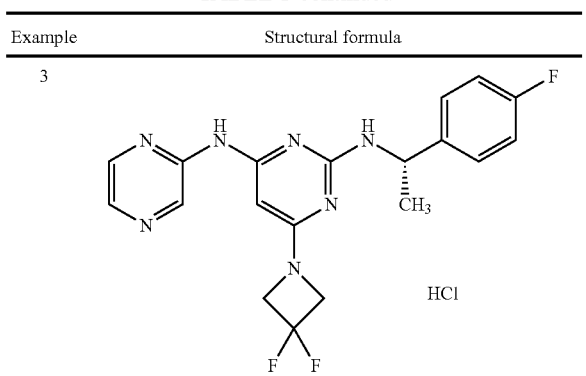 |
| 4 | 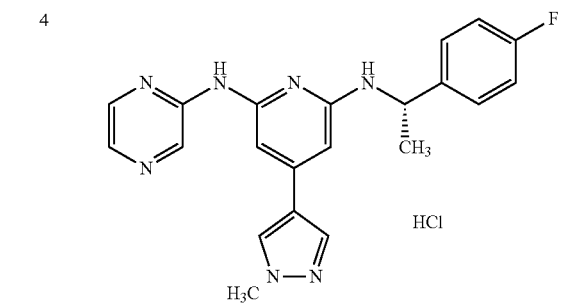 |
| 5 | 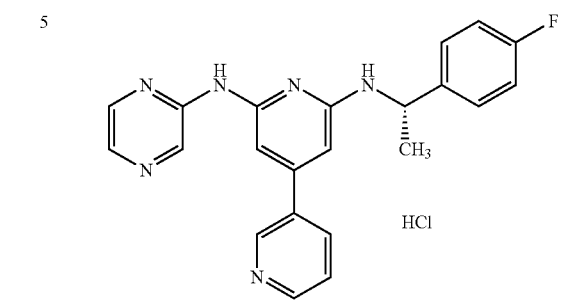 |
| 6 | 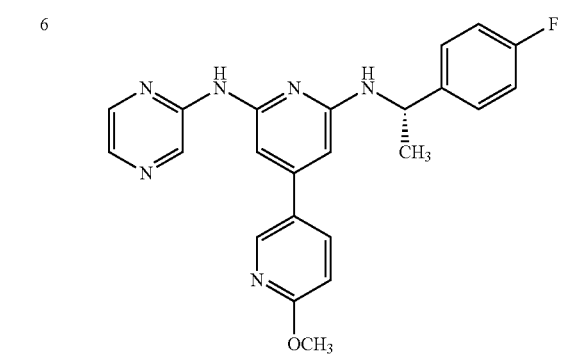 |

TABLE 1-continued

| Example | Structural formula |
|---|---|
| 7 | (pyrazinyl-NH-pyridine-NH-CH(CH3)-4-fluorophenyl, with 2-hydroxypyridin-5-yl substituent) · HCl |
| 8 | (pyrazinyl-NH-pyridazine-NH-CH(CH3)-4-fluorophenyl, with oxazol-5-yl substituent) |
| 9 | (pyrazinyl-NH-pyrimidine-NH-CH(CH3)-4-fluorophenyl, with Cl substituent) |
| 10 | (pyrazinyl-NH-pyrimidine-NH-CH(CH3)-4-fluorophenyl, with 4-(methylsulfonyl)phenyl substituent) · HCl |
| 11 | (pyrazinyl-NH-pyrimidine-NH-CH(CH3)-4-fluorophenyl, with 1H-pyrazol-4-yl substituent) · HCl |
| 12 | (pyrazinyl-NH-pyrimidine-NH-CH(CH3)-4-fluorophenyl, with O-CH2CH2-OH substituent) · HCl |
| 13 | (pyrazinyl-NH-pyrimidine-NH-CH(CH3)-4-fluorophenyl, with pyridin-3-yl substituent) |
| 14 | (pyrazinyl-NH-pyrimidine-NH-CH(CH3)-4-fluorophenyl, with pyridin-2-yl substituent) |
| 15 | (pyrazinyl-NH-pyrimidine-NH-CH(CH3)-4-fluorophenyl, with pyridin-4-yl substituent) |
| 16 | (pyrazinyl-NH-pyrimidine-NH-CH(CH3)-4-fluorophenyl, with 2-oxopyrrolidin-1-yl substituent) |

TABLE 1-continued
| Example | Structural formula |
|---|---|
| 17 | 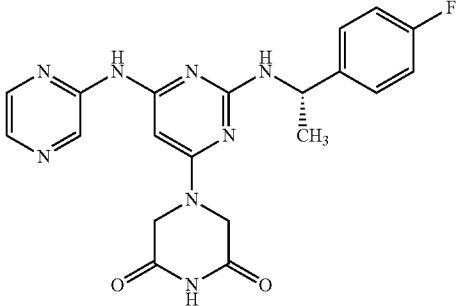 [SMILES: C[C@H](Nc1nc(Nc2cnccn2)cc(N2CC(=O)NC(=O)C2)n1)c1ccc(F)cc1] |
| 18 | 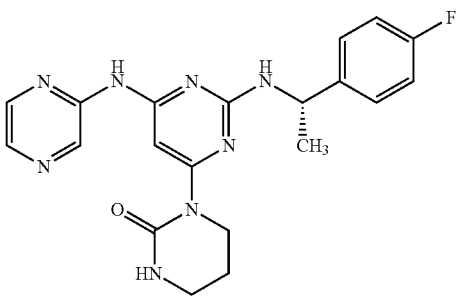 [SMILES: C[C@H](Nc1nc(Nc2cnccn2)cc(N2CCCNC2=O)n1)c1ccc(F)cc1] |
| 19 | 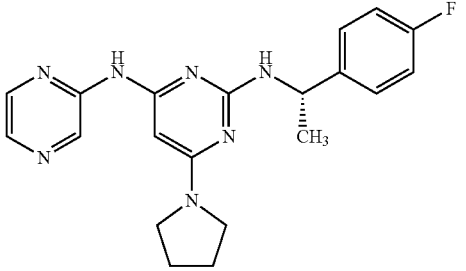 [SMILES: C[C@H](Nc1nc(Nc2cnccn2)cc(N2CCCC2)n1)c1ccc(F)cc1] |
| 20 | 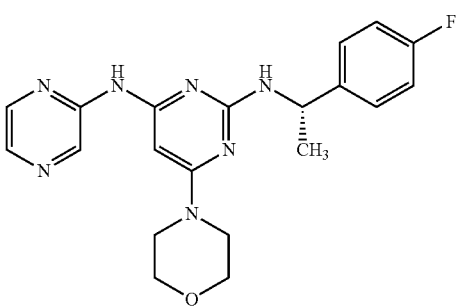 [SMILES: C[C@H](Nc1nc(Nc2cnccn2)cc(N2CCOCC2)n1)c1ccc(F)cc1] |
| 21 | 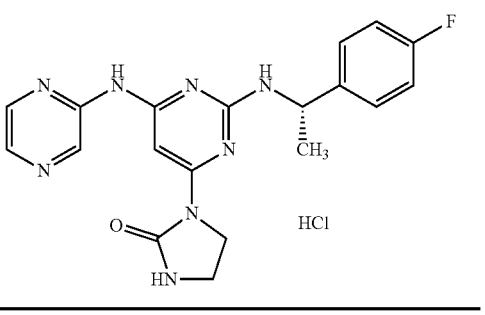 HCl |
TABLE 2
| Example | Structural formula |
|---|---|
| 22 | 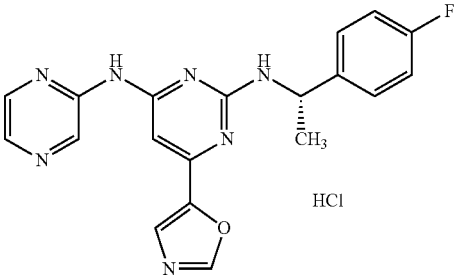 [SMILES: C[C@H](Nc1nc(Nc2cnccn2)cc(-c2cnco2)n1)c1ccc(F)cc1 ; Cl] HCl |
| 23 | 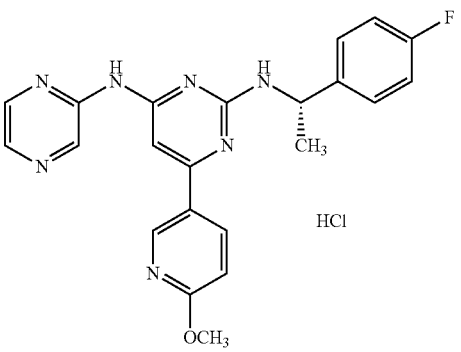 [SMILES: COc1ccc(-c2cc(Nc3cnccn3)nc(N[C@@H](C)c3ccc(F)cc3)n2)cn1 ; Cl] HCl |
| 24 | 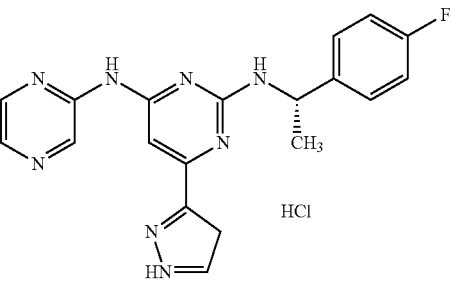 [SMILES: C[C@H](Nc1nc(Nc2cnccn2)cc(C2=NN=CC2)n1)c1ccc(F)cc1 ; Cl] HCl |
| 25 | 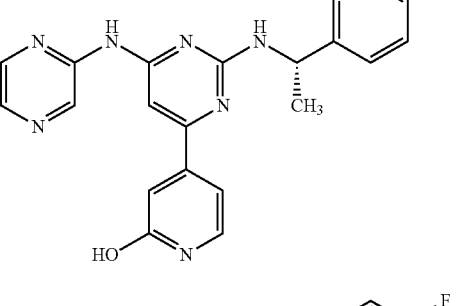 |
| 26 | 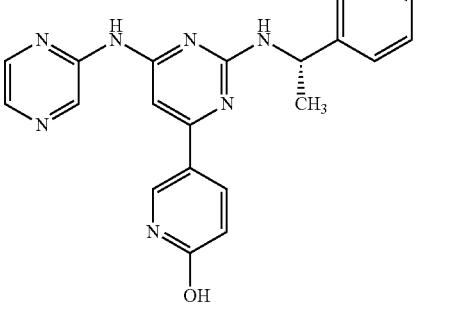 |

TABLE 2-continued

| Example | Structural formula |
|---|---|
| 27 | (structure: pyrazinyl-NH-pyrimidine-NH-CH(CH₃)-(4-F-phenyl), with pyrrolidine-NHCOCH₃ substituent) · HCl |
| 28 | (structure: pyrazinyl-NH-pyridine-NH-CH(CH₃)-(4-F-phenyl), with 1H-pyrazol-4-yl substituent) |
| 29 | (structure: pyrazinyl-NH-pyridine-NH-CH(CH₃)-(4-F-phenyl), with 1H-pyrazol-3-yl substituent) |
| 30 | (structure: pyrazinyl-NH-pyridine-NH-CH(CH₃)-(4-F-phenyl), with methylpyrazolyl substituent) · maleic acid |
| 31 | (structure: pyrazinyl-NH-pyrimidine-NH-CH(CH₃)-(4-F-phenyl), with morpholino substituent) · maleic acid |
| 32 | (structure: pyrazinyl-NH-pyrimidine-NH-CH(CH₃)-(4-F-phenyl), with pyridin-3-yl substituent) · ½ maleic acid |
| 33 | (structure: pyrazinyl-NH-pyrimidine-NH-CH(CH₃)-(4-F-phenyl), with pyrrolidine-NHCOCH₃ substituent) · maleic acid |
| 34 | (structure: pyrazinyl-NH-pyrimidine-NH-CH(CH₃)-(4-F-phenyl), with 1H-pyrazol-4-yl substituent) · maleic acid |
| 35 | (structure: pyrazinyl-NH-pyrimidine-NH-CH(CH₃)-(4-F-phenyl), with 3-(methylsulfonyl)phenyl substituent) · HCl |
| 36 | (structure: pyrazinyl-NH-pyridine-NH-CH(CH₃)-(4-F-phenyl), with 4-(methylsulfonyl)phenyl substituent) · HCl |

TABLE 2-continued

| Example | Structural formula |
|---|---|
| 37 | (structure) HCl |
| 38 | (structure) HCl |
| 39 | (structure) |
| 40 | (structure) |
| 41 | (structure) HCl |
| 42 | (structure) |

TABLE 3

| Example | Structural formula |
|---|---|
| 43 | (structure) |
| 44 | (structure) |
| 45 | (structure) |

TABLE 3-continued

| Example | Structural formula |
|---|---|
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |
| 55 | (structure) |

TABLE 3-continued

| Example | Structural formula |
|---|---|
| 56 | (pyrazin-2-ylamino)-pyrimidine with (S)-1-(4-fluorophenyl)ethylamine and 4-carbamoylpiperidine; HCl |
| 57 | (pyrazin-2-ylamino)-pyrimidine with (S)-1-(4-fluorophenyl)ethylamine and 6-carbamoylpyridin-3-yl |
| 58 | (pyrazin-2-ylamino)-pyrimidine with (S)-1-(4-fluorophenyl)ethylamine and 3-carbamoylpiperazin-1-yl |
| 59 | (pyrazin-2-ylamino)-pyrimidine with (S)-1-(4-fluorophenyl)ethylamine and 3-aminopyrrolidin-1-yl |
| 60 | (pyrazin-2-ylamino)-pyrimidine with (S)-1-(4-fluorophenyl)ethylamine and 3-(methylsulfonylamino)pyrrolidin-1-yl |
| 61 | (pyrazin-2-ylamino)-pyrimidine with (S)-1-(4-fluorophenyl)ethylamine and bis(2-hydroxyethyl)amino; HCl |
| 62 | (pyrazin-2-ylamino)-pyrimidine with (S)-1-(4-fluorophenyl)ethylamine and 2-(dimethylamino)ethylamino; 2HCl |
| 63 | (pyrazin-2-ylamino)-pyrimidine with (S)-1-(4-fluorophenyl)ethylamine and 3-carbamoylpiperidin-1-yl; HCl |

TABLE 4

| Example | Structural formula |
|---|---|
| 64 | (structure) HCl |
| 65 | (structure) HCl |
| 66 | (structure) |
| 67 | (structure) |
| 68 | (structure) |
| 69 | (structure) HCl |
| 70 | (structure) HCl |
| 71 | (structure) HCl |
| 72 | (structure) HCl |

TABLE 4-continued

| Example | Structural formula |
|---|---|
| 73 | (structure) HCl |
| 74 | (structure) |
| 75 | (structure) |
| 76 | (structure) 2HCl |
| 77 | (structure) HCl |
| 78 | (structure) HCl |
| 79 | (structure) HCl |
| 80 | (structure) HCl |
| 81 | (structure) |
| 82 | (structure) HCl |

TABLE 4-continued

| Example | Structural formula |
|---|---|
| 83 | *(structure)* |
| 84 | *(structure)* |

TABLE 5

| Example | Structural formula |
|---|---|
| 85 | *(structure)* |
| 86 | *(structure)* |

TABLE 5-continued

| Example | Structural formula |
|---|---|
| 87 | *(structure)* |
| 88 | *(structure)* |
| 89 | *(structure)* 2HCl |
| 90 | *(structure)* |

TABLE 5-continued

| Example | Structural formula |
|---------|-------------------|
| 91 | |
| 92 | HCl |
| 93 | |
| 94 | |
| 95 | HCl |
| 96 | |
| 97 | |
| 98 | |
| 99 | HCl |
| 100 | HCl |

TABLE 5-continued
| Example | Structural formula |
|---|---|
| 101 | 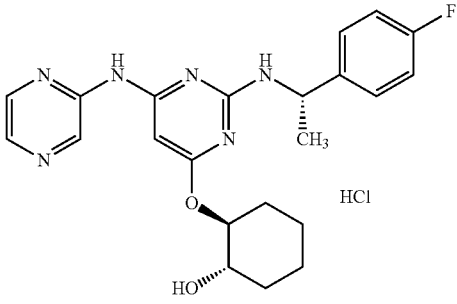 [SMILES: C[C@H](Nc1nc(Nc2cnccn2)cc(O[C@H]2CCCC[C@@H]2O)n1)c1ccc(F)cc1 ; Cl] HCl |
| 102 | 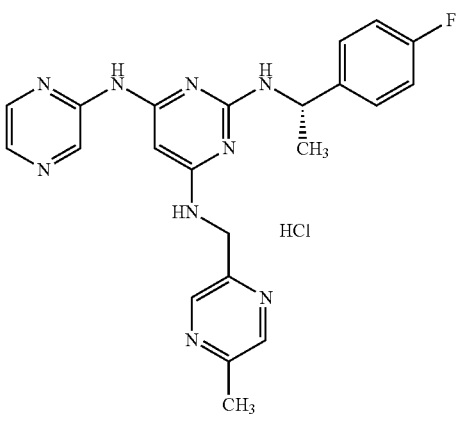 [SMILES: Cc1cnc(CNc2cc(Nc3cnccn3)nc(N[C@@H](C)c3ccc(F)cc3)n2)cn1 ; Cl] HCl |
| 103 | 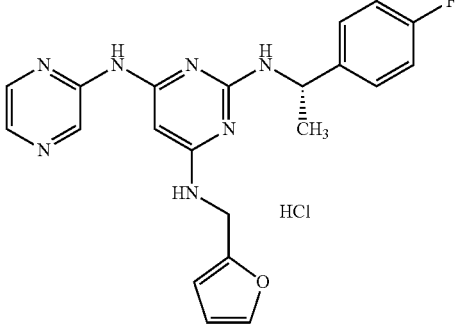 HCl |
| 104 | 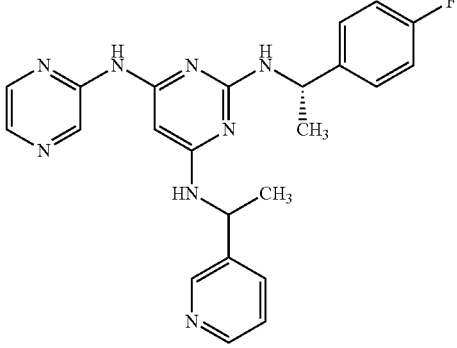 |
TABLE 5-continued
| Example | Structural formula |
|---|---|
| 105 | 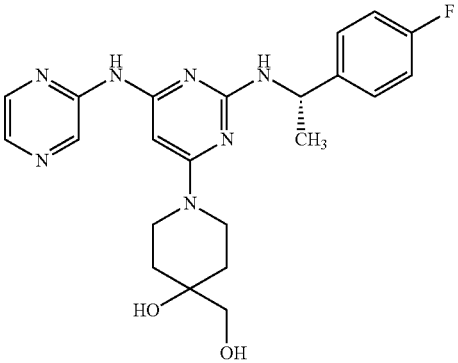 [SMILES: C[C@H](Nc1nc(Nc2cnccn2)cc(N2CCC(O)(CO)CC2)n1)c1ccc(F)cc1] |
TABLE 6
| Example | Structural formula |
|---|---|
| 106 | 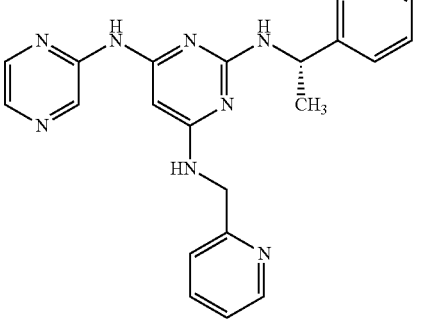 |
| 107 | 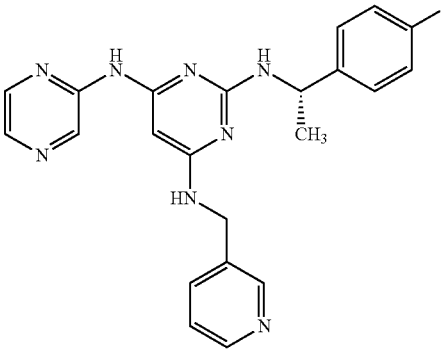 |
| 108 | 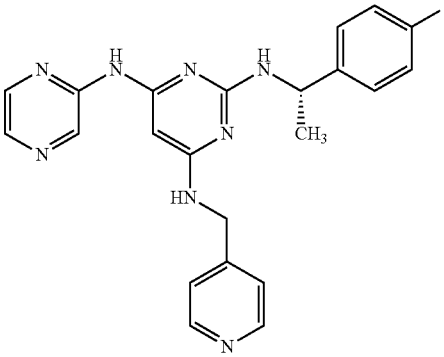 |

TABLE 6-continued

| Example | Structural formula |
|---|---|
| 109 | |
| 110 | |
| 111 | |
| 112 | |
| 113 | |
| 114 | |
| 115 | |
| 116 | |

TABLE 6-continued
| Example | Structural formula |
|---|---|
| 117 | 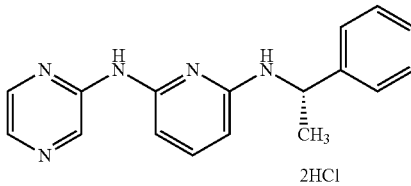 2HCl |
| 118 | HCl |
| 119 | HCl |
| 120 | HCl |
| 121 | HCl |
| 122 | 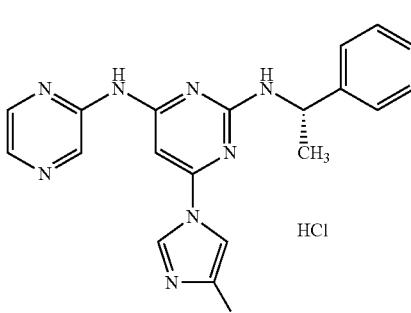 |
| 123 | |
| 124 | HCl |
| 125 | |

TABLE 6-continued

| Example | Structural formula |
|---|---|
| 126 | |

TABLE 7

| Example | Structural formula |
|---|---|
| 127 | |
| 128 | |
| 129 | |

TABLE 7-continued

| Example | Structural formula |
|---|---|
| 130 | |
| 131 | |
| 132 | |
| 133 | |
| 134 | |

TABLE 7-continued

| Example | Structural formula |
|---|---|
| 135 | (structure) HCl |
| 136 | (structure) 2HCl |
| 137 | (structure) |
| 138 | (structure) |
| 139 | (structure) HCl |
| 140 | (structure) |
| 141 | (structure) |
| 142 | (structure) HCl |
| 143 | (structure) |
| 144 | (structure) |

TABLE 7-continued

| Example | Structural formula |
|---|---|
| 145 | (structure) |
| 146 | (structure) HCl |
| 147 | (structure) HCl |

TABLE 8

| Example | Structural formula |
|---|---|
| 148 | (structure) |
| 149 | (structure) |
| 150 | (structure) |
| 151 | (structure) |
| 152 | (structure) |
| 153 | (structure) |
| 154 | (structure) |

TABLE 8-continued
| Example | Structural formula |
|---|---|
| 155 | 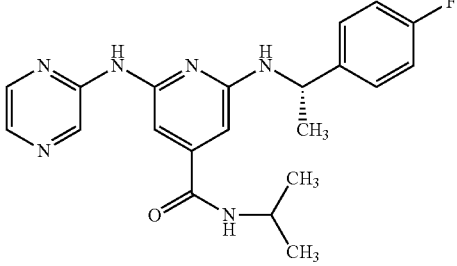 |
| 156 | 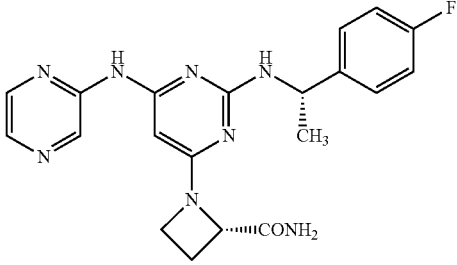 [SMILES: C[C@H](Nc1nc(Nc2cnccn2)cc(N2CC[C@H]2C(N)=O)n1)c1ccc(F)cc1] |
| 157 | 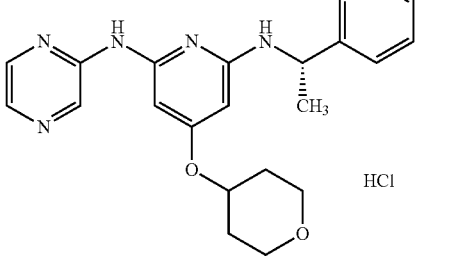 HCl |
| 158 | 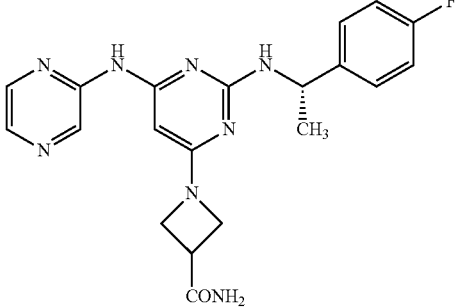 |
| 159 | 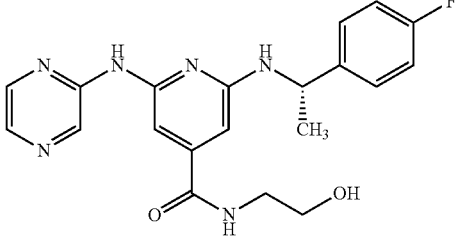 |
| 160 | 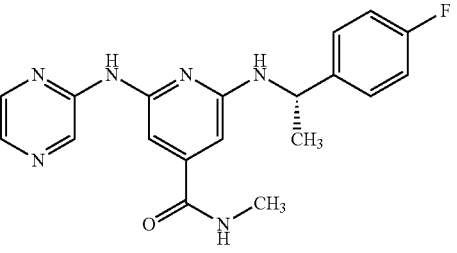 [SMILES: CNC(=O)c1cc(Nc2cnccn2)nc(N[C@@H](C)c2ccc(F)cc2)c1] |
| 161 | 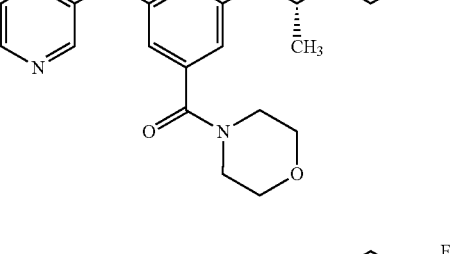 |
| 162 | 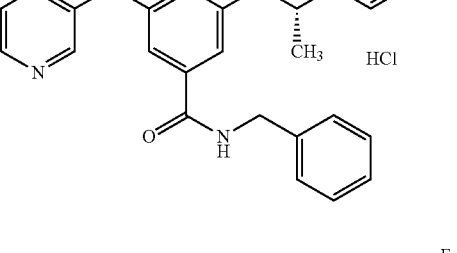 HCl |
| 163 | 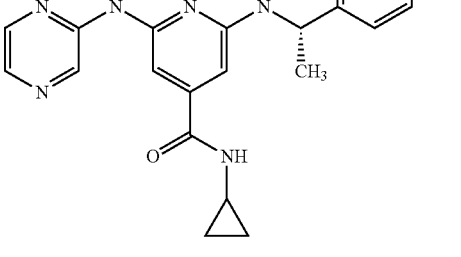 |
| 164 | 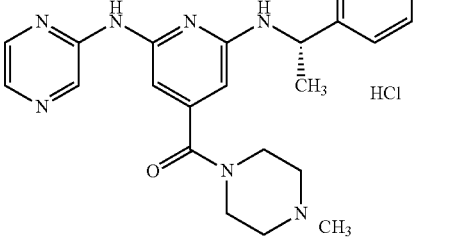 HCl |

TABLE 8-continued
| Example | Structural formula |
|---|---|
| 165 | |
| 166 | |
| 167 | |
| 168 | |
TABLE 9
| Example | Structural formula |
|---|---|
| 169 | |
TABLE 9-continued
| Example | Structural formula |
|---|---|
| 170 | |
| 171 | |
| 172 | |
| 173 | |
| 174 | 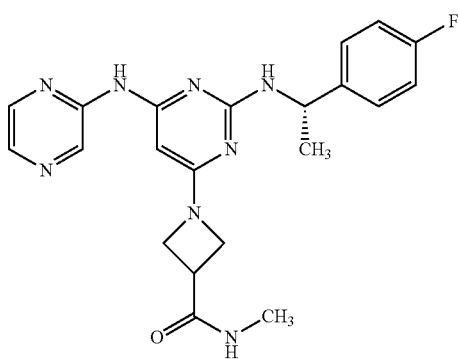 [SMILES: CNC(=O)C1CN(c2cc(Nc3cnccn3)nc(N[C@@H](C)c3ccc(F)cc3)n2)C1] |

TABLE 9-continued
| Example | Structural formula |
|---|---|
| 175 | 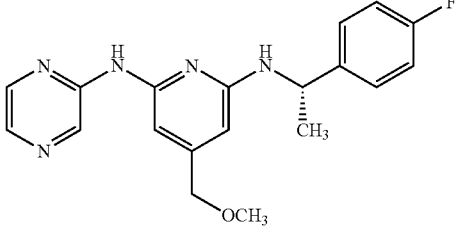 |
| 176 | 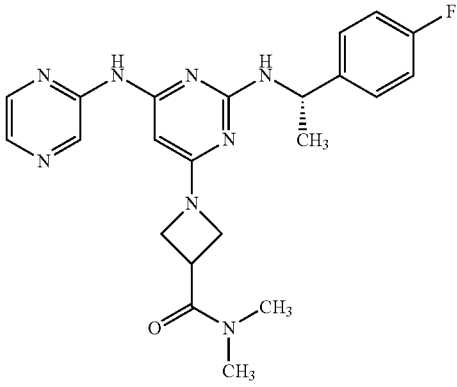 [SMILES: C[C@H](Nc1nc(Nc2cnccn2)cc(N2CC(C(=O)N(C)C)C2)n1)c1ccc(F)cc1] |
| 177 | 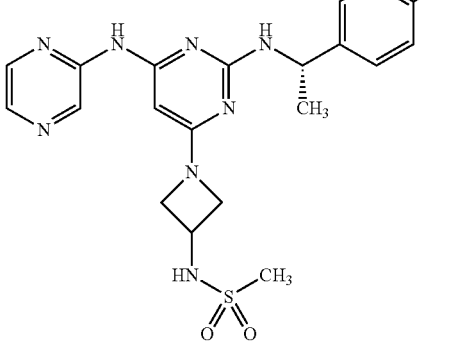 |
| 178 | 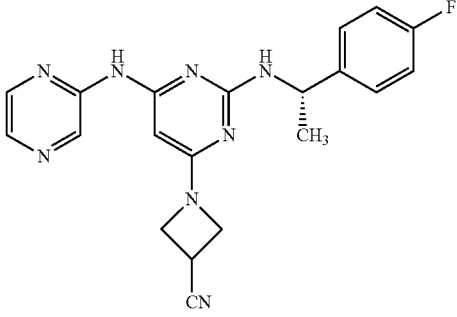 [SMILES: C[C@H](Nc1nc(Nc2cnccn2)cc(N2CC(C#N)C2)n1)c1ccc(F)cc1] |
| 179 | 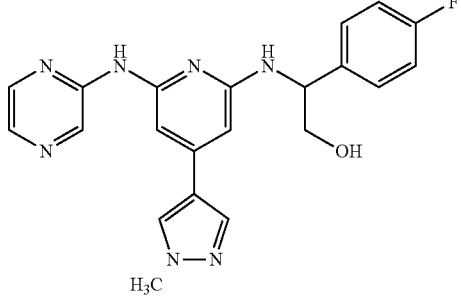 |
| 180 | 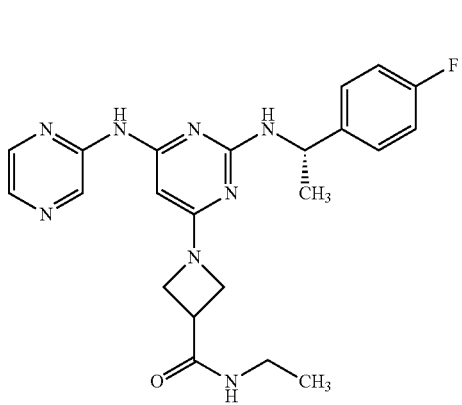 [SMILES: CCNC(=O)C1CN(c2cc(Nc3cnccn3)nc(N[C@@H](C)c3ccc(F)cc3)n2)C1] |
| 181 | 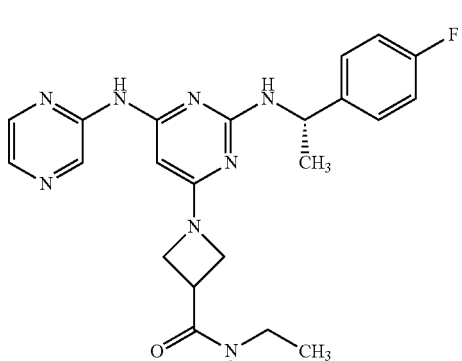 [SMILES: C[C@H](Nc1nc(Nc2cnccn2)cc(N2CC(N(C)C)C2)n1)c1ccc(F)cc1] |
| 182 | 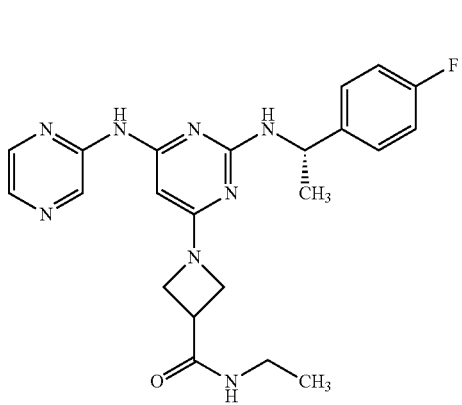 [SMILES: CCNC(=O)C1CN(c2cc(Nc3cnccn3)nc(N[C@@H](C)c3ccc(F)cc3)n2)C1] |

TABLE 9-continued

| Example | Structural formula |
|---|---|
| 183 | (structure: 4-pyrazinylamino-6-(3-methoxyazetidin-1-yl)-2-[(1S)-1-(4-fluorophenyl)ethylamino]pyrimidine, HCl) |
| 184 | (structure: 4-pyrazinylamino-6-(3-hydroxy-3-methylazetidin-1-yl)-2-[(1S)-1-(4-fluorophenyl)ethylamino]pyrimidine, HCl) |
| 185 | (structure: 6-pyrazinylamino-2-[(1S)-1-(4-fluorophenyl)ethylamino]-N-methylpyridine-3-carboxamide) |
| 186 | (structure: 6-pyrazinylamino-2-[(1S)-1-(4-fluorophenyl)ethylamino]-N,N-dimethylpyridine-3-carboxamide) |
| 187 | (structure: 6-pyrazinylamino-2-[(1S)-1-(4-fluorophenyl)ethylamino]pyridine-3-carboxamide) |

TABLE 9-continued

| Example | Structural formula |
|---|---|
| 188 | (structure: 6-pyrazinylamino-2-[(1S)-1-(4-fluorophenyl)ethylamino]-3-(morpholine-4-carbonyl)pyridine, 2HCl) |
| 189 | (structure: 6-pyrazinylamino-2-[(1S)-1-(4-fluorophenyl)ethylamino]-N-(cyclopropylmethyl)pyridine-3-carboxamide) |

TABLE 10

| Example | Structural formula |
|---|---|
| 190 | (structure: 4-pyrazinylamino-6-[3-(ethylsulfonylamino)azetidin-1-yl]-2-[(1S)-1-(4-fluorophenyl)ethylamino]pyrimidine) |
| 191 | (structure: 4-pyrazinylamino-6-[3-(isopropylcarbamoyl)azetidin-1-yl]-2-[(1S)-1-(4-fluorophenyl)ethylamino]pyrimidine) |

TABLE 10-continued
| Example | Structural formula |
|---|---|
| 192 | 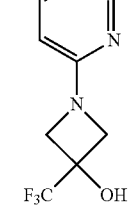 |
| 193 | |
| 194 | |
| 195 | |
TABLE 10-continued
| Example | Structural formula |
|---|---|
| 196 | 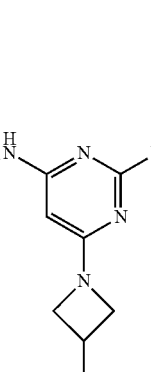 |
| 197 | |
| 198 | |
| 199 | |

TABLE 10-continued

| Example | Structural formula |
|---|---|
| 200 | (pyrazine-NH-pyrimidine with NH-CH(CH3)-(4-F-phenyl) and N-azetidine-3-cyclopropyl-3-OH) · HCl |
| 201 | (pyrazine-NH-pyrimidine with NH-CH(CH3)-(4-F-phenyl) and N-azetidine-3-isopropyl-3-OH) · HCl |
| 202 | (pyrazine-NH-pyrimidine with NH-CH(CH3)-(4-F-phenyl) and N-azetidin-3-ol) · HCl |
| 203 | (pyrazine-NH-pyrimidine with NH-CH(CH3)-(4-F-phenyl) and N-azetidine-3-cyclopropyl-3-OH) · HCl |
| 204 | (pyrazine-NH-pyridine with NH-CH(CH3)-(4-F-phenyl) and N-azetidine-3-isopropyl-3-OH) · HCl |
| 205 | (pyrazine-NH-pyridine with NH-CH(CH3)-(4-F-phenyl) and N-azetidine-3-methyl-3-OH) · HCl |
| 206 | (pyrazine-NH-pyridine with NH-CH(CH3)-(4-F-phenyl) and N-azetidine-3-CF3-3-OH) · HCl |
| 207 | (pyrazine-NH-pyridine with NH-CH(CH3)-(4-F-phenyl) and N-3,3-difluoroazetidine) · HCl |
| 208 | (pyrazine-NH-pyridine with NH-CH(CH3)-(4-F-phenyl) and NH-C(=O)CH3) |

TABLE 10-continued
| Example | Structural formula |
|---|---|
| 209 | 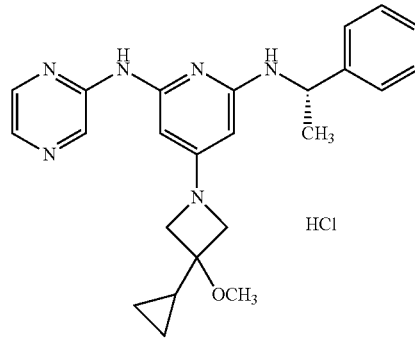 |
| 210 | |
TABLE 11
| Example | Structural formula |
|---|---|
| 211 | 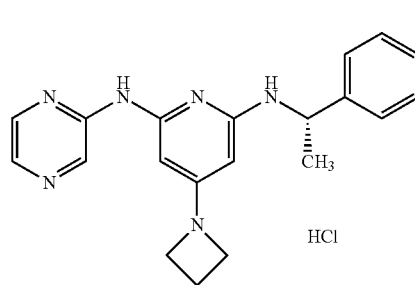 |
| 212 | |
TABLE 11-continued
| Example | Structural formula |
|---|---|
| 213 | 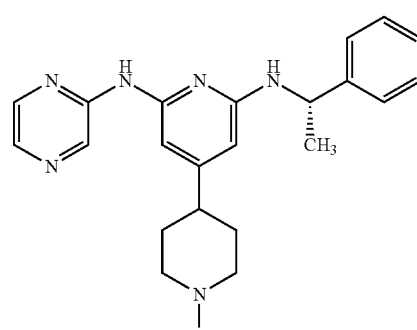 |
| 214 | |
| 215 | 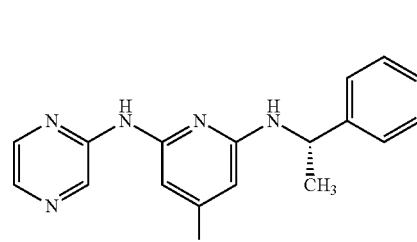 |
| 216 | |

TABLE 11-continued

| Example | Structural formula |
|---------|-------------------|
| 217 | (pyrazin-2-ylamino)-pyridine with (S)-1-(4-fluorophenyl)ethylamino and 1-(2-methoxyethyl)-1H-pyrazol-4-yl substituent |
| 218 | (pyrazin-2-ylamino)-pyridine with (S)-1-(4-fluorophenyl)ethylamino and 1-cyclopropyl-1H-pyrazol-4-yl substituent |
| 219 | (pyrazin-2-ylamino)-pyridine with (S)-1-(4-fluorophenyl)ethylamino and 1-(methoxymethyl)-1H-pyrazol-4-yl substituent |
| 220 | (pyrazin-2-ylamino)-pyrimidine with (S)-1-(4-fluorophenyl)ethylamino and 3-(dimethylamino)azetidin-1-yl substituent |
| 221 | (pyrazin-2-ylamino)-pyrimidine with (S)-1-(4-fluorophenyl)ethylamino and 3-(methylamino)azetidin-1-yl substituent |
| 222 | (pyrazin-2-ylamino)-pyrimidine with (S)-1-(4-fluorophenyl)ethylamino and 3-(pyrrolidin-1-yl)azetidin-1-yl substituent |
| 223 | (pyrazin-2-ylamino)-pyrimidine with (S)-1-(4-fluorophenyl)ethylamino and 3-morpholinoazetidin-1-yl substituent |
| 224 | (pyrazin-2-ylamino)-pyrimidine with (S)-1-(4-fluorophenyl)ethylamino and 3-(4-methylpiperazin-1-yl)azetidin-1-yl substituent |

TABLE 11-continued

| Example | Structural formula |
|---|---|
| 225 | (chemical structure) |
| 226 | (chemical structure) |
| 227 | (chemical structure) |
| 228 | (chemical structure) |
| 229 | (chemical structure) |
| 230 | (chemical structure) |
| 231 | (chemical structure) |

TABLE 12

| Example | Structural formula |
|---|---|
| 232 | (chemical structure) |

TABLE 12-continued

| Example | Structural formula |
|---|---|
| 233 | (structure: pyrazine-NH-pyridine-NH-CH(CH3)-C6H4-F, with azetidine-N-morpholine substituent) |
| 234 | (structure: pyrazine-NH-pyridine-NH-CH(CH3)-C6H4-F, with azetidine-N-piperidine-OH substituent) |

Test 1: Test for inhibitory activity to JAK2 and JAK3 tyrosine kinase

1. Preparation of Test Material

The test material was dissolved in dimethylsulfoxide (DMSO) to be 10 mM, and further diluted with DMSO to be 100-fold concentrations for measurement (1000, 300, 100, 30, 10, 3, 1, 0.3, 0.1, 0.03, 0.01 μM). In addition, solutions diluted with an assay buffer up to 20 times were used as solutions of the test material. As a negative control, a solution of DMSO diluted 20 times with an assay buffer was used. As the assay buffer, 15 mM Tris-Cl (pH 7.5), 0.01 v/v % Tween-20, and 1 mM dithiothreitol were used.

2. Measurement of the Activities of JAK2 and JAK3 Tyrosine Kinases

The activity was determined by ELISA. The solution of the test material (10 μl each; n=2) was placed in a streptavidine-coated 96 well plate (DELFIA Strip Plate 8×12 wells; Perkin Elmer), to which 20 μl each of substrate solution (625 nM biotin-labeled peptide substrate, 25 μM ATP, 25 mM MgCl$_2$, 15 mM Tris-Cl (pH 7.5), 0.01 v/v % Tween-20, and 1 mM dithiothreitol), was added and stirred. Finally, 20 μl each of JAK2 tyrosine kinase (Carnabioscience Co.) (diluted to 0.75 nM with assay buffer) or JAK3 tyrosine kinase (Carnabioscience Co.) (diluted to 0.75 nM with assay buffer) was added, stirred and allowed to stand at 30° C. for 1 hour. The plate was washed 4 times with a washing buffer (50 mM Tris-Cl, pH 7.5, 150 mM NaCl, 0.02 v/v % Tween-20), and then a blocking buffer (0.1% Bovine Serum Albumin, 50 mM Tris-Cl, pH 7.5, 150 mM NaCl, 0.02 v/v % Tween-20)(150 μl each) was added for blocking at 30° C. for 30 minutes. Blocking buffer was removed, and there was added 100 μl each of horse radish peroxidase-labeled anti-phosphorylated tyrosin kinase antibody (BD Bioscience Co.) (diluted 10,000 times with blocking buffer). The plate was incubated at 30° C. for 30 minutes and then washed 4 times with a washing buffer, and 100 μl each of 3,3',5,5'-tetramethylbenzidine (Sigma-Aldrich Co.) was added to develop color for 10 minutes. 0.1 M sulfuric acid (100 μl each) was added to stop the reaction. The absorbance was measured by means of a micro-plate reader (BIO-RAD; Model 3550) at 450 nm.

3. Analysis of the Results of the Measurement

The measured absorbance was subjected to a non-linear regression analysis by means of a SAS system (SAS Institute Inc.), and the concentration (IC$_{50}$) of the test material which inhibited 50% of the activity of each tyrosine kinase was estimated. Tables 13 to 18 show the results.

TABLE 13

| test material | inhibitory activity to JAK2 tyrosine kinase (IC$_{50}$, nM) | inhibitory activity to JAK3 tyrosine kinase (IC$_{50}$, nM) |
|---|---|---|
| Example 1 | 0.94 | 45 |
| Example 2 | 0.49 | 43 |
| Example 3 | 1.2 | 130 |
| Example 4 | 0.59 | 44 |
| Example 5 | 0.62 | 62 |
| Example 6 | 5.7 | 500 |
| Example 7 | 0.42 | 39 |
| Example 8 | 1.1 | 82 |
| Example 9 | 16 | 360 |
| Example 10 | 0.89 | 95 |
| Example 11 | 0.82 | 36 |
| Example 12 | 0.92 | 79 |
| Example 13 | 1.3 | 71 |
| Example 14 | 1.9 | 120 |
| Example 15 | 1.3 | 72 |
| Example 16 | 8.0 | 630 |
| Example 17 | 4.4 | 340 |
| Example 18 | 3.0 | 130 |
| Example 19 | 2.6 | 59 |
| Example 20 | 0.69 | 21 |
| Example 21 | 8.7 | 950 |
| Example 22 | 1.6 | 88 |
| Example 23 | 4.2 | 210 |
| Example 24 | 1.1 | 53 |
| Example 25 | 0.97 | 100 |
| Example 26 | 0.27 | 28 |
| Example 27 | 0.52 | 42 |
| Example 28 | 1.2 | 110 |
| Example 29 | 2.0 | 160 |
| Example 30 | 1.5 | 75 |
| Example 31 | 0.41 | 26 |
| Example 32 | 0.50 | 68 |
| Example 33 | 0.40 | 30 |
| Example 34 | 0.51 | 59 |
| Example 35 | 2.5 | 440 |
| Example 36 | 2.8 | 200 |
| Example 37 | 3.2 | 130 |
| Example 38 | 2.3 | 85 |
| Example 39 | 0.93 | 90 |
| Example 40 | 3.4 | 310 |
| Example 41 | 1.1 | 51 |
| Example 42 | 1.0 | 66 |
| Example 43 | 1.2 | 130 |

TABLE 14

| test material | inhibitory activity to JAK2 tyrosine kinase ($IC_{50}$, nM) | inhibitory activity to JAK3 tyrosine kinase ($IC_{50}$, nM) |
|---|---|---|
| Example 44 | 2.1 | 140 |
| Example 45 | 9.0 | 2300 |
| Example 46 | 3.7 | 93 |
| Example 47 | 12 | 1300 |
| Example 48 | 6.0 | 140 |
| Example 49 | 2.3 | 170 |
| Example 50 | 0.84 | 29 |
| Example 51 | 3.1 | 51 |
| Example 52 | 2.0 | 160 |
| Example 53 | 5.9 | 390 |
| Example 54 | 22 | 1800 |
| Example 55 | 2.0 | 190 |
| Example 56 | 0.79 | 24 |
| Example 57 | 1.3 | 82 |
| Example 58 | 0.69 | 26 |
| Example 59 | 1.7 | 60 |
| Example 60 | 0.71 | 28 |
| Example 61 | 6.0 | 150 |
| Example 62 | 2.2 | 65 |
| Example 63 | 1.0 | 36 |
| Example 64 | 7.0 | 220 |
| Example 65 | 0.27 | 8.9 |
| Example 66 | 1.8 | 37 |
| Example 67 | 11 | 470 |
| Example 68 | 1.5 | 34 |
| Example 69 | 2.6 | 83 |
| Example 70 | 1.5 | 65 |
| Example 71 | 0.72 | 26 |
| Example 72 | 0.96 | 31 |
| Example 73 | 1.3 | 48 |
| Example 74 | 3.8 | 230 |
| Example 75 | 12 | 630 |
| Example 76 | 2.5 | 57 |
| Example 77 | 0.73 | 37 |
| Example 78 | 1.4 | 35 |
| Example 79 | 4.3 | 140 |
| Example 80 | 1.1 | 60 |
| Example 81 | 5.6 | 480 |
| Example 82 | 1.7 | 99 |
| Example 83 | 3.7 | 58 |
| Example 84 | 2.0 | 170 |
| Example 85 | 0.51 | 20 |
| Example 86 | 2.4 | 87 |

TABLE 15

| test material | inhibitory activity to JAK2 tyrosine kinase ($IC_{50}$, nM) | inhibitory activity to JAK3 tyrosine kinase ($IC_{50}$, nM) |
|---|---|---|
| Example 87 | 14 | 450 |
| Example 88 | 13 | 200 |
| Example 89 | 3.8 | 150 |
| Example 90 | 6.1 | 380 |
| Example 91 | 1.4 | 97 |
| Example 92 | 9.8 | 460 |
| Example 93 | 3.0 | 220 |
| Example 94 | 1.7 | 77 |
| Example 95 | 2.2 | 110 |
| Example 96 | 1.4 | 33 |
| Example 97 | 37 | 610 |
| Example 98 | 19 | 1300 |
| Example 99 | 2.4 | 200 |
| Example 100 | 0.52 | 47 |
| Example 101 | 11 | 600 |
| Example 102 | 2.6 | 140 |
| Example 103 | 4.1 | 310 |
| Example 104 | 1.0 | 39 |
| Example 105 | 0.55 | 27 |
| Example 106 | 1.9 | 110 |
| Example 107 | 0.77 | 56 |
| Example 108 | 1.1 | 56 |
| Example 109 | 2.4 | 130 |
| Example 110 | 0.67 | 44 |
| Example 111 | 1.6 | 110 |
| Example 112 | 0.69 | 67 |
| Example 113 | 4.9 | 200 |
| Example 114 | 4.8 | 66 |
| Example 115 | 2.3 | 210 |
| Example 116 | 5.3 | 340 |
| Example 117 | 2.7 | 190 |
| Example 118 | 1.6 | 290 |
| Example 119 | 28 | 1600 |
| Example 120 | 23 | 1700 |
| Example 121 | 2.7 | 170 |
| Example 122 | 0.40 | 30 |
| Example 123 | 5.4 | 330 |
| Example 124 | 1.3 | 66 |
| Example 125 | 1.6 | 130 |
| Example 126 | 8.8 | 630 |

TABLE 16

| test material | inhibitory activity to JAK2 tyrosine kinase ($IC_{50}$, M) | inhibitory activity to JAK3 tyrosine kinase ($IC_{50}$, nM) |
|---|---|---|
| Example 127 | 2.9 | 200 |
| Example 128 | 0.65 | 46 |
| Example 129 | 3.4 | 380 |
| Example 130 | 7.7 | 570 |
| Example 131 | 2.8 | 180 |
| Example 132 | 7.8 | 350 |
| Example 133 | 3.0 | 230 |
| Example 134 | 9.2 | 620 |
| Example 135 | 2.6 | 320 |
| Example 136 | 1.1 | 170 |
| Example 137 | 2.2 | 160 |
| Example 138 | 3.4 | 420 |
| Example 139 | 5.0 | 290 |
| Example 140 | 1.4 | 61 |
| Example 141 | 14 | 440 |
| Example 142 | 1.2 | 66 |
| Example 143 | 14 | 2100 |
| Example 144 | 2.1 | 210 |
| Example 145 | 0.34 | 36 |
| Example 146 | 9.5 | 1400 |
| Example 147 | 9.2 | 920 |
| Example 148 | 21 | 810 |
| Example 149 | 2.6 | 690 |
| Example 150 | 1.7 | 150 |
| Example 151 | 7.4 | 490 |
| Example 152 | 0.71 | 93 |
| Example 153 | 8.4 | 300 |
| Example 154 | 16 | 340 |
| Example 155 | 2.4 | 390 |
| Example 156 | 6.7 | 580 |
| Example 157 | 2.0 | 150 |
| Example 158 | 0.65 | 39 |
| Example 159 | 1.0 | 170 |
| Example 160 | 1.0 | 100 |
| Example 161 | 12 | 230 |
| Example 162 | 3.4 | 370 |
| Example 163 | 0.74 | 170 |
| Example 164 | 12 | 470 |
| Example 165 | 3.1 | 360 |

TABLE 17

| test material | inhibitory activity to JAK2 tyrosine kinase (IC$_{50}$, nM) | inhibitory activity to JAK3 tyrosine kinase (IC$_{50}$, nM) |
| --- | --- | --- |
| Example 166 | 2.2 | 380 |
| Example 167 | 1.6 | 350 |
| Example 168 | 17 | 1300 |
| Example 169 | 3.0 | 500 |
| Example 170 | 1.2 | 180 |
| Example 171 | 1.9 | 570 |
| Example 172 | 0.85 | 150 |
| Example 173 | 1.5 | 200 |
| Example 174 | 0.99 | 47 |
| Example 175 | 4.9 | 400 |
| Example 176 | 0.96 | 35 |
| Example 177 | 0.74 | 87 |
| Example 178 | 1.0 | 82 |
| Example 179 | 2.6 | 330 |
| Example 180 | 2.5 | 52 |
| Example 181 | 2.2 | 56 |
| Example 182 | 6.4 | 440 |
| Example 183 | 1.8 | 59 |
| Example 184 | 0.92 | 45 |
| Example 185 | 4.2 | 380 |
| Example 186 | 5.5 | 240 |
| Example 187 | 2.4 | 400 |
| Example 188 | 3.7 | 120 |
| Example 189 | 12 | 1500 |
| Example 190 | 1.2 | 58 |
| Example 191 | 1.4 | 31 |
| Example 192 | 1.9 | 120 |
| Example 193 | 0.80 | 35 |
| Example 194 | 0.79 | 84 |
| Example 195 | 1.2 | 50 |
| Example 196 | 0.64 | 35 |
| Example 197 | 1.6 | 58 |
| Example 198 | 1.6 | 60 |
| Example 199 | 1.6 | 64 |
| Example 200 | 0.39 | 26 |
| Example 201 | 0.41 | 35 |
| Example 202 | 4.7 | 470 |
| Example 203 | 4.5 | 120 |
| Example 204 | 8.1 | 220 |

TABLE 18

| test material | inhibitory activity to JAK2 tyrosine kinase (IC$_{50}$, nM) | inhibitory activity to JAK3 tyrosine kinase (IC$_{50}$, nM) |
| --- | --- | --- |
| Example 205 | 2.8 | 170 |
| Example 206 | 10 | 360 |
| Example 207 | 7.0 | 300 |
| Example 208 | 1.4 | 100 |
| Example 209 | 7.1 | 440 |
| Example 210 | 3.2 | 180 |
| Example 211 | 5.6 | 86 |
| Example 212 | 15 | 160 |
| Example 213 | 3.2 | 130 |
| Example 214 | 5.5 | 380 |
| Example 215 | 2.3 | 210 |
| Example 216 | 1.4 | 49 |
| Example 217 | 1.5 | 36 |
| Example 218 | 2.2 | 85 |
| Example 219 | 2.6 | 69 |
| Example 220 | 0.98 | 24 |
| Example 221 | 1.5 | 59 |
| Example 222 | 0.75 | 18 |
| Example 223 | 0.65 | 11 |
| Example 224 | 1.1 | 16 |
| Example 225 | 0.69 | 13 |
| Example 226 | 1.1 | 24 |
| Example 227 | 1.1 | 20 |
| Example 228 | 1.1 | 19 |
| Example 229 | 3.9 | 180 |
| Example 230 | 1.2 | 63 |
| Example 231 | 0.59 | 33 |
| Example 232 | 0.55 | 32 |
| Example 233 | 5.8 | 140 |
| Example 234 | 5.4 | 170 |

As mentioned above, the compounds of the invention or pharmaceutically acceptable salts thereof exhibit a high JAK2 tyrosine kinase inhibitory activity with a low JAK3 tyrosine kinase inhibitory activity; thus, pharmaceutical compositions containing the compounds of the invention or pharmaceutically acceptable salts thereof can be used as preventives or therapeutics for cancers (e.g. hematic cancers (e.g. polycythemia vera, essential thrombocythemia, myeloidproliferative neoplasms such as idiopathic myelofibrosis (chronic myeloid proliferative diseases), osteomyelodysplasia syndrome, acute lymphocytic leukemia, acute myeloid leukemia, chronic myeloid leukemia, multiple myeloma), solid cancers (e.g. prostatic cancer, breast cancer)), inflammatory diseases (e.g. rheumatoid arthritis, inflammatory bowel disease, osteoporosis, multiple sclerosis), and angiopathy (e.g., pulmonary hypertension, arteriosclerosis, aneurysm, varicose vein).

Further, the compounds of the invention or pharmaceutically acceptable salts thereof are excellent also from the viewpoint of adverse effects, since their inhibitory activity to other families of tyrosine kinases is weak.

Test 2: Growth inhibitory action against variant JAK2 expressed cells

BaF3 cells into which JAK2 V617F gene was introduced (BaF3/JAK3 V617F cells) were inoculated on a 96-well plate in an amount of 1×10$^3$ cells/well and allowed to stand in a CO$_2$ incubator. Next day, the test material was added to the cells. The test material was serially diluted with DMSO to give 10 mM, 6 mM, 3 mM, 1 mM, 600 µM, 300 µM, 100 µM, 60 µM, 30 µM, or 10 µM solution. This was diluted 100 times with distilled water to give 100 µM, 60 µM, 30 µM, 10 µM, 6 µM, 3 µM, 1 µM, 600 nM, 300 nM, or 100 nM solution. This solution of test material was added to the well in an amount of 10 µl/well. As a negative control, 1% DMSO solution was added to the well in an amount of 10 µl/well. In the above operation, the final concentration of the test material became 10 µM, 6 µM, 3 µM, 1 µM, 600 nM, 300 nM, 100 nM, 60 nM, 30 nM, 10 nM, or 0 nM (0.1% DMSO solution). The addition of the test material solution to each well was made in triplicate.

After continuous incubation for 3 days, the viable count was determined by an MTT method. The MTT method was carried out as follows. First, 10 µl each of solution containing 5 mg/ml of MTT (3-(4,5-dimethylthiazol-2-yl)-2,5-diphenyltetrazolium bromide) was added to each well. The plate was allowed to stand in a CO$_2$ incubator for 4 hours, and then 100 µl of 0.04N HCl/2-propanol solution was added to each well to stop the reaction. The generated MTT-formazan was dissolved well with a multi-channel pipette, and the absorbance at 595 nm was measured with reference to that at 655 nm (Thermo Co.; Multiskan FC). Non-linear regression analysis was made by means of a SAS system (SAS Institute Inc.), and the concentration (IC$_{50}$) of the test material which inhibited 50% of the cell growth was estimated. Table 19 shows the results.

TABLE 19

| test material | (IC$_{50}$, nM) |
|---|---|
| Example 1 | 83 |
| Example 2 | 70 |
| Example 4 | 71 |
| Example 7 | 90 |
| Example 11 | 100 |
| Example 20 | 55 |
| Example 24 | 100 |
| Example 27 | 89 |
| Example 28 | 94 |
| Example 30 | 60 |
| Example 31 | 87 |
| Example 50 | 53 |
| Example 56 | 81 |
| Example 60 | 80 |
| Example 65 | 93 |
| Example 71 | 100 |
| Example 105 | 60 |
| Example 112 | 64 |
| Example 152 | 100 |
| Example 166 | 64 |
| Example 167 | 63 |
| Example 170 | 77 |
| Example 200 | 70 |
| Example 220 | 64 |
| Example 222 | 66 |
| Example 223 | 57 |
| Example 224 | 94 |
| Example 225 | 64 |
| Example 228 | 89 |
| Example 231 | 97 |
| Example 232 | 88 |

Formulation Example 1

Tablets (for oral administration)

Formulation: Each tablet (80 mg) contains the following

| | |
|---|---|
| Compound of Example 1 | 5.0 mg |
| Corn starch | 46.6 mg |
| Crystalline cellulose | 24.0 mg |
| Methyl cellulose | 4.0 mg |
| Magnesium stearate | 0.4 mg |

The mixed powder in the above ratio is made into tablets by a conventional method to prepare tablets for oral administration.

Formulation Example 2

Tablets (for oral administration)

Formulation: Each tablet (80 mg) contains the following

| | |
|---|---|
| Compound of Example 2 | 5.0 mg |
| Corn starch | 46.6 mg |
| Crystalline cellulose | 24.0 mg |
| Methyl cellulose | 4.0 mg |
| Magnesium stearate | 0.4 mg |

The mixed powder in the above ratio is made into tablets by a conventional method to prepare tablets for oral administration.

As mentioned above, the compounds of the invention or pharmaceutically acceptable salts thereof exhibit a high JAK2 tyrosine kinase inhibitory activity; thus, pharmaceutical compositions containing the compounds of the invention or pharmaceutically acceptable salts thereof can be used as preventives or therapeutics for cancers (e.g. hematic cancers (e.g. polycythemia vera, essential thrombocythemia, myeloidproliferative neoplasms such as idiopathic myelofibrosis (chronic myeloid proliferative diseases), osteomyelodysplasia syndrome, acute lymphocytic leukemia, acute myeloid leukemia, chronic myeloid leukemia, multiple myeloma), solid cancers (e.g. prostatic cancer, breast cancer)), inflammatory diseases (e.g. rheumatoid arthritis, inflammatory bowel disease, osteoporosis, multiple sclerosis), and angiopathy (e.g., pulmonary hypertension, arteriosclerosis, aneurysm, varicose vein).

What is claimed is:

1. A compound (S)—$N^2$-[1-(4-fluorophenyl)ethyl]-4-(1-methyl-1H-pyrazol-4-yl)-$N^6$-(pyrazin-2-yl)pyridine-2,6-diamine or a pharmaceutically acceptable salt thereof.

2. The pharmaceutically acceptable salt according to claim 1, which is (S)—$N^2$-[1-(4-fluorophenyl)ethyl]-4-(1-methyl-1H-pyrazol-4-yl)-$N^6$-(pyrazin-2-yl)pyridine-2,6-diamine maleate.

3. A pharmaceutical composition, comprising the compound or pharmaceutically acceptable salt thereof according to claim 1 as an active ingredient.

4. A pharmaceutical composition, comprising the pharmaceutically acceptable salt according to claim 2 as an active ingredient.

5. A method of treating polycythemia vera, essential thrombocythemia, or idiopathic myelofibrosis, comprising the step of administering the compound or pharmaceutically acceptable salt thereof according to claim 1 to a human subject.

6. The method of treating polycythemia vera, essential thrombocythemia, or idiopathic myelofibrosis according to claim 5, wherein what is administered is (S)—$N^2$-[1-(4-fluorophenyl)ethyl]-4-(1-methyl-1H-pyrazol-4-yl)-$N^6$-(pyrazin-2-yl)pyridine-2,6-diamine maleate.

7. The method of treating polycythemia vera, essential thrombocythemia, or idiopathic myelofibrosis according to claim 5, wherein what is treated is polycythemia vera.

8. The method of treating polycythemia vera according to claim 7, wherein what is administered is (S)—$N^2$-[1-(4-fluorophenyl)ethyl]-4-(1-methyl-1H-pyrazol-4-yl)-$N^6$-(pyrazin-2-yl)pyridine-2,6-diamine maleate.

9. The method of treating polycythemia vera, essential thrombocythemia, or idiopathic myelofibrosis according to claim 5, wherein what is treated is essential thrombocythemia.

10. The method of treating essential thrombocythemia according to claim 9, wherein what is administered is (S)—$N^2$-[1-(4-fluorophenyl)ethyl]-4-(1-methyl-1H-pyrazol-4-yl)-$N^6$-(pyrazin-2-yl)pyridine-2,6-diamine maleate.

11. The method of treating polycythemia vera, essential thrombocythemia, or idiopathic myelofibrosis according to claim 5, wherein what is treated is idiopathic myelofibrosis.

12. The method of treating idiopathic myelofibrosis according to claim 11, wherein what is administered is (S)—$N^2$-[1-(4-fluorophenyl)ethyl]-4-(1-methyl-1H-pyrazol-4-yl)-$N^6$-(pyrazin-2-yl)pyridine-2,6-diamine maleate.

* * * * *